US010158089B2

(12) United States Patent
Ma et al.

(10) Patent No.: US 10,158,089 B2
(45) Date of Patent: Dec. 18, 2018

(54) ORGANIC ELECTROLUMINESCENT MATERIALS AND DEVICES

(71) Applicant: Universal Display Corporation, Ewing, NJ (US)

(72) Inventors: Bin Ma, Plainsboro, NJ (US); Alan DeAngelis, Pennington, NJ (US); Chuanjun Xia, Lawrenceville, NJ (US); Bert Alleyne, Newtown, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 812 days.

(21) Appl. No.: 13/974,490

(22) Filed: Aug. 23, 2013

(65) Prior Publication Data

US 2013/0341609 A1 Dec. 26, 2013

Related U.S. Application Data

(63) Continuation-in-part of application No. 13/480,176, filed on May 24, 2012.

(60) Provisional application No. 61/572,276, filed on May 27, 2011.

(51) Int. Cl.
| *H01L 51/50* | (2006.01) |
| *H01L 51/00* | (2006.01) |
| *C07F 15/00* | (2006.01) |
| *C09K 11/06* | (2006.01) |
| *H05B 33/14* | (2006.01) |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1007* (2013.01); *C09K 2211/1011* (2013.01); *C09K 2211/1029* (2013.01); *C09K 2211/185* (2013.01); *H01L 51/0054* (2013.01); *H01L 51/0074* (2013.01); *H01L 51/5016* (2013.01)

(58) Field of Classification Search
CPC ............. H01L 51/5016; H01L 51/0085; H01L 51/0054; H01L 51/0074; C09K 11/06; C09K 2211/1007; C09K 2211/1011; C09K 2211/1029; C09K 2211/185; H05B 33/14; C07F 33/0015; C07F 15/0033
USPC ............... 428/690, 691, 917; 427/58, 66; 313/500–512; 257/40, 88–104; 257/E51.001–E51.052; 252/301.16–301.35; 546/4
See application file for complete search history.

(56) References Cited

U.S. PATENT DOCUMENTS

| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,519,384 B2 | 8/2013 | Xia et al. |
| 8,557,400 B2 | 10/2013 | Xia et al. |
| 2002/0024293 A1 | 2/2002 | Igarashi et al. |
| 2002/0034656 A1 | 3/2002 | Thompson et al. |
| 2002/0134984 A1 | 9/2002 | Igarashi |

(Continued)

FOREIGN PATENT DOCUMENTS

| EP | 0650955 | 5/1995 |
| EP | 1239526 | 9/2002 |

(Continued)

OTHER PUBLICATIONS

Xu et al., "Synthesis and characterization of phosphorescent cyclometalated iridium complexes containing 2,5-diphenylpyridine based ligands", Applied Organometallic Chemistry. 2005; 19: 1225-1231.

(Continued)

*Primary Examiner* — Andrew K Bohaty
*Assistant Examiner* — Dylan C Kershner
(74) *Attorney, Agent, or Firm* — Duane Morris LLP

(57) ABSTRACT

Novel heteroleptic iridium complexes are described. These iridium compounds contain alkyl substituted phenylpyridine ligands, which provide these compounds with beneficial properties when the iridium complexes are incorporated into OLED devices.

19 Claims, 3 Drawing Sheets

(56) References Cited

U.S. PATENT DOCUMENTS

| | | | |
|---|---|---|---|
| 2002/0158242 A1 | 10/2002 | Son et al. | |
| 2002/0182441 A1* | 12/2002 | Lamansky | C07F 15/0033 428/690 |
| 2002/0197511 A1 | 12/2002 | D'Andrade et al. | |
| 2003/0068536 A1* | 4/2003 | Tsuboyama | C07F 15/0033 428/704 |
| 2003/0138657 A1 | 7/2003 | Li et al. | |
| 2003/0151042 A1 | 8/2003 | Marks et al. | |
| 2003/0152802 A1 | 8/2003 | Tsuboyama et al. | |
| 2003/0162053 A1 | 8/2003 | Marks et al. | |
| 2003/0170491 A1* | 9/2003 | Liao | H01L 51/5036 428/690 |
| 2003/0175553 A1 | 9/2003 | Thompson et al. | |
| 2003/0230980 A1 | 12/2003 | Forrest et al. | |
| 2004/0013905 A1 | 1/2004 | Tsuboyama et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2004/0214038 A1 | 10/2004 | Kwong et al. | |
| 2005/0025993 A1 | 2/2005 | Thompson et al. | |
| 2005/0112401 A1 | 5/2005 | Lee et al. | |
| 2005/0112407 A1 | 5/2005 | Ogasawara et al. | |
| 2005/0123794 A1 | 6/2005 | Deaton et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0134459 A1* | 6/2006 | Huo | C07F 15/0033 428/690 |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0247061 A1 | 10/2007 | Adamovich et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2009/0315454 A1 | 12/2009 | Igarashi | |
| 2010/0270916 A1* | 10/2010 | Xia | C07F 15/0033 313/504 |
| 2011/0049496 A1 | 3/2011 | Fukuzaki | |
| 2012/0262542 A1 | 10/2012 | Veera et al. | |
| 2013/0341609 A1 | 12/2013 | Ma et al. | |

FOREIGN PATENT DOCUMENTS

| | | |
|---|---|---|
| EP | 1610398 | 12/2005 |
| EP | 1725079 | 11/2006 |
| EP | 2034538 | 3/2009 |
| JP | 200511610 | 1/2005 |
| JP | 2007123392 | 5/2007 |
| JP | 2007184348 | 7/2007 |
| JP | 2007254297 | 10/2007 |
| JP | 2008074939 | 4/2008 |
| JP | 2009059997 | 3/2009 |
| JP | 2014-512144 | 5/2014 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008029935 | 3/2008 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010013780 | 2/2010 |
| WO | 2010027583 | 3/2010 |
| WO | 2010028151 | 3/2010 |
| WO | 2010028262 | 3/2010 |
| WO | 2010129323 | 11/2010 |
| WO | 20100129323 | 11/2010 |

OTHER PUBLICATIONS

International Search Report corresponding to the PCT/US2012/039607 application.

U.S. Appl. No. 61/572,276, filed May 27, 2011.

Kim, Jae Jin et al., Dendritic Ir(III) complexes functionalized with triphenylsilylphenyl groups: Synthesis, DFT calculation and comprehensive structure-property correlation, J. Mater. Chem., 2009,19, 8347-8359.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

(56) References Cited

OTHER PUBLICATIONS

Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5'-Bis(dimesitylboryl)-2,2'5',2''-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett, 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Notice for Reasons for Rejection dated Apr. 25, 2017 for corresponding JP Application No. JP 2016-139860.

* cited by examiner

Compound 2

Formula I

ORGANIC ELECTROLUMINESCENT MATERIALS AND DEVICES

CROSS REFERENCE TO RELATED APPLICATIONS

This application is a continuation-in-part application of U.S. application Ser. No. 13/480,176, filed May 24, 2012, which claims priority to U.S. application No. 61/572,276, filed May 27, 2011, the entire disclosures of which are expressly incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to heteroleptic iridium complexes containing phenylpyridine ligands. These heteroleptic iridium complexes are useful as dopants in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

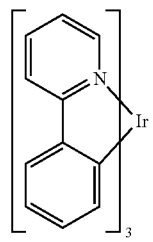

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A compound comprising a heteroleptic iridium complex is provided. In one aspect, the compound is a compound of Formula I.

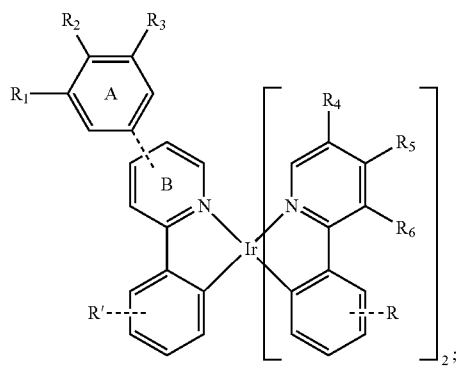

Formula I

In the compound of Formula I, $R_1$, $R_2$, $R_3$, $R_4$, $R_5$, and $R_6$, are independently selected from the group consisting of hydrogen, deuterium, cycloalkyl, deuterated cycloalkyl, alkyl, and deuterated alkyl. At least one of $R_1$, $R_2$, $R_3$, $R_4$, $R_5$, and $R_6$ is cycloalkyl, deuterated cycloalkyl, alkyl or deuterated alkyl, and any two adjacent $R_1$, $R_2$, $R_3$, $R_4$, $R_5$, and $R_6$ are optionally linked together to form a ring. Ring A is attached to the 4- or 5-position of ring B. R and R' represent mono-, di-, tri- or tetra-substitution and are independently selected from the group consisting of: hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound is a compound of Formula II.

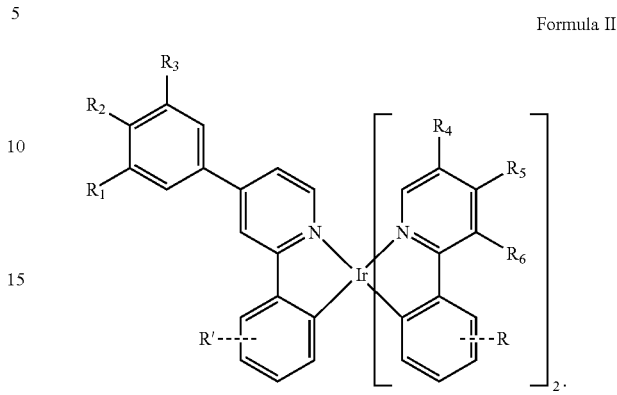

Formula II

In another aspect, the compound is a compound of Formula III.

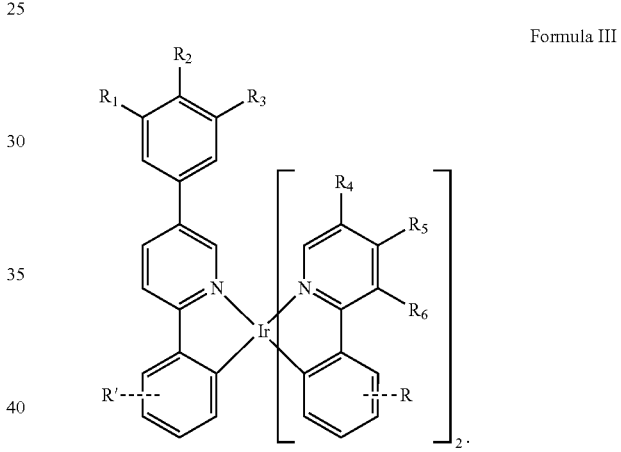

Formula III

In one aspect, $R_1$ is alkyl. In one aspect, $R_2$ is alkyl. In one aspect, $R_3$ is alkyl. In one aspect, $R_4$ is alkyl. In one aspect, $R_5$ is alkyl. In one aspect, $R_6$ is alkyl. In one aspect, at least one of $R_1$, $R_2$, and $R_3$ is alkyl. In one aspect, at least one of $R_4$, $R_5$, and $R_6$ is alkyl. In another aspect, at least one of $R_1$, $R_2$, and $R_3$ is alkyl and at least one of $R_4$, $R_5$, and $R_6$ is alkyl.

In one aspect, the alkyl contains at least 2 carbons, at least 3 carbons, or at most 6 carbons. In another aspect, the alkyl contains greater than 10 carbons.

In one aspect, the compound emits yellow light with a full width at half maximum between about 70 nm to about 110 nm when the light has a peak wavelength between about 530 nm to about 580 nm.

Specific non-limiting compounds are provided. In one aspect, the compound is selected from Compound 1-Compound 89.

In one aspect, the compound comprising a heteroleptic iridium complex has the formula $IrL_A(L_B)_2$, wherein $L_A$ is selected from the group consisting of

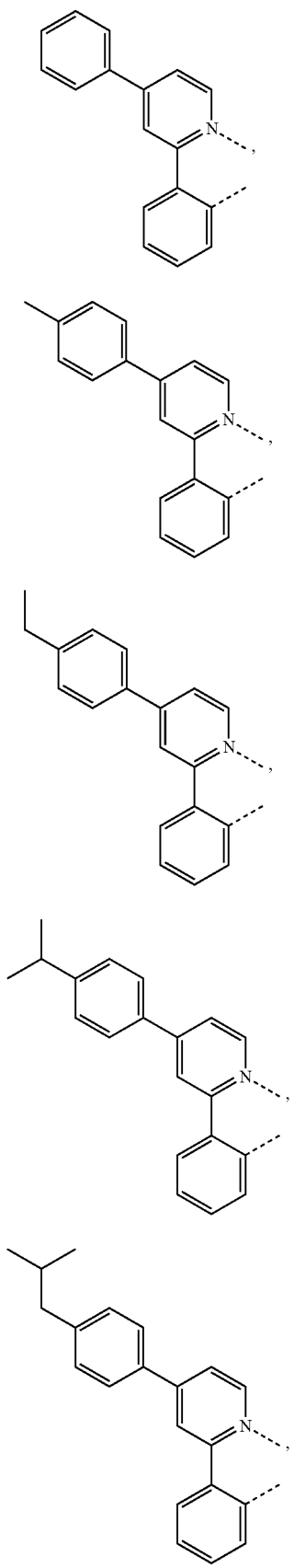
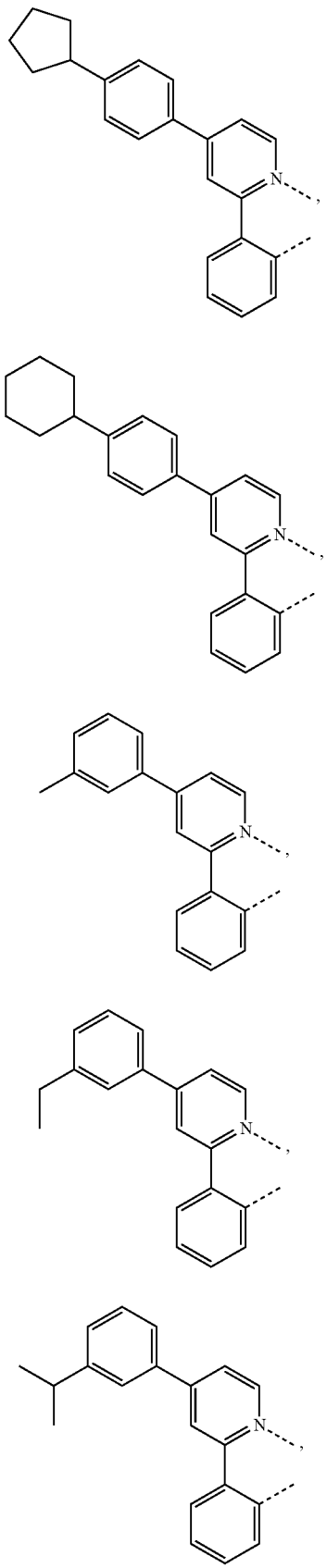

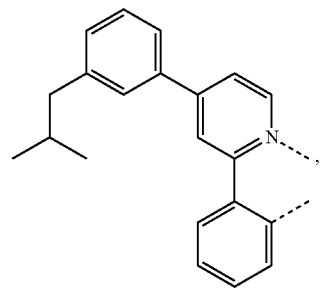
L_{A11}
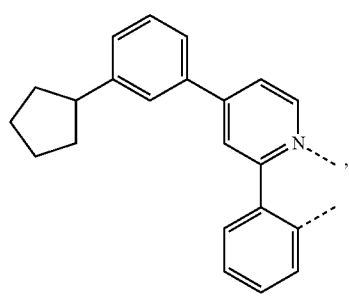
L_{A12}
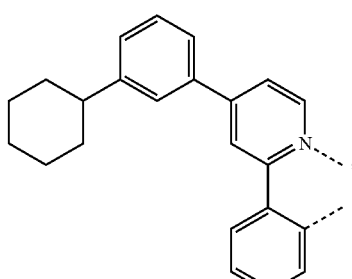
L_{A13}
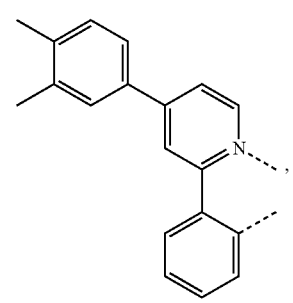
L_{A14}
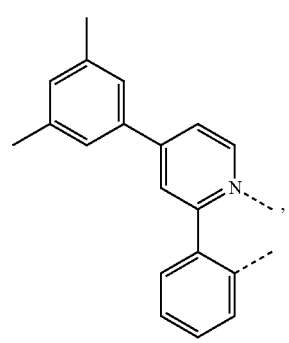
L_{A15}
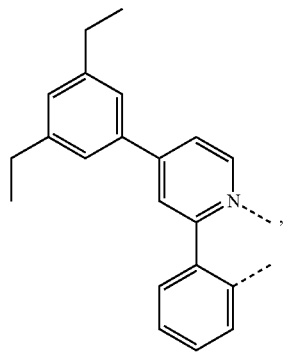
L_{A16}
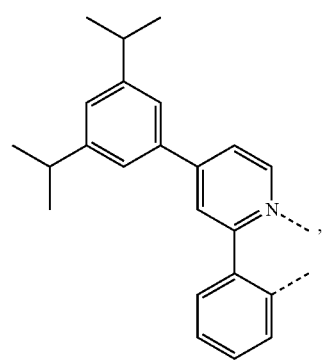
L_{A17}
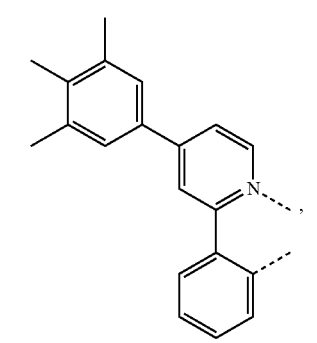
L_{A18}
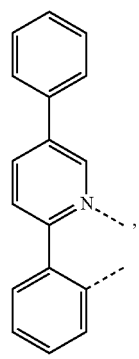
L_{A19}

L_{A20}
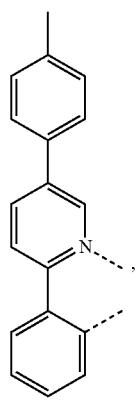
L_{A21}
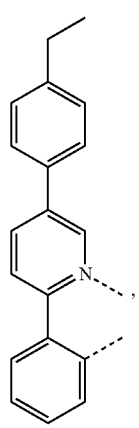
L_{A22}
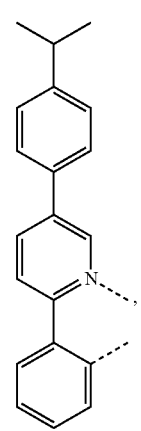
L_{A23}
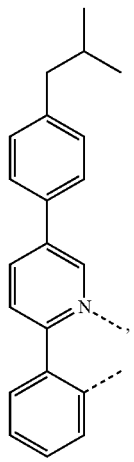
L_{A24}
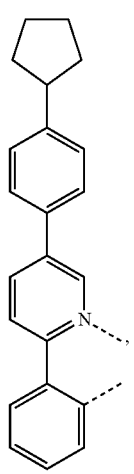
L_{A25}
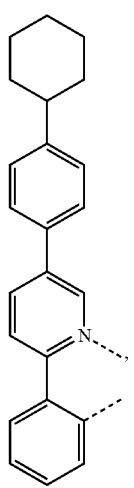

-continued
| | |
|---|---|
| 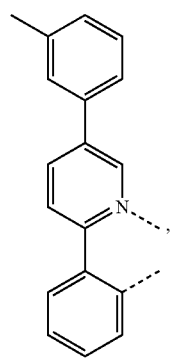 L<sub>A26</sub> | 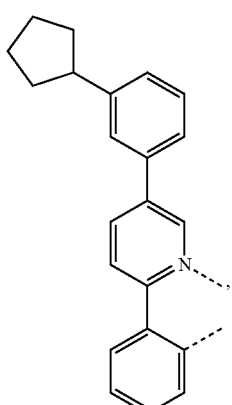 L$_{A30}$ |
| 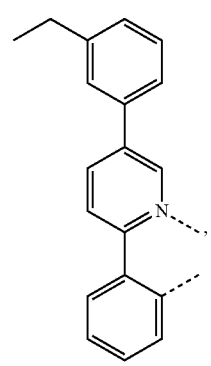 L$_{A27}$ | 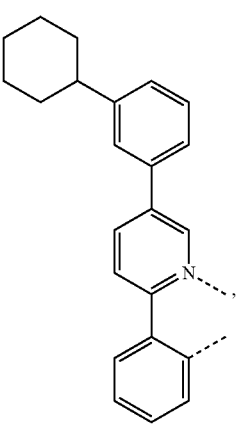 L$_{A31}$ |
| 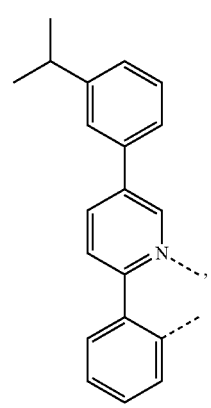 L$_{A28}$ | 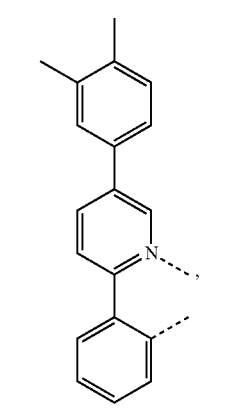 L$_{A32}$ |
| 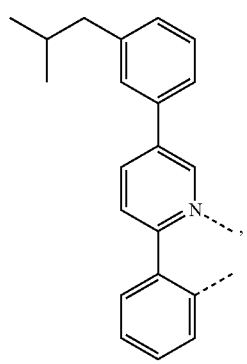 L$_{A29}$ | 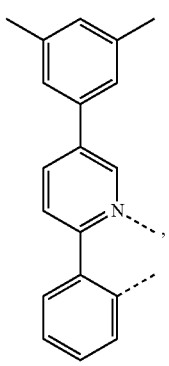 L$_{A33}$ |

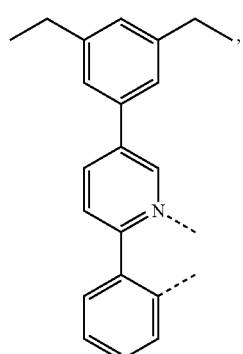 L_{A34}
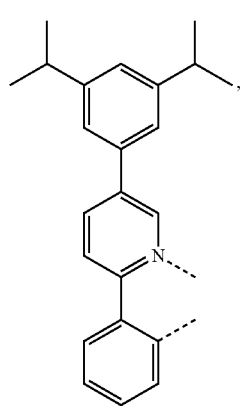 L_{A35}
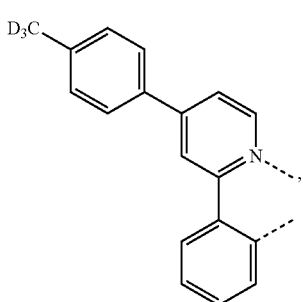 L_{A36}
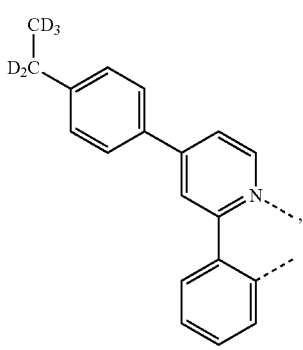 L_{A37}
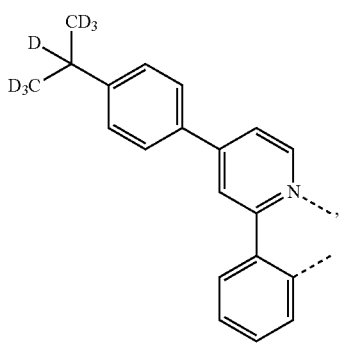 L_{A38}
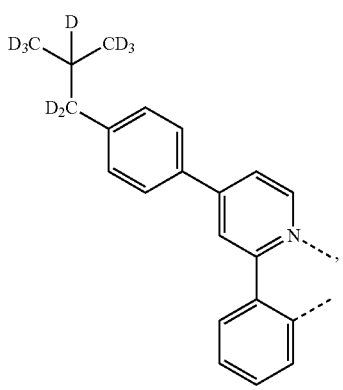 L_{A39}
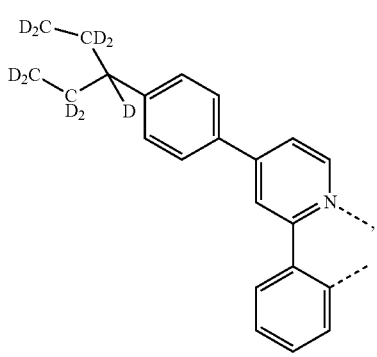 L_{A40}
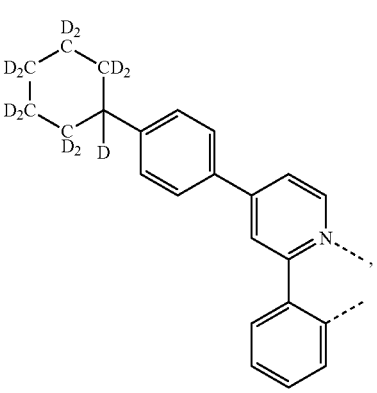 L_{A41}

-continued

L<sub>A42</sub>

L<sub>A43</sub>

L<sub>A44</sub>

L<sub>A45</sub>

L<sub>A46</sub>

-continued

L<sub>A47</sub>

L<sub>A48</sub>

L<sub>A49</sub>

L<sub>A50</sub>

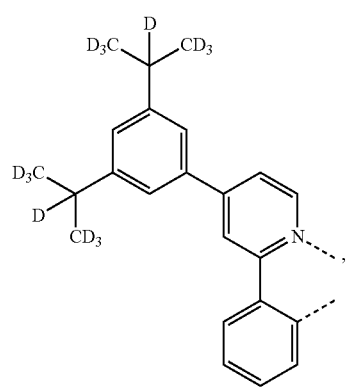 L<sub>A51</sub>
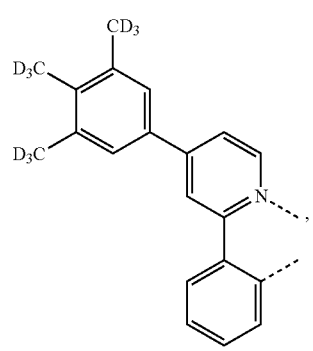 L<sub>A52</sub>
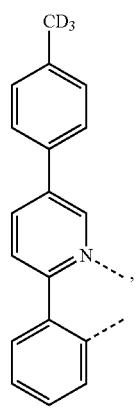 L<sub>A53</sub>
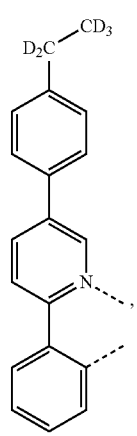 L<sub>A54</sub>
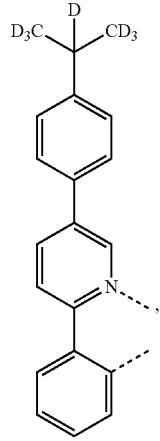 L<sub>A55</sub>
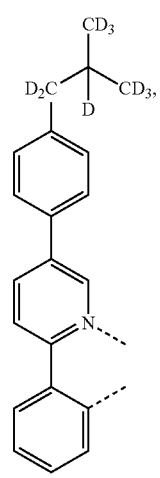 L<sub>A56</sub>
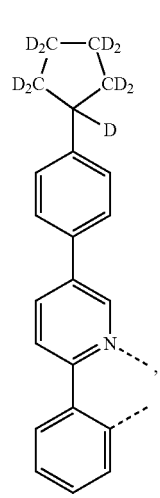 L<sub>A57</sub>

-continued
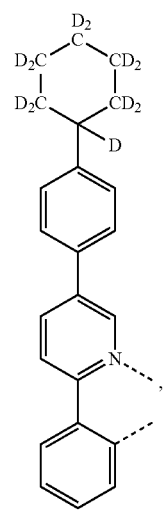 L_{A58}
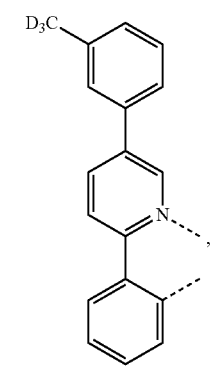 L_{A59}
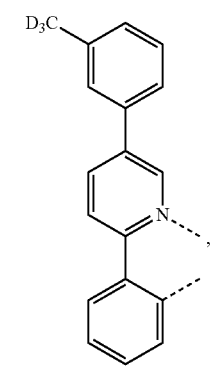 L_{A60}
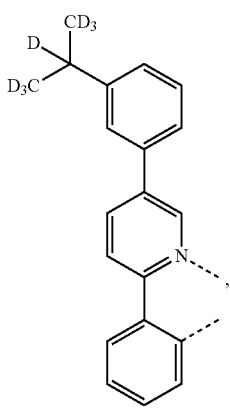 L_{A61}
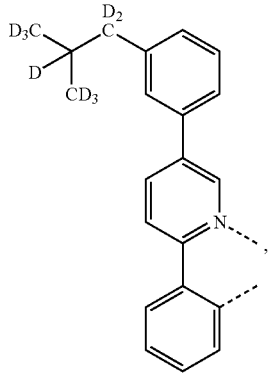 L_{A62}
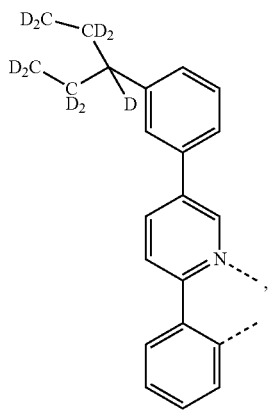 L_{A63}
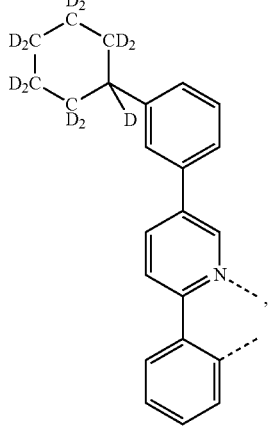 L_{A64}

L<sub>A65</sub> 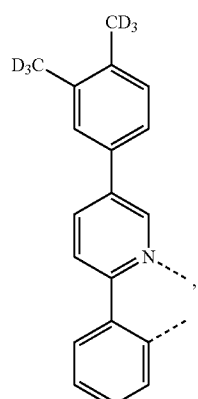
L<sub>A66</sub> 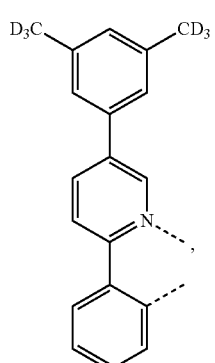
L<sub>A67</sub> 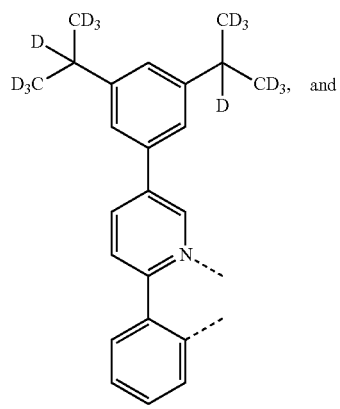
L<sub>A68</sub>
L<sub>A69</sub> 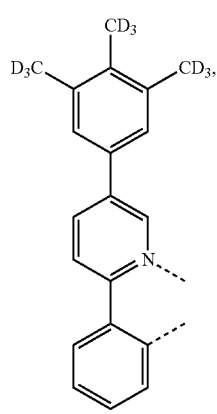
L<sub>B</sub> is selected from the group consisting of
L<sub>B1</sub> 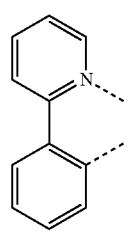
L<sub>B2</sub> 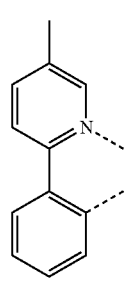
L<sub>B3</sub> 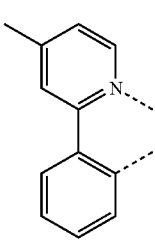
L<sub>B4</sub> 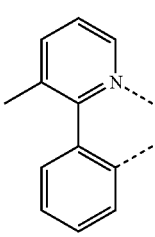

L<sub>B5</sub>
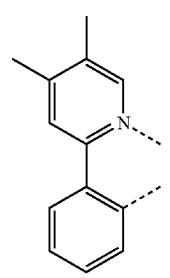
L<sub>B6</sub>
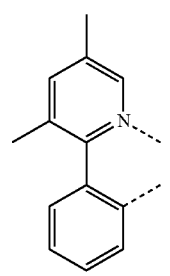
L<sub>B7</sub>
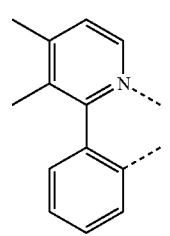
L<sub>B8</sub>
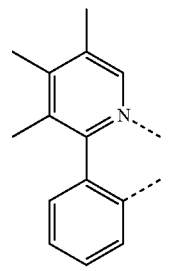
L<sub>B9</sub>
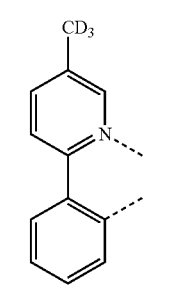
L<sub>B10</sub>
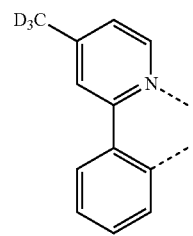
L<sub>B11</sub>
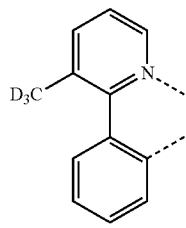
L<sub>B12</sub>
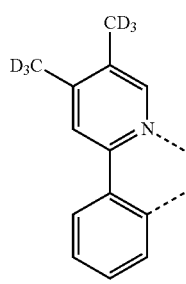
L<sub>B13</sub>
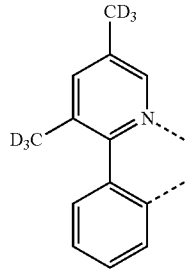
L<sub>B14</sub>
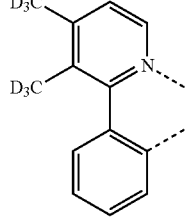
L<sub>B15</sub>
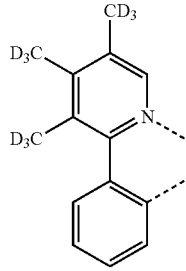
L<sub>B16</sub>
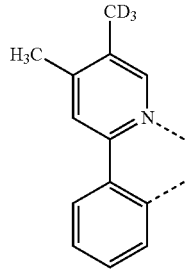

L_{B17}
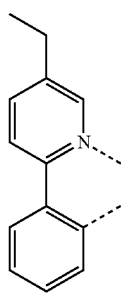
L_{B18}
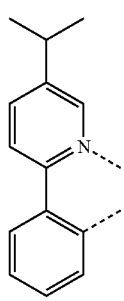
L_{B19}
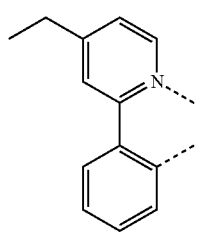
L_{B20}
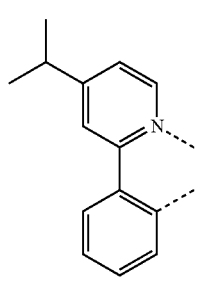
L_{B21}
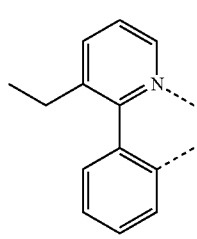
L_{B22}
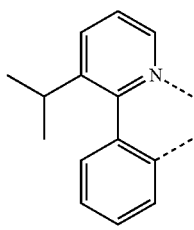
L_{B23}
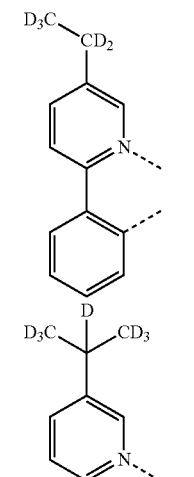
L_{B24}
L_{B25}
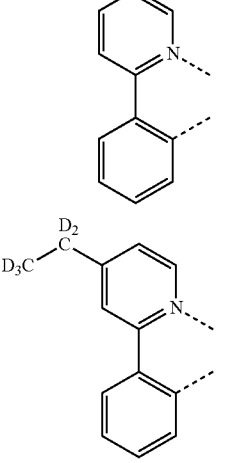
L_{B26}
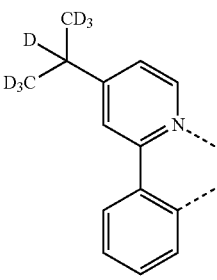
L_{B27}
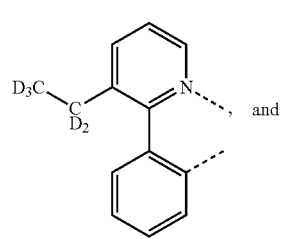, and $L_{B28}$

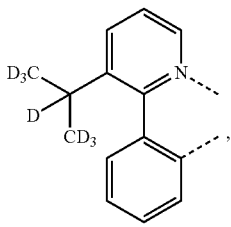

and the heteroleptic iridium complex is selected from the group consisting of Compound II-1 through Compound II-1846, and Compound II-1847 listed in the following table:

| Compound Number | $L_A$ | $L_B$ |
|---|---|---|
| II-1. | $L_{A6}$ | $L_{B1}$ |
| II-2. | $L_{A12}$ | $L_{B1}$ |
| II-3. | $L_{A13}$ | $L_{B1}$ |
| II-4. | $L_{A16}$ | $L_{B1}$ |
| II-5. | $L_{A17}$ | $L_{B1}$ |
| II-6. | $L_{A24}$ | $L_{B1}$ |
| II-7. | $L_{A30}$ | $L_{B1}$ |
| II-8. | $L_{A31}$ | $L_{B1}$ |
| II-9. | $L_{A34}$ | $L_{B1}$ |
| II-10. | $L_{A35}$ | $L_{B1}$ |
| II-11. | $L_{A36}$ | $L_{B1}$ |
| II-12. | $L_{A38}$ | $L_{B1}$ |
| II-13. | $L_{A39}$ | $L_{B1}$ |
| II-14. | $L_{A40}$ | $L_{B1}$ |
| II-15. | $L_{A41}$ | $L_{B1}$ |
| II-16. | $L_{A42}$ | $L_{B1}$ |
| II-17. | $L_{A43}$ | $L_{B1}$ |
| II-18. | $L_{A44}$ | $L_{B1}$ |
| II-19. | $L_{A45}$ | $L_{B1}$ |
| II-20. | $L_{A46}$ | $L_{B1}$ |
| II-21. | $L_{A47}$ | $L_{B1}$ |
| II-22. | $L_{A48}$ | $L_{B1}$ |
| II-23. | $L_{A49}$ | $L_{B1}$ |
| II-24. | $L_{A50}$ | $L_{B1}$ |
| II-25. | $L_{A51}$ | $L_{B1}$ |
| II-26. | $L_{A52}$ | $L_{B1}$ |
| II-27. | $L_{A53}$ | $L_{B1}$ |
| II-28. | $L_{A54}$ | $L_{B1}$ |
| II-29. | $L_{A55}$ | $L_{B1}$ |
| II-30. | $L_{A56}$ | $L_{B1}$ |
| II-31. | $L_{A57}$ | $L_{B1}$ |
| II-32. | $L_{A58}$ | $L_{B1}$ |
| II-33. | $L_{A59}$ | $L_{B1}$ |
| II-34. | $L_{A60}$ | $L_{B1}$ |
| II-35. | $L_{A61}$ | $L_{B1}$ |
| II-36. | $L_{A62}$ | $L_{B1}$ |
| II-37. | $L_{A63}$ | $L_{B1}$ |
| II-38. | $L_{A64}$ | $L_{B1}$ |
| II-39. | $L_{A65}$ | $L_{B1}$ |
| II-40. | $L_{A66}$ | $L_{B1}$ |
| II-41. | $L_{A67}$ | $L_{B1}$ |
| II-42. | $L_{A68}$ | $L_{B1}$ |
| II-43. | $L_{A69}$ | $L_{B1}$ |
| II-44. | $L_{A6}$ | $L_{B2}$ |
| II-45. | $L_{A7}$ | $L_{B2}$ |
| II-46. | $L_{A9}$ | $L_{B2}$ |
| II-47. | $L_{A10}$ | $L_{B2}$ |
| II-48. | $L_{A11}$ | $L_{B2}$ |
| II-49. | $L_{A12}$ | $L_{B2}$ |
| II-50. | $L_{A13}$ | $L_{B2}$ |
| II-51. | $L_{A16}$ | $L_{B2}$ |
| II-52. | $L_{A17}$ | $L_{B2}$ |
| II-53. | $L_{A21}$ | $L_{B2}$ |
| II-54. | $L_{A22}$ | $L_{B2}$ |
| II-55. | $L_{A23}$ | $L_{B2}$ |
| II-56. | $L_{A24}$ | $L_{B2}$ |
| II-57. | $L_{A27}$ | $L_{B2}$ |
| II-58. | $L_{A28}$ | $L_{B2}$ |
| II-59. | $L_{A29}$ | $L_{B2}$ |
| II-60. | $L_{A30}$ | $L_{B2}$ |
| II-61. | $L_{A31}$ | $L_{B2}$ |
| II-62. | $L_{A34}$ | $L_{B2}$ |
| II-63. | $L_{A35}$ | $L_{B2}$ |
| II-64. | $L_{A36}$ | $L_{B2}$ |
| II-65. | $L_{A38}$ | $L_{B2}$ |
| II-66. | $L_{A39}$ | $L_{B2}$ |
| II-67. | $L_{A40}$ | $L_{B2}$ |
| II-68. | $L_{A41}$ | $L_{B2}$ |
| II-69. | $L_{A42}$ | $L_{B2}$ |
| II-70. | $L_{A43}$ | $L_{B2}$ |
| II-71. | $L_{A44}$ | $L_{B2}$ |
| II-72. | $L_{A45}$ | $L_{B2}$ |
| II-73. | $L_{A46}$ | $L_{B2}$ |
| II-74. | $L_{A47}$ | $L_{B2}$ |
| II-75. | $L_{A48}$ | $L_{B2}$ |
| II-76. | $L_{A49}$ | $L_{B2}$ |
| II-77. | $L_{A50}$ | $L_{B2}$ |
| II-78. | $L_{A51}$ | $L_{B2}$ |
| II-79. | $L_{A52}$ | $L_{B2}$ |
| II-80. | $L_{A53}$ | $L_{B2}$ |
| II-81. | $L_{A54}$ | $L_{B2}$ |
| II-82. | $L_{A55}$ | $L_{B2}$ |
| II-83. | $L_{A56}$ | $L_{B2}$ |
| II-84. | $L_{A57}$ | $L_{B2}$ |
| II-85. | $L_{A58}$ | $L_{B2}$ |
| II-86. | $L_{A59}$ | $L_{B2}$ |
| II-87. | $L_{A60}$ | $L_{B2}$ |
| II-88. | $L_{A61}$ | $L_{B2}$ |
| II-89. | $L_{A62}$ | $L_{B2}$ |
| II-90. | $L_{A63}$ | $L_{B2}$ |
| II-91. | $L_{A64}$ | $L_{B2}$ |
| II-92. | $L_{A65}$ | $L_{B2}$ |
| II-93. | $L_{A66}$ | $L_{B2}$ |
| II-94. | $L_{A67}$ | $L_{B2}$ |
| II-95. | $L_{A68}$ | $L_{B2}$ |
| II-96. | $L_{A69}$ | $L_{B2}$ |
| II-97. | $L_{A2}$ | $L_{B3}$ |
| II-98. | $L_{A3}$ | $L_{B3}$ |
| II-99. | $L_{A4}$ | $L_{B3}$ |
| II-100. | $L_{A5}$ | $L_{B3}$ |
| II-101. | $L_{A6}$ | $L_{B3}$ |
| II-102. | $L_{A7}$ | $L_{B3}$ |
| II-103. | $L_{A8}$ | $L_{B3}$ |
| II-104. | $L_{A9}$ | $L_{B3}$ |
| II-105. | $L_{A10}$ | $L_{B3}$ |
| II-106. | $L_{A11}$ | $L_{B3}$ |
| II-107. | $L_{A12}$ | $L_{B3}$ |
| II-108. | $L_{A13}$ | $L_{B3}$ |
| II-109. | $L_{A14}$ | $L_{B3}$ |
| II-110. | $L_{A15}$ | $L_{B3}$ |
| II-111. | $L_{A16}$ | $L_{B3}$ |
| II-112. | $L_{A17}$ | $L_{B3}$ |
| II-113. | $L_{A18}$ | $L_{B3}$ |
| II-114. | $L_{A20}$ | $L_{B3}$ |
| II-115. | $L_{A21}$ | $L_{B3}$ |
| II-116. | $L_{A22}$ | $L_{B3}$ |
| II-117. | $L_{A23}$ | $L_{B3}$ |
| II-118. | $L_{A24}$ | $L_{B3}$ |
| II-119. | $L_{A25}$ | $L_{B3}$ |
| II-120. | $L_{A26}$ | $L_{B3}$ |
| II-121. | $L_{A27}$ | $L_{B3}$ |
| II-122. | $L_{A28}$ | $L_{B3}$ |
| II-123. | $L_{A29}$ | $L_{B3}$ |
| II-124. | $L_{A30}$ | $L_{B3}$ |
| II-125. | $L_{A31}$ | $L_{B3}$ |
| II-126. | $L_{A32}$ | $L_{B3}$ |
| II-127. | $L_{A33}$ | $L_{B3}$ |
| II-128. | $L_{A34}$ | $L_{B3}$ |
| II-129. | $L_{A35}$ | $L_{B3}$ |
| II-130. | $L_{A36}$ | $L_{B3}$ |
| II-131. | $L_{A37}$ | $L_{B3}$ |
| II-132. | $L_{A38}$ | $L_{B3}$ |
| II-133. | $L_{A39}$ | $L_{B3}$ |

| Compound Number | $L_A$ | $L_B$ |
|---|---|---|
| II-134. | $L_{A40}$ | $L_{B3}$ |
| II-135. | $L_{A41}$ | $L_{B3}$ |
| II-136. | $L_{A42}$ | $L_{B3}$ |
| II-137. | $L_{A43}$ | $L_{B3}$ |
| II-138. | $L_{A44}$ | $L_{B3}$ |
| II-139. | $L_{A45}$ | $L_{B3}$ |
| II-140. | $L_{A46}$ | $L_{B3}$ |
| II-141. | $L_{A47}$ | $L_{B3}$ |
| II-142. | $L_{A48}$ | $L_{B3}$ |
| II-143. | $L_{A49}$ | $L_{B3}$ |
| II-144. | $L_{A50}$ | $L_{B3}$ |
| II-145. | $L_{A51}$ | $L_{B3}$ |
| II-146. | $L_{A52}$ | $L_{B3}$ |
| II-147. | $L_{A53}$ | $L_{B3}$ |
| II-148. | $L_{A54}$ | $L_{B3}$ |
| II-149. | $L_{A55}$ | $L_{B3}$ |
| II-150. | $L_{A56}$ | $L_{B3}$ |
| II-151. | $L_{A57}$ | $L_{B3}$ |
| II-152. | $L_{A58}$ | $L_{B3}$ |
| II-153. | $L_{A59}$ | $L_{B3}$ |
| II-154. | $L_{A60}$ | $L_{B3}$ |
| II-155. | $L_{A61}$ | $L_{B3}$ |
| II-156. | $L_{A62}$ | $L_{B3}$ |
| II-157. | $L_{A63}$ | $L_{B3}$ |
| II-158. | $L_{A64}$ | $L_{B3}$ |
| II-159. | $L_{A65}$ | $L_{B3}$ |
| II-160. | $L_{A66}$ | $L_{B3}$ |
| II-161. | $L_{A67}$ | $L_{B3}$ |
| II-162. | $L_{A68}$ | $L_{B3}$ |
| II-163. | $L_{A69}$ | $L_{B3}$ |
| II-164. | $L_{A2}$ | $L_{B4}$ |
| II-165. | $L_{A3}$ | $L_{B4}$ |
| II-166. | $L_{A4}$ | $L_{B4}$ |
| II-167. | $L_{A5}$ | $L_{B4}$ |
| II-168. | $L_{A6}$ | $L_{B4}$ |
| II-169. | $L_{A7}$ | $L_{B4}$ |
| II-170. | $L_{A8}$ | $L_{B4}$ |
| II-171. | $L_{A9}$ | $L_{B4}$ |
| II-172. | $L_{A10}$ | $L_{B4}$ |
| II-173. | $L_{A11}$ | $L_{B4}$ |
| II-174. | $L_{A12}$ | $L_{B4}$ |
| II-175. | $L_{A13}$ | $L_{B4}$ |
| II-176. | $L_{A14}$ | $L_{B4}$ |
| II-177. | $L_{A15}$ | $L_{B4}$ |
| II-178. | $L_{A16}$ | $L_{B4}$ |
| II-179. | $L_{A17}$ | $L_{B4}$ |
| II-180. | $L_{A18}$ | $L_{B4}$ |
| II-181. | $L_{A20}$ | $L_{B4}$ |
| II-182. | $L_{A21}$ | $L_{B4}$ |
| II-183. | $L_{A22}$ | $L_{B4}$ |
| II-184. | $L_{A23}$ | $L_{B4}$ |
| II-185. | $L_{A24}$ | $L_{B4}$ |
| II-186. | $L_{A25}$ | $L_{B4}$ |
| II-187. | $L_{A26}$ | $L_{B4}$ |
| II-188. | $L_{A27}$ | $L_{B4}$ |
| II-189. | $L_{A28}$ | $L_{B4}$ |
| II-190. | $L_{A29}$ | $L_{B4}$ |
| II-191. | $L_{A30}$ | $L_{B4}$ |
| II-192. | $L_{A31}$ | $L_{B4}$ |
| II-193. | $L_{A32}$ | $L_{B4}$ |
| II-194. | $L_{A33}$ | $L_{B4}$ |
| II-195. | $L_{A34}$ | $L_{B4}$ |
| II-196. | $L_{A35}$ | $L_{B4}$ |
| II-197. | $L_{A36}$ | $L_{B4}$ |
| II-198. | $L_{A37}$ | $L_{B4}$ |
| II-199. | $L_{A38}$ | $L_{B4}$ |
| II-200. | $L_{A39}$ | $L_{B4}$ |
| II-201. | $L_{A40}$ | $L_{B4}$ |
| II-202. | $L_{A41}$ | $L_{B4}$ |
| II-203. | $L_{A42}$ | $L_{B4}$ |
| II-204. | $L_{A43}$ | $L_{B4}$ |
| II-205. | $L_{A44}$ | $L_{B4}$ |
| II-206. | $L_{A45}$ | $L_{B4}$ |
| II-207. | $L_{A46}$ | $L_{B4}$ |
| II-208. | $L_{A47}$ | $L_{B4}$ |
| II-209. | $L_{A48}$ | $L_{B4}$ |
| II-210. | $L_{A49}$ | $L_{B4}$ |
| II-211. | $L_{A50}$ | $L_{B4}$ |
| II-212. | $L_{A51}$ | $L_{B4}$ |
| II-213. | $L_{A52}$ | $L_{B4}$ |
| II-214. | $L_{A53}$ | $L_{B4}$ |
| II-215. | $L_{A54}$ | $L_{B4}$ |
| II-216. | $L_{A55}$ | $L_{B4}$ |
| II-217. | $L_{A56}$ | $L_{B4}$ |
| II-218. | $L_{A57}$ | $L_{B4}$ |
| II-219. | $L_{A58}$ | $L_{B4}$ |
| II-220. | $L_{A59}$ | $L_{B4}$ |
| II-221. | $L_{A60}$ | $L_{B4}$ |
| II-222. | $L_{A61}$ | $L_{B4}$ |
| II-223. | $L_{A62}$ | $L_{B4}$ |
| II-224. | $L_{A63}$ | $L_{B4}$ |
| II-225. | $L_{A64}$ | $L_{B4}$ |
| II-226. | $L_{A65}$ | $L_{B4}$ |
| II-227. | $L_{A66}$ | $L_{B4}$ |
| II-228. | $L_{A67}$ | $L_{B4}$ |
| II-229. | $L_{A68}$ | $L_{B4}$ |
| II-230. | $L_{A69}$ | $L_{B4}$ |
| II-231. | $L_{A3}$ | $L_{B5}$ |
| II-232. | $L_{A4}$ | $L_{B5}$ |
| II-233. | $L_{A5}$ | $L_{B5}$ |
| II-234. | $L_{A6}$ | $L_{B5}$ |
| II-235. | $L_{A7}$ | $L_{B5}$ |
| II-236. | $L_{A8}$ | $L_{B5}$ |
| II-237. | $L_{A9}$ | $L_{B5}$ |
| II-238. | $L_{A10}$ | $L_{B5}$ |
| II-239. | $L_{A11}$ | $L_{B5}$ |
| II-240. | $L_{A12}$ | $L_{B5}$ |
| II-241. | $L_{A13}$ | $L_{B5}$ |
| II-242. | $L_{A14}$ | $L_{B5}$ |
| II-243. | $L_{A15}$ | $L_{B5}$ |
| II-244. | $L_{A16}$ | $L_{B5}$ |
| II-245. | $L_{A17}$ | $L_{B5}$ |
| II-246. | $L_{A18}$ | $L_{B5}$ |
| II-247. | $L_{A20}$ | $L_{B5}$ |
| II-248. | $L_{A21}$ | $L_{B5}$ |
| II-249. | $L_{A22}$ | $L_{B5}$ |
| II-250. | $L_{A23}$ | $L_{B5}$ |
| II-251. | $L_{A24}$ | $L_{B5}$ |
| II-252. | $L_{A25}$ | $L_{B5}$ |
| II-253. | $L_{A26}$ | $L_{B5}$ |
| II-254. | $L_{A27}$ | $L_{B5}$ |
| II-255. | $L_{A28}$ | $L_{B5}$ |
| II-256. | $L_{A29}$ | $L_{B5}$ |
| II-257. | $L_{A30}$ | $L_{B5}$ |
| II-258. | $L_{A31}$ | $L_{B5}$ |
| II-259. | $L_{A32}$ | $L_{B5}$ |
| II-260. | $L_{A33}$ | $L_{B5}$ |
| II-261. | $L_{A34}$ | $L_{B5}$ |
| II-262. | $L_{A35}$ | $L_{B5}$ |
| II-263. | $L_{A36}$ | $L_{B5}$ |
| II-264. | $L_{A37}$ | $L_{B5}$ |
| II-265. | $L_{A38}$ | $L_{B5}$ |
| II-266. | $L_{A39}$ | $L_{B5}$ |
| II-267. | $L_{A40}$ | $L_{B5}$ |
| II-268. | $L_{A41}$ | $L_{B5}$ |
| II-269. | $L_{A42}$ | $L_{B5}$ |
| II-270. | $L_{A43}$ | $L_{B5}$ |
| II-271. | $L_{A44}$ | $L_{B5}$ |
| II-272. | $L_{A45}$ | $L_{B5}$ |
| II-273. | $L_{A46}$ | $L_{B5}$ |
| II-274. | $L_{A47}$ | $L_{B5}$ |
| II-275. | $L_{A48}$ | $L_{B5}$ |
| II-276. | $L_{A49}$ | $L_{B5}$ |
| II-277. | $L_{A50}$ | $L_{B5}$ |
| II-278. | $L_{A51}$ | $L_{B5}$ |
| II-279. | $L_{A52}$ | $L_{B5}$ |
| II-280. | $L_{A53}$ | $L_{B5}$ |
| II-281. | $L_{A54}$ | $L_{B5}$ |
| II-282. | $L_{A55}$ | $L_{B5}$ |
| II-283. | $L_{A56}$ | $L_{B5}$ |
| II-284. | $L_{A57}$ | $L_{B5}$ |
| II-285. | $L_{A58}$ | $L_{B5}$ |

| Compound Number | $L_A$ | $L_B$ |
| --- | --- | --- |
| II-286. | $L_{A59}$ | $L_{B5}$ |
| II-287. | $L_{A60}$ | $L_{B5}$ |
| II-288. | $L_{A61}$ | $L_{B5}$ |
| II-289. | $L_{A62}$ | $L_{B5}$ |
| II-290. | $L_{A63}$ | $L_{B5}$ |
| II-291. | $L_{A64}$ | $L_{B5}$ |
| II-292. | $L_{A65}$ | $L_{B5}$ |
| II-293. | $L_{A66}$ | $L_{B5}$ |
| II-294. | $L_{A67}$ | $L_{B5}$ |
| II-295. | $L_{A68}$ | $L_{B5}$ |
| II-296. | $L_{A69}$ | $L_{B5}$ |
| II-297. | $L_{A2}$ | $L_{B6}$ |
| II-298. | $L_{A3}$ | $L_{B6}$ |
| II-299. | $L_{A4}$ | $L_{B6}$ |
| II-300. | $L_{A5}$ | $L_{B6}$ |
| II-301. | $L_{A6}$ | $L_{B6}$ |
| II-302. | $L_{A7}$ | $L_{B6}$ |
| II-303. | $L_{A8}$ | $L_{B6}$ |
| II-304. | $L_{A9}$ | $L_{B6}$ |
| II-305. | $L_{A10}$ | $L_{B6}$ |
| II-306. | $L_{A11}$ | $L_{B6}$ |
| II-307. | $L_{A12}$ | $L_{B6}$ |
| II-308. | $L_{A13}$ | $L_{B6}$ |
| II-309. | $L_{A14}$ | $L_{B6}$ |
| II-310. | $L_{A15}$ | $L_{B6}$ |
| II-311. | $L_{A16}$ | $L_{B6}$ |
| II-312. | $L_{A17}$ | $L_{B6}$ |
| II-313. | $L_{A18}$ | $L_{B6}$ |
| II-314. | $L_{A20}$ | $L_{B6}$ |
| II-315. | $L_{A21}$ | $L_{B6}$ |
| II-316. | $L_{A22}$ | $L_{B6}$ |
| II-317. | $L_{A23}$ | $L_{B6}$ |
| II-318. | $L_{A24}$ | $L_{B6}$ |
| II-319. | $L_{A25}$ | $L_{B6}$ |
| II-320. | $L_{A26}$ | $L_{B6}$ |
| II-321. | $L_{A27}$ | $L_{B6}$ |
| II-322. | $L_{A28}$ | $L_{B6}$ |
| II-323. | $L_{A29}$ | $L_{B6}$ |
| II-324. | $L_{A30}$ | $L_{B6}$ |
| II-325. | $L_{A31}$ | $L_{B6}$ |
| II-326. | $L_{A32}$ | $L_{B6}$ |
| II-327. | $L_{A33}$ | $L_{B6}$ |
| II-328. | $L_{A34}$ | $L_{B6}$ |
| II-329. | $L_{A35}$ | $L_{B6}$ |
| II-330. | $L_{A36}$ | $L_{B6}$ |
| II-331. | $L_{A37}$ | $L_{B6}$ |
| II-332. | $L_{A38}$ | $L_{B6}$ |
| II-333. | $L_{A39}$ | $L_{B6}$ |
| II-334. | $L_{A40}$ | $L_{B6}$ |
| II-335. | $L_{A41}$ | $L_{B6}$ |
| II-336. | $L_{A42}$ | $L_{B6}$ |
| II-337. | $L_{A43}$ | $L_{B6}$ |
| II-338. | $L_{A44}$ | $L_{B6}$ |
| II-339. | $L_{A45}$ | $L_{B6}$ |
| II-340. | $L_{A46}$ | $L_{B6}$ |
| II-341. | $L_{A47}$ | $L_{B6}$ |
| II-342. | $L_{A48}$ | $L_{B6}$ |
| II-343. | $L_{A49}$ | $L_{B6}$ |
| II-344. | $L_{A50}$ | $L_{B6}$ |
| II-345. | $L_{A51}$ | $L_{B6}$ |
| II-346. | $L_{A52}$ | $L_{B6}$ |
| II-347. | $L_{A53}$ | $L_{B6}$ |
| II-348. | $L_{A54}$ | $L_{B6}$ |
| II-349. | $L_{A55}$ | $L_{B6}$ |
| II-350. | $L_{A56}$ | $L_{B6}$ |
| II-351. | $L_{A57}$ | $L_{B6}$ |
| II-352. | $L_{A58}$ | $L_{B6}$ |
| II-353. | $L_{A59}$ | $L_{B6}$ |
| II-354. | $L_{A60}$ | $L_{B6}$ |
| II-355. | $L_{A61}$ | $L_{B6}$ |
| II-356. | $L_{A62}$ | $L_{B6}$ |
| II-357. | $L_{A63}$ | $L_{B6}$ |
| II-358. | $L_{A64}$ | $L_{B6}$ |
| II-359. | $L_{A65}$ | $L_{B6}$ |
| II-360. | $L_{A66}$ | $L_{B6}$ |
| II-361. | $L_{A67}$ | $L_{B6}$ |
| II-362. | $L_{A68}$ | $L_{B6}$ |
| II-363. | $L_{A69}$ | $L_{B6}$ |
| II-364. | $L_{A2}$ | $L_{B7}$ |
| II-365. | $L_{A3}$ | $L_{B7}$ |
| II-366. | $L_{A4}$ | $L_{B7}$ |
| II-367. | $L_{A5}$ | $L_{B7}$ |
| II-368. | $L_{A6}$ | $L_{B7}$ |
| II-369. | $L_{A7}$ | $L_{B7}$ |
| II-370. | $L_{A8}$ | $L_{B7}$ |
| II-371. | $L_{A9}$ | $L_{B7}$ |
| II-372. | $L_{A10}$ | $L_{B7}$ |
| II-373. | $L_{A11}$ | $L_{B7}$ |
| II-374. | $L_{A12}$ | $L_{B7}$ |
| II-375. | $L_{A13}$ | $L_{B7}$ |
| II-376. | $L_{A14}$ | $L_{B7}$ |
| II-377. | $L_{A15}$ | $L_{B7}$ |
| II-378. | $L_{A16}$ | $L_{B7}$ |
| II-379. | $L_{A17}$ | $L_{B7}$ |
| II-380. | $L_{A18}$ | $L_{B7}$ |
| II-381. | $L_{A20}$ | $L_{B7}$ |
| II-382. | $L_{A21}$ | $L_{B7}$ |
| II-383. | $L_{A22}$ | $L_{B7}$ |
| II-384. | $L_{A23}$ | $L_{B7}$ |
| II-385. | $L_{A24}$ | $L_{B7}$ |
| II-386. | $L_{A25}$ | $L_{B7}$ |
| II-387. | $L_{A26}$ | $L_{B7}$ |
| II-388. | $L_{A27}$ | $L_{B7}$ |
| II-389. | $L_{A28}$ | $L_{B7}$ |
| II-390. | $L_{A29}$ | $L_{B7}$ |
| II-391. | $L_{A30}$ | $L_{B7}$ |
| II-392. | $L_{A31}$ | $L_{B7}$ |
| II-393. | $L_{A32}$ | $L_{B7}$ |
| II-394. | $L_{A33}$ | $L_{B7}$ |
| II-395. | $L_{A34}$ | $L_{B7}$ |
| II-396. | $L_{A35}$ | $L_{B7}$ |
| II-397. | $L_{A36}$ | $L_{B7}$ |
| II-398. | $L_{A37}$ | $L_{B7}$ |
| II-399. | $L_{A38}$ | $L_{B7}$ |
| II-400. | $L_{A39}$ | $L_{B7}$ |
| II-401. | $L_{A40}$ | $L_{B7}$ |
| II-402. | $L_{A41}$ | $L_{B7}$ |
| II-403. | $L_{A42}$ | $L_{B7}$ |
| II-404. | $L_{A43}$ | $L_{B7}$ |
| II-405. | $L_{A44}$ | $L_{B7}$ |
| II-406. | $L_{A45}$ | $L_{B7}$ |
| II-407. | $L_{A46}$ | $L_{B7}$ |
| II-408. | $L_{A47}$ | $L_{B7}$ |
| II-409. | $L_{A48}$ | $L_{B7}$ |
| II-410. | $L_{A49}$ | $L_{B7}$ |
| II-411. | $L_{A50}$ | $L_{B7}$ |
| II-412. | $L_{A51}$ | $L_{B7}$ |
| II-413. | $L_{A52}$ | $L_{B7}$ |
| II-414. | $L_{A53}$ | $L_{B7}$ |
| II-415. | $L_{A54}$ | $L_{B7}$ |
| II-416. | $L_{A55}$ | $L_{B7}$ |
| II-417. | $L_{A56}$ | $L_{B7}$ |
| II-418. | $L_{A57}$ | $L_{B7}$ |
| II-419. | $L_{A58}$ | $L_{B7}$ |
| II-420. | $L_{A59}$ | $L_{B7}$ |
| II-421. | $L_{A60}$ | $L_{B7}$ |
| II-422. | $L_{A61}$ | $L_{B7}$ |
| II-423. | $L_{A62}$ | $L_{B7}$ |
| II-424. | $L_{A63}$ | $L_{B7}$ |
| II-425. | $L_{A64}$ | $L_{B7}$ |
| II-426. | $L_{A65}$ | $L_{B7}$ |
| II-427. | $L_{A66}$ | $L_{B7}$ |
| II-428. | $L_{A67}$ | $L_{B7}$ |
| II-429. | $L_{A68}$ | $L_{B7}$ |
| II-430. | $L_{A69}$ | $L_{B7}$ |
| II-431. | $L_{A2}$ | $L_{B8}$ |
| II-432. | $L_{A3}$ | $L_{B8}$ |
| II-433. | $L_{A4}$ | $L_{B8}$ |
| II-434. | $L_{A5}$ | $L_{B8}$ |
| II-435. | $L_{A6}$ | $L_{B8}$ |
| II-436. | $L_{A7}$ | $L_{B8}$ |
| II-437. | $L_{A8}$ | $L_{B8}$ |

-continued

| Compound Number | $L_A$ | $L_B$ |
|---|---|---|
| II-438. | $L_{A9}$ | $L_{B8}$ |
| II-439. | $L_{A10}$ | $L_{B8}$ |
| II-440. | $L_{A11}$ | $L_{B8}$ |
| II-441. | $L_{A12}$ | $L_{B8}$ |
| II-442. | $L_{A13}$ | $L_{B8}$ |
| II-443. | $L_{A14}$ | $L_{B8}$ |
| II-444. | $L_{A15}$ | $L_{B8}$ |
| II-445. | $L_{A16}$ | $L_{B8}$ |
| II-446. | $L_{A17}$ | $L_{B8}$ |
| II-447. | $L_{A18}$ | $L_{B8}$ |
| II-448. | $L_{A20}$ | $L_{B8}$ |
| II-449. | $L_{A21}$ | $L_{B8}$ |
| II-450. | $L_{A22}$ | $L_{B8}$ |
| II-451. | $L_{A23}$ | $L_{B8}$ |
| II-452. | $L_{A24}$ | $L_{B8}$ |
| II-453. | $L_{A25}$ | $L_{B8}$ |
| II-454. | $L_{A26}$ | $L_{B8}$ |
| II-455. | $L_{A27}$ | $L_{B8}$ |
| II-456. | $L_{A28}$ | $L_{B8}$ |
| II-457. | $L_{A29}$ | $L_{B8}$ |
| II-458. | $L_{A30}$ | $L_{B8}$ |
| II-459. | $L_{A31}$ | $L_{B8}$ |
| II-460. | $L_{A32}$ | $L_{B8}$ |
| II-461. | $L_{A33}$ | $L_{B8}$ |
| II-462. | $L_{A34}$ | $L_{B8}$ |
| II-463. | $L_{A35}$ | $L_{B8}$ |
| II-464. | $L_{A36}$ | $L_{B8}$ |
| II-465. | $L_{A37}$ | $L_{B8}$ |
| II-466. | $L_{A38}$ | $L_{B8}$ |
| II-467. | $L_{A39}$ | $L_{B8}$ |
| II-468. | $L_{A40}$ | $L_{B8}$ |
| II-469. | $L_{A41}$ | $L_{B8}$ |
| II-470. | $L_{A42}$ | $L_{B8}$ |
| II-471. | $L_{A43}$ | $L_{B8}$ |
| II-472. | $L_{A44}$ | $L_{B8}$ |
| II-473. | $L_{A45}$ | $L_{B8}$ |
| II-474. | $L_{A46}$ | $L_{B8}$ |
| II-475. | $L_{A47}$ | $L_{B8}$ |
| II-476. | $L_{A48}$ | $L_{B8}$ |
| II-477. | $L_{A49}$ | $L_{B8}$ |
| II-478. | $L_{A50}$ | $L_{B8}$ |
| II-479. | $L_{A51}$ | $L_{B8}$ |
| II-480. | $L_{A52}$ | $L_{B8}$ |
| II-481. | $L_{A53}$ | $L_{B8}$ |
| II-482. | $L_{A54}$ | $L_{B8}$ |
| II-483. | $L_{A55}$ | $L_{B8}$ |
| II-484. | $L_{A56}$ | $L_{B8}$ |
| II-485. | $L_{A57}$ | $L_{B8}$ |
| II-486. | $L_{A58}$ | $L_{B8}$ |
| II-487. | $L_{A59}$ | $L_{B8}$ |
| II-488. | $L_{A60}$ | $L_{B8}$ |
| II-489. | $L_{A61}$ | $L_{B8}$ |
| II-490. | $L_{A62}$ | $L_{B8}$ |
| II-491. | $L_{A63}$ | $L_{B8}$ |
| II-492. | $L_{A64}$ | $L_{B8}$ |
| II-493. | $L_{A65}$ | $L_{B8}$ |
| II-494. | $L_{A66}$ | $L_{B8}$ |
| II-495. | $L_{A67}$ | $L_{B8}$ |
| II-496. | $L_{A68}$ | $L_{B8}$ |
| II-497. | $L_{A69}$ | $L_{B8}$ |
| II-498. | $L_{A3}$ | $L_{B9}$ |
| II-499. | $L_{A4}$ | $L_{B9}$ |
| II-500. | $L_{A5}$ | $L_{B9}$ |
| II-501. | $L_{A6}$ | $L_{B9}$ |
| II-502. | $L_{A7}$ | $L_{B9}$ |
| II-503. | $L_{A8}$ | $L_{B9}$ |
| II-504. | $L_{A9}$ | $L_{B9}$ |
| II-505. | $L_{A10}$ | $L_{B9}$ |
| II-506. | $L_{A11}$ | $L_{B9}$ |
| II-507. | $L_{A12}$ | $L_{B9}$ |
| II-508. | $L_{A13}$ | $L_{B9}$ |
| II-509. | $L_{A14}$ | $L_{B9}$ |
| II-510. | $L_{A15}$ | $L_{B9}$ |
| II-511. | $L_{A16}$ | $L_{B9}$ |
| II-512. | $L_{A17}$ | $L_{B9}$ |
| II-513. | $L_{A18}$ | $L_{B9}$ |
| II-514. | $L_{A21}$ | $L_{B9}$ |
| II-515. | $L_{A22}$ | $L_{B9}$ |
| II-516. | $L_{A23}$ | $L_{B9}$ |
| II-517. | $L_{A24}$ | $L_{B9}$ |
| II-518. | $L_{A25}$ | $L_{B9}$ |
| II-519. | $L_{A26}$ | $L_{B9}$ |
| II-520. | $L_{A27}$ | $L_{B9}$ |
| II-521. | $L_{A28}$ | $L_{B9}$ |
| II-522. | $L_{A29}$ | $L_{B9}$ |
| II-523. | $L_{A30}$ | $L_{B9}$ |
| II-524. | $L_{A31}$ | $L_{B9}$ |
| II-525. | $L_{A32}$ | $L_{B9}$ |
| II-526. | $L_{A33}$ | $L_{B9}$ |
| II-527. | $L_{A34}$ | $L_{B9}$ |
| II-528. | $L_{A35}$ | $L_{B9}$ |
| II-529. | $L_{A37}$ | $L_{B9}$ |
| II-530. | $L_{A38}$ | $L_{B9}$ |
| II-531. | $L_{A39}$ | $L_{B9}$ |
| II-532. | $L_{A40}$ | $L_{B9}$ |
| II-533. | $L_{A41}$ | $L_{B9}$ |
| II-534. | $L_{A42}$ | $L_{B9}$ |
| II-535. | $L_{A43}$ | $L_{B9}$ |
| II-536. | $L_{A44}$ | $L_{B9}$ |
| II-537. | $L_{A45}$ | $L_{B9}$ |
| II-538. | $L_{A46}$ | $L_{B9}$ |
| II-539. | $L_{A47}$ | $L_{B9}$ |
| II-540. | $L_{A48}$ | $L_{B9}$ |
| II-541. | $L_{A49}$ | $L_{B9}$ |
| II-542. | $L_{A50}$ | $L_{B9}$ |
| II-543. | $L_{A51}$ | $L_{B9}$ |
| II-544. | $L_{A52}$ | $L_{B9}$ |
| II-545. | $L_{A54}$ | $L_{B9}$ |
| II-546. | $L_{A55}$ | $L_{B9}$ |
| II-547. | $L_{A56}$ | $L_{B9}$ |
| II-548. | $L_{A57}$ | $L_{B9}$ |
| II-549. | $L_{A58}$ | $L_{B9}$ |
| II-550. | $L_{A59}$ | $L_{B9}$ |
| II-551. | $L_{A60}$ | $L_{B9}$ |
| II-552. | $L_{A61}$ | $L_{B9}$ |
| II-553. | $L_{A62}$ | $L_{B9}$ |
| II-554. | $L_{A63}$ | $L_{B9}$ |
| II-555. | $L_{A64}$ | $L_{B9}$ |
| II-556. | $L_{A65}$ | $L_{B9}$ |
| II-557. | $L_{A66}$ | $L_{B9}$ |
| II-558. | $L_{A67}$ | $L_{B9}$ |
| II-559. | $L_{A68}$ | $L_{B9}$ |
| II-560. | $L_{A69}$ | $L_{B9}$ |
| II-561. | $L_{A1}$ | $L_{B10}$ |
| II-562. | $L_{A2}$ | $L_{B10}$ |
| II-563. | $L_{A3}$ | $L_{B10}$ |
| II-564. | $L_{A4}$ | $L_{B10}$ |
| II-565. | $L_{A5}$ | $L_{B10}$ |
| II-566. | $L_{A6}$ | $L_{B10}$ |
| II-567. | $L_{A7}$ | $L_{B10}$ |
| II-568. | $L_{A8}$ | $L_{B10}$ |
| II-569. | $L_{A9}$ | $L_{B10}$ |
| II-570. | $L_{A10}$ | $L_{B10}$ |
| II-571. | $L_{A11}$ | $L_{B10}$ |
| II-572. | $L_{A12}$ | $L_{B10}$ |
| II-573. | $L_{A13}$ | $L_{B10}$ |
| II-574. | $L_{A14}$ | $L_{B10}$ |
| II-575. | $L_{A15}$ | $L_{B10}$ |
| II-576. | $L_{A16}$ | $L_{B10}$ |
| II-577. | $L_{A17}$ | $L_{B10}$ |
| II-578. | $L_{A18}$ | $L_{B10}$ |
| II-579. | $L_{A19}$ | $L_{B10}$ |
| II-580. | $L_{A20}$ | $L_{B10}$ |
| II-581. | $L_{A21}$ | $L_{B10}$ |
| II-582. | $L_{A22}$ | $L_{B10}$ |
| II-583. | $L_{A23}$ | $L_{B10}$ |
| II-584. | $L_{A24}$ | $L_{B10}$ |
| II-585. | $L_{A25}$ | $L_{B10}$ |
| II-586. | $L_{A26}$ | $L_{B10}$ |
| II-587. | $L_{A27}$ | $L_{B10}$ |
| II-588. | $L_{A28}$ | $L_{B10}$ |
| II-589. | $L_{A29}$ | $L_{B10}$ |

| Compound Number | $L_A$ | $L_B$ |
|---|---|---|
| II-590. | $L_{A30}$ | $L_{B10}$ |
| II-591. | $L_{A31}$ | $L_{B10}$ |
| II-592. | $L_{A32}$ | $L_{B10}$ |
| II-593. | $L_{A33}$ | $L_{B10}$ |
| II-594. | $L_{A34}$ | $L_{B10}$ |
| II-595. | $L_{A35}$ | $L_{B10}$ |
| II-596. | $L_{A36}$ | $L_{B10}$ |
| II-597. | $L_{A37}$ | $L_{B10}$ |
| II-598. | $L_{A38}$ | $L_{B10}$ |
| II-599. | $L_{A39}$ | $L_{B10}$ |
| II-600. | $L_{A40}$ | $L_{B10}$ |
| II-601. | $L_{A41}$ | $L_{B10}$ |
| II-602. | $L_{A42}$ | $L_{B10}$ |
| II-603. | $L_{A43}$ | $L_{B10}$ |
| II-604. | $L_{A44}$ | $L_{B10}$ |
| II-605. | $L_{A45}$ | $L_{B10}$ |
| II-606. | $L_{A46}$ | $L_{B10}$ |
| II-607. | $L_{A47}$ | $L_{B10}$ |
| II-608. | $L_{A48}$ | $L_{B10}$ |
| II-609. | $L_{A49}$ | $L_{B10}$ |
| II-610. | $L_{A50}$ | $L_{B10}$ |
| II-611. | $L_{A51}$ | $L_{B10}$ |
| II-612. | $L_{A52}$ | $L_{B10}$ |
| II-613. | $L_{A53}$ | $L_{B10}$ |
| II-614. | $L_{A54}$ | $L_{B10}$ |
| II-615. | $L_{A55}$ | $L_{B10}$ |
| II-616. | $L_{A56}$ | $L_{B10}$ |
| II-617. | $L_{A57}$ | $L_{B10}$ |
| II-618. | $L_{A58}$ | $L_{B10}$ |
| II-619. | $L_{A59}$ | $L_{B10}$ |
| II-620. | $L_{A60}$ | $L_{B10}$ |
| II-621. | $L_{A61}$ | $L_{B10}$ |
| II-622. | $L_{A62}$ | $L_{B10}$ |
| II-623. | $L_{A63}$ | $L_{B10}$ |
| II-624. | $L_{A64}$ | $L_{B10}$ |
| II-625. | $L_{A65}$ | $L_{B10}$ |
| II-626. | $L_{A66}$ | $L_{B10}$ |
| II-627. | $L_{A67}$ | $L_{B10}$ |
| II-628. | $L_{A68}$ | $L_{B10}$ |
| II-629. | $L_{A69}$ | $L_{B10}$ |
| II-630. | $L_{A1}$ | $L_{B11}$ |
| II-631. | $L_{A2}$ | $L_{B11}$ |
| II-632. | $L_{A3}$ | $L_{B11}$ |
| II-633. | $L_{A4}$ | $L_{B11}$ |
| II-634. | $L_{A5}$ | $L_{B11}$ |
| II-635. | $L_{A6}$ | $L_{B11}$ |
| II-636. | $L_{A7}$ | $L_{B11}$ |
| II-637. | $L_{A8}$ | $L_{B11}$ |
| II-638. | $L_{A9}$ | $L_{B11}$ |
| II-639. | $L_{A10}$ | $L_{B11}$ |
| II-640. | $L_{A11}$ | $L_{B11}$ |
| II-641. | $L_{A12}$ | $L_{B11}$ |
| II-642. | $L_{A13}$ | $L_{B11}$ |
| II-643. | $L_{A14}$ | $L_{B11}$ |
| II-644. | $L_{A15}$ | $L_{B11}$ |
| II-645. | $L_{A16}$ | $L_{B11}$ |
| II-646. | $L_{A17}$ | $L_{B11}$ |
| II-647. | $L_{A18}$ | $L_{B11}$ |
| II-648. | $L_{A19}$ | $L_{B11}$ |
| II-649. | $L_{A20}$ | $L_{B11}$ |
| II-650. | $L_{A21}$ | $L_{B11}$ |
| II-651. | $L_{A22}$ | $L_{B11}$ |
| II-652. | $L_{A23}$ | $L_{B11}$ |
| II-653. | $L_{A24}$ | $L_{B11}$ |
| II-654. | $L_{A25}$ | $L_{B11}$ |
| II-655. | $L_{A26}$ | $L_{B11}$ |
| II-656. | $L_{A27}$ | $L_{B11}$ |
| II-657. | $L_{A28}$ | $L_{B11}$ |
| II-658. | $L_{A29}$ | $L_{B11}$ |
| II-659. | $L_{A30}$ | $L_{B11}$ |
| II-660. | $L_{A31}$ | $L_{B11}$ |
| II-661. | $L_{A32}$ | $L_{B11}$ |
| II-662. | $L_{A33}$ | $L_{B11}$ |
| II-663. | $L_{A34}$ | $L_{B11}$ |
| II-664. | $L_{A35}$ | $L_{B11}$ |
| II-665. | $L_{A36}$ | $L_{B11}$ |
| II-666. | $L_{A37}$ | $L_{B11}$ |
| II-667. | $L_{A38}$ | $L_{B11}$ |
| II-668. | $L_{A39}$ | $L_{B11}$ |
| II-669. | $L_{A40}$ | $L_{B11}$ |
| II-670. | $L_{A41}$ | $L_{B11}$ |
| II-671. | $L_{A42}$ | $L_{B11}$ |
| II-672. | $L_{A43}$ | $L_{B11}$ |
| II-673. | $L_{A44}$ | $L_{B11}$ |
| II-674. | $L_{A45}$ | $L_{B11}$ |
| II-675. | $L_{A46}$ | $L_{B11}$ |
| II-676. | $L_{A47}$ | $L_{B11}$ |
| II-677. | $L_{A48}$ | $L_{B11}$ |
| II-678. | $L_{A49}$ | $L_{B11}$ |
| II-679. | $L_{A50}$ | $L_{B11}$ |
| II-680. | $L_{A51}$ | $L_{B11}$ |
| II-681. | $L_{A52}$ | $L_{B11}$ |
| II-682. | $L_{A53}$ | $L_{B11}$ |
| II-683. | $L_{A54}$ | $L_{B11}$ |
| II-684. | $L_{A55}$ | $L_{B11}$ |
| II-685. | $L_{A56}$ | $L_{B11}$ |
| II-686. | $L_{A57}$ | $L_{B11}$ |
| II-687. | $L_{A58}$ | $L_{B11}$ |
| II-688. | $L_{A59}$ | $L_{B11}$ |
| II-689. | $L_{A60}$ | $L_{B11}$ |
| II-690. | $L_{A61}$ | $L_{B11}$ |
| II-691. | $L_{A62}$ | $L_{B11}$ |
| II-692. | $L_{A63}$ | $L_{B11}$ |
| II-693. | $L_{A64}$ | $L_{B11}$ |
| II-694. | $L_{A65}$ | $L_{B11}$ |
| II-695. | $L_{A66}$ | $L_{B11}$ |
| II-696. | $L_{A67}$ | $L_{B11}$ |
| II-697. | $L_{A68}$ | $L_{B11}$ |
| II-698. | $L_{A69}$ | $L_{B11}$ |
| II-699. | $L_{A3}$ | $L_{B12}$ |
| II-700. | $L_{A4}$ | $L_{B12}$ |
| II-701. | $L_{A5}$ | $L_{B12}$ |
| II-702. | $L_{A6}$ | $L_{B12}$ |
| II-703. | $L_{A7}$ | $L_{B12}$ |
| II-704. | $L_{A8}$ | $L_{B12}$ |
| II-705. | $L_{A9}$ | $L_{B12}$ |
| II-706. | $L_{A10}$ | $L_{B12}$ |
| II-707. | $L_{A11}$ | $L_{B12}$ |
| II-708. | $L_{A12}$ | $L_{B12}$ |
| II-709. | $L_{A13}$ | $L_{B12}$ |
| II-710. | $L_{A14}$ | $L_{B12}$ |
| II-711. | $L_{A15}$ | $L_{B12}$ |
| II-712. | $L_{A16}$ | $L_{B12}$ |
| II-713. | $L_{A17}$ | $L_{B12}$ |
| II-714. | $L_{A18}$ | $L_{B12}$ |
| II-715. | $L_{A21}$ | $L_{B12}$ |
| II-716. | $L_{A22}$ | $L_{B12}$ |
| II-717. | $L_{A23}$ | $L_{B12}$ |
| II-718. | $L_{A24}$ | $L_{B12}$ |
| II-719. | $L_{A25}$ | $L_{B12}$ |
| II-720. | $L_{A26}$ | $L_{B12}$ |
| II-721. | $L_{A27}$ | $L_{B12}$ |
| II-722. | $L_{A28}$ | $L_{B12}$ |
| II-723. | $L_{A29}$ | $L_{B12}$ |
| II-724. | $L_{A30}$ | $L_{B12}$ |
| II-725. | $L_{A31}$ | $L_{B12}$ |
| II-726. | $L_{A32}$ | $L_{B12}$ |
| II-727. | $L_{A33}$ | $L_{B12}$ |
| II-728. | $L_{A34}$ | $L_{B12}$ |
| II-729. | $L_{A35}$ | $L_{B12}$ |
| II-730. | $L_{A37}$ | $L_{B12}$ |
| II-731. | $L_{A38}$ | $L_{B12}$ |
| II-732. | $L_{A39}$ | $L_{B12}$ |
| II-733. | $L_{A40}$ | $L_{B12}$ |
| II-734. | $L_{A41}$ | $L_{B12}$ |
| II-735. | $L_{A42}$ | $L_{B12}$ |
| II-736. | $L_{A43}$ | $L_{B12}$ |
| II-737. | $L_{A44}$ | $L_{B12}$ |
| II-738. | $L_{A45}$ | $L_{B12}$ |
| II-739. | $L_{A46}$ | $L_{B12}$ |
| II-740. | $L_{A47}$ | $L_{B12}$ |
| II-741. | $L_{A48}$ | $L_{B12}$ |

| Compound Number | $L_A$ | $L_B$ |
|---|---|---|
| II-742. | $L_{A49}$ | $L_{B12}$ |
| II-743. | $L_{A50}$ | $L_{B12}$ |
| II-744. | $L_{A51}$ | $L_{B12}$ |
| II-745. | $L_{A52}$ | $L_{B12}$ |
| II-746. | $L_{A54}$ | $L_{B12}$ |
| II-747. | $L_{A55}$ | $L_{B12}$ |
| II-748. | $L_{A56}$ | $L_{B12}$ |
| II-749. | $L_{A57}$ | $L_{B12}$ |
| II-750. | $L_{A58}$ | $L_{B12}$ |
| II-751. | $L_{A59}$ | $L_{B12}$ |
| II-752. | $L_{A60}$ | $L_{B12}$ |
| II-753. | $L_{A61}$ | $L_{B12}$ |
| II-754. | $L_{A62}$ | $L_{B12}$ |
| II-755. | $L_{A63}$ | $L_{B12}$ |
| II-756. | $L_{A64}$ | $L_{B12}$ |
| II-757. | $L_{A65}$ | $L_{B12}$ |
| II-758. | $L_{A66}$ | $L_{B12}$ |
| II-759. | $L_{A67}$ | $L_{B12}$ |
| II-760. | $L_{A68}$ | $L_{B12}$ |
| II-761. | $L_{A69}$ | $L_{B12}$ |
| II-762. | $L_{A1}$ | $L_{B13}$ |
| II-763. | $L_{A2}$ | $L_{B13}$ |
| II-764. | $L_{A3}$ | $L_{B13}$ |
| II-765. | $L_{A4}$ | $L_{B13}$ |
| II-766. | $L_{A5}$ | $L_{B13}$ |
| II-767. | $L_{A6}$ | $L_{B13}$ |
| II-768. | $L_{A7}$ | $L_{B13}$ |
| II-769. | $L_{A8}$ | $L_{B13}$ |
| II-770. | $L_{A9}$ | $L_{B13}$ |
| II-771. | $L_{A10}$ | $L_{B13}$ |
| II-772. | $L_{A11}$ | $L_{B13}$ |
| II-773. | $L_{A12}$ | $L_{B13}$ |
| II-774. | $L_{A13}$ | $L_{B13}$ |
| II-775. | $L_{A14}$ | $L_{B13}$ |
| II-776. | $L_{A15}$ | $L_{B13}$ |
| II-777. | $L_{A16}$ | $L_{B13}$ |
| II-778. | $L_{A17}$ | $L_{B13}$ |
| II-779. | $L_{A18}$ | $L_{B13}$ |
| II-780. | $L_{A19}$ | $L_{B13}$ |
| II-781. | $L_{A20}$ | $L_{B13}$ |
| II-782. | $L_{A21}$ | $L_{B13}$ |
| II-783. | $L_{A22}$ | $L_{B13}$ |
| II-784. | $L_{A23}$ | $L_{B13}$ |
| II-785. | $L_{A24}$ | $L_{B13}$ |
| II-786. | $L_{A25}$ | $L_{B13}$ |
| II-787. | $L_{A26}$ | $L_{B13}$ |
| II-788. | $L_{A27}$ | $L_{B13}$ |
| II-789. | $L_{A28}$ | $L_{B13}$ |
| II-790. | $L_{A29}$ | $L_{B13}$ |
| II-791. | $L_{A30}$ | $L_{B13}$ |
| II-792. | $L_{A31}$ | $L_{B13}$ |
| II-793. | $L_{A32}$ | $L_{B13}$ |
| II-794. | $L_{A33}$ | $L_{B13}$ |
| II-795. | $L_{A34}$ | $L_{B13}$ |
| II-796. | $L_{A35}$ | $L_{B13}$ |
| II-797. | $L_{A36}$ | $L_{B13}$ |
| II-798. | $L_{A37}$ | $L_{B13}$ |
| II-799. | $L_{A38}$ | $L_{B13}$ |
| II-800. | $L_{A39}$ | $L_{B13}$ |
| II-801. | $L_{A40}$ | $L_{B13}$ |
| II-802. | $L_{A41}$ | $L_{B13}$ |
| II-803. | $L_{A42}$ | $L_{B13}$ |
| II-804. | $L_{A43}$ | $L_{B13}$ |
| II-805. | $L_{A44}$ | $L_{B13}$ |
| II-806. | $L_{A45}$ | $L_{B13}$ |
| II-807. | $L_{A46}$ | $L_{B13}$ |
| II-808. | $L_{A47}$ | $L_{B13}$ |
| II-809. | $L_{A48}$ | $L_{B13}$ |
| II-810. | $L_{A49}$ | $L_{B13}$ |
| II-811. | $L_{A50}$ | $L_{B13}$ |
| II-812. | $L_{A51}$ | $L_{B13}$ |
| II-813. | $L_{A52}$ | $L_{B13}$ |
| II-814. | $L_{A53}$ | $L_{B13}$ |
| II-815. | $L_{A54}$ | $L_{B13}$ |
| II-816. | $L_{A55}$ | $L_{B13}$ |
| II-817. | $L_{A56}$ | $L_{B13}$ |
| II-818. | $L_{A57}$ | $L_{B13}$ |
| II-819. | $L_{A58}$ | $L_{B13}$ |
| II-820. | $L_{A59}$ | $L_{B13}$ |
| II-821. | $L_{A60}$ | $L_{B13}$ |
| II-822. | $L_{A61}$ | $L_{B13}$ |
| II-823. | $L_{A62}$ | $L_{B13}$ |
| II-824. | $L_{A63}$ | $L_{B13}$ |
| II-825. | $L_{A64}$ | $L_{B13}$ |
| II-826. | $L_{A65}$ | $L_{B13}$ |
| II-827. | $L_{A66}$ | $L_{B13}$ |
| II-828. | $L_{A67}$ | $L_{B13}$ |
| II-829. | $L_{A68}$ | $L_{B13}$ |
| II-830. | $L_{A69}$ | $L_{B13}$ |
| II-831. | $L_{A1}$ | $L_{B14}$ |
| II-832. | $L_{A2}$ | $L_{B14}$ |
| II-833. | $L_{A3}$ | $L_{B14}$ |
| II-834. | $L_{A4}$ | $L_{B14}$ |
| II-835. | $L_{A5}$ | $L_{B14}$ |
| II-836. | $L_{A6}$ | $L_{B14}$ |
| II-837. | $L_{A7}$ | $L_{B14}$ |
| II-838. | $L_{A8}$ | $L_{B14}$ |
| II-839. | $L_{A9}$ | $L_{B14}$ |
| II-840. | $L_{A10}$ | $L_{B14}$ |
| II-841. | $L_{A11}$ | $L_{B14}$ |
| II-842. | $L_{A12}$ | $L_{B14}$ |
| II-843. | $L_{A13}$ | $L_{B14}$ |
| II-844. | $L_{A14}$ | $L_{B14}$ |
| II-845. | $L_{A15}$ | $L_{B14}$ |
| II-846. | $L_{A16}$ | $L_{B14}$ |
| II-847. | $L_{A17}$ | $L_{B14}$ |
| II-848. | $L_{A18}$ | $L_{B14}$ |
| II-849. | $L_{A19}$ | $L_{B14}$ |
| II-850. | $L_{A20}$ | $L_{B14}$ |
| II-851. | $L_{A21}$ | $L_{B14}$ |
| II-852. | $L_{A22}$ | $L_{B14}$ |
| II-853. | $L_{A23}$ | $L_{B14}$ |
| II-854. | $L_{A24}$ | $L_{B14}$ |
| II-855. | $L_{A25}$ | $L_{B14}$ |
| II-856. | $L_{A26}$ | $L_{B14}$ |
| II-857. | $L_{A27}$ | $L_{B14}$ |
| II-858. | $L_{A28}$ | $L_{B14}$ |
| II-859. | $L_{A29}$ | $L_{B14}$ |
| II-860. | $L_{A30}$ | $L_{B14}$ |
| II-861. | $L_{A31}$ | $L_{B14}$ |
| II-862. | $L_{A32}$ | $L_{B14}$ |
| II-863. | $L_{A33}$ | $L_{B14}$ |
| II-864. | $L_{A34}$ | $L_{B14}$ |
| II-865. | $L_{A35}$ | $L_{B14}$ |
| II-866. | $L_{A36}$ | $L_{B14}$ |
| II-867. | $L_{A37}$ | $L_{B14}$ |
| II-868. | $L_{A38}$ | $L_{B14}$ |
| II-869. | $L_{A39}$ | $L_{B14}$ |
| II-870. | $L_{A40}$ | $L_{B14}$ |
| II-871. | $L_{A41}$ | $L_{B14}$ |
| II-872. | $L_{A42}$ | $L_{B14}$ |
| II-873. | $L_{A43}$ | $L_{B14}$ |
| II-874. | $L_{A44}$ | $L_{B14}$ |
| II-875. | $L_{A45}$ | $L_{B14}$ |
| II-876. | $L_{A46}$ | $L_{B14}$ |
| II-877. | $L_{A47}$ | $L_{B14}$ |
| II-878. | $L_{A48}$ | $L_{B14}$ |
| II-879. | $L_{A49}$ | $L_{B14}$ |
| II-880. | $L_{A50}$ | $L_{B14}$ |
| II-881. | $L_{A51}$ | $L_{B14}$ |
| II-882. | $L_{A52}$ | $L_{B14}$ |
| II-883. | $L_{A53}$ | $L_{B14}$ |
| II-884. | $L_{A54}$ | $L_{B14}$ |
| II-885. | $L_{A55}$ | $L_{B14}$ |
| II-886. | $L_{A56}$ | $L_{B14}$ |
| II-887. | $L_{A57}$ | $L_{B14}$ |
| II-888. | $L_{A58}$ | $L_{B14}$ |
| II-889. | $L_{A59}$ | $L_{B14}$ |
| II-890. | $L_{A60}$ | $L_{B14}$ |
| II-891. | $L_{A61}$ | $L_{B14}$ |
| II-892. | $L_{A62}$ | $L_{B14}$ |
| II-893. | $L_{A63}$ | $L_{B14}$ |

| Compound Number | $L_A$ | $L_B$ |
|---|---|---|
| II-894. | $L_{A64}$ | $L_{B14}$ |
| II-895. | $L_{A65}$ | $L_{B14}$ |
| II-896. | $L_{A66}$ | $L_{B14}$ |
| II-897. | $L_{A67}$ | $L_{B14}$ |
| II-898. | $L_{A68}$ | $L_{B14}$ |
| II-899. | $L_{A69}$ | $L_{B14}$ |
| II-900. | $L_{A1}$ | $L_{B15}$ |
| II-901. | $L_{A2}$ | $L_{B15}$ |
| II-902. | $L_{A3}$ | $L_{B15}$ |
| II-903. | $L_{A4}$ | $L_{B15}$ |
| II-904. | $L_{A5}$ | $L_{B15}$ |
| II-905. | $L_{A6}$ | $L_{B15}$ |
| II-906. | $L_{A7}$ | $L_{B15}$ |
| II-907. | $L_{A8}$ | $L_{B15}$ |
| II-908. | $L_{A9}$ | $L_{B15}$ |
| II-909. | $L_{A10}$ | $L_{B15}$ |
| II-910. | $L_{A11}$ | $L_{B15}$ |
| II-911. | $L_{A12}$ | $L_{B15}$ |
| II-912. | $L_{A13}$ | $L_{B15}$ |
| II-913. | $L_{A14}$ | $L_{B15}$ |
| II-914. | $L_{A15}$ | $L_{B15}$ |
| II-915. | $L_{A16}$ | $L_{B15}$ |
| II-916. | $L_{A17}$ | $L_{B15}$ |
| II-917. | $L_{A18}$ | $L_{B15}$ |
| II-918. | $L_{A19}$ | $L_{B15}$ |
| II-919. | $L_{A20}$ | $L_{B15}$ |
| II-920. | $L_{A21}$ | $L_{B15}$ |
| II-921. | $L_{A22}$ | $L_{B15}$ |
| II-922. | $L_{A23}$ | $L_{B15}$ |
| II-923. | $L_{A24}$ | $L_{B15}$ |
| II-924. | $L_{A25}$ | $L_{B15}$ |
| II-925. | $L_{A26}$ | $L_{B15}$ |
| II-926. | $L_{A27}$ | $L_{B15}$ |
| II-927. | $L_{A28}$ | $L_{B15}$ |
| II-928. | $L_{A29}$ | $L_{B15}$ |
| II-929. | $L_{A30}$ | $L_{B15}$ |
| II-930. | $L_{A31}$ | $L_{B15}$ |
| II-931. | $L_{A32}$ | $L_{B15}$ |
| II-932. | $L_{A33}$ | $L_{B15}$ |
| II-933. | $L_{A34}$ | $L_{B15}$ |
| II-934. | $L_{A35}$ | $L_{B15}$ |
| II-935. | $L_{A36}$ | $L_{B15}$ |
| II-936. | $L_{A37}$ | $L_{B15}$ |
| II-937. | $L_{A38}$ | $L_{B15}$ |
| II-938. | $L_{A39}$ | $L_{B15}$ |
| II-939. | $L_{A40}$ | $L_{B15}$ |
| II-940. | $L_{A41}$ | $L_{B15}$ |
| II-941. | $L_{A42}$ | $L_{B15}$ |
| II-942. | $L_{A43}$ | $L_{B15}$ |
| II-943. | $L_{A44}$ | $L_{B15}$ |
| II-944. | $L_{A45}$ | $L_{B15}$ |
| II-945. | $L_{A46}$ | $L_{B15}$ |
| II-946. | $L_{A47}$ | $L_{B15}$ |
| II-947. | $L_{A48}$ | $L_{B15}$ |
| II-948. | $L_{A49}$ | $L_{B15}$ |
| II-949. | $L_{A50}$ | $L_{B15}$ |
| II-950. | $L_{A51}$ | $L_{B15}$ |
| II-951. | $L_{A52}$ | $L_{B15}$ |
| II-952. | $L_{A53}$ | $L_{B15}$ |
| II-953. | $L_{A54}$ | $L_{B15}$ |
| II-954. | $L_{A55}$ | $L_{B15}$ |
| II-955. | $L_{A56}$ | $L_{B15}$ |
| II-956. | $L_{A57}$ | $L_{B15}$ |
| II-957. | $L_{A58}$ | $L_{B15}$ |
| II-958. | $L_{A59}$ | $L_{B15}$ |
| II-959. | $L_{A60}$ | $L_{B15}$ |
| II-960. | $L_{A61}$ | $L_{B15}$ |
| II-961. | $L_{A62}$ | $L_{B15}$ |
| II-962. | $L_{A63}$ | $L_{B15}$ |
| II-963. | $L_{A64}$ | $L_{B15}$ |
| II-964. | $L_{A65}$ | $L_{B15}$ |
| II-965. | $L_{A66}$ | $L_{B15}$ |
| II-966. | $L_{A67}$ | $L_{B15}$ |
| II-967. | $L_{A68}$ | $L_{B15}$ |
| II-968. | $L_{A69}$ | $L_{B15}$ |
| II-969. | $L_{A3}$ | $L_{B16}$ |
| II-970. | $L_{A4}$ | $L_{B16}$ |
| II-971. | $L_{A5}$ | $L_{B16}$ |
| II-972. | $L_{A6}$ | $L_{B16}$ |
| II-973. | $L_{A7}$ | $L_{B16}$ |
| II-974. | $L_{A8}$ | $L_{B16}$ |
| II-975. | $L_{A9}$ | $L_{B16}$ |
| II-976. | $L_{A10}$ | $L_{B16}$ |
| II-977. | $L_{A11}$ | $L_{B16}$ |
| II-978. | $L_{A12}$ | $L_{B16}$ |
| II-979. | $L_{A13}$ | $L_{B16}$ |
| II-980. | $L_{A14}$ | $L_{B16}$ |
| II-981. | $L_{A15}$ | $L_{B16}$ |
| II-982. | $L_{A16}$ | $L_{B16}$ |
| II-983. | $L_{A17}$ | $L_{B16}$ |
| II-984. | $L_{A18}$ | $L_{B16}$ |
| II-985. | $L_{A21}$ | $L_{B16}$ |
| II-986. | $L_{A22}$ | $L_{B16}$ |
| II-987. | $L_{A23}$ | $L_{B16}$ |
| II-988. | $L_{A24}$ | $L_{B16}$ |
| II-989. | $L_{A25}$ | $L_{B16}$ |
| II-990. | $L_{A26}$ | $L_{B16}$ |
| II-991. | $L_{A27}$ | $L_{B16}$ |
| II-992. | $L_{A28}$ | $L_{B16}$ |
| II-993. | $L_{A29}$ | $L_{B16}$ |
| II-994. | $L_{A30}$ | $L_{B16}$ |
| II-995. | $L_{A31}$ | $L_{B16}$ |
| II-996. | $L_{A32}$ | $L_{B16}$ |
| II-997. | $L_{A33}$ | $L_{B16}$ |
| II-998. | $L_{A34}$ | $L_{B16}$ |
| II-999. | $L_{A35}$ | $L_{B16}$ |
| II-1000. | $L_{A37}$ | $L_{B16}$ |
| II-1001. | $L_{A38}$ | $L_{B16}$ |
| II-1002. | $L_{A39}$ | $L_{B16}$ |
| II-1003. | $L_{A40}$ | $L_{B16}$ |
| II-1004. | $L_{A41}$ | $L_{B16}$ |
| II-1005. | $L_{A42}$ | $L_{B16}$ |
| II-1006. | $L_{A43}$ | $L_{B16}$ |
| II-1007. | $L_{A44}$ | $L_{B16}$ |
| II-1008. | $L_{A45}$ | $L_{B16}$ |
| II-1009. | $L_{A46}$ | $L_{B16}$ |
| II-1010. | $L_{A47}$ | $L_{B16}$ |
| II-1011. | $L_{A48}$ | $L_{B16}$ |
| II-1012. | $L_{A49}$ | $L_{B16}$ |
| II-1013. | $L_{A50}$ | $L_{B16}$ |
| II-1014. | $L_{A51}$ | $L_{B16}$ |
| II-1015. | $L_{A52}$ | $L_{B16}$ |
| II-1016. | $L_{A54}$ | $L_{B16}$ |
| II-1017. | $L_{A55}$ | $L_{B16}$ |
| II-1018. | $L_{A56}$ | $L_{B16}$ |
| II-1019. | $L_{A57}$ | $L_{B16}$ |
| II-1020. | $L_{A58}$ | $L_{B16}$ |
| II-1021. | $L_{A59}$ | $L_{B16}$ |
| II-1022. | $L_{A60}$ | $L_{B16}$ |
| II-1023. | $L_{A61}$ | $L_{B16}$ |
| II-1024. | $L_{A62}$ | $L_{B16}$ |
| II-1025. | $L_{A63}$ | $L_{B16}$ |
| II-1026. | $L_{A64}$ | $L_{B16}$ |
| II-1027. | $L_{A65}$ | $L_{B16}$ |
| II-1028. | $L_{A66}$ | $L_{B16}$ |
| II-1029. | $L_{A67}$ | $L_{B16}$ |
| II-1030. | $L_{A68}$ | $L_{B16}$ |
| II-1031. | $L_{A69}$ | $L_{B16}$ |
| II-1032. | $L_{A2}$ | $L_{B17}$ |
| II-1033. | $L_{A3}$ | $L_{B17}$ |
| II-1034. | $L_{A4}$ | $L_{B17}$ |
| II-1035. | $L_{A5}$ | $L_{B17}$ |
| II-1036. | $L_{A6}$ | $L_{B17}$ |
| II-1037. | $L_{A7}$ | $L_{B17}$ |
| II-1038. | $L_{A8}$ | $L_{B17}$ |
| II-1039. | $L_{A9}$ | $L_{B17}$ |
| II-1040. | $L_{A10}$ | $L_{B17}$ |
| II-1041. | $L_{A11}$ | $L_{B17}$ |
| II-1042. | $L_{A12}$ | $L_{B17}$ |
| II-1043. | $L_{A13}$ | $L_{B17}$ |
| II-1044. | $L_{A14}$ | $L_{B17}$ |
| II-1045. | $L_{A15}$ | $L_{B17}$ |

| Compound Number | $L_A$ | $L_B$ |
|---|---|---|
| II-1046. | $L_{A16}$ | $L_{B17}$ |
| II-1047. | $L_{A17}$ | $L_{B17}$ |
| II-1048. | $L_{A18}$ | $L_{B17}$ |
| II-1049. | $L_{A20}$ | $L_{B17}$ |
| II-1050. | $L_{A21}$ | $L_{B17}$ |
| II-1051. | $L_{A22}$ | $L_{B17}$ |
| II-1052. | $L_{A23}$ | $L_{B17}$ |
| II-1053. | $L_{A24}$ | $L_{B17}$ |
| II-1054. | $L_{A25}$ | $L_{B17}$ |
| II-1055. | $L_{A26}$ | $L_{B17}$ |
| II-1056. | $L_{A27}$ | $L_{B17}$ |
| II-1057. | $L_{A28}$ | $L_{B17}$ |
| II-1058. | $L_{A29}$ | $L_{B17}$ |
| II-1059. | $L_{A30}$ | $L_{B17}$ |
| II-1060. | $L_{A31}$ | $L_{B17}$ |
| II-1061. | $L_{A32}$ | $L_{B17}$ |
| II-1062. | $L_{A33}$ | $L_{B17}$ |
| II-1063. | $L_{A34}$ | $L_{B17}$ |
| II-1064. | $L_{A35}$ | $L_{B17}$ |
| II-1065. | $L_{A36}$ | $L_{B17}$ |
| II-1066. | $L_{A37}$ | $L_{B17}$ |
| II-1067. | $L_{A38}$ | $L_{B17}$ |
| II-1068. | $L_{A39}$ | $L_{B17}$ |
| II-1069. | $L_{A40}$ | $L_{B17}$ |
| II-1070. | $L_{A41}$ | $L_{B17}$ |
| II-1071. | $L_{A42}$ | $L_{B17}$ |
| II-1072. | $L_{A43}$ | $L_{B17}$ |
| II-1073. | $L_{A44}$ | $L_{B17}$ |
| II-1074. | $L_{A45}$ | $L_{B17}$ |
| II-1075. | $L_{A46}$ | $L_{B17}$ |
| II-1076. | $L_{A47}$ | $L_{B17}$ |
| II-1077. | $L_{A48}$ | $L_{B17}$ |
| II-1078. | $L_{A49}$ | $L_{B17}$ |
| II-1079. | $L_{A50}$ | $L_{B17}$ |
| II-1080. | $L_{A51}$ | $L_{B17}$ |
| II-1081. | $L_{A52}$ | $L_{B17}$ |
| II-1082. | $L_{A53}$ | $L_{B17}$ |
| II-1083. | $L_{A54}$ | $L_{B17}$ |
| II-1084. | $L_{A55}$ | $L_{B17}$ |
| II-1085. | $L_{A56}$ | $L_{B17}$ |
| II-1086. | $L_{A57}$ | $L_{B17}$ |
| II-1087. | $L_{A58}$ | $L_{B17}$ |
| II-1088. | $L_{A59}$ | $L_{B17}$ |
| II-1089. | $L_{A60}$ | $L_{B17}$ |
| II-1090. | $L_{A61}$ | $L_{B17}$ |
| II-1091. | $L_{A62}$ | $L_{B17}$ |
| II-1092. | $L_{A63}$ | $L_{B17}$ |
| II-1093. | $L_{A64}$ | $L_{B17}$ |
| II-1094. | $L_{A65}$ | $L_{B17}$ |
| II-1095. | $L_{A66}$ | $L_{B17}$ |
| II-1096. | $L_{A67}$ | $L_{B17}$ |
| II-1097. | $L_{A68}$ | $L_{B17}$ |
| II-1098. | $L_{A69}$ | $L_{B17}$ |
| II-1099. | $L_{A2}$ | $L_{B18}$ |
| II-1100. | $L_{A3}$ | $L_{B18}$ |
| II-1101. | $L_{A4}$ | $L_{B18}$ |
| II-1102. | $L_{A5}$ | $L_{B18}$ |
| II-1103. | $L_{A6}$ | $L_{B18}$ |
| II-1104. | $L_{A7}$ | $L_{B18}$ |
| II-1105. | $L_{A8}$ | $L_{B18}$ |
| II-1106. | $L_{A9}$ | $L_{B18}$ |
| II-1107. | $L_{A10}$ | $L_{B18}$ |
| II-1108. | $L_{A11}$ | $L_{B18}$ |
| II-1109. | $L_{A12}$ | $L_{B18}$ |
| II-1110. | $L_{A13}$ | $L_{B18}$ |
| II-1111. | $L_{A14}$ | $L_{B18}$ |
| II-1112. | $L_{A15}$ | $L_{B18}$ |
| II-1113. | $L_{A16}$ | $L_{B18}$ |
| II-1114. | $L_{A17}$ | $L_{B18}$ |
| II-1115. | $L_{A18}$ | $L_{B18}$ |
| II-1116. | $L_{A20}$ | $L_{B18}$ |
| II-1117. | $L_{A21}$ | $L_{B18}$ |
| II-1118. | $L_{A22}$ | $L_{B18}$ |
| II-1119. | $L_{A23}$ | $L_{B18}$ |
| II-1120. | $L_{A24}$ | $L_{B18}$ |
| II-1121. | $L_{A25}$ | $L_{B18}$ |
| II-1122. | $L_{A26}$ | $L_{B18}$ |
| II-1123. | $L_{A27}$ | $L_{B18}$ |
| II-1124. | $L_{A28}$ | $L_{B18}$ |
| II-1125. | $L_{A29}$ | $L_{B18}$ |
| II-1126. | $L_{A30}$ | $L_{B18}$ |
| II-1127. | $L_{A31}$ | $L_{B18}$ |
| II-1128. | $L_{A32}$ | $L_{B18}$ |
| II-1129. | $L_{A33}$ | $L_{B18}$ |
| II-1130. | $L_{A34}$ | $L_{B18}$ |
| II-1131. | $L_{A35}$ | $L_{B18}$ |
| II-1132. | $L_{A36}$ | $L_{B18}$ |
| II-1133. | $L_{A37}$ | $L_{B18}$ |
| II-1134. | $L_{A38}$ | $L_{B18}$ |
| II-1135. | $L_{A39}$ | $L_{B18}$ |
| II-1136. | $L_{A40}$ | $L_{B18}$ |
| II-1137. | $L_{A41}$ | $L_{B18}$ |
| II-1138. | $L_{A42}$ | $L_{B18}$ |
| II-1139. | $L_{A43}$ | $L_{B18}$ |
| II-1140. | $L_{A44}$ | $L_{B18}$ |
| II-1141. | $L_{A45}$ | $L_{B18}$ |
| II-1142. | $L_{A46}$ | $L_{B18}$ |
| II-1143. | $L_{A47}$ | $L_{B18}$ |
| II-1144. | $L_{A48}$ | $L_{B18}$ |
| II-1145. | $L_{A49}$ | $L_{B18}$ |
| II-1146. | $L_{A50}$ | $L_{B18}$ |
| II-1147. | $L_{A51}$ | $L_{B18}$ |
| II-1148. | $L_{A52}$ | $L_{B18}$ |
| II-1149. | $L_{A53}$ | $L_{B18}$ |
| II-1150. | $L_{A54}$ | $L_{B18}$ |
| II-1151. | $L_{A55}$ | $L_{B18}$ |
| II-1152. | $L_{A56}$ | $L_{B18}$ |
| II-1153. | $L_{A57}$ | $L_{B18}$ |
| II-1154. | $L_{A58}$ | $L_{B18}$ |
| II-1155. | $L_{A59}$ | $L_{B18}$ |
| II-1156. | $L_{A60}$ | $L_{B18}$ |
| II-1157. | $L_{A61}$ | $L_{B18}$ |
| II-1158. | $L_{A62}$ | $L_{B18}$ |
| II-1159. | $L_{A63}$ | $L_{B18}$ |
| II-1160. | $L_{A64}$ | $L_{B18}$ |
| II-1161. | $L_{A65}$ | $L_{B18}$ |
| II-1162. | $L_{A66}$ | $L_{B18}$ |
| II-1163. | $L_{A67}$ | $L_{B18}$ |
| II-1164. | $L_{A68}$ | $L_{B18}$ |
| II-1165. | $L_{A69}$ | $L_{B18}$ |
| II-1166. | $L_{A2}$ | $L_{B19}$ |
| II-1167. | $L_{A3}$ | $L_{B19}$ |
| II-1168. | $L_{A4}$ | $L_{B19}$ |
| II-1169. | $L_{A5}$ | $L_{B19}$ |
| II-1170. | $L_{A6}$ | $L_{B19}$ |
| II-1171. | $L_{A7}$ | $L_{B19}$ |
| II-1172. | $L_{A8}$ | $L_{B19}$ |
| II-1173. | $L_{A9}$ | $L_{B19}$ |
| II-1174. | $L_{A10}$ | $L_{B19}$ |
| II-1175. | $L_{A11}$ | $L_{B19}$ |
| II-1176. | $L_{A12}$ | $L_{B19}$ |
| II-1177. | $L_{A13}$ | $L_{B19}$ |
| II-1178. | $L_{A14}$ | $L_{B19}$ |
| II-1179. | $L_{A15}$ | $L_{B19}$ |
| II-1180. | $L_{A16}$ | $L_{B19}$ |
| II-1181. | $L_{A17}$ | $L_{B19}$ |
| II-1182. | $L_{A18}$ | $L_{B19}$ |
| II-1183. | $L_{A20}$ | $L_{B19}$ |
| II-1184. | $L_{A21}$ | $L_{B19}$ |
| II-1185. | $L_{A22}$ | $L_{B19}$ |
| II-1186. | $L_{A23}$ | $L_{B19}$ |
| II-1187. | $L_{A24}$ | $L_{B19}$ |
| II-1188. | $L_{A25}$ | $L_{B19}$ |
| II-1189. | $L_{A26}$ | $L_{B19}$ |
| II-1190. | $L_{A27}$ | $L_{B19}$ |
| II-1191. | $L_{A28}$ | $L_{B19}$ |
| II-1192. | $L_{A29}$ | $L_{B19}$ |
| II-1193. | $L_{A30}$ | $L_{B19}$ |
| II-1194. | $L_{A31}$ | $L_{B19}$ |
| II-1195. | $L_{A32}$ | $L_{B19}$ |
| II-1196. | $L_{A33}$ | $L_{B19}$ |
| II-1197. | $L_{A34}$ | $L_{B19}$ |

-continued

| Compound Number | $L_A$ | $L_B$ |
|---|---|---|
| II-1198. | $L_{A35}$ | $L_{B19}$ |
| II-1199. | $L_{A36}$ | $L_{B19}$ |
| II-1200. | $L_{A37}$ | $L_{B19}$ |
| II-1201. | $L_{A38}$ | $L_{B19}$ |
| II-1202. | $L_{A39}$ | $L_{B19}$ |
| II-1203. | $L_{A40}$ | $L_{B19}$ |
| II-1204. | $L_{A41}$ | $L_{B19}$ |
| II-1205. | $L_{A42}$ | $L_{B19}$ |
| II-1206. | $L_{A43}$ | $L_{B19}$ |
| II-1207. | $L_{A44}$ | $L_{B19}$ |
| II-1208. | $L_{A45}$ | $L_{B19}$ |
| II-1209. | $L_{A46}$ | $L_{B19}$ |
| II-1210. | $L_{A47}$ | $L_{B19}$ |
| II-1211. | $L_{A48}$ | $L_{B19}$ |
| II-1212. | $L_{A49}$ | $L_{B19}$ |
| II-1213. | $L_{A50}$ | $L_{B19}$ |
| II-1214. | $L_{A51}$ | $L_{B19}$ |
| II-1215. | $L_{A52}$ | $L_{B19}$ |
| II-1216. | $L_{A53}$ | $L_{B19}$ |
| II-1217. | $L_{A54}$ | $L_{B19}$ |
| II-1218. | $L_{A55}$ | $L_{B19}$ |
| II-1219. | $L_{A56}$ | $L_{B19}$ |
| II-1220. | $L_{A57}$ | $L_{B19}$ |
| II-1221. | $L_{A58}$ | $L_{B19}$ |
| II-1222. | $L_{A59}$ | $L_{B19}$ |
| II-1223. | $L_{A60}$ | $L_{B19}$ |
| II-1224. | $L_{A61}$ | $L_{B19}$ |
| II-1225. | $L_{A62}$ | $L_{B19}$ |
| II-1226. | $L_{A63}$ | $L_{B19}$ |
| II-1227. | $L_{A64}$ | $L_{B19}$ |
| II-1228. | $L_{A65}$ | $L_{B19}$ |
| II-1229. | $L_{A66}$ | $L_{B19}$ |
| II-1230. | $L_{A67}$ | $L_{B19}$ |
| II-1231. | $L_{A68}$ | $L_{B19}$ |
| II-1232. | $L_{A69}$ | $L_{B19}$ |
| II-1233. | $L_{A2}$ | $L_{B20}$ |
| II-1234. | $L_{A3}$ | $L_{B20}$ |
| II-1235. | $L_{A4}$ | $L_{B20}$ |
| II-1236. | $L_{A5}$ | $L_{B20}$ |
| II-1237. | $L_{A6}$ | $L_{B20}$ |
| II-1238. | $L_{A7}$ | $L_{B20}$ |
| II-1239. | $L_{A8}$ | $L_{B20}$ |
| II-1240. | $L_{A9}$ | $L_{B20}$ |
| II-1241. | $L_{A10}$ | $L_{B20}$ |
| II-1242. | $L_{A11}$ | $L_{B20}$ |
| II-1243. | $L_{A12}$ | $L_{B20}$ |
| II-1244. | $L_{A13}$ | $L_{B20}$ |
| II-1245. | $L_{A14}$ | $L_{B20}$ |
| II-1246. | $L_{A15}$ | $L_{B20}$ |
| II-1247. | $L_{A16}$ | $L_{B20}$ |
| II-1248. | $L_{A17}$ | $L_{B20}$ |
| II-1249. | $L_{A18}$ | $L_{B20}$ |
| II-1250. | $L_{A20}$ | $L_{B20}$ |
| II-1251. | $L_{A21}$ | $L_{B20}$ |
| II-1252. | $L_{A22}$ | $L_{B20}$ |
| II-1253. | $L_{A23}$ | $L_{B20}$ |
| II-1254. | $L_{A24}$ | $L_{B20}$ |
| II-1255. | $L_{A25}$ | $L_{B20}$ |
| II-1256. | $L_{A26}$ | $L_{B20}$ |
| II-1257. | $L_{A27}$ | $L_{B20}$ |
| II-1258. | $L_{A28}$ | $L_{B20}$ |
| II-1259. | $L_{A29}$ | $L_{B20}$ |
| II-1260. | $L_{A30}$ | $L_{B20}$ |
| II-1261. | $L_{A31}$ | $L_{B20}$ |
| II-1262. | $L_{A32}$ | $L_{B20}$ |
| II-1263. | $L_{A33}$ | $L_{B20}$ |
| II-1264. | $L_{A34}$ | $L_{B20}$ |
| II-1265. | $L_{A35}$ | $L_{B20}$ |
| II-1266. | $L_{A36}$ | $L_{B20}$ |
| II-1267. | $L_{A37}$ | $L_{B20}$ |
| II-1268. | $L_{A38}$ | $L_{B20}$ |
| II-1269. | $L_{A39}$ | $L_{B20}$ |
| II-1270. | $L_{A40}$ | $L_{B20}$ |
| II-1271. | $L_{A41}$ | $L_{B20}$ |
| II-1272. | $L_{A42}$ | $L_{B20}$ |
| II-1273. | $L_{A43}$ | $L_{B20}$ |
| II-1274. | $L_{A44}$ | $L_{B20}$ |
| II-1275. | $L_{A45}$ | $L_{B20}$ |
| II-1276. | $L_{A46}$ | $L_{B20}$ |
| II-1277. | $L_{A47}$ | $L_{B20}$ |
| II-1278. | $L_{A48}$ | $L_{B20}$ |
| II-1279. | $L_{A49}$ | $L_{B20}$ |
| II-1280. | $L_{A50}$ | $L_{B20}$ |
| II-1281. | $L_{A51}$ | $L_{B20}$ |
| II-1282. | $L_{A52}$ | $L_{B20}$ |
| II-1283. | $L_{A53}$ | $L_{B20}$ |
| II-1284. | $L_{A54}$ | $L_{B20}$ |
| II-1285. | $L_{A55}$ | $L_{B20}$ |
| II-1286. | $L_{A56}$ | $L_{B20}$ |
| II-1287. | $L_{A57}$ | $L_{B20}$ |
| II-1288. | $L_{A58}$ | $L_{B20}$ |
| II-1289. | $L_{A59}$ | $L_{B20}$ |
| II-1290. | $L_{A60}$ | $L_{B20}$ |
| II-1291. | $L_{A61}$ | $L_{B20}$ |
| II-1292. | $L_{A62}$ | $L_{B20}$ |
| II-1293. | $L_{A63}$ | $L_{B20}$ |
| II-1294. | $L_{A64}$ | $L_{B20}$ |
| II-1295. | $L_{A65}$ | $L_{B20}$ |
| II-1296. | $L_{A66}$ | $L_{B20}$ |
| II-1297. | $L_{A67}$ | $L_{B20}$ |
| II-1298. | $L_{A68}$ | $L_{B20}$ |
| II-1299. | $L_{A69}$ | $L_{B20}$ |
| II-1300. | $L_{A2}$ | $L_{B21}$ |
| II-1301. | $L_{A3}$ | $L_{B21}$ |
| II-1302. | $L_{A4}$ | $L_{B21}$ |
| II-1303. | $L_{A5}$ | $L_{B21}$ |
| II-1304. | $L_{A6}$ | $L_{B21}$ |
| II-1305. | $L_{A7}$ | $L_{B21}$ |
| II-1306. | $L_{A8}$ | $L_{B21}$ |
| II-1307. | $L_{A9}$ | $L_{B21}$ |
| II-1308. | $L_{A10}$ | $L_{B21}$ |
| II-1309. | $L_{A11}$ | $L_{B21}$ |
| II-1310. | $L_{A12}$ | $L_{B21}$ |
| II-1311. | $L_{A13}$ | $L_{B21}$ |
| II-1312. | $L_{A14}$ | $L_{B21}$ |
| II-1313. | $L_{A15}$ | $L_{B21}$ |
| II-1314. | $L_{A16}$ | $L_{B21}$ |
| II-1315. | $L_{A17}$ | $L_{B21}$ |
| II-1316. | $L_{A18}$ | $L_{B21}$ |
| II-1317. | $L_{A20}$ | $L_{B21}$ |
| II-1318. | $L_{A21}$ | $L_{B21}$ |
| II-1319. | $L_{A22}$ | $L_{B21}$ |
| II-1320. | $L_{A23}$ | $L_{B21}$ |
| II-1321. | $L_{A24}$ | $L_{B21}$ |
| II-1322. | $L_{A25}$ | $L_{B21}$ |
| II-1323. | $L_{A26}$ | $L_{B21}$ |
| II-1324. | $L_{A27}$ | $L_{B21}$ |
| II-1325. | $L_{A28}$ | $L_{B21}$ |
| II-1326. | $L_{A29}$ | $L_{B21}$ |
| II-1327. | $L_{A30}$ | $L_{B21}$ |
| II-1328. | $L_{A31}$ | $L_{B21}$ |
| II-1329. | $L_{A32}$ | $L_{B21}$ |
| II-1330. | $L_{A33}$ | $L_{B21}$ |
| II-1331. | $L_{A34}$ | $L_{B21}$ |
| II-1332. | $L_{A35}$ | $L_{B21}$ |
| II-1333. | $L_{A36}$ | $L_{B21}$ |
| II-1334. | $L_{A37}$ | $L_{B21}$ |
| II-1335. | $L_{A38}$ | $L_{B21}$ |
| II-1336. | $L_{A39}$ | $L_{B21}$ |
| II-1337. | $L_{A40}$ | $L_{B21}$ |
| II-1338. | $L_{A41}$ | $L_{B21}$ |
| II-1339. | $L_{A42}$ | $L_{B21}$ |
| II-1340. | $L_{A43}$ | $L_{B21}$ |
| II-1341. | $L_{A44}$ | $L_{B21}$ |
| II-1342. | $L_{A45}$ | $L_{B21}$ |
| II-1343. | $L_{A46}$ | $L_{B21}$ |
| II-1344. | $L_{A47}$ | $L_{B21}$ |
| II-1345. | $L_{A48}$ | $L_{B21}$ |
| II-1346. | $L_{A49}$ | $L_{B21}$ |
| II-1347. | $L_{A50}$ | $L_{B21}$ |
| II-1348. | $L_{A51}$ | $L_{B21}$ |
| II-1349. | $L_{A52}$ | $L_{B21}$ |

| Compound Number | $L_A$ | $L_B$ |
|---|---|---|
| II-1350. | $L_{A53}$ | $L_{B21}$ |
| II-1351. | $L_{A54}$ | $L_{B21}$ |
| II-1352. | $L_{A55}$ | $L_{B21}$ |
| II-1353. | $L_{A56}$ | $L_{B21}$ |
| II-1354. | $L_{A57}$ | $L_{B21}$ |
| II-1355. | $L_{A58}$ | $L_{B21}$ |
| II-1356. | $L_{A59}$ | $L_{B21}$ |
| II-1357. | $L_{A60}$ | $L_{B21}$ |
| II-1358. | $L_{A61}$ | $L_{B21}$ |
| II-1359. | $L_{A62}$ | $L_{B21}$ |
| II-1360. | $L_{A63}$ | $L_{B21}$ |
| II-1361. | $L_{A64}$ | $L_{B21}$ |
| II-1362. | $L_{A65}$ | $L_{B21}$ |
| II-1363. | $L_{A66}$ | $L_{B21}$ |
| II-1364. | $L_{A67}$ | $L_{B21}$ |
| II-1365. | $L_{A68}$ | $L_{B21}$ |
| II-1366. | $L_{A69}$ | $L_{B21}$ |
| II-1367. | $L_{A2}$ | $L_{B22}$ |
| II-1368. | $L_{A3}$ | $L_{B22}$ |
| II-1369. | $L_{A4}$ | $L_{B22}$ |
| II-1370. | $L_{A5}$ | $L_{B22}$ |
| II-1371. | $L_{A6}$ | $L_{B22}$ |
| II-1372. | $L_{A7}$ | $L_{B22}$ |
| II-1373. | $L_{A8}$ | $L_{B22}$ |
| II-1374. | $L_{A9}$ | $L_{B22}$ |
| II-1375. | $L_{A10}$ | $L_{B22}$ |
| II-1376. | $L_{A11}$ | $L_{B22}$ |
| II-1377. | $L_{A12}$ | $L_{B22}$ |
| II-1378. | $L_{A13}$ | $L_{B22}$ |
| II-1379. | $L_{A14}$ | $L_{B22}$ |
| II-1380. | $L_{A15}$ | $L_{B22}$ |
| II-1381. | $L_{A16}$ | $L_{B22}$ |
| II-1382. | $L_{A17}$ | $L_{B22}$ |
| II-1383. | $L_{A18}$ | $L_{B22}$ |
| II-1384. | $L_{A20}$ | $L_{B22}$ |
| II-1385. | $L_{A21}$ | $L_{B22}$ |
| II-1386. | $L_{A22}$ | $L_{B22}$ |
| II-1387. | $L_{A23}$ | $L_{B22}$ |
| II-1388. | $L_{A24}$ | $L_{B22}$ |
| II-1389. | $L_{A25}$ | $L_{B22}$ |
| II-1390. | $L_{A26}$ | $L_{B22}$ |
| II-1391. | $L_{A27}$ | $L_{B22}$ |
| II-1392. | $L_{A28}$ | $L_{B22}$ |
| II-1393. | $L_{A29}$ | $L_{B22}$ |
| II-1394. | $L_{A30}$ | $L_{B22}$ |
| II-1395. | $L_{A31}$ | $L_{B22}$ |
| II-1396. | $L_{A32}$ | $L_{B22}$ |
| II-1397. | $L_{A33}$ | $L_{B22}$ |
| II-1398. | $L_{A34}$ | $L_{B22}$ |
| II-1399. | $L_{A35}$ | $L_{B22}$ |
| II-1400. | $L_{A36}$ | $L_{B22}$ |
| II-1401. | $L_{A37}$ | $L_{B22}$ |
| II-1402. | $L_{A38}$ | $L_{B22}$ |
| II-1403. | $L_{A39}$ | $L_{B22}$ |
| II-1404. | $L_{A40}$ | $L_{B22}$ |
| II-1405. | $L_{A41}$ | $L_{B22}$ |
| II-1406. | $L_{A42}$ | $L_{B22}$ |
| II-1407. | $L_{A43}$ | $L_{B22}$ |
| II-1408. | $L_{A44}$ | $L_{B22}$ |
| II-1409. | $L_{A45}$ | $L_{B22}$ |
| II-1410. | $L_{A46}$ | $L_{B22}$ |
| II-1411. | $L_{A47}$ | $L_{B22}$ |
| II-1412. | $L_{A48}$ | $L_{B22}$ |
| II-1413. | $L_{A49}$ | $L_{B22}$ |
| II-1414. | $L_{A50}$ | $L_{B22}$ |
| II-1415. | $L_{A51}$ | $L_{B22}$ |
| II-1416. | $L_{A52}$ | $L_{B22}$ |
| II-1417. | $L_{A53}$ | $L_{B22}$ |
| II-1418. | $L_{A54}$ | $L_{B22}$ |
| II-1419. | $L_{A55}$ | $L_{B22}$ |
| II-1420. | $L_{A56}$ | $L_{B22}$ |
| II-1421. | $L_{A57}$ | $L_{B22}$ |
| II-1422. | $L_{A58}$ | $L_{B22}$ |
| II-1423. | $L_{A59}$ | $L_{B22}$ |
| II-1424. | $L_{A60}$ | $L_{B22}$ |
| II-1425. | $L_{A61}$ | $L_{B22}$ |
| II-1426. | $L_{A62}$ | $L_{B22}$ |
| II-1427. | $L_{A63}$ | $L_{B22}$ |
| II-1428. | $L_{A64}$ | $L_{B22}$ |
| II-1429. | $L_{A65}$ | $L_{B22}$ |
| II-1430. | $L_{A66}$ | $L_{B22}$ |
| II-1431. | $L_{A67}$ | $L_{B22}$ |
| II-1432. | $L_{A68}$ | $L_{B22}$ |
| II-1433. | $L_{A69}$ | $L_{B22}$ |
| II-1434. | $L_{A1}$ | $L_{B23}$ |
| II-1435. | $L_{A2}$ | $L_{B23}$ |
| II-1436. | $L_{A3}$ | $L_{B23}$ |
| II-1437. | $L_{A4}$ | $L_{B23}$ |
| II-1438. | $L_{A5}$ | $L_{B23}$ |
| II-1439. | $L_{A6}$ | $L_{B23}$ |
| II-1440. | $L_{A7}$ | $L_{B23}$ |
| II-1441. | $L_{A8}$ | $L_{B23}$ |
| II-1442. | $L_{A9}$ | $L_{B23}$ |
| II-1443. | $L_{A10}$ | $L_{B23}$ |
| II-1444. | $L_{A11}$ | $L_{B23}$ |
| II-1445. | $L_{A12}$ | $L_{B23}$ |
| II-1446. | $L_{A13}$ | $L_{B23}$ |
| II-1447. | $L_{A14}$ | $L_{B23}$ |
| II-1448. | $L_{A15}$ | $L_{B23}$ |
| II-1449. | $L_{A16}$ | $L_{B23}$ |
| II-1450. | $L_{A17}$ | $L_{B23}$ |
| II-1451. | $L_{A18}$ | $L_{B23}$ |
| II-1452. | $L_{A19}$ | $L_{B23}$ |
| II-1453. | $L_{A20}$ | $L_{B23}$ |
| II-1454. | $L_{A21}$ | $L_{B23}$ |
| II-1455. | $L_{A22}$ | $L_{B23}$ |
| II-1456. | $L_{A23}$ | $L_{B23}$ |
| II-1457. | $L_{A24}$ | $L_{B23}$ |
| II-1458. | $L_{A25}$ | $L_{B23}$ |
| II-1459. | $L_{A26}$ | $L_{B23}$ |
| II-1460. | $L_{A27}$ | $L_{B23}$ |
| II-1461. | $L_{A28}$ | $L_{B23}$ |
| II-1462. | $L_{A29}$ | $L_{B23}$ |
| II-1463. | $L_{A30}$ | $L_{B23}$ |
| II-1464. | $L_{A31}$ | $L_{B23}$ |
| II-1465. | $L_{A32}$ | $L_{B23}$ |
| II-1466. | $L_{A33}$ | $L_{B23}$ |
| II-1467. | $L_{A34}$ | $L_{B23}$ |
| II-1468. | $L_{A35}$ | $L_{B23}$ |
| II-1469. | $L_{A36}$ | $L_{B23}$ |
| II-1470. | $L_{A37}$ | $L_{B23}$ |
| II-1471. | $L_{A38}$ | $L_{B23}$ |
| II-1472. | $L_{A39}$ | $L_{B23}$ |
| II-1473. | $L_{A40}$ | $L_{B23}$ |
| II-1474. | $L_{A41}$ | $L_{B23}$ |
| II-1475. | $L_{A42}$ | $L_{B23}$ |
| II-1476. | $L_{A43}$ | $L_{B23}$ |
| II-1477. | $L_{A44}$ | $L_{B23}$ |
| II-1478. | $L_{A45}$ | $L_{B23}$ |
| II-1479. | $L_{A46}$ | $L_{B23}$ |
| II-1480. | $L_{A47}$ | $L_{B23}$ |
| II-1481. | $L_{A48}$ | $L_{B23}$ |
| II-1482. | $L_{A49}$ | $L_{B23}$ |
| II-1483. | $L_{A50}$ | $L_{B23}$ |
| II-1484. | $L_{A51}$ | $L_{B23}$ |
| II-1485. | $L_{A52}$ | $L_{B23}$ |
| II-1486. | $L_{A53}$ | $L_{B23}$ |
| II-1487. | $L_{A54}$ | $L_{B23}$ |
| II-1488. | $L_{A55}$ | $L_{B23}$ |
| II-1489. | $L_{A56}$ | $L_{B23}$ |
| II-1490. | $L_{A57}$ | $L_{B23}$ |
| II-1491. | $L_{A58}$ | $L_{B23}$ |
| II-1492. | $L_{A59}$ | $L_{B23}$ |
| II-1493. | $L_{A60}$ | $L_{B23}$ |
| II-1494. | $L_{A61}$ | $L_{B23}$ |
| II-1495. | $L_{A62}$ | $L_{B23}$ |
| II-1496. | $L_{A63}$ | $L_{B23}$ |
| II-1497. | $L_{A64}$ | $L_{B23}$ |
| II-1498. | $L_{A65}$ | $L_{B23}$ |
| II-1499. | $L_{A66}$ | $L_{B23}$ |
| II-1500. | $L_{A67}$ | $L_{B23}$ |
| II-1501. | $L_{A68}$ | $L_{B23}$ |

| Compound Number | $L_A$ | $L_B$ |
|---|---|---|
| II-1502. | $L_{A69}$ | $L_{B23}$ |
| II-1503. | $L_{A1}$ | $L_{B24}$ |
| II-1504. | $L_{A2}$ | $L_{B24}$ |
| II-1505. | $L_{A3}$ | $L_{B24}$ |
| II-1506. | $L_{A4}$ | $L_{B24}$ |
| II-1507. | $L_{A5}$ | $L_{B24}$ |
| II-1508. | $L_{A6}$ | $L_{B24}$ |
| II-1509. | $L_{A7}$ | $L_{B24}$ |
| II-1510. | $L_{A8}$ | $L_{B24}$ |
| II-1511. | $L_{A9}$ | $L_{B24}$ |
| II-1512. | $L_{A10}$ | $L_{B24}$ |
| II-1513. | $L_{A11}$ | $L_{B24}$ |
| II-1514. | $L_{A12}$ | $L_{B24}$ |
| II-1515. | $L_{A13}$ | $L_{B24}$ |
| II-1516. | $L_{A14}$ | $L_{B24}$ |
| II-1517. | $L_{A15}$ | $L_{B24}$ |
| II-1518. | $L_{A16}$ | $L_{B24}$ |
| II-1519. | $L_{A17}$ | $L_{B24}$ |
| II-1520. | $L_{A18}$ | $L_{B24}$ |
| II-1521. | $L_{A19}$ | $L_{B24}$ |
| II-1522. | $L_{A20}$ | $L_{B24}$ |
| II-1523. | $L_{A21}$ | $L_{B24}$ |
| II-1524. | $L_{A22}$ | $L_{B24}$ |
| II-1525. | $L_{A23}$ | $L_{B24}$ |
| II-1526. | $L_{A24}$ | $L_{B24}$ |
| II-1527. | $L_{A25}$ | $L_{B24}$ |
| II-1528. | $L_{A26}$ | $L_{B24}$ |
| II-1529. | $L_{A27}$ | $L_{B24}$ |
| II-1530. | $L_{A28}$ | $L_{B24}$ |
| II-1531. | $L_{A29}$ | $L_{B24}$ |
| II-1532. | $L_{A30}$ | $L_{B24}$ |
| II-1533. | $L_{A31}$ | $L_{B24}$ |
| II-1534. | $L_{A32}$ | $L_{B24}$ |
| II-1535. | $L_{A33}$ | $L_{B24}$ |
| II-1536. | $L_{A34}$ | $L_{B24}$ |
| II-1537. | $L_{A35}$ | $L_{B24}$ |
| II-1538. | $L_{A36}$ | $L_{B24}$ |
| II-1539. | $L_{A37}$ | $L_{B24}$ |
| II-1540. | $L_{A38}$ | $L_{B24}$ |
| II-1541. | $L_{A39}$ | $L_{B24}$ |
| II-1542. | $L_{A40}$ | $L_{B24}$ |
| II-1543. | $L_{A41}$ | $L_{B24}$ |
| II-1544. | $L_{A42}$ | $L_{B24}$ |
| II-1545. | $L_{A43}$ | $L_{B24}$ |
| II-1546. | $L_{A44}$ | $L_{B24}$ |
| II-1547. | $L_{A45}$ | $L_{B24}$ |
| II-1548. | $L_{A46}$ | $L_{B24}$ |
| II-1549. | $L_{A47}$ | $L_{B24}$ |
| II-1550. | $L_{A48}$ | $L_{B24}$ |
| II-1551. | $L_{A49}$ | $L_{B24}$ |
| II-1552. | $L_{A50}$ | $L_{B24}$ |
| II-1553. | $L_{A51}$ | $L_{B24}$ |
| II-1554. | $L_{A52}$ | $L_{B24}$ |
| II-1555. | $L_{A53}$ | $L_{B24}$ |
| II-1556. | $L_{A54}$ | $L_{B24}$ |
| II-1557. | $L_{A55}$ | $L_{B24}$ |
| II-1558. | $L_{A56}$ | $L_{B24}$ |
| II-1559. | $L_{A57}$ | $L_{B24}$ |
| II-1560. | $L_{A58}$ | $L_{B24}$ |
| II-1561. | $L_{A59}$ | $L_{B24}$ |
| II-1562. | $L_{A60}$ | $L_{B24}$ |
| II-1563. | $L_{A61}$ | $L_{B24}$ |
| II-1564. | $L_{A62}$ | $L_{B24}$ |
| II-1565. | $L_{A63}$ | $L_{B24}$ |
| II-1566. | $L_{A64}$ | $L_{B24}$ |
| II-1567. | $L_{A65}$ | $L_{B24}$ |
| II-1568. | $L_{A66}$ | $L_{B24}$ |
| II-1569. | $L_{A67}$ | $L_{B24}$ |
| II-1570. | $L_{A68}$ | $L_{B24}$ |
| II-1571. | $L_{A69}$ | $L_{B24}$ |
| II-1572. | $L_{A1}$ | $L_{B25}$ |
| II-1573. | $L_{A2}$ | $L_{B25}$ |
| II-1574. | $L_{A3}$ | $L_{B25}$ |
| II-1575. | $L_{A4}$ | $L_{B25}$ |
| II-1576. | $L_{A5}$ | $L_{B25}$ |
| II-1577. | $L_{A6}$ | $L_{B25}$ |
| II-1578. | $L_{A7}$ | $L_{B25}$ |
| II-1579. | $L_{A8}$ | $L_{B25}$ |
| II-1580. | $L_{A9}$ | $L_{B25}$ |
| II-1581. | $L_{A10}$ | $L_{B25}$ |
| II-1582. | $L_{A11}$ | $L_{B25}$ |
| II-1583. | $L_{A12}$ | $L_{B25}$ |
| II-1584. | $L_{A13}$ | $L_{B25}$ |
| II-1585. | $L_{A14}$ | $L_{B25}$ |
| II-1586. | $L_{A15}$ | $L_{B25}$ |
| II-1587. | $L_{A16}$ | $L_{B25}$ |
| II-1588. | $L_{A17}$ | $L_{B25}$ |
| II-1589. | $L_{A18}$ | $L_{B25}$ |
| II-1590. | $L_{A19}$ | $L_{B25}$ |
| II-1591. | $L_{A20}$ | $L_{B25}$ |
| II-1592. | $L_{A21}$ | $L_{B25}$ |
| II-1593. | $L_{A22}$ | $L_{B25}$ |
| II-1594. | $L_{A23}$ | $L_{B25}$ |
| II-1595. | $L_{A24}$ | $L_{B25}$ |
| II-1596. | $L_{A25}$ | $L_{B25}$ |
| II-1597. | $L_{A26}$ | $L_{B25}$ |
| II-1598. | $L_{A27}$ | $L_{B25}$ |
| II-1599. | $L_{A28}$ | $L_{B25}$ |
| II-1600. | $L_{A29}$ | $L_{B25}$ |
| II-1601. | $L_{A30}$ | $L_{B25}$ |
| II-1602. | $L_{A31}$ | $L_{B25}$ |
| II-1603. | $L_{A32}$ | $L_{B25}$ |
| II-1604. | $L_{A33}$ | $L_{B25}$ |
| II-1605. | $L_{A34}$ | $L_{B25}$ |
| II-1606. | $L_{A35}$ | $L_{B25}$ |
| II-1607. | $L_{A36}$ | $L_{B25}$ |
| II-1608. | $L_{A37}$ | $L_{B25}$ |
| II-1609. | $L_{A38}$ | $L_{B25}$ |
| II-1610. | $L_{A39}$ | $L_{B25}$ |
| II-1611. | $L_{A40}$ | $L_{B25}$ |
| II-1612. | $L_{A41}$ | $L_{B25}$ |
| II-1613. | $L_{A42}$ | $L_{B25}$ |
| II-1614. | $L_{A43}$ | $L_{B25}$ |
| II-1615. | $L_{A44}$ | $L_{B25}$ |
| II-1616. | $L_{A45}$ | $L_{B25}$ |
| II-1617. | $L_{A46}$ | $L_{B25}$ |
| II-1618. | $L_{A47}$ | $L_{B25}$ |
| II-1619. | $L_{A48}$ | $L_{B25}$ |
| II-1620. | $L_{A49}$ | $L_{B25}$ |
| II-1621. | $L_{A50}$ | $L_{B25}$ |
| II-1622. | $L_{A51}$ | $L_{B25}$ |
| II-1623. | $L_{A52}$ | $L_{B25}$ |
| II-1624. | $L_{A53}$ | $L_{B25}$ |
| II-1625. | $L_{A54}$ | $L_{B25}$ |
| II-1626. | $L_{A55}$ | $L_{B25}$ |
| II-1627. | $L_{A56}$ | $L_{B25}$ |
| II-1628. | $L_{A57}$ | $L_{B25}$ |
| II-1629. | $L_{A58}$ | $L_{B25}$ |
| II-1630. | $L_{A59}$ | $L_{B25}$ |
| II-1631. | $L_{A60}$ | $L_{B25}$ |
| II-1632. | $L_{A61}$ | $L_{B25}$ |
| II-1633. | $L_{A62}$ | $L_{B25}$ |
| II-1634. | $L_{A63}$ | $L_{B25}$ |
| II-1635. | $L_{A64}$ | $L_{B25}$ |
| II-1636. | $L_{A65}$ | $L_{B25}$ |
| II-1637. | $L_{A66}$ | $L_{B25}$ |
| II-1638. | $L_{A67}$ | $L_{B25}$ |
| II-1639. | $L_{A68}$ | $L_{B25}$ |
| II-1640. | $L_{A69}$ | $L_{B25}$ |
| II-1641. | $L_{A1}$ | $L_{B26}$ |
| II-1642. | $L_{A2}$ | $L_{B26}$ |
| II-1643. | $L_{A3}$ | $L_{B26}$ |
| II-1644. | $L_{A4}$ | $L_{B26}$ |
| II-1645. | $L_{A5}$ | $L_{B26}$ |
| II-1646. | $L_{A6}$ | $L_{B26}$ |
| II-1647. | $L_{A7}$ | $L_{B26}$ |
| II-1648. | $L_{A8}$ | $L_{B26}$ |
| II-1649. | $L_{A9}$ | $L_{B26}$ |
| II-1650. | $L_{A10}$ | $L_{B26}$ |
| II-1651. | $L_{A11}$ | $L_{B26}$ |
| II-1652. | $L_{A12}$ | $L_{B26}$ |
| II-1653. | $L_{A13}$ | $L_{B26}$ |

| Compound Number | $L_A$ | $L_B$ |
|---|---|---|
| II-1654. | $L_{A14}$ | $L_{B26}$ |
| II-1655. | $L_{A15}$ | $L_{B26}$ |
| II-1656. | $L_{A16}$ | $L_{B26}$ |
| II-1657. | $L_{A17}$ | $L_{B26}$ |
| II-1658. | $L_{A18}$ | $L_{B26}$ |
| II-1659. | $L_{A19}$ | $L_{B26}$ |
| II-1660. | $L_{A20}$ | $L_{B26}$ |
| II-1661. | $L_{A21}$ | $L_{B26}$ |
| II-1662. | $L_{A22}$ | $L_{B26}$ |
| II-1663. | $L_{A23}$ | $L_{B26}$ |
| II-1664. | $L_{A24}$ | $L_{B26}$ |
| II-1665. | $L_{A25}$ | $L_{B26}$ |
| II-1666. | $L_{A26}$ | $L_{B26}$ |
| II-1667. | $L_{A27}$ | $L_{B26}$ |
| II-1668. | $L_{A28}$ | $L_{B26}$ |
| II-1669. | $L_{A29}$ | $L_{B26}$ |
| II-1670. | $L_{A30}$ | $L_{B26}$ |
| II-1671. | $L_{A31}$ | $L_{B26}$ |
| II-1672. | $L_{A32}$ | $L_{B26}$ |
| II-1673. | $L_{A33}$ | $L_{B26}$ |
| II-1674. | $L_{A34}$ | $L_{B26}$ |
| II-1675. | $L_{A35}$ | $L_{B26}$ |
| II-1676. | $L_{A36}$ | $L_{B26}$ |
| II-1677. | $L_{A37}$ | $L_{B26}$ |
| II-1678. | $L_{A38}$ | $L_{B26}$ |
| II-1679. | $L_{A39}$ | $L_{B26}$ |
| II-1680. | $L_{A40}$ | $L_{B26}$ |
| II-1681. | $L_{A41}$ | $L_{B26}$ |
| II-1682. | $L_{A42}$ | $L_{B26}$ |
| II-1683. | $L_{A43}$ | $L_{B26}$ |
| II-1684. | $L_{A44}$ | $L_{B26}$ |
| II-1685. | $L_{A45}$ | $L_{B26}$ |
| II-1686. | $L_{A46}$ | $L_{B26}$ |
| II-1687. | $L_{A47}$ | $L_{B26}$ |
| II-1688. | $L_{A48}$ | $L_{B26}$ |
| II-1689. | $L_{A49}$ | $L_{B26}$ |
| II-1690. | $L_{A50}$ | $L_{B26}$ |
| II-1691. | $L_{A51}$ | $L_{B26}$ |
| II-1692. | $L_{A52}$ | $L_{B26}$ |
| II-1693. | $L_{A53}$ | $L_{B26}$ |
| II-1694. | $L_{A54}$ | $L_{B26}$ |
| II-1695. | $L_{A55}$ | $L_{B26}$ |
| II-1696. | $L_{A56}$ | $L_{B26}$ |
| II-1697. | $L_{A57}$ | $L_{B26}$ |
| II-1698. | $L_{A58}$ | $L_{B26}$ |
| II-1699. | $L_{A59}$ | $L_{B26}$ |
| II-1700. | $L_{A60}$ | $L_{B26}$ |
| II-1701. | $L_{A61}$ | $L_{B26}$ |
| II-1702. | $L_{A62}$ | $L_{B26}$ |
| II-1703. | $L_{A63}$ | $L_{B26}$ |
| II-1704. | $L_{A64}$ | $L_{B26}$ |
| II-1705. | $L_{A65}$ | $L_{B26}$ |
| II-1706. | $L_{A66}$ | $L_{B26}$ |
| II-1707. | $L_{A67}$ | $L_{B26}$ |
| II-1708. | $L_{A68}$ | $L_{B26}$ |
| II-1709. | $L_{A69}$ | $L_{B26}$ |
| II-1710. | $L_{A1}$ | $L_{B27}$ |
| II-1711. | $L_{A2}$ | $L_{B27}$ |
| II-1712. | $L_{A3}$ | $L_{B27}$ |
| II-1713. | $L_{A4}$ | $L_{B27}$ |
| II-1714. | $L_{A5}$ | $L_{B27}$ |
| II-1715. | $L_{A6}$ | $L_{B27}$ |
| II-1716. | $L_{A7}$ | $L_{B27}$ |
| II-1717. | $L_{A8}$ | $L_{B27}$ |
| II-1718. | $L_{A9}$ | $L_{B27}$ |
| II-1719. | $L_{A10}$ | $L_{B27}$ |
| II-1720. | $L_{A11}$ | $L_{B27}$ |
| II-1721. | $L_{A12}$ | $L_{B27}$ |
| II-1722. | $L_{A13}$ | $L_{B27}$ |
| II-1723. | $L_{A14}$ | $L_{B27}$ |
| II-1724. | $L_{A15}$ | $L_{B27}$ |
| II-1725. | $L_{A16}$ | $L_{B27}$ |
| II-1726. | $L_{A17}$ | $L_{B27}$ |
| II-1727. | $L_{A18}$ | $L_{B27}$ |
| II-1728. | $L_{A19}$ | $L_{B27}$ |
| II-1729. | $L_{A20}$ | $L_{B27}$ |
| II-1730. | $L_{A21}$ | $L_{B27}$ |
| II-1731. | $L_{A22}$ | $L_{B27}$ |
| II-1732. | $L_{A23}$ | $L_{B27}$ |
| II-1733. | $L_{A24}$ | $L_{B27}$ |
| II-1734. | $L_{A25}$ | $L_{B27}$ |
| II-1735. | $L_{A26}$ | $L_{B27}$ |
| II-1736. | $L_{A27}$ | $L_{B27}$ |
| II-1737. | $L_{A28}$ | $L_{B27}$ |
| II-1738. | $L_{A29}$ | $L_{B27}$ |
| II-1739. | $L_{A30}$ | $L_{B27}$ |
| II-1740. | $L_{A31}$ | $L_{B27}$ |
| II-1741. | $L_{A32}$ | $L_{B27}$ |
| II-1742. | $L_{A33}$ | $L_{B27}$ |
| II-1743. | $L_{A34}$ | $L_{B27}$ |
| II-1744. | $L_{A35}$ | $L_{B27}$ |
| II-1745. | $L_{A36}$ | $L_{B27}$ |
| II-1746. | $L_{A37}$ | $L_{B27}$ |
| II-1747. | $L_{A38}$ | $L_{B27}$ |
| II-1748. | $L_{A39}$ | $L_{B27}$ |
| II-1749. | $L_{A40}$ | $L_{B27}$ |
| II-1750. | $L_{A41}$ | $L_{B27}$ |
| II-1751. | $L_{A42}$ | $L_{B27}$ |
| II-1752. | $L_{A43}$ | $L_{B27}$ |
| II-1753. | $L_{A44}$ | $L_{B27}$ |
| II-1754. | $L_{A45}$ | $L_{B27}$ |
| II-1755. | $L_{A46}$ | $L_{B27}$ |
| II-1756. | $L_{A47}$ | $L_{B27}$ |
| II-1757. | $L_{A48}$ | $L_{B27}$ |
| II-1758. | $L_{A49}$ | $L_{B27}$ |
| II-1759. | $L_{A50}$ | $L_{B27}$ |
| II-1760. | $L_{A51}$ | $L_{B27}$ |
| II-1761. | $L_{A52}$ | $L_{B27}$ |
| II-1762. | $L_{A53}$ | $L_{B27}$ |
| II-1763. | $L_{A54}$ | $L_{B27}$ |
| II-1764. | $L_{A55}$ | $L_{B27}$ |
| II-1765. | $L_{A56}$ | $L_{B27}$ |
| II-1766. | $L_{A57}$ | $L_{B27}$ |
| II-1767. | $L_{A58}$ | $L_{B27}$ |
| II-1768. | $L_{A59}$ | $L_{B27}$ |
| II-1769. | $L_{A60}$ | $L_{B27}$ |
| II-1770. | $L_{A61}$ | $L_{B27}$ |
| II-1771. | $L_{A62}$ | $L_{B27}$ |
| II-1772. | $L_{A63}$ | $L_{B27}$ |
| II-1773. | $L_{A64}$ | $L_{B27}$ |
| II-1774. | $L_{A65}$ | $L_{B27}$ |
| II-1775. | $L_{A66}$ | $L_{B27}$ |
| II-1776. | $L_{A67}$ | $L_{B27}$ |
| II-1777. | $L_{A68}$ | $L_{B27}$ |
| II-1778. | $L_{A69}$ | $L_{B27}$ |
| II-1779. | $L_{A1}$ | $L_{B28}$ |
| II-1780. | $L_{A2}$ | $L_{B28}$ |
| II-1781. | $L_{A3}$ | $L_{B28}$ |
| II-1782. | $L_{A4}$ | $L_{B28}$ |
| II-1783. | $L_{A5}$ | $L_{B28}$ |
| II-1784. | $L_{A6}$ | $L_{B28}$ |
| II-1785. | $L_{A7}$ | $L_{B28}$ |
| II-1786. | $L_{A8}$ | $L_{B28}$ |
| II-1787. | $L_{A9}$ | $L_{B28}$ |
| II-1788. | $L_{A10}$ | $L_{B28}$ |
| II-1789. | $L_{A11}$ | $L_{B28}$ |
| II-1790. | $L_{A12}$ | $L_{B28}$ |
| II-1791. | $L_{A13}$ | $L_{B28}$ |
| II-1792. | $L_{A14}$ | $L_{B28}$ |
| II-1793. | $L_{A15}$ | $L_{B28}$ |
| II-1794. | $L_{A16}$ | $L_{B28}$ |
| II-1795. | $L_{A17}$ | $L_{B28}$ |
| II-1796. | $L_{A18}$ | $L_{B28}$ |
| II-1797. | $L_{A19}$ | $L_{B28}$ |
| II-1798. | $L_{A20}$ | $L_{B28}$ |
| II-1799. | $L_{A21}$ | $L_{B28}$ |
| II-1800. | $L_{A22}$ | $L_{B28}$ |
| II-1801. | $L_{A23}$ | $L_{B28}$ |
| II-1802. | $L_{A24}$ | $L_{B28}$ |
| II-1803. | $L_{A25}$ | $L_{B28}$ |
| II-1804. | $L_{A26}$ | $L_{B28}$ |
| II-1805. | $L_{A27}$ | $L_{B28}$ |

-continued

| Compound Number | $L_A$ | $L_B$ |
|---|---|---|
| II-1806. | $L_{A28}$ | $L_{B28}$ |
| II-1807. | $L_{A29}$ | $L_{B28}$ |
| II-1808. | $L_{A30}$ | $L_{B28}$ |
| II-1809. | $L_{A31}$ | $L_{B28}$ |
| II-1810. | $L_{A32}$ | $L_{B28}$ |
| II-1811. | $L_{A33}$ | $L_{B28}$ |
| II-1812. | $L_{A34}$ | $L_{B28}$ |
| II-1813. | $L_{A35}$ | $L_{B28}$ |
| II-1814. | $L_{A36}$ | $L_{B28}$ |
| II-1815. | $L_{A37}$ | $L_{B28}$ |
| II-1816. | $L_{A38}$ | $L_{B28}$ |
| II-1817. | $L_{A39}$ | $L_{B28}$ |
| II-1818. | $L_{A40}$ | $L_{B28}$ |
| II-1819. | $L_{A41}$ | $L_{B28}$ |
| II-1820. | $L_{A42}$ | $L_{B28}$ |
| II-1821. | $L_{A43}$ | $L_{B28}$ |
| II-1822. | $L_{A44}$ | $L_{B28}$ |
| II-1823. | $L_{A45}$ | $L_{B28}$ |
| II-1824. | $L_{A46}$ | $L_{B28}$ |
| II-1825. | $L_{A47}$ | $L_{B28}$ |
| II-1826. | $L_{A48}$ | $L_{B28}$ |
| II-1827. | $L_{A49}$ | $L_{B28}$ |
| II-1828. | $L_{A50}$ | $L_{B28}$ |
| II-1829. | $L_{A51}$ | $L_{B28}$ |
| II-1830. | $L_{A52}$ | $L_{B28}$ |
| II-1831. | $L_{A53}$ | $L_{B28}$ |
| II-1832. | $L_{A54}$ | $L_{B28}$ |
| II-1833. | $L_{A55}$ | $L_{B28}$ |
| II-1834. | $L_{A56}$ | $L_{B28}$ |
| II-1835. | $L_{A57}$ | $L_{B28}$ |
| II-1836. | $L_{A58}$ | $L_{B28}$ |
| II-1837. | $L_{A59}$ | $L_{B28}$ |
| II-1838. | $L_{A60}$ | $L_{B28}$ |
| II-1839. | $L_{A61}$ | $L_{B28}$ |
| II-1840. | $L_{A62}$ | $L_{B28}$ |
| II-1841. | $L_{A63}$ | $L_{B28}$ |
| II-1842. | $L_{A64}$ | $L_{B28}$ |
| II-1843. | $L_{A65}$ | $L_{B28}$ |
| II-1844. | $L_{A66}$ | $L_{B28}$ |
| II-1845. | $L_{A67}$ | $L_{B28}$ |
| II-1846. | $L_{A68}$ | $L_{B28}$ |
| II-1847. | $L_{A69}$ | $L_{B28}$ |

In one preferred embodiment, the heteroleptic iridium complex is selected from the group of compounds that have one ore more deuterated ligands. The group consists of Compound II-11 through Compound II-43, Compound II-64 through Compound II-96, Compound II-130 through Compound II-163, Compound II-197 through Compound II-230, Compound II-263 through Compound II-296, Compound II-330 through Compound II-363, Compound II-397 through Compound II-430, Compound II-464 through Compound II-1031, Compound II-1065 through Compound II-1098, Compound II-1132 through Compound II-1165, Compound II-1199 through Compound II-1232, Compound II-1266 through Compound II-1299, Compound II-1333 through Compound II-1366, Compound II-1400 through Compound II-1846, and Compound II-1847.

In one aspect, a first device is provided. The first device comprises a first organic light emitting device, and contains an anode, a cathode, and an organic layer, disposed between the anode and the cathode. The organic layer comprises a heteroleptic iridium complex having the formula $IrL_A(L_B)_2$, wherein $L_A$ is selected from the group consisting of the ligands $L_{A1}$ through $L_{A69}$ defined herein, $L_B$ is selected from the group consisting of the ligands $L_{B1}$ through $L_{B28}$, and the heteroleptic iridium complex is selected from the group consisting of Compound II-1 through Compound II-1846, and Compound II-1847 as defined herein.

In one preferred embodiment, the heteroleptic iridium complex in the organic layer of the first device is selected from the group of compounds having one or more deuterated ligands. Such group consists of Compound II-11 through Compound II-43, Compound II-64 through Compound II-96, Compound II-130 through Compound II-163, Compound II-197 through Compound II-230, Compound II-263 through Compound II-296, Compound II-330 through Compound II-363, Compound II-397 through Compound II-430, Compound II-464 through Compound II-1031, Compound II-1065 through Compound II-1098, Compound II-1132 through Compound II-1165, Compound II-1199 through Compound II-1232, Compound II-1266 through Compound II-1299, Compound II-1333 through Compound II-1366, Compound II-1400 through Compound II-1846, and Compound II-1847, as defined herein.

In one aspect, the organic layer is an emissive layer and the compound is an emissive dopant. In another aspect, the organic layer is an emissive layer and the compound is an non-emissive dopant.

In another aspect, the organic layer further comprises a host. In one aspect, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1$-$Ar_2$, $C_nH_{2n}$-$Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10. In one aspect, the host has the formula:

Compound H

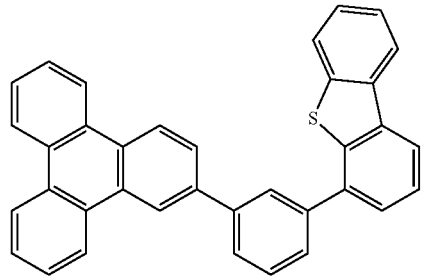

In one aspect, the host is a metal complex.

In one aspect, the first device is a consumer product. In another aspect, the first device is an organic light-emitting device. In another aspect, the first device comprises a lighting panel.

In one aspect, the first device further comprises a second emissive dopant having a peak wavelength of between 400 to 500 nanometers. In one aspect, the second emissive dopant is a fluorescent emitter. In another aspect, the second emissive dopant is a phosphorescent emitter.

In one aspect, the first device further comprises a first organic light-emitting device comprising a compound of Formula I and a second light emitting device separate from the first organic light-emitting device comprising an emissive dopant having a peak wavelength of between 400 to 500 nanometers. In another aspect, the first device comprises an organic-light emitting device having a first emissive layer comprising a compound of Formula I and a second emissive layer comprising an emissive dopant having a peak wavelength of between 400 to 500 nanometers.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-1") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
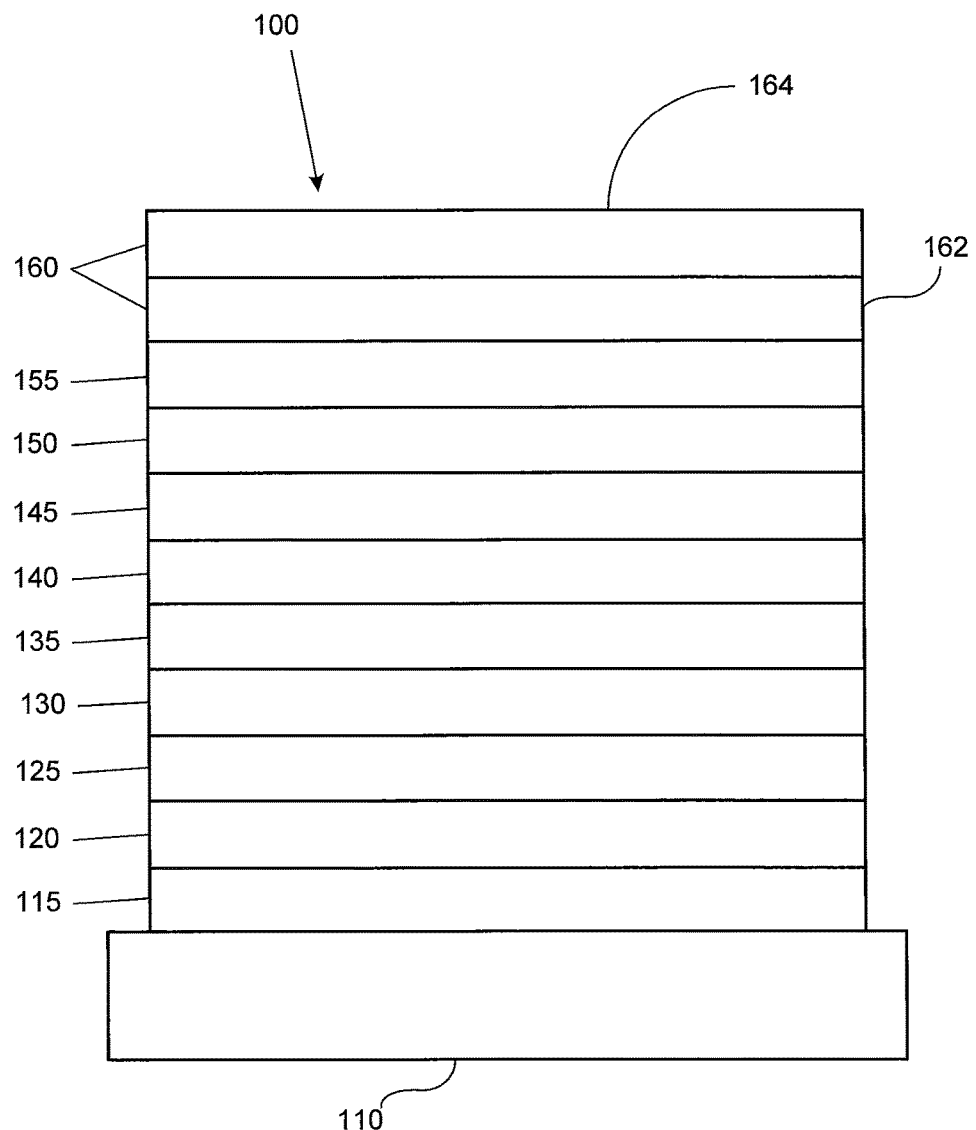
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
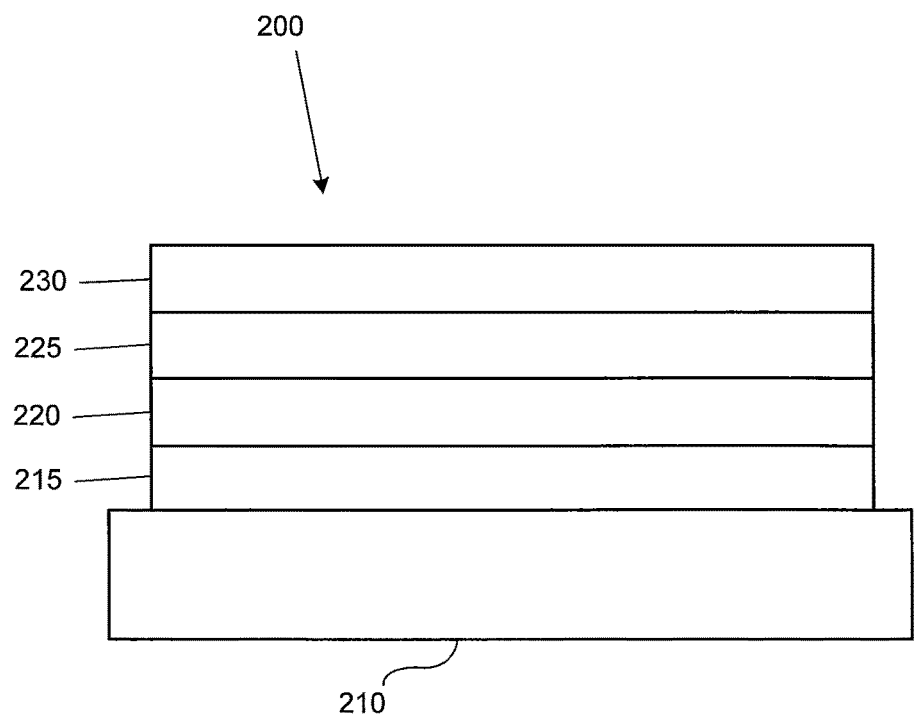
FIG. 2 shows an inverted organic light emitting device that does not have a separate electron transport layer.
Figure 3:
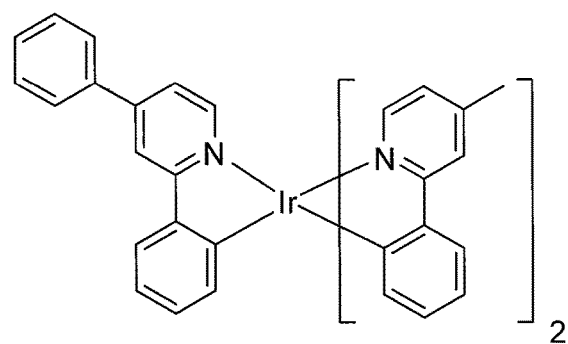
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

A compound comprising a heteroleptic iridium complex is provided. In one embodiment, the compound is a compound of Formula I.

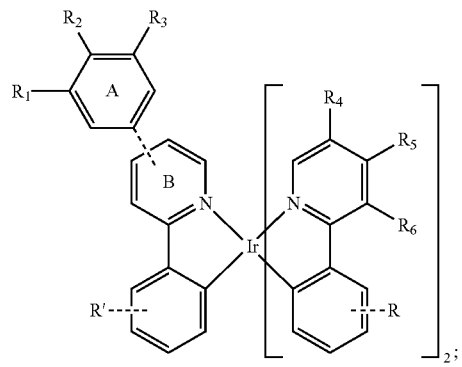

Formula I

In the compound of Formula I, $R_1$, $R_2$, $R_3$, $R_4$, $R_5$, and $R_6$, are independently selected from the group consisting of hydrogen, deuterium, cycloalkyl, deuterated cycloalkyl, alkyl, and deuterated alkyl. At least one of $R_1$, $R_2$, $R_3$, $R_4$, $R_5$, and $R_6$ is cycloalkyl, deuterated cycloalkyl, alkyl or deuterated alkyl, and any two adjacent $R_1$, $R_2$, $R_3$, $R_4$, $R_5$, and $R_6$ are optionally linked together to form a ring. Thus, any of $R_1$ and $R_2$, $R_2$ and $R_3$, $R_3$ and $R_4$, $R_4$ and $R_5$, or $R_5$ and $R_6$ can be linked to form a ring. Ring A is attached to the 4- or 5-position of ring B. R and R' represent mono-, di-, tri- or tetra-substitution and are independently selected from the group consisting of: hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

Ring B is numbered according to the following scheme:

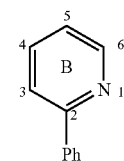

Thus, the 4-position is para to the pyridine nitrogen in ring B, and the 5-position is para to the phenyl ring attached to ring B.

In one embodiment, the compound is a compound of Formula II.

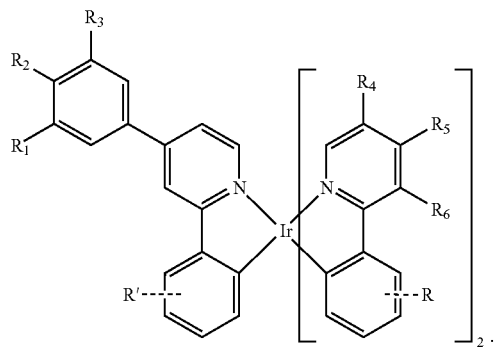

Formula II

In another embodiment, the compound is a compound of Formula III.

Formula III

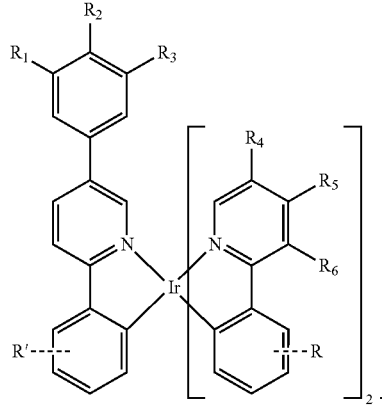

In one embodiment, $R_1$ is alkyl. In one embodiment, $R_2$ is alkyl. In one embodiment, $R_3$ is alkyl. In one embodiment, $R_4$ is alkyl. In one embodiment, $R_5$ is alkyl. In one embodiment, $R_6$ is alkyl. In one embodiment, at least one of $R_1$, $R_2$, and $R_3$ is alkyl. In one embodiment, at least one of $R_4$, $R_5$, and $R_6$ is alkyl. In another embodiment, at least one of $R_1$, $R_2$, and $R_3$ is alkyl and at least one of $R_4$, $R_5$, and $R_6$ is alkyl. In any of the foregoing embodiments, the alkyl may be replaced with a partially or fully deuterated alkyl.

In one embodiment, the alkyl contains at least 2 carbons, at least 3 carbons, or at most 6 carbons. Having at least 2 carbons, at least 3 carbons, or at most 6 carbons allows the compounds of Formula I to efficiently emit in the yellow portion of the spectrum, without increasing the sublimation temperature of the compounds. Increased sublimation temperatures can make it difficult to purify compounds. In another embodiment, the alkyl contains greater than 10 carbons. Having an alkyl with greater than 10 carbons is useful in the solution processing of compounds of Formula I, which leads to inexpensive manufacture of OLED devices.

In one embodiment, the compound emits yellow light with a full width at half maximum between about 70 nm to about 110 nm when the light has a peak wavelength between about 530 nm to about 580 nm. When compounds of Formula I have the above range of full width at half maximum (FWHM) with the accompanying range of peak wavelengths, they are efficient yellow emitters with broad line shapes, which is desirable in white light applications.

Specific non-limiting compounds are provided. In one embodiment, the compound is selected from the group consisting of:

Compound 1

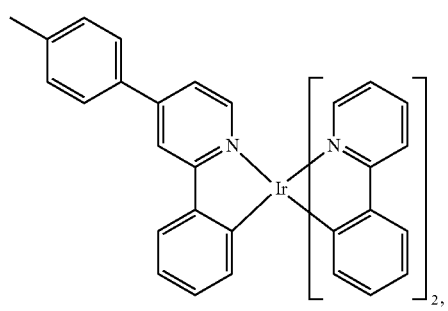

Compound 2

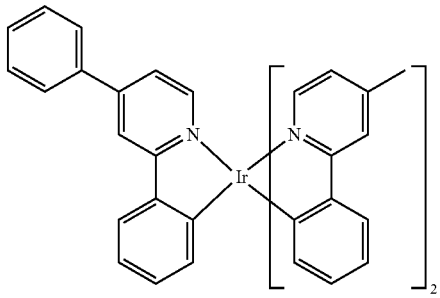

Compound 3

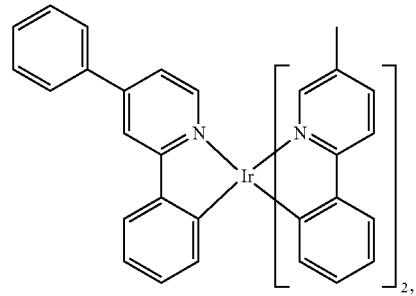

Compound 4

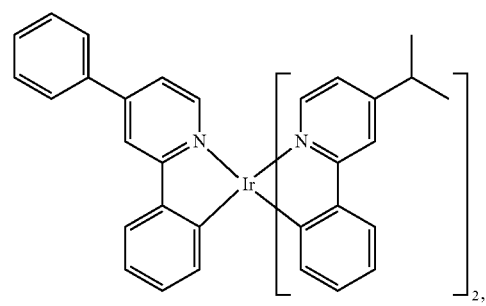

Compound 5

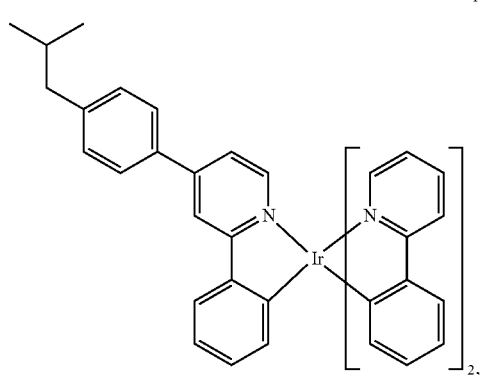

Compound 6

Compound 7
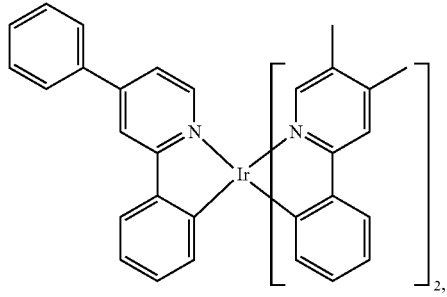
Compound 8
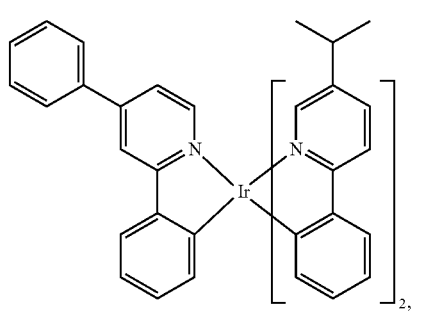
Compound 9
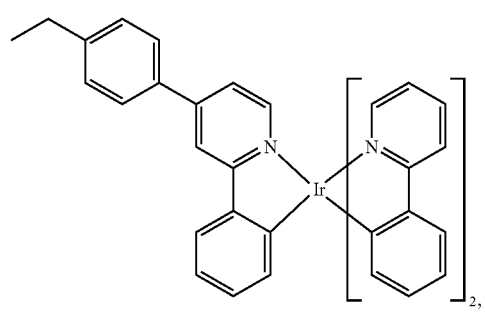
Compound 10
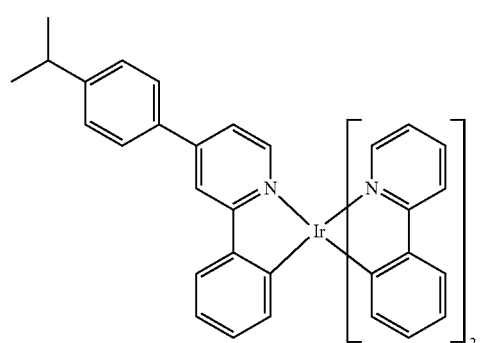
Compound 11
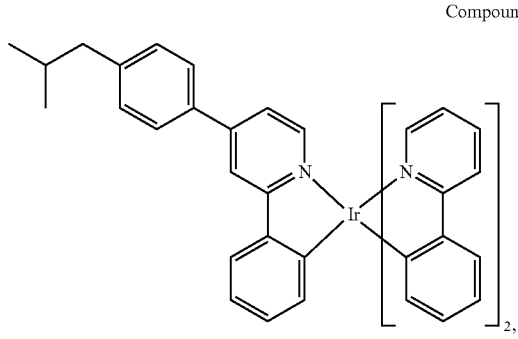
Compound 12
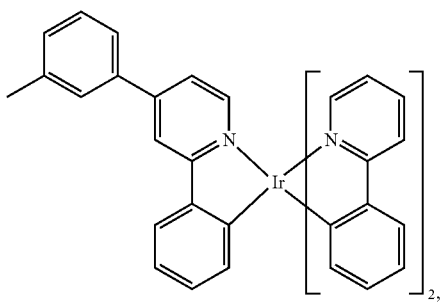
Compound 13
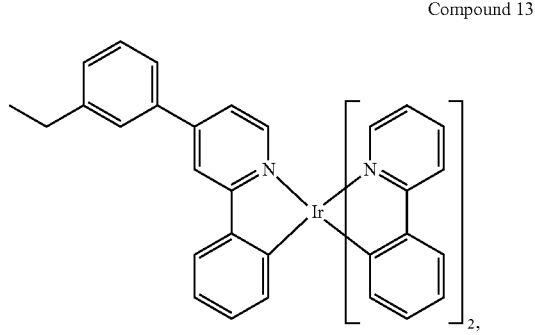
Compound 14
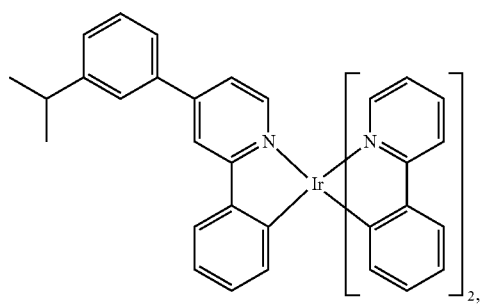
Compound 15
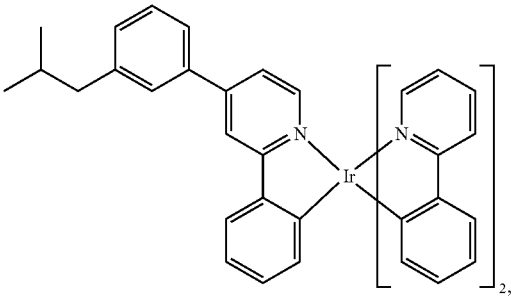

Compound 16
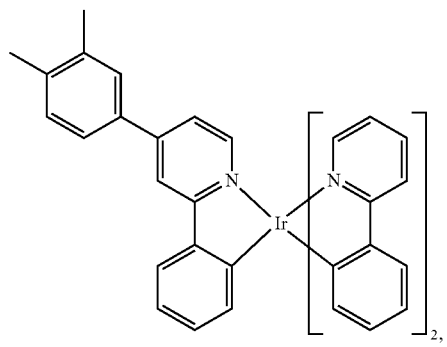
Compound 17
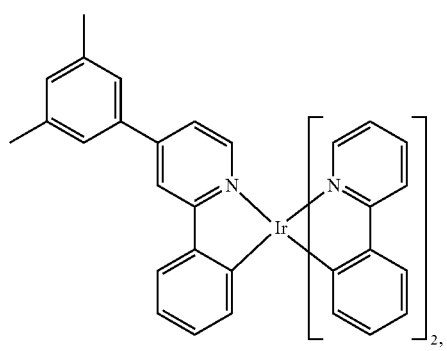
Compound 18
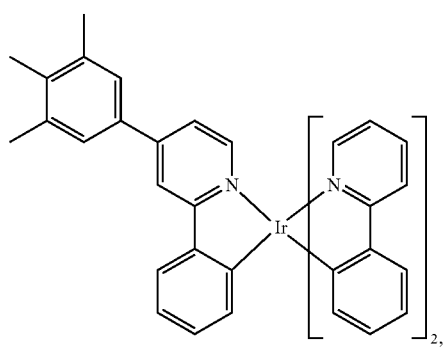
Compound 19
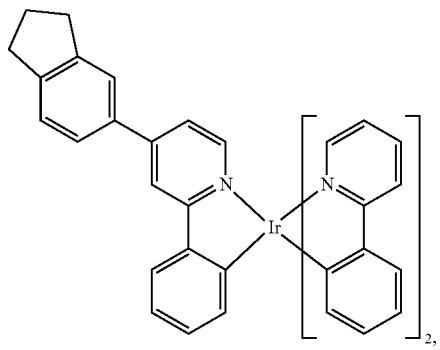
Compound 20
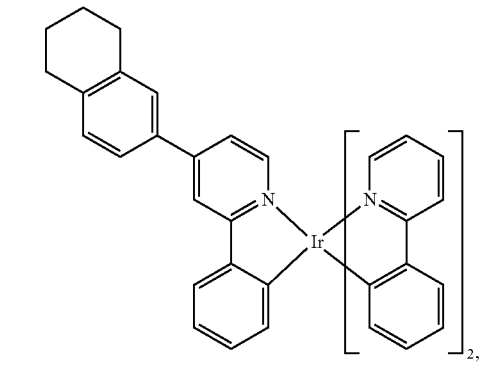
Compound 21
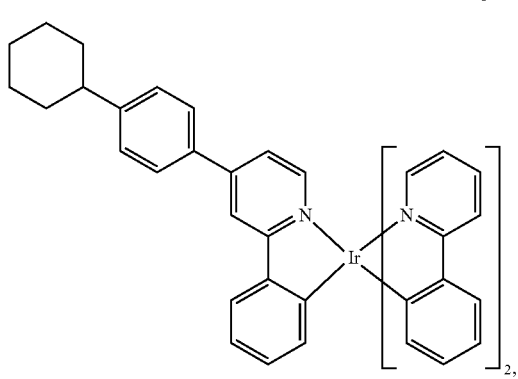
Compound 22
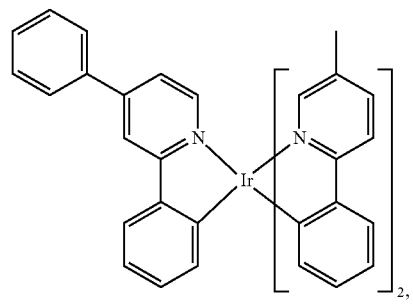
Compound 23
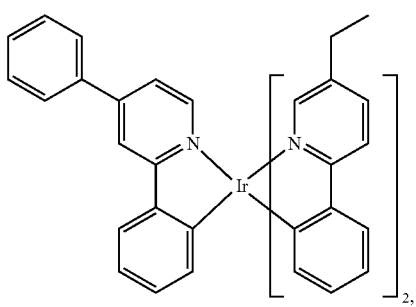

-continued
Compound 24
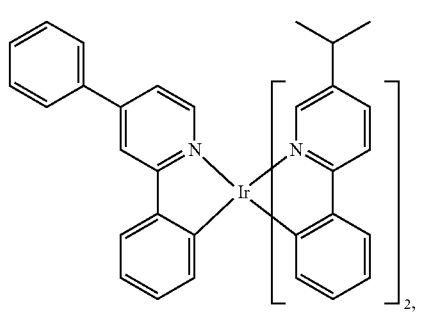
Compound 25
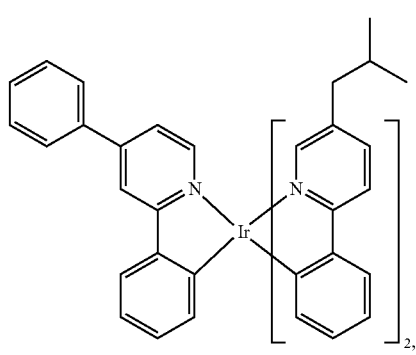
Compound 26
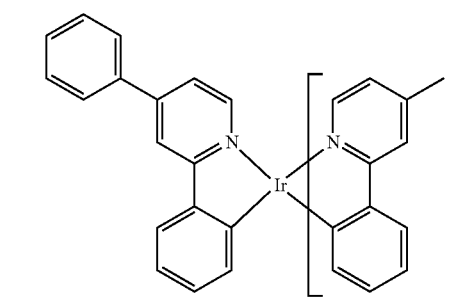
Compound 27
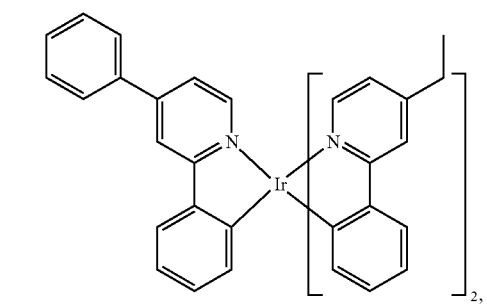
Compound 28
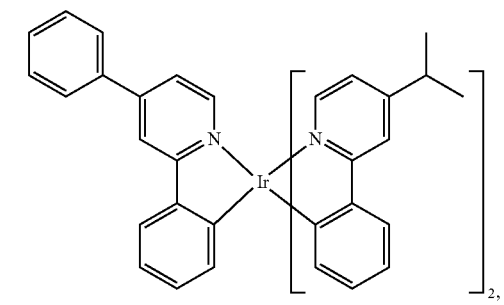
-continued
Compound 29
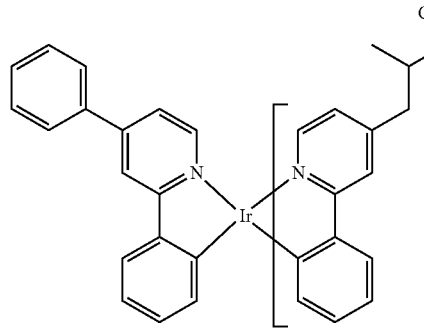
Compound 30
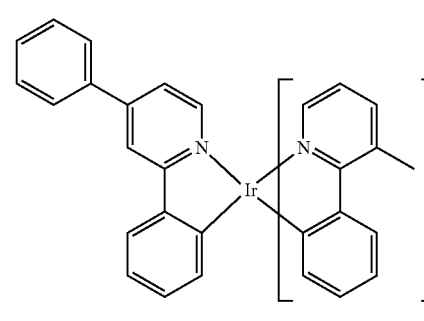
Compound 31
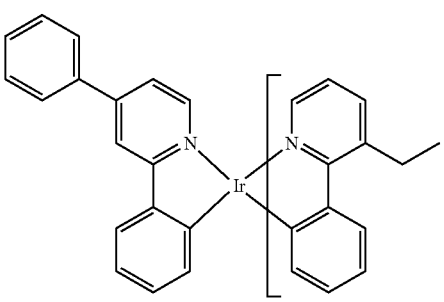
Compound 32
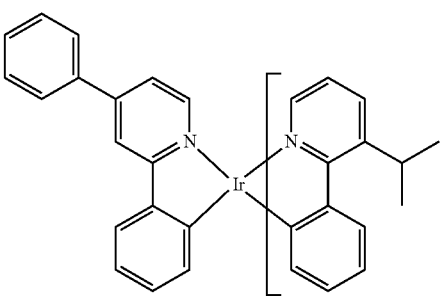
Compound 33
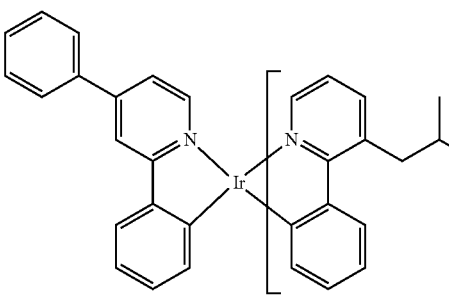

Compound 34
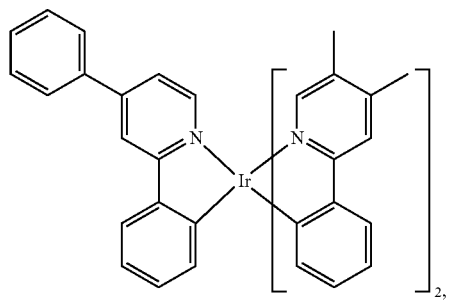
Compound 35
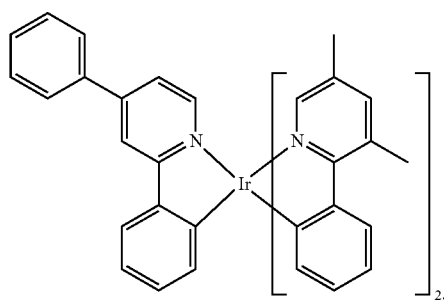
Compound 36
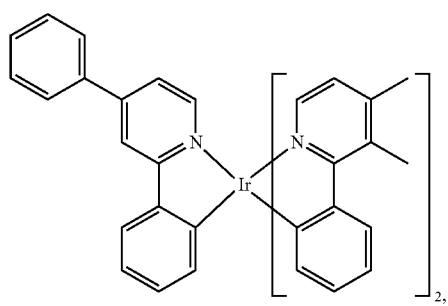
Compound 37
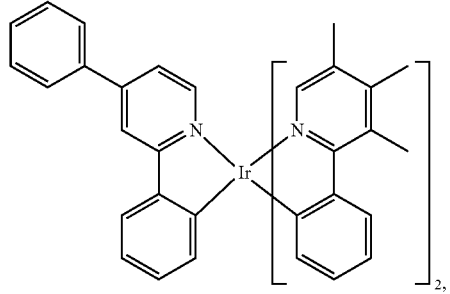
Compound 38
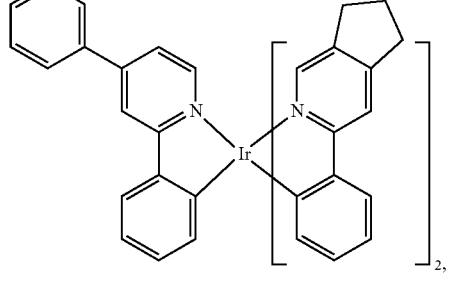
Compound 39
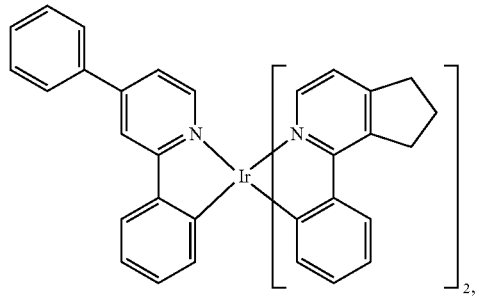
Compound 40
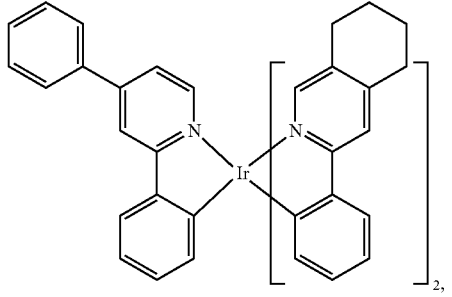
Compound 41
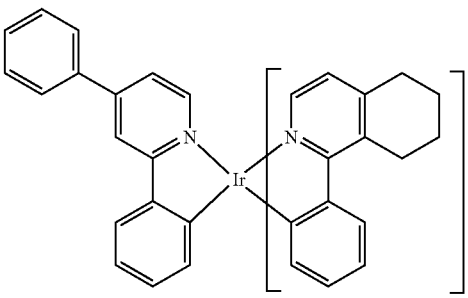
Compound 42
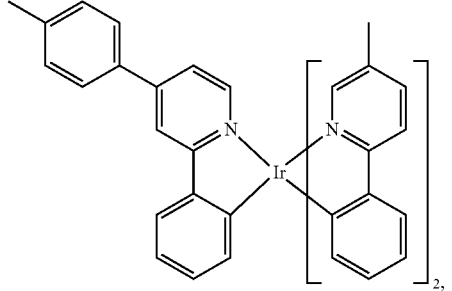
Compound 43
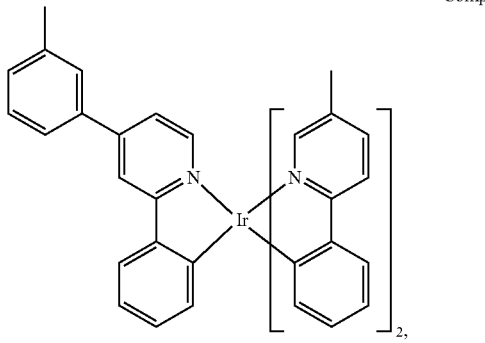

Compound 44
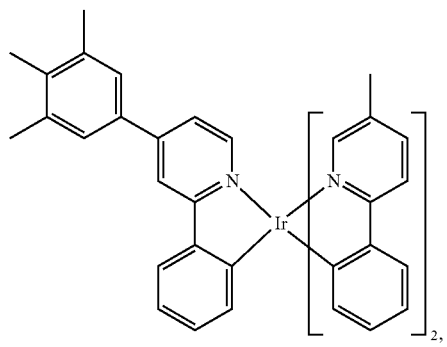
Compound 45
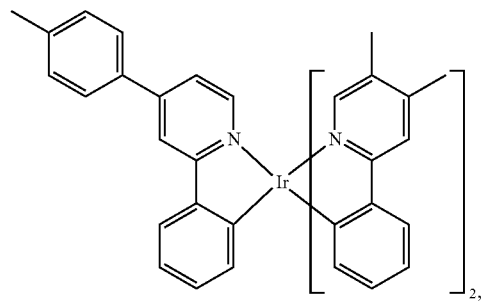
Compound 46
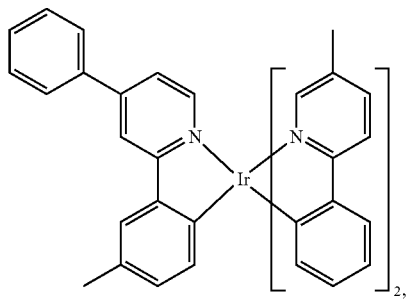
Compound 47
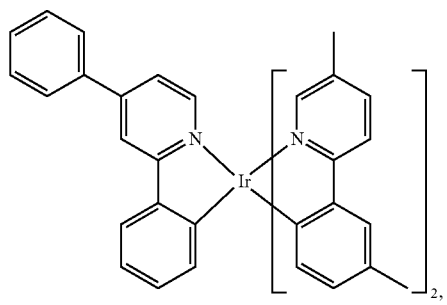
Compound 48
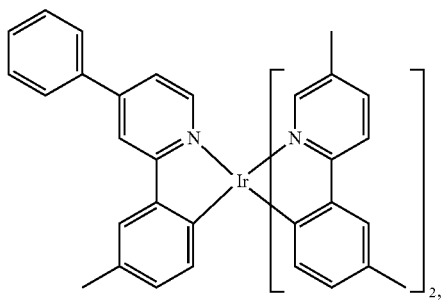
Compound 49
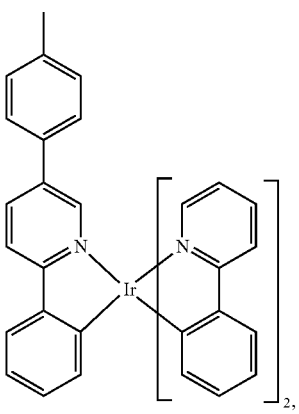
Compound 50
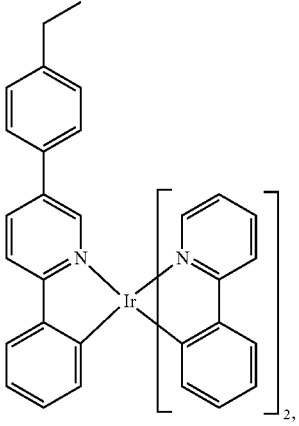
Compound 51
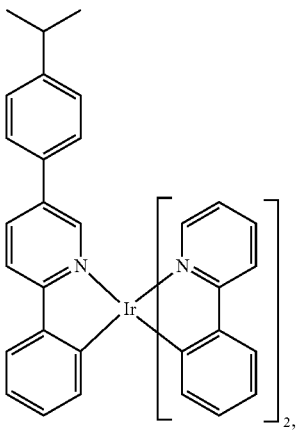

Compound 52
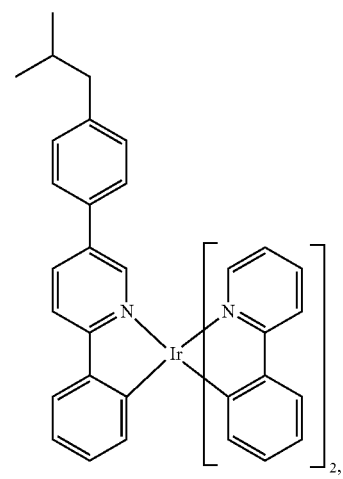
Compound 53
Compound 54
Compound 55
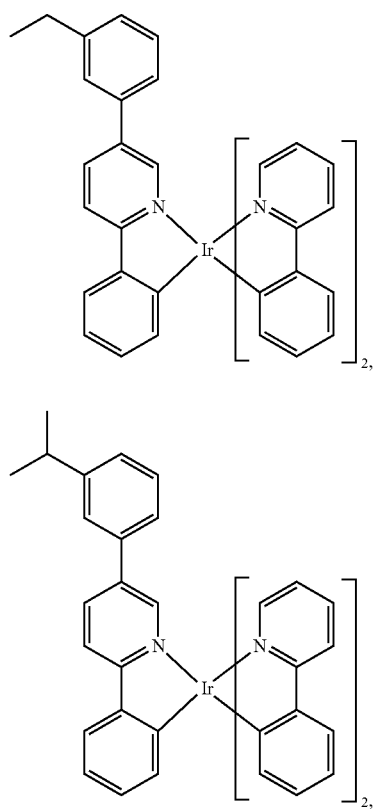
Compound 56
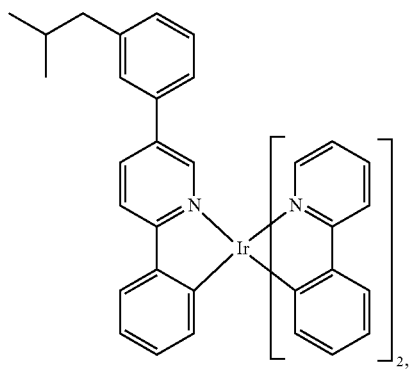
Compound 57
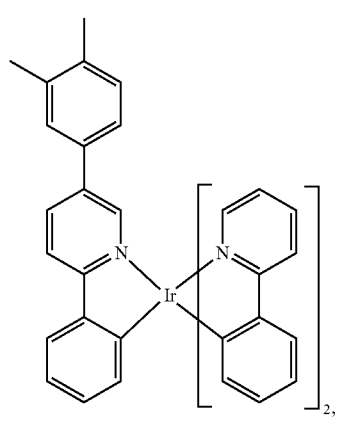
Compound 58
Compound 59

Compound 60
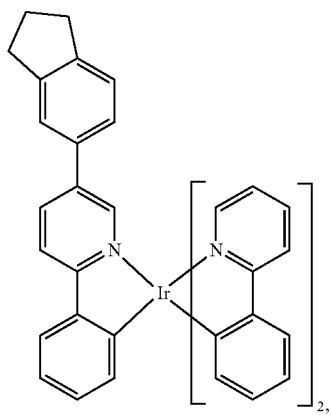
Compound 61
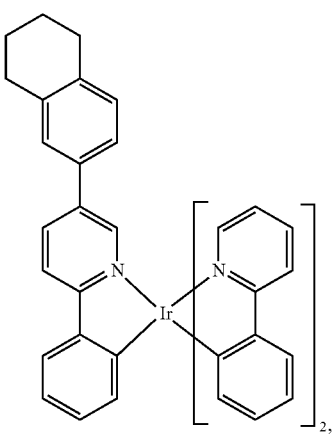
Compound 62
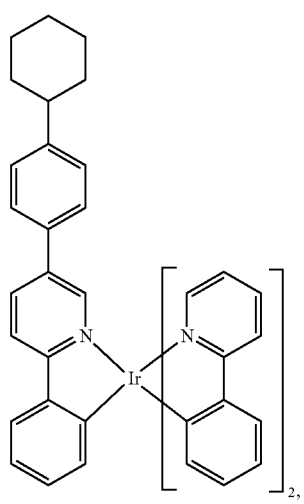
Compound 63
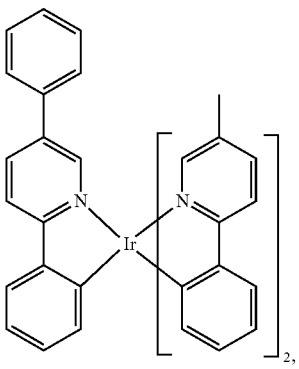
Compound 64
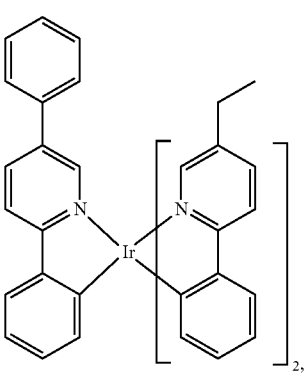
Compound 65
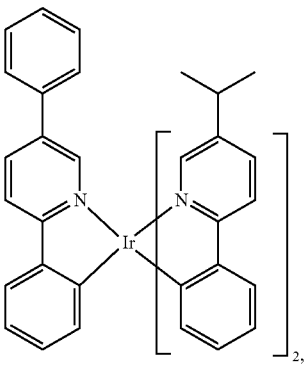
Compound 66
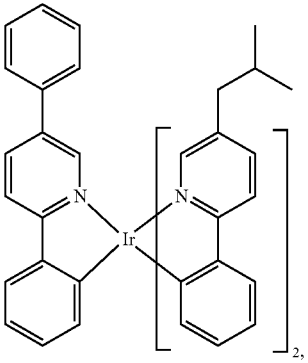

Compound 67
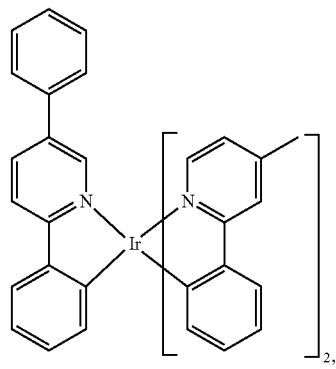
Compound 68
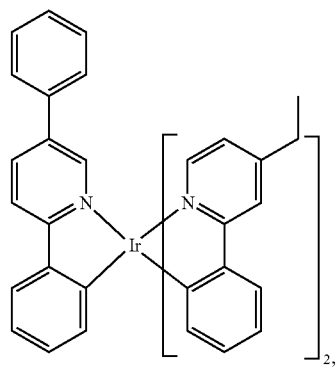
Compound 69
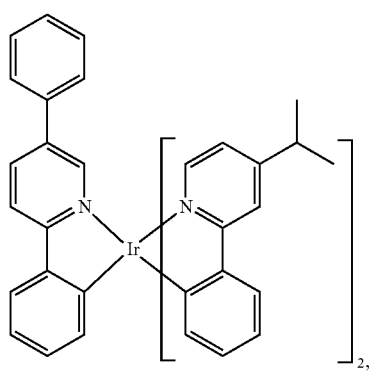
Compound 70
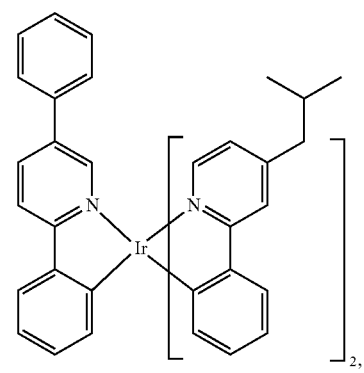
Compound 71
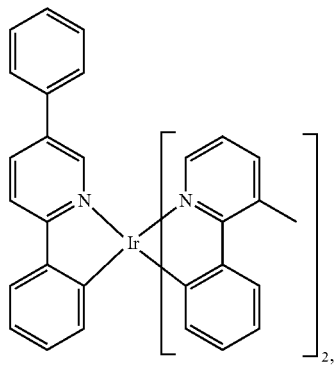
Compound 72
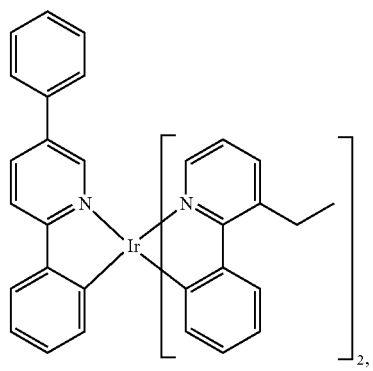
Compound 73
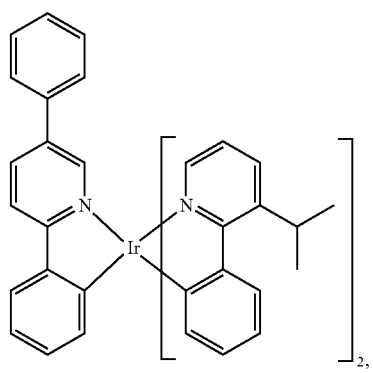
Compound 74
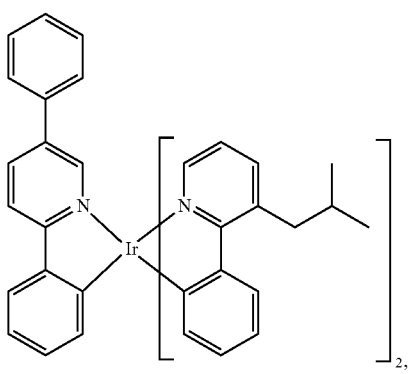

Compound 75
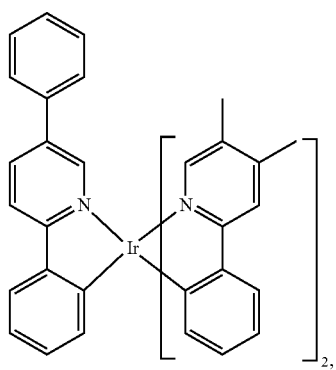
Compound 76
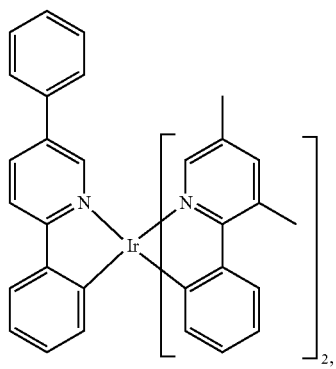
Compound 77
Compound 78
Compound 79
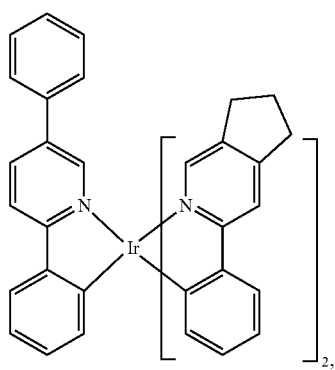
Compound 80
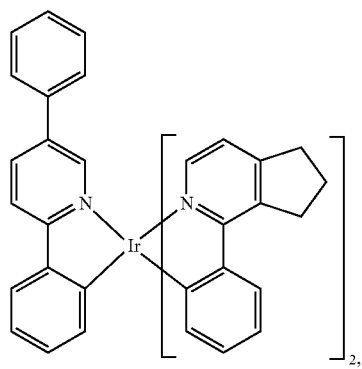
Compound 81
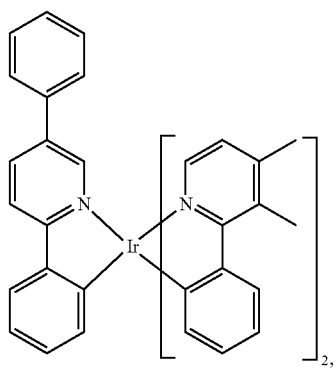
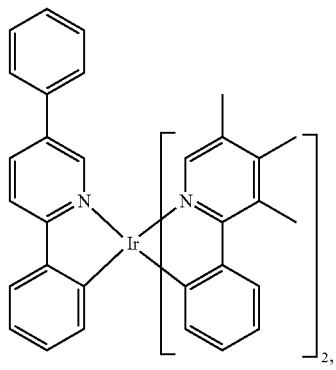
Compound 82
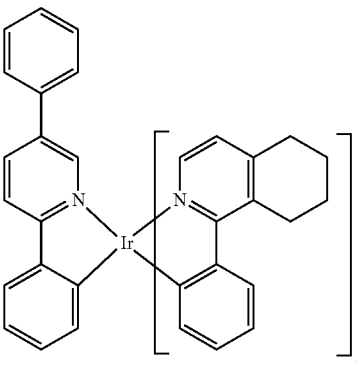

-continued
Compound 83
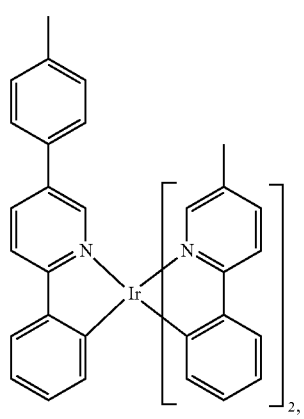
Compound 84
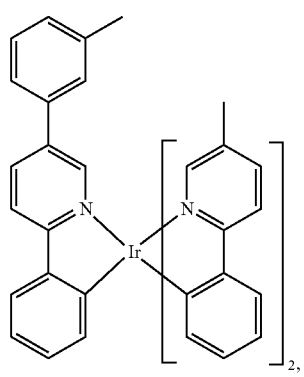
Compound 85
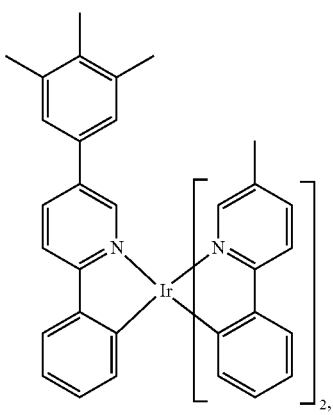
Compound 86
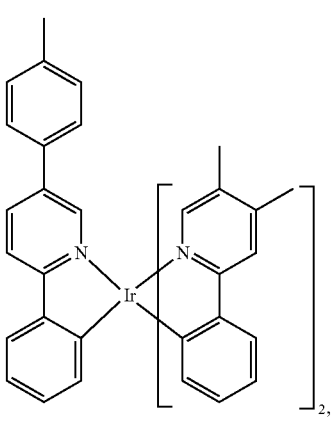
-continued
Compound 87
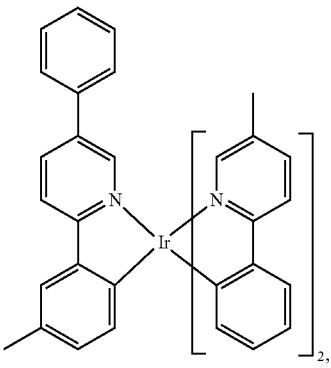
Compound 88
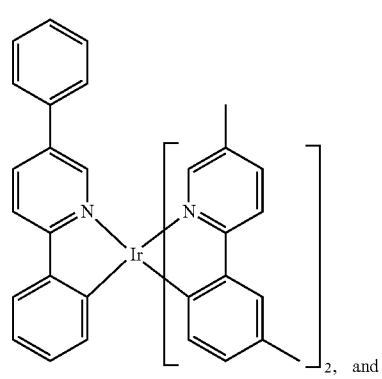, and
Compound 89
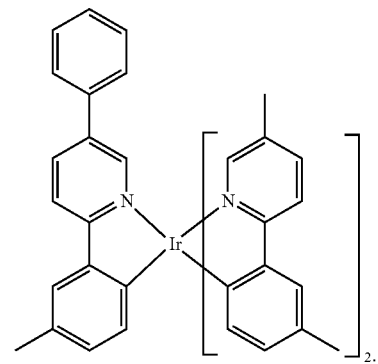.
In one aspect, the compound comprising a heteroleptic iridium complex has the formula $IrL_A(L_B)_2$, wherein $L_A$ is selected from the group consisting of
$L_{A1}$
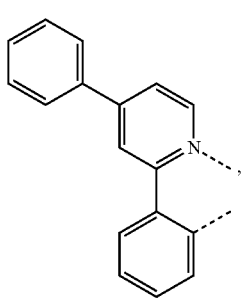

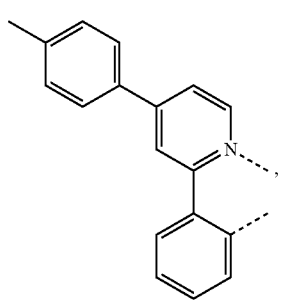 L_{A2}
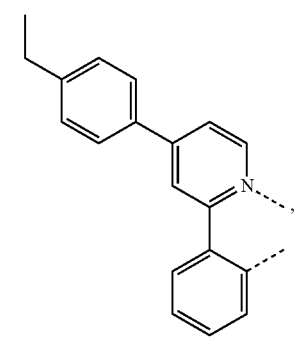 L_{A3}
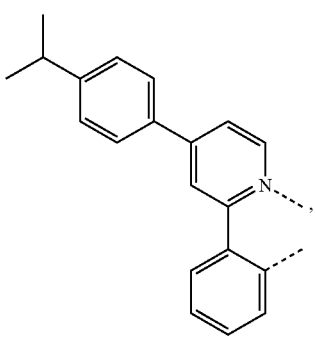 L_{A4}
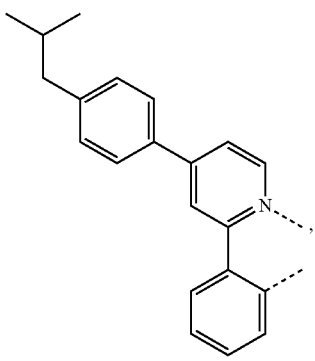 L_{A5}
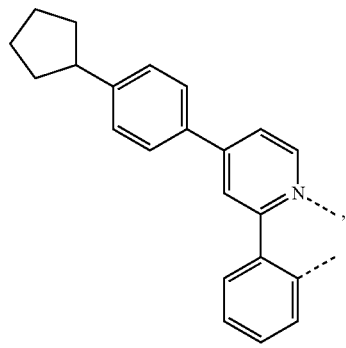 L_{A6}
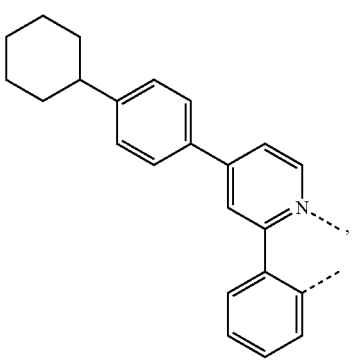 L_{A7}
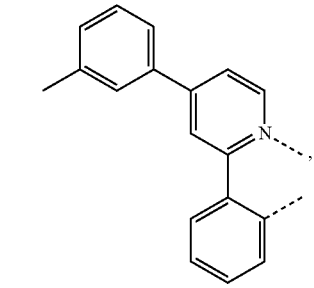 L_{A8}
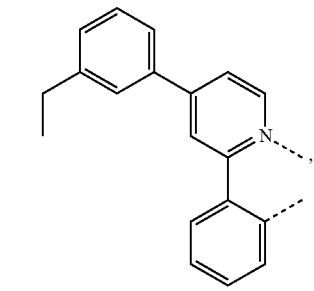 L_{A9}
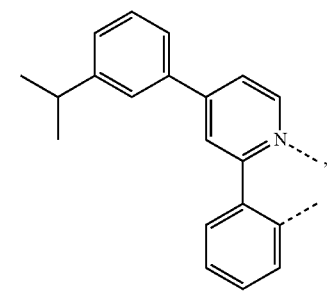 L_{A10}

L<sub>A11</sub>
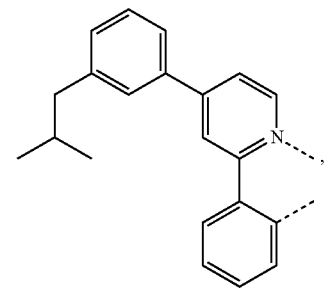
L<sub>A12</sub>
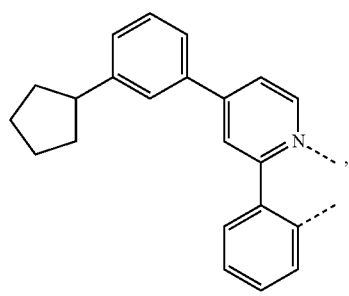
L<sub>A13</sub>
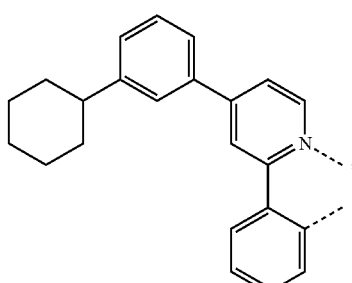
L<sub>A14</sub>
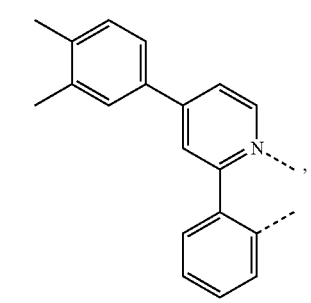
L<sub>A15</sub>
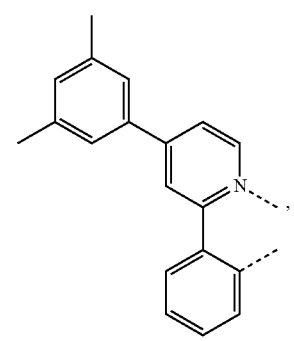
L<sub>A16</sub>
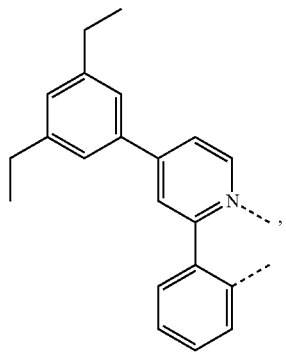
L<sub>A17</sub>
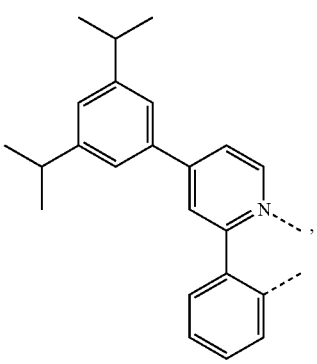
L<sub>A18</sub>
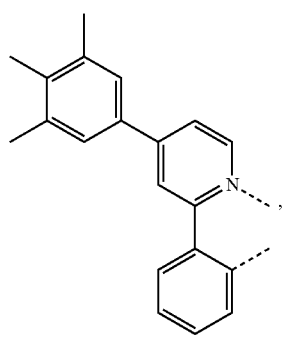
L<sub>A19</sub>
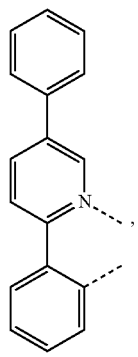

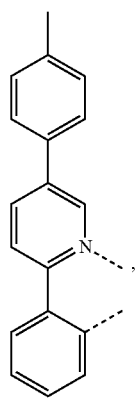
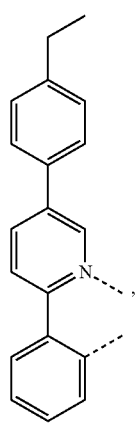
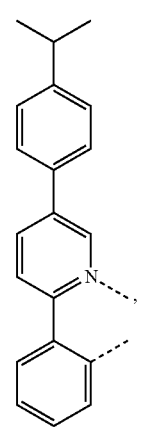
L<sub>A20</sub>
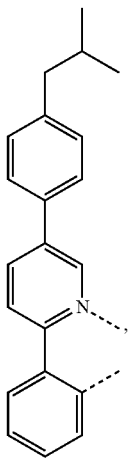
L<sub>A21</sub>
L<sub>A22</sub>
L<sub>A23</sub>
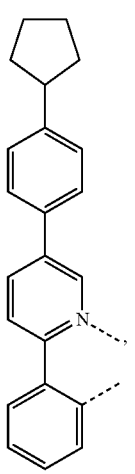
L<sub>A24</sub>
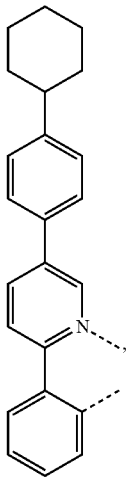
L<sub>A25</sub>

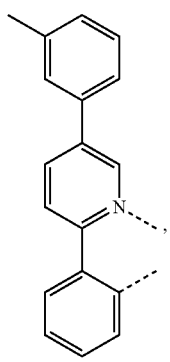
L_{A26}
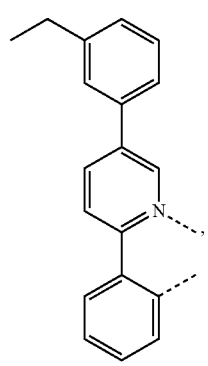
L_{A27}
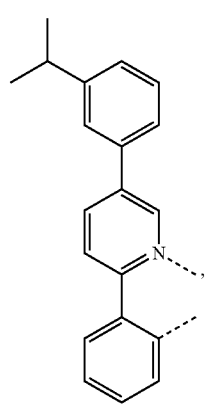
L_{A28}
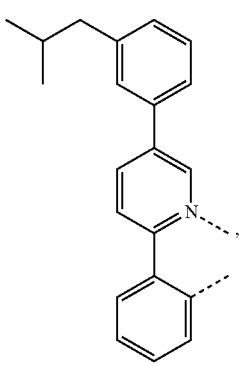
L_{A29}
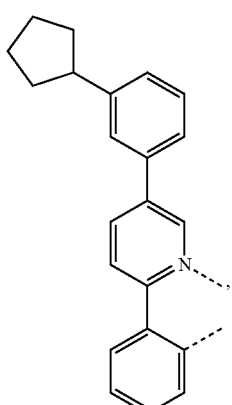
L_{A30}
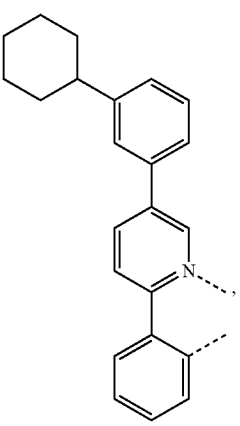
L_{A31}
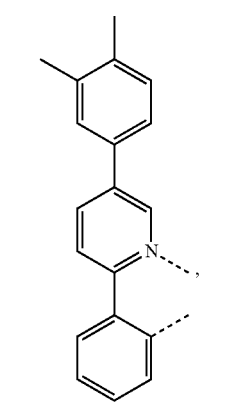
L_{A32}
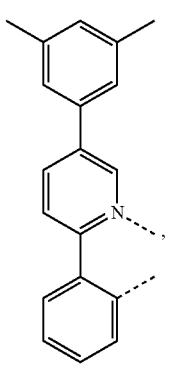
L_{A33}

L<sub>A34</sub>
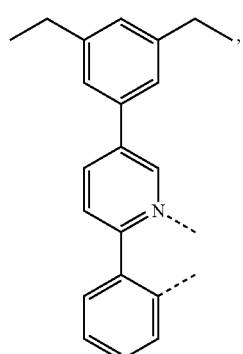
L<sub>A35</sub>
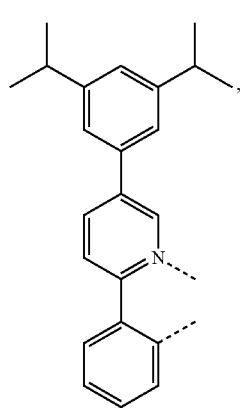
L<sub>A36</sub>
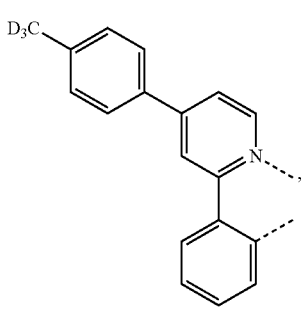
L<sub>A37</sub>
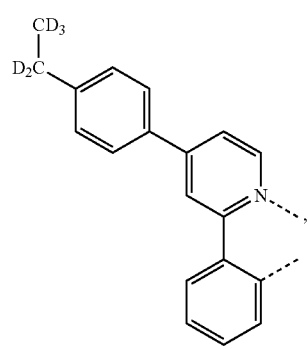
L<sub>A38</sub>
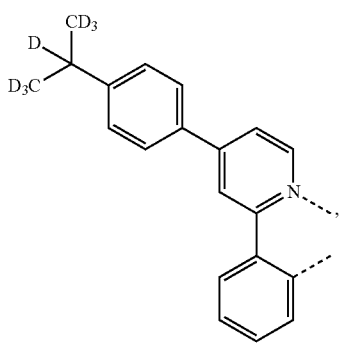
L<sub>A39</sub>
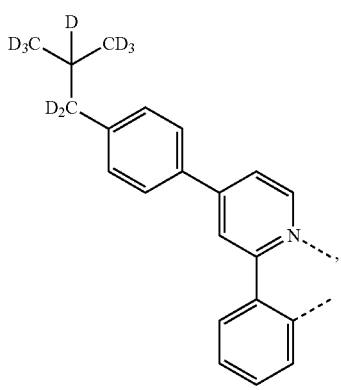
L<sub>A40</sub>
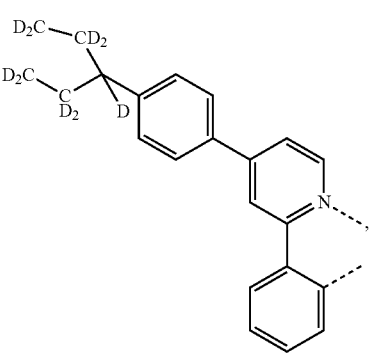
L<sub>A41</sub>
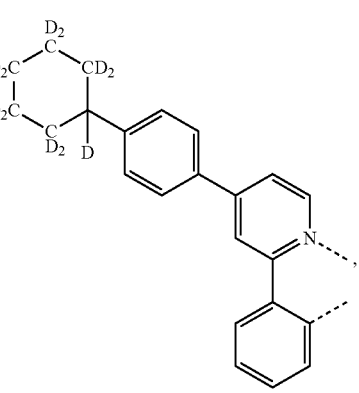

L<sub>A42</sub>
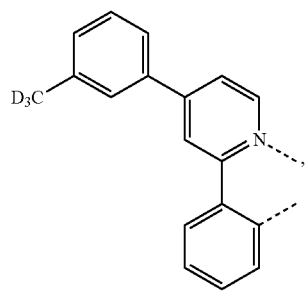
L<sub>A43</sub>
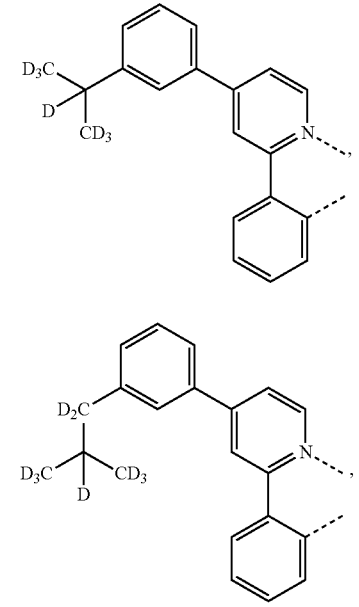
L<sub>A44</sub>
L<sub>A45</sub>
L<sub>A46</sub>
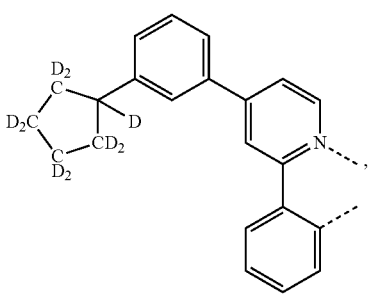
L<sub>A47</sub>
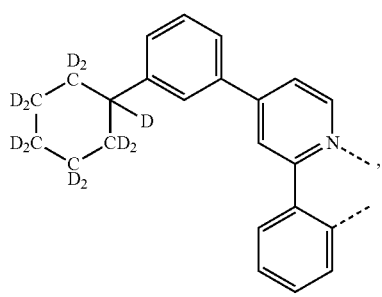
L<sub>A48</sub>
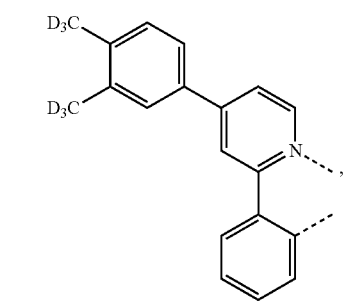
L<sub>A49</sub>
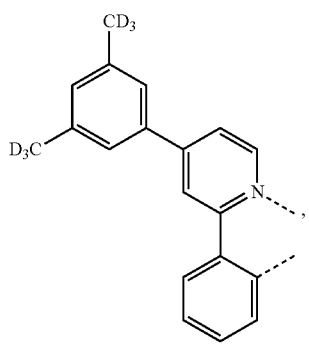
L<sub>A50</sub>
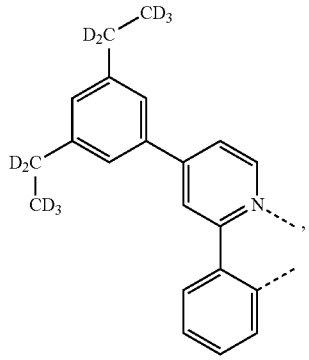

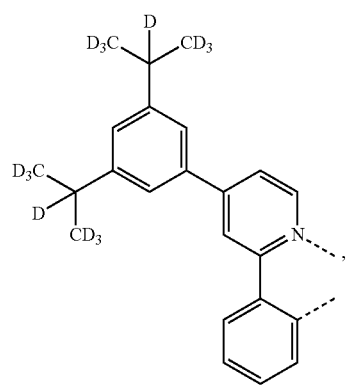 L<sub>A51</sub>
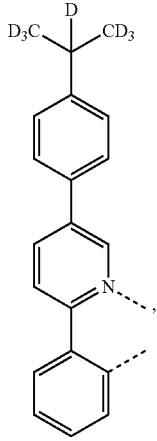 L<sub>A55</sub>
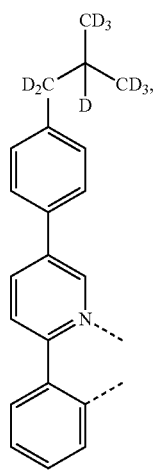 L<sub>A56</sub>
L<sub>A52</sub>
L<sub>A53</sub>
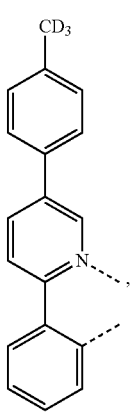 L<sub>A54</sub>
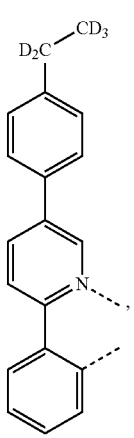 L<sub>A57</sub>

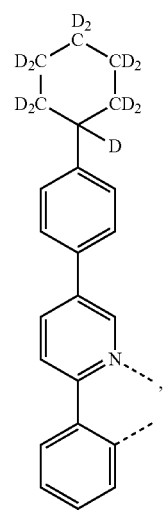
L_{A58}
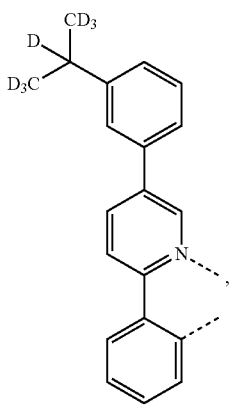
L_{A61}
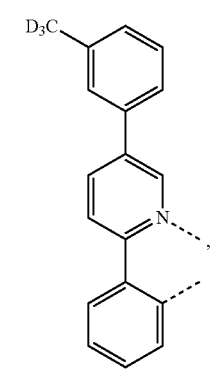
L_{A59}
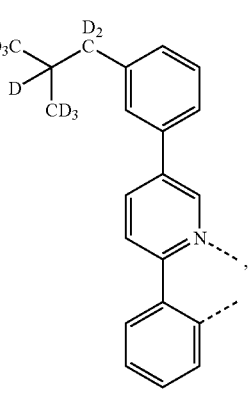
L_{A62}
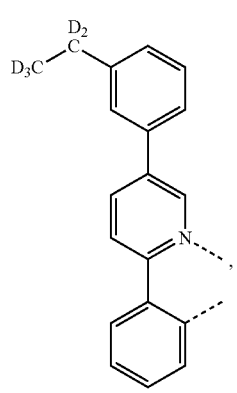
L_{A60}
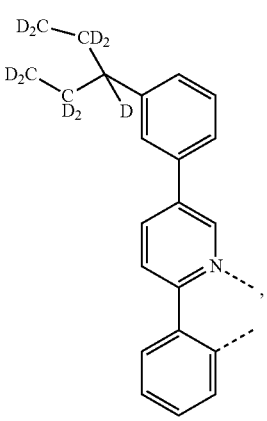
L_{A63}
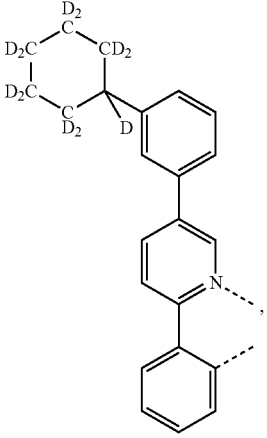
L_{A64}

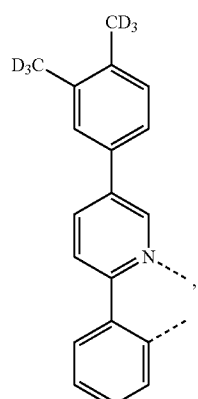
L<sub>A65</sub>
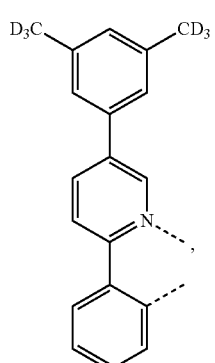
L<sub>A66</sub>
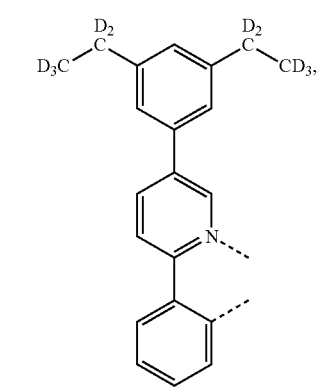
L<sub>A67</sub>
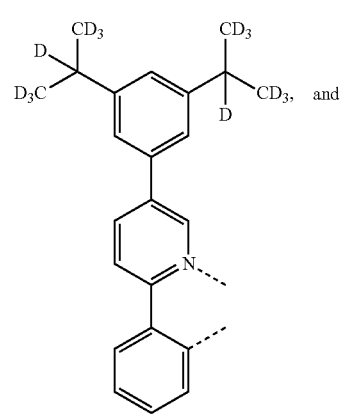
L<sub>A68</sub>
and
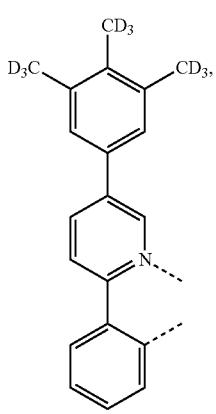
L<sub>A69</sub>
L<sub>B</sub> is selected from the group consisting of
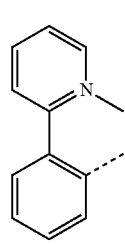
L<sub>B1</sub>
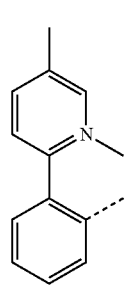
L<sub>B2</sub>
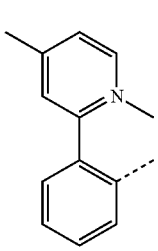
L<sub>B3</sub>
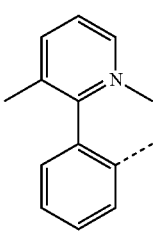
L<sub>B4</sub>

L_{B5}
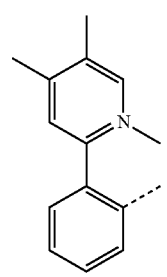
L_{B6}
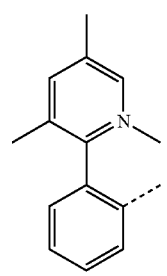
L_{B7}
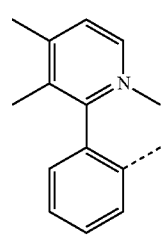
L_{B8}
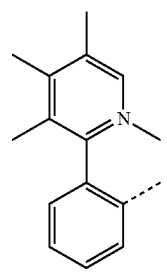
L_{B9}
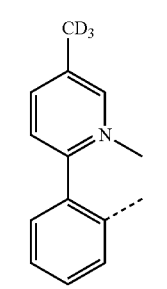
L_{B10}
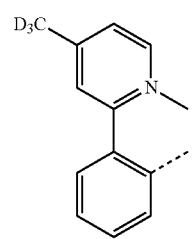
L_{B11}
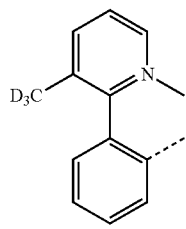
L_{B12}
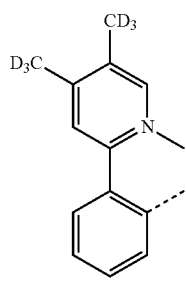
L_{B13}
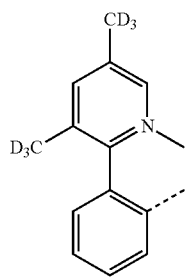
L_{B14}
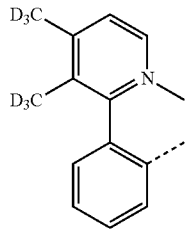
L_{B15}
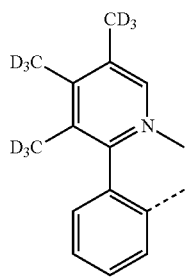
L_{B16}
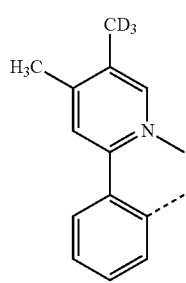

| | |
|---|---|
| 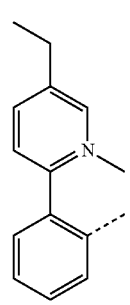 L_{B17} | 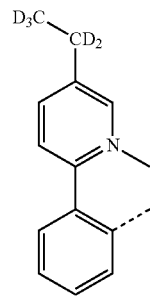 L_{B23} |
| 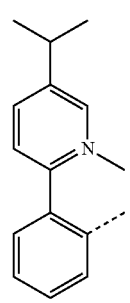 L_{B18} | 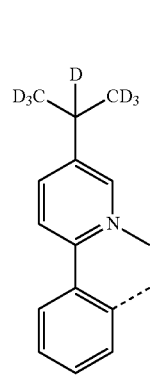 L_{B24} |
| 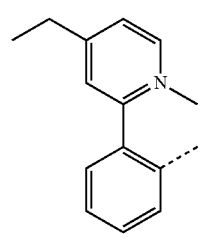 L_{B19} | 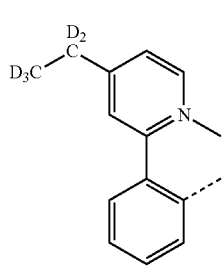 L_{B25} |
| 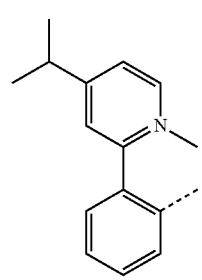 L_{B20} | 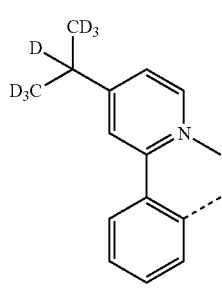 L_{B26} |
| 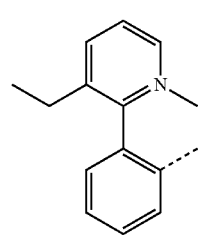 L_{B21} | 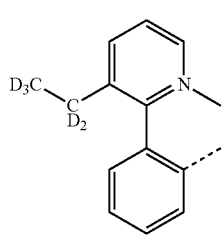 L_{B27} |
| 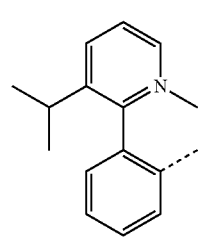 L_{B22} | |

$L_{B28}$

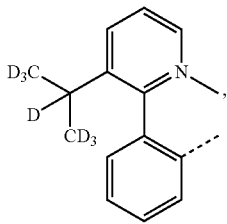

and the heteroleptic iridium complex is selected from the group consisting of Compound II-1 through Compound II-1846, and Compound II-1847 listed in the following table:

| Compound Number | $L_A$ | $L_B$ |
|---|---|---|
| II-1. | $L_{A6}$ | $L_{B1}$ |
| II-2. | $L_{A12}$ | $L_{B1}$ |
| II-3. | $L_{A13}$ | $L_{B1}$ |
| II-4. | $L_{A16}$ | $L_{B1}$ |
| II-5. | $L_{A17}$ | $L_{B1}$ |
| II-6. | $L_{A24}$ | $L_{B1}$ |
| II-7. | $L_{A30}$ | $L_{B1}$ |
| II-8. | $L_{A31}$ | $L_{B1}$ |
| II-9. | $L_{A34}$ | $L_{B1}$ |
| II-10. | $L_{A35}$ | $L_{B1}$ |
| II-11. | $L_{A36}$ | $L_{B1}$ |
| II-12. | $L_{A38}$ | $L_{B1}$ |
| II-13. | $L_{A39}$ | $L_{B1}$ |
| II-14. | $L_{A40}$ | $L_{B1}$ |
| II-15. | $L_{A41}$ | $L_{B1}$ |
| II-16. | $L_{A42}$ | $L_{B1}$ |
| II-17. | $L_{A43}$ | $L_{B1}$ |
| II-18. | $L_{A44}$ | $L_{B1}$ |
| II-19. | $L_{A45}$ | $L_{B1}$ |
| II-20. | $L_{A46}$ | $L_{B1}$ |
| II-21. | $L_{A47}$ | $L_{B1}$ |
| II-22. | $L_{A48}$ | $L_{B1}$ |
| II-23. | $L_{A49}$ | $L_{B1}$ |
| II-24. | $L_{A50}$ | $L_{B1}$ |
| II-25. | $L_{A51}$ | $L_{B1}$ |
| II-26. | $L_{A52}$ | $L_{B1}$ |
| II-27. | $L_{A53}$ | $L_{B1}$ |
| II-28. | $L_{A54}$ | $L_{B1}$ |
| II-29. | $L_{A55}$ | $L_{B1}$ |
| II-30. | $L_{A56}$ | $L_{B1}$ |
| II-31. | $L_{A57}$ | $L_{B1}$ |
| II-32. | $L_{A58}$ | $L_{B1}$ |
| II-33. | $L_{A59}$ | $L_{B1}$ |
| II-34. | $L_{A60}$ | $L_{B1}$ |
| II-35. | $L_{A61}$ | $L_{B1}$ |
| II-36. | $L_{A62}$ | $L_{B1}$ |
| II-37. | $L_{A63}$ | $L_{B1}$ |
| II-38. | $L_{A64}$ | $L_{B1}$ |
| II-39. | $L_{A65}$ | $L_{B1}$ |
| II-40. | $L_{A66}$ | $L_{B1}$ |
| II-41. | $L_{A67}$ | $L_{B1}$ |
| II-42. | $L_{A68}$ | $L_{B1}$ |
| II-43. | $L_{A69}$ | $L_{B1}$ |
| II-44. | $L_{A6}$ | $L_{B2}$ |
| II-45. | $L_{A7}$ | $L_{B2}$ |
| II-46. | $L_{A9}$ | $L_{B2}$ |
| II-47. | $L_{A10}$ | $L_{B2}$ |
| II-48. | $L_{A11}$ | $L_{B2}$ |
| II-49. | $L_{A12}$ | $L_{B2}$ |
| II-50. | $L_{A13}$ | $L_{B2}$ |
| II-51. | $L_{A16}$ | $L_{B2}$ |
| II-52. | $L_{A17}$ | $L_{B2}$ |
| II-53. | $L_{A21}$ | $L_{B2}$ |
| II-54. | $L_{A22}$ | $L_{B2}$ |
| II-55. | $L_{A23}$ | $L_{B2}$ |
| II-56. | $L_{A24}$ | $L_{B2}$ |
| II-57. | $L_{A27}$ | $L_{B2}$ |
| II-58. | $L_{A28}$ | $L_{B2}$ |
| II-59. | $L_{A29}$ | $L_{B2}$ |
| II-60. | $L_{A30}$ | $L_{B2}$ |
| II-61. | $L_{A31}$ | $L_{B2}$ |
| II-62. | $L_{A34}$ | $L_{B2}$ |
| II-63. | $L_{A35}$ | $L_{B2}$ |
| II-64. | $L_{A36}$ | $L_{B2}$ |
| II-65. | $L_{A38}$ | $L_{B2}$ |
| II-66. | $L_{A39}$ | $L_{B2}$ |
| II-67. | $L_{A40}$ | $L_{B2}$ |
| II-68. | $L_{A41}$ | $L_{B2}$ |
| II-69. | $L_{A42}$ | $L_{B2}$ |
| II-70. | $L_{A43}$ | $L_{B2}$ |
| II-71. | $L_{A44}$ | $L_{B2}$ |
| II-72. | $L_{A45}$ | $L_{B2}$ |
| II-73. | $L_{A46}$ | $L_{B2}$ |
| II-74. | $L_{A47}$ | $L_{B2}$ |
| II-75. | $L_{A48}$ | $L_{B2}$ |
| II-76. | $L_{A49}$ | $L_{B2}$ |
| II-77. | $L_{A50}$ | $L_{B2}$ |
| II-78. | $L_{A51}$ | $L_{B2}$ |
| II-79. | $L_{A52}$ | $L_{B2}$ |
| II-80. | $L_{A53}$ | $L_{B2}$ |
| II-81. | $L_{A54}$ | $L_{B2}$ |
| II-82. | $L_{A55}$ | $L_{B2}$ |
| II-83. | $L_{A56}$ | $L_{B2}$ |
| II-84. | $L_{A57}$ | $L_{B2}$ |
| II-85. | $L_{A58}$ | $L_{B2}$ |
| II-86. | $L_{A59}$ | $L_{B2}$ |
| II-87. | $L_{A60}$ | $L_{B2}$ |
| II-88. | $L_{A61}$ | $L_{B2}$ |
| II-89. | $L_{A62}$ | $L_{B2}$ |
| II-90. | $L_{A63}$ | $L_{B2}$ |
| II-91. | $L_{A64}$ | $L_{B2}$ |
| II-92. | $L_{A65}$ | $L_{B2}$ |
| II-93. | $L_{A66}$ | $L_{B2}$ |
| II-94. | $L_{A67}$ | $L_{B2}$ |
| II-95. | $L_{A68}$ | $L_{B2}$ |
| II-96. | $L_{A69}$ | $L_{B2}$ |
| II-97. | $L_{A2}$ | $L_{B3}$ |
| II-98. | $L_{A3}$ | $L_{B3}$ |
| II-99. | $L_{A4}$ | $L_{B3}$ |
| II-100. | $L_{A5}$ | $L_{B3}$ |
| II-101. | $L_{A6}$ | $L_{B3}$ |
| II-102. | $L_{A7}$ | $L_{B3}$ |
| II-103. | $L_{A8}$ | $L_{B3}$ |
| II-104. | $L_{A9}$ | $L_{B3}$ |
| II-105. | $L_{A10}$ | $L_{B3}$ |
| II-106. | $L_{A11}$ | $L_{B3}$ |
| II-107. | $L_{A12}$ | $L_{B3}$ |
| II-108. | $L_{A13}$ | $L_{B3}$ |
| II-109. | $L_{A14}$ | $L_{B3}$ |
| II-110. | $L_{A15}$ | $L_{B3}$ |
| II-111. | $L_{A16}$ | $L_{B3}$ |
| II-112. | $L_{A17}$ | $L_{B3}$ |
| II-113. | $L_{A18}$ | $L_{B3}$ |
| II-114. | $L_{A20}$ | $L_{B3}$ |
| II-115. | $L_{A21}$ | $L_{B3}$ |
| II-116. | $L_{A22}$ | $L_{B3}$ |
| II-117. | $L_{A23}$ | $L_{B3}$ |
| II-118. | $L_{A24}$ | $L_{B3}$ |
| II-119. | $L_{A25}$ | $L_{B3}$ |
| II-120. | $L_{A26}$ | $L_{B3}$ |
| II-121. | $L_{A27}$ | $L_{B3}$ |
| II-122. | $L_{A28}$ | $L_{B3}$ |
| II-123. | $L_{A29}$ | $L_{B3}$ |
| II-124. | $L_{A30}$ | $L_{B3}$ |
| II-125. | $L_{A31}$ | $L_{B3}$ |
| II-126. | $L_{A32}$ | $L_{B3}$ |
| II-127. | $L_{A33}$ | $L_{B3}$ |
| II-128. | $L_{A34}$ | $L_{B3}$ |
| II-129. | $L_{A35}$ | $L_{B3}$ |
| II-130. | $L_{A36}$ | $L_{B3}$ |
| II-131. | $L_{A37}$ | $L_{B3}$ |
| II-132. | $L_{A38}$ | $L_{B3}$ |
| II-133. | $L_{A39}$ | $L_{B3}$ |

-continued

| Compound Number | $L_A$ | $L_B$ |
|---|---|---|
| II-134. | $L_{A40}$ | $L_{B3}$ |
| II-135. | $L_{A41}$ | $L_{B3}$ |
| II-136. | $L_{A42}$ | $L_{B3}$ |
| II-137. | $L_{A43}$ | $L_{B3}$ |
| II-138. | $L_{A44}$ | $L_{B3}$ |
| II-139. | $L_{A45}$ | $L_{B3}$ |
| II-140. | $L_{A46}$ | $L_{B3}$ |
| II-141. | $L_{A47}$ | $L_{B3}$ |
| II-142. | $L_{A48}$ | $L_{B3}$ |
| II-143. | $L_{A49}$ | $L_{B3}$ |
| II-144. | $L_{A50}$ | $L_{B3}$ |
| II-145. | $L_{A51}$ | $L_{B3}$ |
| II-146. | $L_{A52}$ | $L_{B3}$ |
| II-147. | $L_{A53}$ | $L_{B3}$ |
| II-148. | $L_{A54}$ | $L_{B3}$ |
| II-149. | $L_{A55}$ | $L_{B3}$ |
| II-150. | $L_{A56}$ | $L_{B3}$ |
| II-151. | $L_{A57}$ | $L_{B3}$ |
| II-152. | $L_{A58}$ | $L_{B3}$ |
| II-153. | $L_{A59}$ | $L_{B3}$ |
| II-154. | $L_{A60}$ | $L_{B3}$ |
| II-155. | $L_{A61}$ | $L_{B3}$ |
| II-156. | $L_{A62}$ | $L_{B3}$ |
| II-157. | $L_{A63}$ | $L_{B3}$ |
| II-158. | $L_{A64}$ | $L_{B3}$ |
| II-159. | $L_{A65}$ | $L_{B3}$ |
| II-160. | $L_{A66}$ | $L_{B3}$ |
| II-161. | $L_{A67}$ | $L_{B3}$ |
| II-162. | $L_{A68}$ | $L_{B3}$ |
| II-163. | $L_{A69}$ | $L_{B3}$ |
| II-164. | $L_{A2}$ | $L_{B4}$ |
| II-165. | $L_{A3}$ | $L_{B4}$ |
| II-166. | $L_{A4}$ | $L_{B4}$ |
| II-167. | $L_{A5}$ | $L_{B4}$ |
| II-168. | $L_{A6}$ | $L_{B4}$ |
| II-169. | $L_{A7}$ | $L_{B4}$ |
| II-170. | $L_{A8}$ | $L_{B4}$ |
| II-171. | $L_{A9}$ | $L_{B4}$ |
| II-172. | $L_{A10}$ | $L_{B4}$ |
| II-173. | $L_{A11}$ | $L_{B4}$ |
| II-174. | $L_{A12}$ | $L_{B4}$ |
| II-175. | $L_{A13}$ | $L_{B4}$ |
| II-176. | $L_{A14}$ | $L_{B4}$ |
| II-177. | $L_{A15}$ | $L_{B4}$ |
| II-178. | $L_{A16}$ | $L_{B4}$ |
| II-179. | $L_{A17}$ | $L_{B4}$ |
| II-180. | $L_{A18}$ | $L_{B4}$ |
| II-181. | $L_{A20}$ | $L_{B4}$ |
| II-182. | $L_{A21}$ | $L_{B4}$ |
| II-183. | $L_{A22}$ | $L_{B4}$ |
| II-184. | $L_{A23}$ | $L_{B4}$ |
| II-185. | $L_{A24}$ | $L_{B4}$ |
| II-186. | $L_{A25}$ | $L_{B4}$ |
| II-187. | $L_{A26}$ | $L_{B4}$ |
| II-188. | $L_{A27}$ | $L_{B4}$ |
| II-189. | $L_{A28}$ | $L_{B4}$ |
| II-190. | $L_{A29}$ | $L_{B4}$ |
| II-191. | $L_{A30}$ | $L_{B4}$ |
| II-192. | $L_{A31}$ | $L_{B4}$ |
| II-193. | $L_{A32}$ | $L_{B4}$ |
| II-194. | $L_{A33}$ | $L_{B4}$ |
| II-195. | $L_{A34}$ | $L_{B4}$ |
| II-196. | $L_{A35}$ | $L_{B4}$ |
| II-197. | $L_{A36}$ | $L_{B4}$ |
| II-198. | $L_{A37}$ | $L_{B4}$ |
| II-199. | $L_{A38}$ | $L_{B4}$ |
| II-200. | $L_{A39}$ | $L_{B4}$ |
| II-201. | $L_{A40}$ | $L_{B4}$ |
| II-202. | $L_{A41}$ | $L_{B4}$ |
| II-203. | $L_{A42}$ | $L_{B4}$ |
| II-204. | $L_{A43}$ | $L_{B4}$ |
| II-205. | $L_{A44}$ | $L_{B4}$ |
| II-206. | $L_{A45}$ | $L_{B4}$ |
| II-207. | $L_{A46}$ | $L_{B4}$ |
| II-208. | $L_{A47}$ | $L_{B4}$ |
| II-209. | $L_{A48}$ | $L_{B4}$ |

-continued

| Compound Number | $L_A$ | $L_B$ |
|---|---|---|
| II-210. | $L_{A49}$ | $L_{B4}$ |
| II-211. | $L_{A50}$ | $L_{B4}$ |
| II-212. | $L_{A51}$ | $L_{B4}$ |
| II-213. | $L_{A52}$ | $L_{B4}$ |
| II-214. | $L_{A53}$ | $L_{B4}$ |
| II-215. | $L_{A54}$ | $L_{B4}$ |
| II-216. | $L_{A55}$ | $L_{B4}$ |
| II-217. | $L_{A56}$ | $L_{B4}$ |
| II-218. | $L_{A57}$ | $L_{B4}$ |
| II-219. | $L_{A58}$ | $L_{B4}$ |
| II-220. | $L_{A59}$ | $L_{B4}$ |
| II-221. | $L_{A60}$ | $L_{B4}$ |
| II-222. | $L_{A61}$ | $L_{B4}$ |
| II-223. | $L_{A62}$ | $L_{B4}$ |
| II-224. | $L_{A63}$ | $L_{B4}$ |
| II-225. | $L_{A64}$ | $L_{B4}$ |
| II-226. | $L_{A65}$ | $L_{B4}$ |
| II-227. | $L_{A66}$ | $L_{B4}$ |
| II-228. | $L_{A67}$ | $L_{B4}$ |
| II-229. | $L_{A68}$ | $L_{B4}$ |
| II-230. | $L_{A69}$ | $L_{B4}$ |
| II-231. | $L_{A3}$ | $L_{B5}$ |
| II-232. | $L_{A4}$ | $L_{B5}$ |
| II-233. | $L_{A5}$ | $L_{B5}$ |
| II-234. | $L_{A6}$ | $L_{B5}$ |
| II-235. | $L_{A7}$ | $L_{B5}$ |
| II-236. | $L_{A8}$ | $L_{B5}$ |
| II-237. | $L_{A9}$ | $L_{B5}$ |
| II-238. | $L_{A10}$ | $L_{B5}$ |
| II-239. | $L_{A11}$ | $L_{B5}$ |
| II-240. | $L_{A12}$ | $L_{B5}$ |
| II-241. | $L_{A13}$ | $L_{B5}$ |
| II-242. | $L_{A14}$ | $L_{B5}$ |
| II-243. | $L_{A15}$ | $L_{B5}$ |
| II-244. | $L_{A16}$ | $L_{B5}$ |
| II-245. | $L_{A17}$ | $L_{B5}$ |
| II-246. | $L_{A18}$ | $L_{B5}$ |
| II-247. | $L_{A20}$ | $L_{B5}$ |
| II-248. | $L_{A21}$ | $L_{B5}$ |
| II-249. | $L_{A22}$ | $L_{B5}$ |
| II-250. | $L_{A23}$ | $L_{B5}$ |
| II-251. | $L_{A24}$ | $L_{B5}$ |
| II-252. | $L_{A25}$ | $L_{B5}$ |
| II-253. | $L_{A26}$ | $L_{B5}$ |
| II-254. | $L_{A27}$ | $L_{B5}$ |
| II-255. | $L_{A28}$ | $L_{B5}$ |
| II-256. | $L_{A29}$ | $L_{B5}$ |
| II-257. | $L_{A30}$ | $L_{B5}$ |
| II-258. | $L_{A31}$ | $L_{B5}$ |
| II-259. | $L_{A32}$ | $L_{B5}$ |
| II-260. | $L_{A33}$ | $L_{B5}$ |
| II-261. | $L_{A34}$ | $L_{B5}$ |
| II-262. | $L_{A35}$ | $L_{B5}$ |
| II-263. | $L_{A36}$ | $L_{B5}$ |
| II-264. | $L_{A37}$ | $L_{B5}$ |
| II-265. | $L_{A38}$ | $L_{B5}$ |
| II-266. | $L_{A39}$ | $L_{B5}$ |
| II-267. | $L_{A40}$ | $L_{B5}$ |
| II-268. | $L_{A41}$ | $L_{B5}$ |
| II-269. | $L_{A42}$ | $L_{B5}$ |
| II-270. | $L_{A43}$ | $L_{B5}$ |
| II-271. | $L_{A44}$ | $L_{B5}$ |
| II-272. | $L_{A45}$ | $L_{B5}$ |
| II-273. | $L_{A46}$ | $L_{B5}$ |
| II-274. | $L_{A47}$ | $L_{B5}$ |
| II-275. | $L_{A48}$ | $L_{B5}$ |
| II-276. | $L_{A49}$ | $L_{B5}$ |
| II-277. | $L_{A50}$ | $L_{B5}$ |
| II-278. | $L_{A51}$ | $L_{B5}$ |
| II-279. | $L_{A52}$ | $L_{B5}$ |
| II-280. | $L_{A53}$ | $L_{B5}$ |
| II-281. | $L_{A54}$ | $L_{B5}$ |
| II-282. | $L_{A55}$ | $L_{B5}$ |
| II-283. | $L_{A56}$ | $L_{B5}$ |
| II-284. | $L_{A57}$ | $L_{B5}$ |
| II-285. | $L_{A58}$ | $L_{B5}$ |

| Compound Number | $L_A$ | $L_B$ |
|---|---|---|
| II-286. | $L_{A59}$ | $L_{B5}$ |
| II-287. | $L_{A60}$ | $L_{B5}$ |
| II-288. | $L_{A61}$ | $L_{B5}$ |
| II-289. | $L_{A62}$ | $L_{B5}$ |
| II-290. | $L_{A63}$ | $L_{B5}$ |
| II-291. | $L_{A64}$ | $L_{B5}$ |
| II-292. | $L_{A65}$ | $L_{B5}$ |
| II-293. | $L_{A66}$ | $L_{B5}$ |
| II-294. | $L_{A67}$ | $L_{B5}$ |
| II-295. | $L_{A68}$ | $L_{B5}$ |
| II-296. | $L_{A69}$ | $L_{B5}$ |
| II-297. | $L_{A2}$ | $L_{B6}$ |
| II-298. | $L_{A3}$ | $L_{B6}$ |
| II-299. | $L_{A4}$ | $L_{B6}$ |
| II-300. | $L_{A5}$ | $L_{B6}$ |
| II-301. | $L_{A6}$ | $L_{B6}$ |
| II-302. | $L_{A7}$ | $L_{B6}$ |
| II-303. | $L_{A8}$ | $L_{B6}$ |
| II-304. | $L_{A9}$ | $L_{B6}$ |
| II-305. | $L_{A10}$ | $L_{B6}$ |
| II-306. | $L_{A11}$ | $L_{B6}$ |
| II-307. | $L_{A12}$ | $L_{B6}$ |
| II-308. | $L_{A13}$ | $L_{B6}$ |
| II-309. | $L_{A14}$ | $L_{B6}$ |
| II-310. | $L_{A15}$ | $L_{B6}$ |
| II-311. | $L_{A16}$ | $L_{B6}$ |
| II-312. | $L_{A17}$ | $L_{B6}$ |
| II-313. | $L_{A18}$ | $L_{B6}$ |
| II-314. | $L_{A20}$ | $L_{B6}$ |
| II-315. | $L_{A21}$ | $L_{B6}$ |
| II-316. | $L_{A22}$ | $L_{B6}$ |
| II-317. | $L_{A23}$ | $L_{B6}$ |
| II-318. | $L_{A24}$ | $L_{B6}$ |
| II-319. | $L_{A25}$ | $L_{B6}$ |
| II-320. | $L_{A26}$ | $L_{B6}$ |
| II-321. | $L_{A27}$ | $L_{B6}$ |
| II-322. | $L_{A28}$ | $L_{B6}$ |
| II-323. | $L_{A29}$ | $L_{B6}$ |
| II-324. | $L_{A30}$ | $L_{B6}$ |
| II-325. | $L_{A31}$ | $L_{B6}$ |
| II-326. | $L_{A32}$ | $L_{B6}$ |
| II-327. | $L_{A33}$ | $L_{B6}$ |
| II-328. | $L_{A34}$ | $L_{B6}$ |
| II-329. | $L_{A35}$ | $L_{B6}$ |
| II-330. | $L_{A36}$ | $L_{B6}$ |
| II-331. | $L_{A37}$ | $L_{B6}$ |
| II-332. | $L_{A38}$ | $L_{B6}$ |
| II-333. | $L_{A39}$ | $L_{B6}$ |
| II-334. | $L_{A40}$ | $L_{B6}$ |
| II-335. | $L_{A41}$ | $L_{B6}$ |
| II-336. | $L_{A42}$ | $L_{B6}$ |
| II-337. | $L_{A43}$ | $L_{B6}$ |
| II-338. | $L_{A44}$ | $L_{B6}$ |
| II-339. | $L_{A45}$ | $L_{B6}$ |
| II-340. | $L_{A46}$ | $L_{B6}$ |
| II-341. | $L_{A47}$ | $L_{B6}$ |
| II-342. | $L_{A48}$ | $L_{B6}$ |
| II-343. | $L_{A49}$ | $L_{B6}$ |
| II-344. | $L_{A50}$ | $L_{B6}$ |
| II-345. | $L_{A51}$ | $L_{B6}$ |
| II-346. | $L_{A52}$ | $L_{B6}$ |
| II-347. | $L_{A53}$ | $L_{B6}$ |
| II-348. | $L_{A54}$ | $L_{B6}$ |
| II-349. | $L_{A55}$ | $L_{B6}$ |
| II-350. | $L_{A56}$ | $L_{B6}$ |
| II-351. | $L_{A57}$ | $L_{B6}$ |
| II-352. | $L_{A58}$ | $L_{B6}$ |
| II-353. | $L_{A59}$ | $L_{B6}$ |
| II-354. | $L_{A60}$ | $L_{B6}$ |
| II-355. | $L_{A61}$ | $L_{B6}$ |
| II-356. | $L_{A62}$ | $L_{B6}$ |
| II-357. | $L_{A63}$ | $L_{B6}$ |
| II-358. | $L_{A64}$ | $L_{B6}$ |
| II-359. | $L_{A65}$ | $L_{B6}$ |
| II-360. | $L_{A66}$ | $L_{B6}$ |
| II-361. | $L_{A67}$ | $L_{B6}$ |
| II-362. | $L_{A68}$ | $L_{B6}$ |
| II-363. | $L_{A69}$ | $L_{B6}$ |
| II-364. | $L_{A2}$ | $L_{B7}$ |
| II-365. | $L_{A3}$ | $L_{B7}$ |
| II-366. | $L_{A4}$ | $L_{B7}$ |
| II-367. | $L_{A5}$ | $L_{B7}$ |
| II-368. | $L_{A6}$ | $L_{B7}$ |
| II-369. | $L_{A7}$ | $L_{B7}$ |
| II-370. | $L_{A8}$ | $L_{B7}$ |
| II-371. | $L_{A9}$ | $L_{B7}$ |
| II-372. | $L_{A10}$ | $L_{B7}$ |
| II-373. | $L_{A11}$ | $L_{B7}$ |
| II-374. | $L_{A12}$ | $L_{B7}$ |
| II-375. | $L_{A13}$ | $L_{B7}$ |
| II-376. | $L_{A14}$ | $L_{B7}$ |
| II-377. | $L_{A15}$ | $L_{B7}$ |
| II-378. | $L_{A16}$ | $L_{B7}$ |
| II-379. | $L_{A17}$ | $L_{B7}$ |
| II-380. | $L_{A18}$ | $L_{B7}$ |
| II-381. | $L_{A20}$ | $L_{B7}$ |
| II-382. | $L_{A21}$ | $L_{B7}$ |
| II-383. | $L_{A22}$ | $L_{B7}$ |
| II-384. | $L_{A23}$ | $L_{B7}$ |
| II-385. | $L_{A24}$ | $L_{B7}$ |
| II-386. | $L_{A25}$ | $L_{B7}$ |
| II-387. | $L_{A26}$ | $L_{B7}$ |
| II-388. | $L_{A27}$ | $L_{B7}$ |
| II-389. | $L_{A28}$ | $L_{B7}$ |
| II-390. | $L_{A29}$ | $L_{B7}$ |
| II-391. | $L_{A30}$ | $L_{B7}$ |
| II-392. | $L_{A31}$ | $L_{B7}$ |
| II-393. | $L_{A32}$ | $L_{B7}$ |
| II-394. | $L_{A33}$ | $L_{B7}$ |
| II-395. | $L_{A34}$ | $L_{B7}$ |
| II-396. | $L_{A35}$ | $L_{B7}$ |
| II-397. | $L_{A36}$ | $L_{B7}$ |
| II-398. | $L_{A37}$ | $L_{B7}$ |
| II-399. | $L_{A38}$ | $L_{B7}$ |
| II-400. | $L_{A39}$ | $L_{B7}$ |
| II-401. | $L_{A40}$ | $L_{B7}$ |
| II-402. | $L_{A41}$ | $L_{B7}$ |
| II-403. | $L_{A42}$ | $L_{B7}$ |
| II-404. | $L_{A43}$ | $L_{B7}$ |
| II-405. | $L_{A44}$ | $L_{B7}$ |
| II-406. | $L_{A45}$ | $L_{B7}$ |
| II-407. | $L_{A46}$ | $L_{B7}$ |
| II-408. | $L_{A47}$ | $L_{B7}$ |
| II-409. | $L_{A48}$ | $L_{B7}$ |
| II-410. | $L_{A49}$ | $L_{B7}$ |
| II-411. | $L_{A50}$ | $L_{B7}$ |
| II-412. | $L_{A51}$ | $L_{B7}$ |
| II-413. | $L_{A52}$ | $L_{B7}$ |
| II-414. | $L_{A53}$ | $L_{B7}$ |
| II-415. | $L_{A54}$ | $L_{B7}$ |
| II-416. | $L_{A55}$ | $L_{B7}$ |
| II-417. | $L_{A56}$ | $L_{B7}$ |
| II-418. | $L_{A57}$ | $L_{B7}$ |
| II-419. | $L_{A58}$ | $L_{B7}$ |
| II-420. | $L_{A59}$ | $L_{B7}$ |
| II-421. | $L_{A60}$ | $L_{B7}$ |
| II-422. | $L_{A61}$ | $L_{B7}$ |
| II-423. | $L_{A62}$ | $L_{B7}$ |
| II-424. | $L_{A63}$ | $L_{B7}$ |
| II-425. | $L_{A64}$ | $L_{B7}$ |
| II-426. | $L_{A65}$ | $L_{B7}$ |
| II-427. | $L_{A66}$ | $L_{B7}$ |
| II-428. | $L_{A67}$ | $L_{B7}$ |
| II-429. | $L_{A68}$ | $L_{B7}$ |
| II-430. | $L_{A69}$ | $L_{B7}$ |
| II-431. | $L_{A2}$ | $L_{B8}$ |
| II-432. | $L_{A3}$ | $L_{B8}$ |
| II-433. | $L_{A4}$ | $L_{B8}$ |
| II-434. | $L_{A5}$ | $L_{B8}$ |
| II-435. | $L_{A6}$ | $L_{B8}$ |
| II-436. | $L_{A7}$ | $L_{B8}$ |
| II-437. | $L_{A8}$ | $L_{B8}$ |

-continued

| Compound Number | $L_A$ | $L_B$ |
|---|---|---|
| II-438. | $L_{A9}$ | $L_{B8}$ |
| II-439. | $L_{A10}$ | $L_{B8}$ |
| II-440. | $L_{A11}$ | $L_{B8}$ |
| II-441. | $L_{A12}$ | $L_{B8}$ |
| II-442. | $L_{A13}$ | $L_{B8}$ |
| II-443. | $L_{A14}$ | $L_{B8}$ |
| II-444. | $L_{A15}$ | $L_{B8}$ |
| II-445. | $L_{A16}$ | $L_{B8}$ |
| II-446. | $L_{A17}$ | $L_{B8}$ |
| II-447. | $L_{A18}$ | $L_{B8}$ |
| II-448. | $L_{A20}$ | $L_{B8}$ |
| II-449. | $L_{A21}$ | $L_{B8}$ |
| II-450. | $L_{A22}$ | $L_{B8}$ |
| II-451. | $L_{A23}$ | $L_{B8}$ |
| II-452. | $L_{A24}$ | $L_{B8}$ |
| II-453. | $L_{A25}$ | $L_{B8}$ |
| II-454. | $L_{A26}$ | $L_{B8}$ |
| II-455. | $L_{A27}$ | $L_{B8}$ |
| II-456. | $L_{A28}$ | $L_{B8}$ |
| II-457. | $L_{A29}$ | $L_{B8}$ |
| II-458. | $L_{A30}$ | $L_{B8}$ |
| II-459. | $L_{A31}$ | $L_{B8}$ |
| II-460. | $L_{A32}$ | $L_{B8}$ |
| II-461. | $L_{A33}$ | $L_{B8}$ |
| II-462. | $L_{A34}$ | $L_{B8}$ |
| II-463. | $L_{A35}$ | $L_{B8}$ |
| II-464. | $L_{A36}$ | $L_{B8}$ |
| II-465. | $L_{A37}$ | $L_{B8}$ |
| II-466. | $L_{A38}$ | $L_{B8}$ |
| II-467. | $L_{A39}$ | $L_{B8}$ |
| II-468. | $L_{A40}$ | $L_{B8}$ |
| II-469. | $L_{A41}$ | $L_{B8}$ |
| II-470. | $L_{A42}$ | $L_{B8}$ |
| II-471. | $L_{A43}$ | $L_{B8}$ |
| II-472. | $L_{A44}$ | $L_{B8}$ |
| II-473. | $L_{A45}$ | $L_{B8}$ |
| II-474. | $L_{A46}$ | $L_{B8}$ |
| II-475. | $L_{A47}$ | $L_{B8}$ |
| II-476. | $L_{A48}$ | $L_{B8}$ |
| II-477. | $L_{A49}$ | $L_{B8}$ |
| II-478. | $L_{A50}$ | $L_{B8}$ |
| II-479. | $L_{A51}$ | $L_{B8}$ |
| II-480. | $L_{A52}$ | $L_{B8}$ |
| II-481. | $L_{A53}$ | $L_{B8}$ |
| II-482. | $L_{A54}$ | $L_{B8}$ |
| II-483. | $L_{A55}$ | $L_{B8}$ |
| II-484. | $L_{A56}$ | $L_{B8}$ |
| II-485. | $L_{A57}$ | $L_{B8}$ |
| II-486. | $L_{A58}$ | $L_{B8}$ |
| II-487. | $L_{A59}$ | $L_{B8}$ |
| II-488. | $L_{A60}$ | $L_{B8}$ |
| II-489. | $L_{A61}$ | $L_{B8}$ |
| II-490. | $L_{A62}$ | $L_{B8}$ |
| II-491. | $L_{A63}$ | $L_{B8}$ |
| II-492. | $L_{A64}$ | $L_{B8}$ |
| II-493. | $L_{A65}$ | $L_{B8}$ |
| II-494. | $L_{A66}$ | $L_{B8}$ |
| II-495. | $L_{A67}$ | $L_{B8}$ |
| II-496. | $L_{A68}$ | $L_{B8}$ |
| II-497. | $L_{A69}$ | $L_{B8}$ |
| II-498. | $L_{A3}$ | $L_{B9}$ |
| II-499. | $L_{A4}$ | $L_{B9}$ |
| II-500. | $L_{A5}$ | $L_{B9}$ |
| II-501. | $L_{A6}$ | $L_{B9}$ |
| II-502. | $L_{A7}$ | $L_{B9}$ |
| II-503. | $L_{A8}$ | $L_{B9}$ |
| II-504. | $L_{A9}$ | $L_{B9}$ |
| II-505. | $L_{A10}$ | $L_{B9}$ |
| II-506. | $L_{A11}$ | $L_{B9}$ |
| II-507. | $L_{A12}$ | $L_{B9}$ |
| II-508. | $L_{A13}$ | $L_{B9}$ |
| II-509. | $L_{A14}$ | $L_{B9}$ |
| II-510. | $L_{A15}$ | $L_{B9}$ |
| II-511. | $L_{A16}$ | $L_{B9}$ |
| II-512. | $L_{A17}$ | $L_{B9}$ |
| II-513. | $L_{A18}$ | $L_{B9}$ |
| II-514. | $L_{A21}$ | $L_{B9}$ |
| II-515. | $L_{A22}$ | $L_{B9}$ |
| II-516. | $L_{A23}$ | $L_{B9}$ |
| II-517. | $L_{A24}$ | $L_{B9}$ |
| II-518. | $L_{A25}$ | $L_{B9}$ |
| II-519. | $L_{A26}$ | $L_{B9}$ |
| II-520. | $L_{A27}$ | $L_{B9}$ |
| II-521. | $L_{A28}$ | $L_{B9}$ |
| II-522. | $L_{A29}$ | $L_{B9}$ |
| II-523. | $L_{A30}$ | $L_{B9}$ |
| II-524. | $L_{A31}$ | $L_{B9}$ |
| II-525. | $L_{A32}$ | $L_{B9}$ |
| II-526. | $L_{A33}$ | $L_{B9}$ |
| II-527. | $L_{A34}$ | $L_{B9}$ |
| II-528. | $L_{A35}$ | $L_{B9}$ |
| II-529. | $L_{A37}$ | $L_{B9}$ |
| II-530. | $L_{A38}$ | $L_{B9}$ |
| II-531. | $L_{A39}$ | $L_{B9}$ |
| II-532. | $L_{A40}$ | $L_{B9}$ |
| II-533. | $L_{A41}$ | $L_{B9}$ |
| II-534. | $L_{A42}$ | $L_{B9}$ |
| II-535. | $L_{A43}$ | $L_{B9}$ |
| II-536. | $L_{A44}$ | $L_{B9}$ |
| II-537. | $L_{A45}$ | $L_{B9}$ |
| II-538. | $L_{A46}$ | $L_{B9}$ |
| II-539. | $L_{A47}$ | $L_{B9}$ |
| II-540. | $L_{A48}$ | $L_{B9}$ |
| II-541. | $L_{A49}$ | $L_{B9}$ |
| II-542. | $L_{A50}$ | $L_{B9}$ |
| II-543. | $L_{A51}$ | $L_{B9}$ |
| II-544. | $L_{A52}$ | $L_{B9}$ |
| II-545. | $L_{A54}$ | $L_{B9}$ |
| II-546. | $L_{A55}$ | $L_{B9}$ |
| II-547. | $L_{A56}$ | $L_{B9}$ |
| II-548. | $L_{A57}$ | $L_{B9}$ |
| II-549. | $L_{A58}$ | $L_{B9}$ |
| II-550. | $L_{A59}$ | $L_{B9}$ |
| II-551. | $L_{A60}$ | $L_{B9}$ |
| II-552. | $L_{A61}$ | $L_{B9}$ |
| II-553. | $L_{A62}$ | $L_{B9}$ |
| II-554. | $L_{A63}$ | $L_{B9}$ |
| II-555. | $L_{A64}$ | $L_{B9}$ |
| II-556. | $L_{A65}$ | $L_{B9}$ |
| II-557. | $L_{A66}$ | $L_{B9}$ |
| II-558. | $L_{A67}$ | $L_{B9}$ |
| II-559. | $L_{A68}$ | $L_{B9}$ |
| II-560. | $L_{A69}$ | $L_{B9}$ |
| II-561. | $L_{A1}$ | $L_{B10}$ |
| II-562. | $L_{A2}$ | $L_{B10}$ |
| II-563. | $L_{A3}$ | $L_{B10}$ |
| II-564. | $L_{A4}$ | $L_{B10}$ |
| II-565. | $L_{A5}$ | $L_{B10}$ |
| II-566. | $L_{A6}$ | $L_{B10}$ |
| II-567. | $L_{A7}$ | $L_{B10}$ |
| II-568. | $L_{A8}$ | $L_{B10}$ |
| II-569. | $L_{A9}$ | $L_{B10}$ |
| II-570. | $L_{A10}$ | $L_{B10}$ |
| II-571. | $L_{A11}$ | $L_{B10}$ |
| II-572. | $L_{A12}$ | $L_{B10}$ |
| II-573. | $L_{A13}$ | $L_{B10}$ |
| II-574. | $L_{A14}$ | $L_{B10}$ |
| II-575. | $L_{A15}$ | $L_{B10}$ |
| II-576. | $L_{A16}$ | $L_{B10}$ |
| II-577. | $L_{A17}$ | $L_{B10}$ |
| II-578. | $L_{A18}$ | $L_{B10}$ |
| II-579. | $L_{A19}$ | $L_{B10}$ |
| II-580. | $L_{A20}$ | $L_{B10}$ |
| II-581. | $L_{A21}$ | $L_{B10}$ |
| II-582. | $L_{A22}$ | $L_{B10}$ |
| II-583. | $L_{A23}$ | $L_{B10}$ |
| II-584. | $L_{A24}$ | $L_{B10}$ |
| II-585. | $L_{A25}$ | $L_{B10}$ |
| II-586. | $L_{A26}$ | $L_{B10}$ |
| II-587. | $L_{A27}$ | $L_{B10}$ |
| II-588. | $L_{A28}$ | $L_{B10}$ |
| II-589. | $L_{A29}$ | $L_{B10}$ |

| Compound Number | $L_A$ | $L_B$ |
|---|---|---|
| II-590. | $L_{A30}$ | $L_{B10}$ |
| II-591. | $L_{A31}$ | $L_{B10}$ |
| II-592. | $L_{A32}$ | $L_{B10}$ |
| II-593. | $L_{A33}$ | $L_{B10}$ |
| II-594. | $L_{A34}$ | $L_{B10}$ |
| II-595. | $L_{A35}$ | $L_{B10}$ |
| II-596. | $L_{A36}$ | $L_{B10}$ |
| II-597. | $L_{A37}$ | $L_{B10}$ |
| II-598. | $L_{A38}$ | $L_{B10}$ |
| II-599. | $L_{A39}$ | $L_{B10}$ |
| II-600. | $L_{A40}$ | $L_{B10}$ |
| II-601. | $L_{A41}$ | $L_{B10}$ |
| II-602. | $L_{A42}$ | $L_{B10}$ |
| II-603. | $L_{A43}$ | $L_{B10}$ |
| II-604. | $L_{A44}$ | $L_{B10}$ |
| II-605. | $L_{A45}$ | $L_{B10}$ |
| II-606. | $L_{A46}$ | $L_{B10}$ |
| II-607. | $L_{A47}$ | $L_{B10}$ |
| II-608. | $L_{A48}$ | $L_{B10}$ |
| II-609. | $L_{A49}$ | $L_{B10}$ |
| II-610. | $L_{A50}$ | $L_{B10}$ |
| II-611. | $L_{A51}$ | $L_{B10}$ |
| II-612. | $L_{A52}$ | $L_{B10}$ |
| II-613. | $L_{A53}$ | $L_{B10}$ |
| II-614. | $L_{A54}$ | $L_{B10}$ |
| II-615. | $L_{A55}$ | $L_{B10}$ |
| II-616. | $L_{A56}$ | $L_{B10}$ |
| II-617. | $L_{A57}$ | $L_{B10}$ |
| II-618. | $L_{A58}$ | $L_{B10}$ |
| II-619. | $L_{A59}$ | $L_{B10}$ |
| II-620. | $L_{A60}$ | $L_{B10}$ |
| II-621. | $L_{A61}$ | $L_{B10}$ |
| II-622. | $L_{A62}$ | $L_{B10}$ |
| II-623. | $L_{A63}$ | $L_{B10}$ |
| II-624. | $L_{A64}$ | $L_{B10}$ |
| II-625. | $L_{A65}$ | $L_{B10}$ |
| II-626. | $L_{A66}$ | $L_{B10}$ |
| II-627. | $L_{A67}$ | $L_{B10}$ |
| II-628. | $L_{A68}$ | $L_{B10}$ |
| II-629. | $L_{A69}$ | $L_{B10}$ |
| II-630. | $L_{A1}$ | $L_{B11}$ |
| II-631. | $L_{A2}$ | $L_{B11}$ |
| II-632. | $L_{A3}$ | $L_{B11}$ |
| II-633. | $L_{A4}$ | $L_{B11}$ |
| II-634. | $L_{A5}$ | $L_{B11}$ |
| II-635. | $L_{A6}$ | $L_{B11}$ |
| II-636. | $L_{A7}$ | $L_{B11}$ |
| II-637. | $L_{A8}$ | $L_{B11}$ |
| II-638. | $L_{A9}$ | $L_{B11}$ |
| II-639. | $L_{A10}$ | $L_{B11}$ |
| II-640. | $L_{A11}$ | $L_{B11}$ |
| II-641. | $L_{A12}$ | $L_{B11}$ |
| II-642. | $L_{A13}$ | $L_{B11}$ |
| II-643. | $L_{A14}$ | $L_{B11}$ |
| II-644. | $L_{A15}$ | $L_{B11}$ |
| II-645. | $L_{A16}$ | $L_{B11}$ |
| II-646. | $L_{A17}$ | $L_{B11}$ |
| II-647. | $L_{A18}$ | $L_{B11}$ |
| II-648. | $L_{A19}$ | $L_{B11}$ |
| II-649. | $L_{A20}$ | $L_{B11}$ |
| II-650. | $L_{A21}$ | $L_{B11}$ |
| II-651. | $L_{A22}$ | $L_{B11}$ |
| II-652. | $L_{A23}$ | $L_{B11}$ |
| II-653. | $L_{A24}$ | $L_{B11}$ |
| II-654. | $L_{A25}$ | $L_{B11}$ |
| II-655. | $L_{A26}$ | $L_{B11}$ |
| II-656. | $L_{A27}$ | $L_{B11}$ |
| II-657. | $L_{A28}$ | $L_{B11}$ |
| II-658. | $L_{A29}$ | $L_{B11}$ |
| II-659. | $L_{A30}$ | $L_{B11}$ |
| II-660. | $L_{A31}$ | $L_{B11}$ |
| II-661. | $L_{A32}$ | $L_{B11}$ |
| II-662. | $L_{A33}$ | $L_{B11}$ |
| II-663. | $L_{A34}$ | $L_{B11}$ |
| II-664. | $L_{A35}$ | $L_{B11}$ |
| II-665. | $L_{A36}$ | $L_{B11}$ |
| II-666. | $L_{A37}$ | $L_{B11}$ |
| II-667. | $L_{A38}$ | $L_{B11}$ |
| II-668. | $L_{A39}$ | $L_{B11}$ |
| II-669. | $L_{A40}$ | $L_{B11}$ |
| II-670. | $L_{A41}$ | $L_{B11}$ |
| II-671. | $L_{A42}$ | $L_{B11}$ |
| II-672. | $L_{A43}$ | $L_{B11}$ |
| II-673. | $L_{A44}$ | $L_{B11}$ |
| II-674. | $L_{A45}$ | $L_{B11}$ |
| II-675. | $L_{A46}$ | $L_{B11}$ |
| II-676. | $L_{A47}$ | $L_{B11}$ |
| II-677. | $L_{A48}$ | $L_{B11}$ |
| II-678. | $L_{A49}$ | $L_{B11}$ |
| II-679. | $L_{A50}$ | $L_{B11}$ |
| II-680. | $L_{A51}$ | $L_{B11}$ |
| II-681. | $L_{A52}$ | $L_{B11}$ |
| II-682. | $L_{A53}$ | $L_{B11}$ |
| II-683. | $L_{A54}$ | $L_{B11}$ |
| II-684. | $L_{A55}$ | $L_{B11}$ |
| II-685. | $L_{A56}$ | $L_{B11}$ |
| II-686. | $L_{A57}$ | $L_{B11}$ |
| II-687. | $L_{A58}$ | $L_{B11}$ |
| II-688. | $L_{A59}$ | $L_{B11}$ |
| II-689. | $L_{A60}$ | $L_{B11}$ |
| II-690. | $L_{A61}$ | $L_{B11}$ |
| II-691. | $L_{A62}$ | $L_{B11}$ |
| II-692. | $L_{A63}$ | $L_{B11}$ |
| II-693. | $L_{A64}$ | $L_{B11}$ |
| II-694. | $L_{A65}$ | $L_{B11}$ |
| II-695. | $L_{A66}$ | $L_{B11}$ |
| II-696. | $L_{A67}$ | $L_{B11}$ |
| II-697. | $L_{A68}$ | $L_{B11}$ |
| II-698. | $L_{A69}$ | $L_{B11}$ |
| II-699. | $L_{A3}$ | $L_{B12}$ |
| II-700. | $L_{A4}$ | $L_{B12}$ |
| II-701. | $L_{A5}$ | $L_{B12}$ |
| II-702. | $L_{A6}$ | $L_{B12}$ |
| II-703. | $L_{A7}$ | $L_{B12}$ |
| II-704. | $L_{A8}$ | $L_{B12}$ |
| II-705. | $L_{A9}$ | $L_{B12}$ |
| II-706. | $L_{A10}$ | $L_{B12}$ |
| II-707. | $L_{A11}$ | $L_{B12}$ |
| II-708. | $L_{A12}$ | $L_{B12}$ |
| II-709. | $L_{A13}$ | $L_{B12}$ |
| II-710. | $L_{A14}$ | $L_{B12}$ |
| II-711. | $L_{A15}$ | $L_{B12}$ |
| II-712. | $L_{A16}$ | $L_{B12}$ |
| II-713. | $L_{A17}$ | $L_{B12}$ |
| II-714. | $L_{A18}$ | $L_{B12}$ |
| II-715. | $L_{A21}$ | $L_{B12}$ |
| II-716. | $L_{A22}$ | $L_{B12}$ |
| II-717. | $L_{A23}$ | $L_{B12}$ |
| II-718. | $L_{A24}$ | $L_{B12}$ |
| II-719. | $L_{A25}$ | $L_{B12}$ |
| II-720. | $L_{A26}$ | $L_{B12}$ |
| II-721. | $L_{A27}$ | $L_{B12}$ |
| II-722. | $L_{A28}$ | $L_{B12}$ |
| II-723. | $L_{A29}$ | $L_{B12}$ |
| II-724. | $L_{A30}$ | $L_{B12}$ |
| II-725. | $L_{A31}$ | $L_{B12}$ |
| II-726. | $L_{A32}$ | $L_{B12}$ |
| II-727. | $L_{A33}$ | $L_{B12}$ |
| II-728. | $L_{A34}$ | $L_{B12}$ |
| II-729. | $L_{A35}$ | $L_{B12}$ |
| II-730. | $L_{A36}$ | $L_{B12}$ |
| II-731. | $L_{A37}$ | $L_{B12}$ |
| II-732. | $L_{A38}$ | $L_{B12}$ |
| II-733. | $L_{A40}$ | $L_{B12}$ |
| II-734. | $L_{A41}$ | $L_{B12}$ |
| II-735. | $L_{A42}$ | $L_{B12}$ |
| II-736. | $L_{A43}$ | $L_{B12}$ |
| II-737. | $L_{A44}$ | $L_{B12}$ |
| II-738. | $L_{A45}$ | $L_{B12}$ |
| II-739. | $L_{A46}$ | $L_{B12}$ |
| II-740. | $L_{A47}$ | $L_{B12}$ |
| II-741. | $L_{A48}$ | $L_{B12}$ |

-continued

| Compound Number | $L_A$ | $L_B$ |
|---|---|---|
| II-742. | $L_{A49}$ | $L_{B12}$ |
| II-743. | $L_{A50}$ | $L_{B12}$ |
| II-744. | $L_{A51}$ | $L_{B12}$ |
| II-745. | $L_{A52}$ | $L_{B12}$ |
| II-746. | $L_{A54}$ | $L_{B12}$ |
| II-747. | $L_{A55}$ | $L_{B12}$ |
| II-748. | $L_{A56}$ | $L_{B12}$ |
| II-749. | $L_{A57}$ | $L_{B12}$ |
| II-750. | $L_{A58}$ | $L_{B12}$ |
| II-751. | $L_{A59}$ | $L_{B12}$ |
| II-752. | $L_{A60}$ | $L_{B12}$ |
| II-753. | $L_{A61}$ | $L_{B12}$ |
| II-754. | $L_{A62}$ | $L_{B12}$ |
| II-755. | $L_{A63}$ | $L_{B12}$ |
| II-756. | $L_{A64}$ | $L_{B12}$ |
| II-757. | $L_{A65}$ | $L_{B12}$ |
| II-758. | $L_{A66}$ | $L_{B12}$ |
| II-759. | $L_{A67}$ | $L_{B12}$ |
| II-760. | $L_{A68}$ | $L_{B12}$ |
| II-761. | $L_{A69}$ | $L_{B12}$ |
| II-762. | $L_{A1}$ | $L_{B13}$ |
| II-763. | $L_{A2}$ | $L_{B13}$ |
| II-764. | $L_{A3}$ | $L_{B13}$ |
| II-765. | $L_{A4}$ | $L_{B13}$ |
| II-766. | $L_{A5}$ | $L_{B13}$ |
| II-767. | $L_{A6}$ | $L_{B13}$ |
| II-768. | $L_{A7}$ | $L_{B13}$ |
| II-769. | $L_{A8}$ | $L_{B13}$ |
| II-770. | $L_{A9}$ | $L_{B13}$ |
| II-771. | $L_{A10}$ | $L_{B13}$ |
| II-772. | $L_{A11}$ | $L_{B13}$ |
| II-773. | $L_{A12}$ | $L_{B13}$ |
| II-774. | $L_{A13}$ | $L_{B13}$ |
| II-775. | $L_{A14}$ | $L_{B13}$ |
| II-776. | $L_{A15}$ | $L_{B13}$ |
| II-777. | $L_{A16}$ | $L_{B13}$ |
| II-778. | $L_{A17}$ | $L_{B13}$ |
| II-779. | $L_{A18}$ | $L_{B13}$ |
| II-780. | $L_{A19}$ | $L_{B13}$ |
| II-781. | $L_{A20}$ | $L_{B13}$ |
| II-782. | $L_{A21}$ | $L_{B13}$ |
| II-783. | $L_{A22}$ | $L_{B13}$ |
| II-784. | $L_{A23}$ | $L_{B13}$ |
| II-785. | $L_{A24}$ | $L_{B13}$ |
| II-786. | $L_{A25}$ | $L_{B13}$ |
| II-787. | $L_{A26}$ | $L_{B13}$ |
| II-788. | $L_{A27}$ | $L_{B13}$ |
| II-789. | $L_{A28}$ | $L_{B13}$ |
| II-790. | $L_{A29}$ | $L_{B13}$ |
| II-791. | $L_{A30}$ | $L_{B13}$ |
| II-792. | $L_{A31}$ | $L_{B13}$ |
| II-793. | $L_{A32}$ | $L_{B13}$ |
| II-794. | $L_{A33}$ | $L_{B13}$ |
| II-795. | $L_{A34}$ | $L_{B13}$ |
| II-796. | $L_{A35}$ | $L_{B13}$ |
| II-797. | $L_{A36}$ | $L_{B13}$ |
| II-798. | $L_{A37}$ | $L_{B13}$ |
| II-799. | $L_{A38}$ | $L_{B13}$ |
| II-800. | $L_{A39}$ | $L_{B13}$ |
| II-801. | $L_{A40}$ | $L_{B13}$ |
| II-802. | $L_{A41}$ | $L_{B13}$ |
| II-803. | $L_{A42}$ | $L_{B13}$ |
| II-804. | $L_{A43}$ | $L_{B13}$ |
| II-805. | $L_{A44}$ | $L_{B13}$ |
| II-806. | $L_{A45}$ | $L_{B13}$ |
| II-807. | $L_{A46}$ | $L_{B13}$ |
| II-808. | $L_{A47}$ | $L_{B13}$ |
| II-809. | $L_{A48}$ | $L_{B13}$ |
| II-810. | $L_{A49}$ | $L_{B13}$ |
| II-811. | $L_{A50}$ | $L_{B13}$ |
| II-812. | $L_{A51}$ | $L_{B13}$ |
| II-813. | $L_{A52}$ | $L_{B13}$ |
| II-814. | $L_{A53}$ | $L_{B13}$ |
| II-815. | $L_{A54}$ | $L_{B13}$ |
| II-816. | $L_{A55}$ | $L_{B13}$ |
| II-817. | $L_{A56}$ | $L_{B13}$ |

-continued

| Compound Number | $L_A$ | $L_B$ |
|---|---|---|
| II-818. | $L_{A57}$ | $L_{B13}$ |
| II-819. | $L_{A58}$ | $L_{B13}$ |
| II-820. | $L_{A59}$ | $L_{B13}$ |
| II-821. | $L_{A60}$ | $L_{B13}$ |
| II-822. | $L_{A61}$ | $L_{B13}$ |
| II-823. | $L_{A62}$ | $L_{B13}$ |
| II-824. | $L_{A63}$ | $L_{B13}$ |
| II-825. | $L_{A64}$ | $L_{B13}$ |
| II-826. | $L_{A65}$ | $L_{B13}$ |
| II-827. | $L_{A66}$ | $L_{B13}$ |
| II-828. | $L_{A67}$ | $L_{B13}$ |
| II-829. | $L_{A68}$ | $L_{B13}$ |
| II-830. | $L_{A69}$ | $L_{B13}$ |
| II-831. | $L_{A1}$ | $L_{B14}$ |
| II-832. | $L_{A2}$ | $L_{B14}$ |
| II-833. | $L_{A3}$ | $L_{B14}$ |
| II-834. | $L_{A4}$ | $L_{B14}$ |
| II-835. | $L_{A5}$ | $L_{B14}$ |
| II-836. | $L_{A6}$ | $L_{B14}$ |
| II-837. | $L_{A7}$ | $L_{B14}$ |
| II-838. | $L_{A8}$ | $L_{B14}$ |
| II-839. | $L_{A9}$ | $L_{B14}$ |
| II-840. | $L_{A10}$ | $L_{B14}$ |
| II-841. | $L_{A11}$ | $L_{B14}$ |
| II-842. | $L_{A12}$ | $L_{B14}$ |
| II-843. | $L_{A13}$ | $L_{B14}$ |
| II-844. | $L_{A14}$ | $L_{B14}$ |
| II-845. | $L_{A15}$ | $L_{B14}$ |
| II-846. | $L_{A16}$ | $L_{B14}$ |
| II-847. | $L_{A17}$ | $L_{B14}$ |
| II-848. | $L_{A18}$ | $L_{B14}$ |
| II-849. | $L_{A19}$ | $L_{B14}$ |
| II-850. | $L_{A20}$ | $L_{B14}$ |
| II-851. | $L_{A21}$ | $L_{B14}$ |
| II-852. | $L_{A22}$ | $L_{B14}$ |
| II-853. | $L_{A23}$ | $L_{B14}$ |
| II-854. | $L_{A24}$ | $L_{B14}$ |
| II-855. | $L_{A25}$ | $L_{B14}$ |
| II-856. | $L_{A26}$ | $L_{B14}$ |
| II-857. | $L_{A27}$ | $L_{B14}$ |
| II-858. | $L_{A28}$ | $L_{B14}$ |
| II-859. | $L_{A29}$ | $L_{B14}$ |
| II-860. | $L_{A30}$ | $L_{B14}$ |
| II-861. | $L_{A31}$ | $L_{B14}$ |
| II-862. | $L_{A32}$ | $L_{B14}$ |
| II-863. | $L_{A33}$ | $L_{B14}$ |
| II-864. | $L_{A34}$ | $L_{B14}$ |
| II-865. | $L_{A35}$ | $L_{B14}$ |
| II-866. | $L_{A36}$ | $L_{B14}$ |
| II-867. | $L_{A37}$ | $L_{B14}$ |
| II-868. | $L_{A38}$ | $L_{B14}$ |
| II-869. | $L_{A39}$ | $L_{B14}$ |
| II-870. | $L_{A40}$ | $L_{B14}$ |
| II-871. | $L_{A41}$ | $L_{B14}$ |
| II-872. | $L_{A42}$ | $L_{B14}$ |
| II-873. | $L_{A43}$ | $L_{B14}$ |
| II-874. | $L_{A44}$ | $L_{B14}$ |
| II-875. | $L_{A45}$ | $L_{B14}$ |
| II-876. | $L_{A46}$ | $L_{B14}$ |
| II-877. | $L_{A47}$ | $L_{B14}$ |
| II-878. | $L_{A48}$ | $L_{B14}$ |
| II-879. | $L_{A49}$ | $L_{B14}$ |
| II-880. | $L_{A50}$ | $L_{B14}$ |
| II-881. | $L_{A51}$ | $L_{B14}$ |
| II-882. | $L_{A52}$ | $L_{B14}$ |
| II-883. | $L_{A53}$ | $L_{B14}$ |
| II-884. | $L_{A54}$ | $L_{B14}$ |
| II-885. | $L_{A55}$ | $L_{B14}$ |
| II-886. | $L_{A56}$ | $L_{B14}$ |
| II-887. | $L_{A57}$ | $L_{B14}$ |
| II-888. | $L_{A58}$ | $L_{B14}$ |
| II-889. | $L_{A59}$ | $L_{B14}$ |
| II-890. | $L_{A60}$ | $L_{B14}$ |
| II-891. | $L_{A61}$ | $L_{B14}$ |
| II-892. | $L_{A62}$ | $L_{B14}$ |
| II-893. | $L_{A63}$ | $L_{B14}$ |

| Compound Number | $L_A$ | $L_B$ |
|---|---|---|
| II-894. | $L_{A64}$ | $L_{B14}$ |
| II-895. | $L_{A65}$ | $L_{B14}$ |
| II-896. | $L_{A66}$ | $L_{B14}$ |
| II-897. | $L_{A67}$ | $L_{B14}$ |
| II-898. | $L_{A68}$ | $L_{B14}$ |
| II-899. | $L_{A69}$ | $L_{B14}$ |
| II-900. | $L_{A1}$ | $L_{B15}$ |
| II-901. | $L_{A2}$ | $L_{B15}$ |
| II-902. | $L_{A3}$ | $L_{B15}$ |
| II-903. | $L_{A4}$ | $L_{B15}$ |
| II-904. | $L_{A5}$ | $L_{B15}$ |
| II-905. | $L_{A6}$ | $L_{B15}$ |
| II-906. | $L_{A7}$ | $L_{B15}$ |
| II-907. | $L_{A8}$ | $L_{B15}$ |
| II-908. | $L_{A9}$ | $L_{B15}$ |
| II-909. | $L_{A10}$ | $L_{B15}$ |
| II-910. | $L_{A11}$ | $L_{B15}$ |
| II-911. | $L_{A12}$ | $L_{B15}$ |
| II-912. | $L_{A13}$ | $L_{B15}$ |
| II-913. | $L_{A14}$ | $L_{B15}$ |
| II-914. | $L_{A15}$ | $L_{B15}$ |
| II-915. | $L_{A16}$ | $L_{B15}$ |
| II-916. | $L_{A17}$ | $L_{B15}$ |
| II-917. | $L_{A18}$ | $L_{B15}$ |
| II-918. | $L_{A19}$ | $L_{B15}$ |
| II-919. | $L_{A20}$ | $L_{B15}$ |
| II-920. | $L_{A21}$ | $L_{B15}$ |
| II-921. | $L_{A22}$ | $L_{B15}$ |
| II-922. | $L_{A23}$ | $L_{B15}$ |
| II-923. | $L_{A24}$ | $L_{B15}$ |
| II-924. | $L_{A25}$ | $L_{B15}$ |
| II-1387. | $L_{A26}$ | $L_{B15}$ |
| II-1388. | $L_{A27}$ | $L_{B15}$ |
| II-1389. | $L_{A28}$ | $L_{B15}$ |
| II-1390. | $L_{A29}$ | $L_{B15}$ |
| II-1391. | $L_{A30}$ | $L_{B15}$ |
| II-1392. | $L_{A31}$ | $L_{B15}$ |
| II-1393. | $L_{A32}$ | $L_{B15}$ |
| II-1394. | $L_{A33}$ | $L_{B15}$ |
| II-1395. | $L_{A34}$ | $L_{B15}$ |
| II-1396. | $L_{A35}$ | $L_{B15}$ |
| II-1397. | $L_{A36}$ | $L_{B15}$ |
| II-1398. | $L_{A37}$ | $L_{B15}$ |
| II-1399. | $L_{A38}$ | $L_{B15}$ |
| II-1400. | $L_{A39}$ | $L_{B15}$ |
| II-1401. | $L_{A40}$ | $L_{B15}$ |
| II-1402. | $L_{A41}$ | $L_{B15}$ |
| II-1403. | $L_{A42}$ | $L_{B15}$ |
| II-1404. | $L_{A43}$ | $L_{B15}$ |
| II-1405. | $L_{A44}$ | $L_{B15}$ |
| II-1406. | $L_{A45}$ | $L_{B15}$ |
| II-1407. | $L_{A46}$ | $L_{B15}$ |
| II-1408. | $L_{A47}$ | $L_{B15}$ |
| II-1409. | $L_{A48}$ | $L_{B15}$ |
| II-1410. | $L_{A49}$ | $L_{B15}$ |
| II-1411. | $L_{A50}$ | $L_{B15}$ |
| II-1412. | $L_{A51}$ | $L_{B15}$ |
| II-1413. | $L_{A52}$ | $L_{B15}$ |
| II-1414. | $L_{A53}$ | $L_{B15}$ |
| II-1415. | $L_{A54}$ | $L_{B15}$ |
| II-1416. | $L_{A55}$ | $L_{B15}$ |
| II-1417. | $L_{A56}$ | $L_{B15}$ |
| II-1418. | $L_{A57}$ | $L_{B15}$ |
| II-1419. | $L_{A58}$ | $L_{B15}$ |
| II-1420. | $L_{A59}$ | $L_{B15}$ |
| II-1421. | $L_{A60}$ | $L_{B15}$ |
| II-1422. | $L_{A61}$ | $L_{B15}$ |
| II-1423. | $L_{A62}$ | $L_{B15}$ |
| II-1424. | $L_{A63}$ | $L_{B15}$ |
| II-1425. | $L_{A64}$ | $L_{B15}$ |
| II-1426. | $L_{A65}$ | $L_{B15}$ |
| II-1427. | $L_{A66}$ | $L_{B15}$ |
| II-1428. | $L_{A67}$ | $L_{B15}$ |
| II-1429. | $L_{A68}$ | $L_{B15}$ |
| II-1430. | $L_{A69}$ | $L_{B15}$ |
| II-1431. | $L_{A3}$ | $L_{B16}$ |
| II-1432. | $L_{A4}$ | $L_{B16}$ |
| II-1433. | $L_{A5}$ | $L_{B16}$ |
| II-1434. | $L_{A6}$ | $L_{B16}$ |
| II-1435. | $L_{A7}$ | $L_{B16}$ |
| II-1436. | $L_{A8}$ | $L_{B16}$ |
| II-1437. | $L_{A9}$ | $L_{B16}$ |
| II-1438. | $L_{A10}$ | $L_{B16}$ |
| II-1439. | $L_{A11}$ | $L_{B16}$ |
| II-1440. | $L_{A12}$ | $L_{B16}$ |
| II-1441. | $L_{A13}$ | $L_{B16}$ |
| II-1442. | $L_{A14}$ | $L_{B16}$ |
| II-1443. | $L_{A15}$ | $L_{B16}$ |
| II-1444. | $L_{A16}$ | $L_{B16}$ |
| II-1445. | $L_{A17}$ | $L_{B16}$ |
| II-1446. | $L_{A18}$ | $L_{B16}$ |
| II-1447. | $L_{A21}$ | $L_{B16}$ |
| II-1448. | $L_{A22}$ | $L_{B16}$ |
| II-1449. | $L_{A23}$ | $L_{B16}$ |
| II-1450. | $L_{A24}$ | $L_{B16}$ |
| II-1451. | $L_{A25}$ | $L_{B16}$ |
| II-1452. | $L_{A26}$ | $L_{B16}$ |
| II-1453. | $L_{A27}$ | $L_{B16}$ |
| II-1454. | $L_{A28}$ | $L_{B16}$ |
| II-1455. | $L_{A29}$ | $L_{B16}$ |
| II-1456. | $L_{A30}$ | $L_{B16}$ |
| II-1457. | $L_{A31}$ | $L_{B16}$ |
| II-1458. | $L_{A32}$ | $L_{B16}$ |
| II-1459. | $L_{A33}$ | $L_{B16}$ |
| II-1460. | $L_{A34}$ | $L_{B16}$ |
| II-1461. | $L_{A35}$ | $L_{B16}$ |
| II-1462. | $L_{A37}$ | $L_{B16}$ |
| II-1463. | $L_{A38}$ | $L_{B16}$ |
| II-1464. | $L_{A39}$ | $L_{B16}$ |
| II-1465. | $L_{A40}$ | $L_{B16}$ |
| II-1466. | $L_{A41}$ | $L_{B16}$ |
| II-1467. | $L_{A42}$ | $L_{B16}$ |
| II-1468. | $L_{A43}$ | $L_{B16}$ |
| II-1469. | $L_{A44}$ | $L_{B16}$ |
| II-1470. | $L_{A45}$ | $L_{B16}$ |
| II-1471. | $L_{A46}$ | $L_{B16}$ |
| II-1472. | $L_{A47}$ | $L_{B16}$ |
| II-1473. | $L_{A48}$ | $L_{B16}$ |
| II-1474. | $L_{A49}$ | $L_{B16}$ |
| II-1475. | $L_{A50}$ | $L_{B16}$ |
| II-1476. | $L_{A51}$ | $L_{B16}$ |
| II-1477. | $L_{A52}$ | $L_{B16}$ |
| II-1478. | $L_{A54}$ | $L_{B16}$ |
| II-1479. | $L_{A55}$ | $L_{B16}$ |
| II-1480. | $L_{A56}$ | $L_{B16}$ |
| II-1481. | $L_{A57}$ | $L_{B16}$ |
| II-1482. | $L_{A58}$ | $L_{B16}$ |
| II-1483. | $L_{A59}$ | $L_{B16}$ |
| II-1484. | $L_{A60}$ | $L_{B16}$ |
| II-1485. | $L_{A61}$ | $L_{B16}$ |
| II-1486. | $L_{A62}$ | $L_{B16}$ |
| II-1487. | $L_{A63}$ | $L_{B16}$ |
| II-1488. | $L_{A64}$ | $L_{B16}$ |
| II-1489. | $L_{A65}$ | $L_{B16}$ |
| II-1490. | $L_{A66}$ | $L_{B16}$ |
| II-1491. | $L_{A67}$ | $L_{B16}$ |
| II-1492. | $L_{A68}$ | $L_{B16}$ |
| II-1493. | $L_{A69}$ | $L_{B16}$ |
| II-1494. | $L_{A2}$ | $L_{B17}$ |
| II-1495. | $L_{A3}$ | $L_{B17}$ |
| II-1496. | $L_{A4}$ | $L_{B17}$ |
| II-1497. | $L_{A5}$ | $L_{B17}$ |
| II-1498. | $L_{A6}$ | $L_{B17}$ |
| II-1499. | $L_{A7}$ | $L_{B17}$ |
| II-1500. | $L_{A8}$ | $L_{B17}$ |
| II-1501. | $L_{A9}$ | $L_{B17}$ |
| II-1502. | $L_{A10}$ | $L_{B17}$ |
| II-1503. | $L_{A11}$ | $L_{B17}$ |
| II-1504. | $L_{A12}$ | $L_{B17}$ |
| II-1505. | $L_{A13}$ | $L_{B17}$ |
| II-1506. | $L_{A14}$ | $L_{B17}$ |
| II-1507. | $L_{A15}$ | $L_{B17}$ |

| Compound Number | $L_A$ | $L_B$ |
|---|---|---|
| II-1508. | $L_{A16}$ | $L_{B17}$ |
| II-1509. | $L_{A17}$ | $L_{B17}$ |
| II-1510. | $L_{A18}$ | $L_{B17}$ |
| II-1511. | $L_{A20}$ | $L_{B17}$ |
| II-1512. | $L_{A21}$ | $L_{B17}$ |
| II-1513. | $L_{A22}$ | $L_{B17}$ |
| II-1514. | $L_{A23}$ | $L_{B17}$ |
| II-1515. | $L_{A24}$ | $L_{B17}$ |
| II-1516. | $L_{A25}$ | $L_{B17}$ |
| II-1517. | $L_{A26}$ | $L_{B17}$ |
| II-1518. | $L_{A27}$ | $L_{B17}$ |
| II-1519. | $L_{A28}$ | $L_{B17}$ |
| II-1520. | $L_{A29}$ | $L_{B17}$ |
| II-1521. | $L_{A30}$ | $L_{B17}$ |
| II-1522. | $L_{A31}$ | $L_{B17}$ |
| II-1523. | $L_{A32}$ | $L_{B17}$ |
| II-1524. | $L_{A33}$ | $L_{B17}$ |
| II-1525. | $L_{A34}$ | $L_{B17}$ |
| II-1526. | $L_{A35}$ | $L_{B17}$ |
| II-1527. | $L_{A36}$ | $L_{B17}$ |
| II-1528. | $L_{A37}$ | $L_{B17}$ |
| II-1529. | $L_{A38}$ | $L_{B17}$ |
| II-1530. | $L_{A39}$ | $L_{B17}$ |
| II-1531. | $L_{A40}$ | $L_{B17}$ |
| II-1532. | $L_{A41}$ | $L_{B17}$ |
| II-1533. | $L_{A42}$ | $L_{B17}$ |
| II-1534. | $L_{A43}$ | $L_{B17}$ |
| II-1535. | $L_{A44}$ | $L_{B17}$ |
| II-1536. | $L_{A45}$ | $L_{B17}$ |
| II-1537. | $L_{A46}$ | $L_{B17}$ |
| II-1538. | $L_{A47}$ | $L_{B17}$ |
| II-1539. | $L_{A48}$ | $L_{B17}$ |
| II-1540. | $L_{A49}$ | $L_{B17}$ |
| II-1541. | $L_{A50}$ | $L_{B17}$ |
| II-1542. | $L_{A51}$ | $L_{B17}$ |
| II-1543. | $L_{A52}$ | $L_{B17}$ |
| II-1544. | $L_{A53}$ | $L_{B17}$ |
| II-1545. | $L_{A54}$ | $L_{B17}$ |
| II-1546. | $L_{A55}$ | $L_{B17}$ |
| II-1547. | $L_{A56}$ | $L_{B17}$ |
| II-1548. | $L_{A57}$ | $L_{B17}$ |
| II-1549. | $L_{A58}$ | $L_{B17}$ |
| II-1550. | $L_{A59}$ | $L_{B17}$ |
| II-1551. | $L_{A60}$ | $L_{B17}$ |
| II-1552. | $L_{A61}$ | $L_{B17}$ |
| II-1553. | $L_{A62}$ | $L_{B17}$ |
| II-1554. | $L_{A63}$ | $L_{B17}$ |
| II-1555. | $L_{A64}$ | $L_{B17}$ |
| II-1556. | $L_{A65}$ | $L_{B17}$ |
| II-1557. | $L_{A66}$ | $L_{B17}$ |
| II-1558. | $L_{A67}$ | $L_{B17}$ |
| II-1559. | $L_{A68}$ | $L_{B17}$ |
| II-1560. | $L_{A69}$ | $L_{B17}$ |
| II-1561. | $L_{A2}$ | $L_{B18}$ |
| II-1562. | $L_{A3}$ | $L_{B18}$ |
| II-1563. | $L_{A4}$ | $L_{B18}$ |
| II-1564. | $L_{A5}$ | $L_{B18}$ |
| II-1565. | $L_{A6}$ | $L_{B18}$ |
| II-1566. | $L_{A7}$ | $L_{B18}$ |
| II-1567. | $L_{A8}$ | $L_{B18}$ |
| II-1568. | $L_{A9}$ | $L_{B18}$ |
| II-1569. | $L_{A10}$ | $L_{B18}$ |
| II-1570. | $L_{A11}$ | $L_{B18}$ |
| II-1571. | $L_{A12}$ | $L_{B18}$ |
| II-1572. | $L_{A13}$ | $L_{B18}$ |
| II-1573. | $L_{A14}$ | $L_{B18}$ |
| II-1574. | $L_{A15}$ | $L_{B18}$ |
| II-1575. | $L_{A16}$ | $L_{B18}$ |
| II-1576. | $L_{A17}$ | $L_{B18}$ |
| II-1577. | $L_{A18}$ | $L_{B18}$ |
| II-1578. | $L_{A20}$ | $L_{B18}$ |
| II-1579. | $L_{A21}$ | $L_{B18}$ |
| II-1580. | $L_{A22}$ | $L_{B18}$ |
| II-1581. | $L_{A23}$ | $L_{B18}$ |
| II-1582. | $L_{A24}$ | $L_{B18}$ |
| II-1583. | $L_{A25}$ | $L_{B18}$ |
| II-1584. | $L_{A26}$ | $L_{B18}$ |
| II-1585. | $L_{A27}$ | $L_{B18}$ |
| II-1586. | $L_{A28}$ | $L_{B18}$ |
| II-1587. | $L_{A29}$ | $L_{B18}$ |
| II-1588. | $L_{A30}$ | $L_{B18}$ |
| II-1589. | $L_{A31}$ | $L_{B18}$ |
| II-1590. | $L_{A32}$ | $L_{B18}$ |
| II-1591. | $L_{A33}$ | $L_{B18}$ |
| II-1592. | $L_{A34}$ | $L_{B18}$ |
| II-1593. | $L_{A35}$ | $L_{B18}$ |
| II-1594. | $L_{A36}$ | $L_{B18}$ |
| II-1595. | $L_{A37}$ | $L_{B18}$ |
| II-1596. | $L_{A38}$ | $L_{B18}$ |
| II-1597. | $L_{A39}$ | $L_{B18}$ |
| II-1598. | $L_{A40}$ | $L_{B18}$ |
| II-1599. | $L_{A41}$ | $L_{B18}$ |
| II-1600. | $L_{A42}$ | $L_{B18}$ |
| II-1601. | $L_{A43}$ | $L_{B18}$ |
| II-1602. | $L_{A44}$ | $L_{B18}$ |
| II-1603. | $L_{A45}$ | $L_{B18}$ |
| II-1604. | $L_{A46}$ | $L_{B18}$ |
| II-1605. | $L_{A47}$ | $L_{B18}$ |
| II-1606. | $L_{A48}$ | $L_{B18}$ |
| II-1607. | $L_{A49}$ | $L_{B18}$ |
| II-1608. | $L_{A50}$ | $L_{B18}$ |
| II-1609. | $L_{A51}$ | $L_{B18}$ |
| II-1610. | $L_{A52}$ | $L_{B18}$ |
| II-1611. | $L_{A53}$ | $L_{B18}$ |
| II-1612. | $L_{A54}$ | $L_{B18}$ |
| II-1613. | $L_{A55}$ | $L_{B18}$ |
| II-1614. | $L_{A56}$ | $L_{B18}$ |
| II-1615. | $L_{A57}$ | $L_{B18}$ |
| II-1616. | $L_{A58}$ | $L_{B18}$ |
| II-1617. | $L_{A59}$ | $L_{B18}$ |
| II-1618. | $L_{A60}$ | $L_{B18}$ |
| II-1619. | $L_{A61}$ | $L_{B18}$ |
| II-1620. | $L_{A62}$ | $L_{B18}$ |
| II-1621. | $L_{A63}$ | $L_{B18}$ |
| II-1622. | $L_{A64}$ | $L_{B18}$ |
| II-1623. | $L_{A65}$ | $L_{B18}$ |
| II-1624. | $L_{A66}$ | $L_{B18}$ |
| II-1625. | $L_{A67}$ | $L_{B18}$ |
| II-1626. | $L_{A68}$ | $L_{B18}$ |
| II-1627. | $L_{A69}$ | $L_{B18}$ |
| II-1628. | $L_{A2}$ | $L_{B19}$ |
| II-1629. | $L_{A3}$ | $L_{B19}$ |
| II-1630. | $L_{A4}$ | $L_{B19}$ |
| II-1631. | $L_{A5}$ | $L_{B19}$ |
| II-1632. | $L_{A6}$ | $L_{B19}$ |
| II-1633. | $L_{A7}$ | $L_{B19}$ |
| II-1634. | $L_{A8}$ | $L_{B19}$ |
| II-1635. | $L_{A9}$ | $L_{B19}$ |
| II-1636. | $L_{A10}$ | $L_{B19}$ |
| II-1637. | $L_{A11}$ | $L_{B19}$ |
| II-1638. | $L_{A12}$ | $L_{B19}$ |
| II-1639. | $L_{A13}$ | $L_{B19}$ |
| II-1640. | $L_{A14}$ | $L_{B19}$ |
| II-1641. | $L_{A15}$ | $L_{B19}$ |
| II-1642. | $L_{A16}$ | $L_{B19}$ |
| II-1643. | $L_{A17}$ | $L_{B19}$ |
| II-1644. | $L_{A18}$ | $L_{B19}$ |
| II-1645. | $L_{A20}$ | $L_{B19}$ |
| II-1646. | $L_{A21}$ | $L_{B19}$ |
| II-1647. | $L_{A22}$ | $L_{B19}$ |
| II-1648. | $L_{A23}$ | $L_{B19}$ |
| II-1649. | $L_{A24}$ | $L_{B19}$ |
| II-1650. | $L_{A25}$ | $L_{B19}$ |
| II-1651. | $L_{A26}$ | $L_{B19}$ |
| II-1652. | $L_{A27}$ | $L_{B19}$ |
| II-1653. | $L_{A28}$ | $L_{B19}$ |
| II-1654. | $L_{A29}$ | $L_{B19}$ |
| II-1655. | $L_{A30}$ | $L_{B19}$ |
| II-1656. | $L_{A31}$ | $L_{B19}$ |
| II-1657. | $L_{A32}$ | $L_{B19}$ |
| II-1658. | $L_{A33}$ | $L_{B19}$ |
| II-1659. | $L_{A34}$ | $L_{B19}$ |

| Compound Number | $L_A$ | $L_B$ |
|---|---|---|
| II-1660. | $L_{A35}$ | $L_{B19}$ |
| II-1661. | $L_{A36}$ | $L_{B19}$ |
| II-1662. | $L_{A37}$ | $L_{B19}$ |
| II-1663. | $L_{A38}$ | $L_{B19}$ |
| II-1664. | $L_{A39}$ | $L_{B19}$ |
| II-1665. | $L_{A40}$ | $L_{B19}$ |
| II-1666. | $L_{A41}$ | $L_{B19}$ |
| II-1667. | $L_{A42}$ | $L_{B19}$ |
| II-1668. | $L_{A43}$ | $L_{B19}$ |
| II-1669. | $L_{A44}$ | $L_{B19}$ |
| II-1670. | $L_{A45}$ | $L_{B19}$ |
| II-1671. | $L_{A46}$ | $L_{B19}$ |
| II-1672. | $L_{A47}$ | $L_{B19}$ |
| II-1673. | $L_{A48}$ | $L_{B19}$ |
| II-1674. | $L_{A49}$ | $L_{B19}$ |
| II-1675. | $L_{A50}$ | $L_{B19}$ |
| II-1676. | $L_{A51}$ | $L_{B19}$ |
| II-1677. | $L_{A52}$ | $L_{B19}$ |
| II-1678. | $L_{A53}$ | $L_{B19}$ |
| II-1679. | $L_{A54}$ | $L_{B19}$ |
| II-1680. | $L_{A55}$ | $L_{B19}$ |
| II-1681. | $L_{A56}$ | $L_{B19}$ |
| II-1682. | $L_{A57}$ | $L_{B19}$ |
| II-1683. | $L_{A58}$ | $L_{B19}$ |
| II-1684. | $L_{A59}$ | $L_{B19}$ |
| II-1685. | $L_{A60}$ | $L_{B19}$ |
| II-1686. | $L_{A61}$ | $L_{B19}$ |
| II-1687. | $L_{A62}$ | $L_{B19}$ |
| II-1688. | $L_{A63}$ | $L_{B19}$ |
| II-1689. | $L_{A64}$ | $L_{B19}$ |
| II-1690. | $L_{A65}$ | $L_{B19}$ |
| II-1691. | $L_{A66}$ | $L_{B19}$ |
| II-1692. | $L_{A67}$ | $L_{B19}$ |
| II-1693. | $L_{A68}$ | $L_{B19}$ |
| II-1694. | $L_{A69}$ | $L_{B19}$ |
| II-1695. | $L_{A2}$ | $L_{B20}$ |
| II-1696. | $L_{A3}$ | $L_{B20}$ |
| II-1697. | $L_{A4}$ | $L_{B20}$ |
| II-1698. | $L_{A5}$ | $L_{B20}$ |
| II-1699. | $L_{A6}$ | $L_{B20}$ |
| II-1700. | $L_{A7}$ | $L_{B20}$ |
| II-1701. | $L_{A8}$ | $L_{B20}$ |
| II-1702. | $L_{A9}$ | $L_{B20}$ |
| II-1703. | $L_{A10}$ | $L_{B20}$ |
| II-1704. | $L_{A11}$ | $L_{B20}$ |
| II-1705. | $L_{A12}$ | $L_{B20}$ |
| II-1706. | $L_{A13}$ | $L_{B20}$ |
| II-1707. | $L_{A14}$ | $L_{B20}$ |
| II-1708. | $L_{A15}$ | $L_{B20}$ |
| II-1709. | $L_{A16}$ | $L_{B20}$ |
| II-1710. | $L_{A17}$ | $L_{B20}$ |
| II-1711. | $L_{A18}$ | $L_{B20}$ |
| II-1712. | $L_{A20}$ | $L_{B20}$ |
| II-1713. | $L_{A21}$ | $L_{B20}$ |
| II-1714. | $L_{A22}$ | $L_{B20}$ |
| II-1715. | $L_{A23}$ | $L_{B20}$ |
| II-1716. | $L_{A24}$ | $L_{B20}$ |
| II-1717. | $L_{A25}$ | $L_{B20}$ |
| II-1718. | $L_{A26}$ | $L_{B20}$ |
| II-1719. | $L_{A27}$ | $L_{B20}$ |
| II-1720. | $L_{A28}$ | $L_{B20}$ |
| II-1721. | $L_{A29}$ | $L_{B20}$ |
| II-1722. | $L_{A30}$ | $L_{B20}$ |
| II-1723. | $L_{A31}$ | $L_{B20}$ |
| II-1724. | $L_{A32}$ | $L_{B20}$ |
| II-1725. | $L_{A33}$ | $L_{B20}$ |
| II-1726. | $L_{A34}$ | $L_{B20}$ |
| II-1727. | $L_{A35}$ | $L_{B20}$ |
| II-1728. | $L_{A36}$ | $L_{B20}$ |
| II-1729. | $L_{A37}$ | $L_{B20}$ |
| II-1730. | $L_{A38}$ | $L_{B20}$ |
| II-1731. | $L_{A39}$ | $L_{B20}$ |
| II-1732. | $L_{A40}$ | $L_{B20}$ |
| II-1733. | $L_{A41}$ | $L_{B20}$ |
| II-1734. | $L_{A42}$ | $L_{B20}$ |
| II-1735. | $L_{A43}$ | $L_{B20}$ |
| II-1736. | $L_{A44}$ | $L_{B20}$ |
| II-1737. | $L_{A45}$ | $L_{B20}$ |
| II-1738. | $L_{A46}$ | $L_{B20}$ |
| II-1739. | $L_{A47}$ | $L_{B20}$ |
| II-1740. | $L_{A48}$ | $L_{B20}$ |
| II-1741. | $L_{A49}$ | $L_{B20}$ |
| II-1742. | $L_{A50}$ | $L_{B20}$ |
| II-1743. | $L_{A51}$ | $L_{B20}$ |
| II-1744. | $L_{A52}$ | $L_{B20}$ |
| II-1745. | $L_{A53}$ | $L_{B20}$ |
| II-1746. | $L_{A54}$ | $L_{B20}$ |
| II-1747. | $L_{A55}$ | $L_{B20}$ |
| II-1748. | $L_{A56}$ | $L_{B20}$ |
| II-1749. | $L_{A57}$ | $L_{B20}$ |
| II-1750. | $L_{A58}$ | $L_{B20}$ |
| II-1751. | $L_{A59}$ | $L_{B20}$ |
| II-1752. | $L_{A60}$ | $L_{B20}$ |
| II-1753. | $L_{A61}$ | $L_{B20}$ |
| II-1754. | $L_{A62}$ | $L_{B20}$ |
| II-1755. | $L_{A63}$ | $L_{B20}$ |
| II-1756. | $L_{A64}$ | $L_{B20}$ |
| II-1757. | $L_{A65}$ | $L_{B20}$ |
| II-1758. | $L_{A66}$ | $L_{B20}$ |
| II-1759. | $L_{A67}$ | $L_{B20}$ |
| II-1760. | $L_{A68}$ | $L_{B20}$ |
| II-1761. | $L_{A69}$ | $L_{B20}$ |
| II-1762. | $L_{A2}$ | $L_{B21}$ |
| II-1763. | $L_{A3}$ | $L_{B21}$ |
| II-1764. | $L_{A4}$ | $L_{B21}$ |
| II-1765. | $L_{A5}$ | $L_{B21}$ |
| II-1766. | $L_{A6}$ | $L_{B21}$ |
| II-1767. | $L_{A7}$ | $L_{B21}$ |
| II-1768. | $L_{A8}$ | $L_{B21}$ |
| II-1769. | $L_{A9}$ | $L_{B21}$ |
| II-1770. | $L_{A10}$ | $L_{B21}$ |
| II-1771. | $L_{A11}$ | $L_{B21}$ |
| II-1772. | $L_{A12}$ | $L_{B21}$ |
| II-1773. | $L_{A13}$ | $L_{B21}$ |
| II-1774. | $L_{A14}$ | $L_{B21}$ |
| II-1775. | $L_{A15}$ | $L_{B21}$ |
| II-1776. | $L_{A16}$ | $L_{B21}$ |
| II-1777. | $L_{A17}$ | $L_{B21}$ |
| II-1778. | $L_{A18}$ | $L_{B21}$ |
| II-1779. | $L_{A20}$ | $L_{B21}$ |
| II-1780. | $L_{A21}$ | $L_{B21}$ |
| II-1781. | $L_{A22}$ | $L_{B21}$ |
| II-1782. | $L_{A23}$ | $L_{B21}$ |
| II-1783. | $L_{A24}$ | $L_{B21}$ |
| II-1784. | $L_{A25}$ | $L_{B21}$ |
| II-1785. | $L_{A26}$ | $L_{B21}$ |
| II-1786. | $L_{A27}$ | $L_{B21}$ |
| II-1787. | $L_{A28}$ | $L_{B21}$ |
| II-1788. | $L_{A29}$ | $L_{B21}$ |
| II-1789. | $L_{A30}$ | $L_{B21}$ |
| II-1790. | $L_{A31}$ | $L_{B21}$ |
| II-1791. | $L_{A32}$ | $L_{B21}$ |
| II-1792. | $L_{A33}$ | $L_{B21}$ |
| II-1793. | $L_{A34}$ | $L_{B21}$ |
| II-1794. | $L_{A35}$ | $L_{B21}$ |
| II-1795. | $L_{A36}$ | $L_{B21}$ |
| II-1796. | $L_{A37}$ | $L_{B21}$ |
| II-1797. | $L_{A38}$ | $L_{B21}$ |
| II-1798. | $L_{A39}$ | $L_{B21}$ |
| II-1799. | $L_{A40}$ | $L_{B21}$ |
| II-1800. | $L_{A41}$ | $L_{B21}$ |
| II-1801. | $L_{A42}$ | $L_{B21}$ |
| II-1802. | $L_{A43}$ | $L_{B21}$ |
| II-1803. | $L_{A44}$ | $L_{B21}$ |
| II-1804. | $L_{A45}$ | $L_{B21}$ |
| II-1805. | $L_{A46}$ | $L_{B21}$ |
| II-1806. | $L_{A47}$ | $L_{B21}$ |
| II-1807. | $L_{A48}$ | $L_{B21}$ |
| II-1808. | $L_{A49}$ | $L_{B21}$ |
| II-1809. | $L_{A50}$ | $L_{B21}$ |
| II-1810. | $L_{A51}$ | $L_{B21}$ |
| II-1811. | $L_{A52}$ | $L_{B21}$ |

| Compound Number | $L_A$ | $L_B$ |
|---|---|---|
| II-1812. | $L_{A53}$ | $L_{B21}$ |
| II-1813. | $L_{A54}$ | $L_{B21}$ |
| II-1814. | $L_{A55}$ | $L_{B21}$ |
| II-1815. | $L_{A56}$ | $L_{B21}$ |
| II-1816. | $L_{A57}$ | $L_{B21}$ |
| II-1817. | $L_{A58}$ | $L_{B21}$ |
| II-1818. | $L_{A59}$ | $L_{B21}$ |
| II-1819. | $L_{A60}$ | $L_{B21}$ |
| II-1820. | $L_{A61}$ | $L_{B21}$ |
| II-1821. | $L_{A62}$ | $L_{B21}$ |
| II-1822. | $L_{A63}$ | $L_{B21}$ |
| II-1823. | $L_{A64}$ | $L_{B21}$ |
| II-1824. | $L_{A65}$ | $L_{B21}$ |
| II-1825. | $L_{A66}$ | $L_{B21}$ |
| II-1826. | $L_{A67}$ | $L_{B21}$ |
| II-1827. | $L_{A68}$ | $L_{B21}$ |
| II-1828. | $L_{A69}$ | $L_{B21}$ |
| II-1829. | $L_{A2}$ | $L_{B22}$ |
| II-1830. | $L_{A3}$ | $L_{B22}$ |
| II-1831. | $L_{A4}$ | $L_{B22}$ |
| II-1832. | $L_{A5}$ | $L_{B22}$ |
| II-1833. | $L_{A6}$ | $L_{B22}$ |
| II-1834. | $L_{A7}$ | $L_{B22}$ |
| II-1835. | $L_{A8}$ | $L_{B22}$ |
| II-1836. | $L_{A9}$ | $L_{B22}$ |
| II-1837. | $L_{A10}$ | $L_{B22}$ |
| II-1838. | $L_{A11}$ | $L_{B22}$ |
| II-1839. | $L_{A12}$ | $L_{B22}$ |
| II-1840. | $L_{A13}$ | $L_{B22}$ |
| II-1841. | $L_{A14}$ | $L_{B22}$ |
| II-1842. | $L_{A15}$ | $L_{B22}$ |
| II-1843. | $L_{A16}$ | $L_{B22}$ |
| II-1844. | $L_{A17}$ | $L_{B22}$ |
| II-1845. | $L_{A18}$ | $L_{B22}$ |
| II-1846. | $L_{A20}$ | $L_{B22}$ |
| II-1847. | $L_{A21}$ | $L_{B22}$ |
| II-1848. | $L_{A22}$ | $L_{B22}$ |
| II-1387. | $L_{A23}$ | $L_{B22}$ |
| II-1388. | $L_{A24}$ | $L_{B22}$ |
| II-1389. | $L_{A25}$ | $L_{B22}$ |
| II-1390. | $L_{A26}$ | $L_{B22}$ |
| II-1391. | $L_{A27}$ | $L_{B22}$ |
| II-1392. | $L_{A28}$ | $L_{B22}$ |
| II-1393. | $L_{A29}$ | $L_{B22}$ |
| II-1394. | $L_{A30}$ | $L_{B22}$ |
| II-1395. | $L_{A31}$ | $L_{B22}$ |
| II-1396. | $L_{A32}$ | $L_{B22}$ |
| II-1397. | $L_{A33}$ | $L_{B22}$ |
| II-1398. | $L_{A34}$ | $L_{B22}$ |
| II-1399. | $L_{A35}$ | $L_{B22}$ |
| II-1400. | $L_{A36}$ | $L_{B22}$ |
| II-1401. | $L_{A37}$ | $L_{B22}$ |
| II-1402. | $L_{A38}$ | $L_{B22}$ |
| II-1403. | $L_{A39}$ | $L_{B22}$ |
| II-1404. | $L_{A40}$ | $L_{B22}$ |
| II-1405. | $L_{A41}$ | $L_{B22}$ |
| II-1406. | $L_{A42}$ | $L_{B22}$ |
| II-1407. | $L_{A43}$ | $L_{B22}$ |
| II-1408. | $L_{A44}$ | $L_{B22}$ |
| II-1409. | $L_{A45}$ | $L_{B22}$ |
| II-1410. | $L_{A46}$ | $L_{B22}$ |
| II-1411. | $L_{A47}$ | $L_{B22}$ |
| II-1412. | $L_{A48}$ | $L_{B22}$ |
| II-1413. | $L_{A49}$ | $L_{B22}$ |
| II-1414. | $L_{A50}$ | $L_{B22}$ |
| II-1415. | $L_{A51}$ | $L_{B22}$ |
| II-1416. | $L_{A52}$ | $L_{B22}$ |
| II-1417. | $L_{A53}$ | $L_{B22}$ |
| II-1418. | $L_{A54}$ | $L_{B22}$ |
| II-1419. | $L_{A55}$ | $L_{B22}$ |
| II-1420. | $L_{A56}$ | $L_{B22}$ |
| II-1421. | $L_{A57}$ | $L_{B22}$ |
| II-1422. | $L_{A58}$ | $L_{B22}$ |
| II-1423. | $L_{A59}$ | $L_{B22}$ |
| II-1424. | $L_{A60}$ | $L_{B22}$ |
| II-1425. | $L_{A61}$ | $L_{B22}$ |
| II-1426. | $L_{A62}$ | $L_{B22}$ |
| II-1427. | $L_{A63}$ | $L_{B22}$ |
| II-1428. | $L_{A64}$ | $L_{B22}$ |
| II-1429. | $L_{A65}$ | $L_{B22}$ |
| II-1430. | $L_{A66}$ | $L_{B22}$ |
| II-1431. | $L_{A67}$ | $L_{B22}$ |
| II-1432. | $L_{A68}$ | $L_{B22}$ |
| II-1433. | $L_{A69}$ | $L_{B22}$ |
| II-1434. | $L_{A1}$ | $L_{B23}$ |
| II-1435. | $L_{A2}$ | $L_{B23}$ |
| II-1436. | $L_{A3}$ | $L_{B23}$ |
| II-1437. | $L_{A4}$ | $L_{B23}$ |
| II-1438. | $L_{A5}$ | $L_{B23}$ |
| II-1439. | $L_{A6}$ | $L_{B23}$ |
| II-1440. | $L_{A7}$ | $L_{B23}$ |
| II-1441. | $L_{A8}$ | $L_{B23}$ |
| II-1442. | $L_{A9}$ | $L_{B23}$ |
| II-1443. | $L_{A10}$ | $L_{B23}$ |
| II-1444. | $L_{A11}$ | $L_{B23}$ |
| II-1445. | $L_{A12}$ | $L_{B23}$ |
| II-1446. | $L_{A13}$ | $L_{B23}$ |
| II-1447. | $L_{A14}$ | $L_{B23}$ |
| II-1448. | $L_{A15}$ | $L_{B23}$ |
| II-1449. | $L_{A16}$ | $L_{B23}$ |
| II-1450. | $L_{A17}$ | $L_{B23}$ |
| II-1451. | $L_{A18}$ | $L_{B23}$ |
| II-1452. | $L_{A19}$ | $L_{B23}$ |
| II-1453. | $L_{A20}$ | $L_{B23}$ |
| II-1454. | $L_{A21}$ | $L_{B23}$ |
| II-1455. | $L_{A22}$ | $L_{B23}$ |
| II-1456. | $L_{A23}$ | $L_{B23}$ |
| II-1457. | $L_{A24}$ | $L_{B23}$ |
| II-1458. | $L_{A25}$ | $L_{B23}$ |
| II-1459. | $L_{A26}$ | $L_{B23}$ |
| II-1460. | $L_{A27}$ | $L_{B23}$ |
| II-1461. | $L_{A28}$ | $L_{B23}$ |
| II-1462. | $L_{A29}$ | $L_{B23}$ |
| II-1463. | $L_{A30}$ | $L_{B23}$ |
| II-1464. | $L_{A31}$ | $L_{B23}$ |
| II-1465. | $L_{A32}$ | $L_{B23}$ |
| II-1466. | $L_{A33}$ | $L_{B23}$ |
| II-1467. | $L_{A34}$ | $L_{B23}$ |
| II-1468. | $L_{A35}$ | $L_{B23}$ |
| II-1469. | $L_{A36}$ | $L_{B23}$ |
| II-1470. | $L_{A37}$ | $L_{B23}$ |
| II-1471. | $L_{A38}$ | $L_{B23}$ |
| II-1472. | $L_{A39}$ | $L_{B23}$ |
| II-1473. | $L_{A40}$ | $L_{B23}$ |
| II-1474. | $L_{A41}$ | $L_{B23}$ |
| II-1475. | $L_{A42}$ | $L_{B23}$ |
| II-1476. | $L_{A43}$ | $L_{B23}$ |
| II-1477. | $L_{A44}$ | $L_{B23}$ |
| II-1478. | $L_{A45}$ | $L_{B23}$ |
| II-1479. | $L_{A46}$ | $L_{B23}$ |
| II-1480. | $L_{A47}$ | $L_{B23}$ |
| II-1481. | $L_{A48}$ | $L_{B23}$ |
| II-1482. | $L_{A49}$ | $L_{B23}$ |
| II-1483. | $L_{A50}$ | $L_{B23}$ |
| II-1484. | $L_{A51}$ | $L_{B23}$ |
| II-1485. | $L_{A52}$ | $L_{B23}$ |
| II-1486. | $L_{A53}$ | $L_{B23}$ |
| II-1487. | $L_{A54}$ | $L_{B23}$ |
| II-1488. | $L_{A55}$ | $L_{B23}$ |
| II-1489. | $L_{A56}$ | $L_{B23}$ |
| II-1490. | $L_{A57}$ | $L_{B23}$ |
| II-1491. | $L_{A58}$ | $L_{B23}$ |
| II-1492. | $L_{A59}$ | $L_{B23}$ |
| II-1493. | $L_{A60}$ | $L_{B23}$ |
| II-1494. | $L_{A61}$ | $L_{B23}$ |
| II-1495. | $L_{A62}$ | $L_{B23}$ |
| II-1496. | $L_{A63}$ | $L_{B23}$ |
| II-1497. | $L_{A64}$ | $L_{B23}$ |
| II-1498. | $L_{A65}$ | $L_{B23}$ |
| II-1499. | $L_{A66}$ | $L_{B23}$ |
| II-1500. | $L_{A67}$ | $L_{B23}$ |
| II-1501. | $L_{A68}$ | $L_{B23}$ |

-continued

| Compound Number | $L_A$ | $L_B$ |
|---|---|---|
| II-1502. | $L_{A69}$ | $L_{B23}$ |
| II-1503. | $L_{A1}$ | $L_{B24}$ |
| II-1504. | $L_{A2}$ | $L_{B24}$ |
| II-1505. | $L_{A3}$ | $L_{B24}$ |
| II-1506. | $L_{A4}$ | $L_{B24}$ |
| II-1507. | $L_{A5}$ | $L_{B24}$ |
| II-1508. | $L_{A6}$ | $L_{B24}$ |
| II-1509. | $L_{A7}$ | $L_{B24}$ |
| II-1510. | $L_{A8}$ | $L_{B24}$ |
| II-1511. | $L_{A9}$ | $L_{B24}$ |
| II-1512. | $L_{A10}$ | $L_{B24}$ |
| II-1513. | $L_{A11}$ | $L_{B24}$ |
| II-1514. | $L_{A12}$ | $L_{B24}$ |
| II-1515. | $L_{A13}$ | $L_{B24}$ |
| II-1516. | $L_{A14}$ | $L_{B24}$ |
| II-1517. | $L_{A15}$ | $L_{B24}$ |
| II-1518. | $L_{A16}$ | $L_{B24}$ |
| II-1519. | $L_{A17}$ | $L_{B24}$ |
| II-1520. | $L_{A18}$ | $L_{B24}$ |
| II-1521. | $L_{A19}$ | $L_{B24}$ |
| II-1522. | $L_{A20}$ | $L_{B24}$ |
| II-1523. | $L_{A21}$ | $L_{B24}$ |
| II-1524. | $L_{A22}$ | $L_{B24}$ |
| II-1525. | $L_{A23}$ | $L_{B24}$ |
| II-1526. | $L_{A24}$ | $L_{B24}$ |
| II-1527. | $L_{A25}$ | $L_{B24}$ |
| II-1528. | $L_{A26}$ | $L_{B24}$ |
| II-1529. | $L_{A27}$ | $L_{B24}$ |
| II-1530. | $L_{A28}$ | $L_{B24}$ |
| II-1531. | $L_{A29}$ | $L_{B24}$ |
| II-1532. | $L_{A30}$ | $L_{B24}$ |
| II-1533. | $L_{A31}$ | $L_{B24}$ |
| II-1534. | $L_{A32}$ | $L_{B24}$ |
| II-1535. | $L_{A33}$ | $L_{B24}$ |
| II-1536. | $L_{A34}$ | $L_{B24}$ |
| II-1537. | $L_{A35}$ | $L_{B24}$ |
| II-1538. | $L_{A36}$ | $L_{B24}$ |
| II-1539. | $L_{A37}$ | $L_{B24}$ |
| II-1540. | $L_{A38}$ | $L_{B24}$ |
| II-1541. | $L_{A39}$ | $L_{B24}$ |
| II-1542. | $L_{A40}$ | $L_{B24}$ |
| II-1543. | $L_{A41}$ | $L_{B24}$ |
| II-1544. | $L_{A42}$ | $L_{B24}$ |
| II-1545. | $L_{A43}$ | $L_{B24}$ |
| II-1546. | $L_{A44}$ | $L_{B24}$ |
| II-1547. | $L_{A45}$ | $L_{B24}$ |
| II-1548. | $L_{A46}$ | $L_{B24}$ |
| II-1549. | $L_{A47}$ | $L_{B24}$ |
| II-1550. | $L_{A48}$ | $L_{B24}$ |
| II-1551. | $L_{A49}$ | $L_{B24}$ |
| II-1552. | $L_{A50}$ | $L_{B24}$ |
| II-1553. | $L_{A51}$ | $L_{B24}$ |
| II-1554. | $L_{A52}$ | $L_{B24}$ |
| II-1555. | $L_{A53}$ | $L_{B24}$ |
| II-1556. | $L_{A54}$ | $L_{B24}$ |
| II-1557. | $L_{A55}$ | $L_{B24}$ |
| II-1558. | $L_{A56}$ | $L_{B24}$ |
| II-1559. | $L_{A57}$ | $L_{B24}$ |
| II-1560. | $L_{A58}$ | $L_{B24}$ |
| II-1561. | $L_{A59}$ | $L_{B24}$ |
| II-1562. | $L_{A60}$ | $L_{B24}$ |
| II-1563. | $L_{A61}$ | $L_{B24}$ |
| II-1564. | $L_{A62}$ | $L_{B24}$ |
| II-1565. | $L_{A63}$ | $L_{B24}$ |
| II-1566. | $L_{A64}$ | $L_{B24}$ |
| II-1567. | $L_{A65}$ | $L_{B24}$ |
| II-1568. | $L_{A66}$ | $L_{B24}$ |
| II-1569. | $L_{A67}$ | $L_{B24}$ |
| II-1570. | $L_{A68}$ | $L_{B24}$ |
| II-1571. | $L_{A69}$ | $L_{B24}$ |
| II-1572. | $L_{A1}$ | $L_{B25}$ |
| II-1573. | $L_{A2}$ | $L_{B25}$ |
| II-1574. | $L_{A3}$ | $L_{B25}$ |
| II-1575. | $L_{A4}$ | $L_{B25}$ |
| II-1576. | $L_{A5}$ | $L_{B25}$ |
| II-1577. | $L_{A6}$ | $L_{B25}$ |
| II-1578. | $L_{A7}$ | $L_{B25}$ |
| II-1579. | $L_{A8}$ | $L_{B25}$ |
| II-1580. | $L_{A9}$ | $L_{B25}$ |
| II-1581. | $L_{A10}$ | $L_{B25}$ |
| II-1582. | $L_{A11}$ | $L_{B25}$ |
| II-1583. | $L_{A12}$ | $L_{B25}$ |
| II-1584. | $L_{A13}$ | $L_{B25}$ |
| II-1585. | $L_{A14}$ | $L_{B25}$ |
| II-1586. | $L_{A15}$ | $L_{B25}$ |
| II-1587. | $L_{A16}$ | $L_{B25}$ |
| II-1588. | $L_{A17}$ | $L_{B25}$ |
| II-1589. | $L_{A18}$ | $L_{B25}$ |
| II-1590. | $L_{A19}$ | $L_{B25}$ |
| II-1591. | $L_{A20}$ | $L_{B25}$ |
| II-1592. | $L_{A21}$ | $L_{B25}$ |
| II-1593. | $L_{A22}$ | $L_{B25}$ |
| II-1594. | $L_{A23}$ | $L_{B25}$ |
| II-1595. | $L_{A24}$ | $L_{B25}$ |
| II-1596. | $L_{A25}$ | $L_{B25}$ |
| II-1597. | $L_{A26}$ | $L_{B25}$ |
| II-1598. | $L_{A27}$ | $L_{B25}$ |
| II-1599. | $L_{A28}$ | $L_{B25}$ |
| II-1600. | $L_{A29}$ | $L_{B25}$ |
| II-1601. | $L_{A30}$ | $L_{B25}$ |
| II-1602. | $L_{A31}$ | $L_{B25}$ |
| II-1603. | $L_{A32}$ | $L_{B25}$ |
| II-1604. | $L_{A33}$ | $L_{B25}$ |
| II-1605. | $L_{A34}$ | $L_{B25}$ |
| II-1606. | $L_{A35}$ | $L_{B25}$ |
| II-1607. | $L_{A36}$ | $L_{B25}$ |
| II-1608. | $L_{A37}$ | $L_{B25}$ |
| II-1609. | $L_{A38}$ | $L_{B25}$ |
| II-1610. | $L_{A39}$ | $L_{B25}$ |
| II-1611. | $L_{A40}$ | $L_{B25}$ |
| II-1612. | $L_{A41}$ | $L_{B25}$ |
| II-1613. | $L_{A42}$ | $L_{B25}$ |
| II-1614. | $L_{A43}$ | $L_{B25}$ |
| II-1615. | $L_{A44}$ | $L_{B25}$ |
| II-1616. | $L_{A45}$ | $L_{B25}$ |
| II-1617. | $L_{A46}$ | $L_{B25}$ |
| II-1618. | $L_{A47}$ | $L_{B25}$ |
| II-1619. | $L_{A48}$ | $L_{B25}$ |
| II-1620. | $L_{A49}$ | $L_{B25}$ |
| II-1621. | $L_{A50}$ | $L_{B25}$ |
| II-1622. | $L_{A51}$ | $L_{B25}$ |
| II-1623. | $L_{A52}$ | $L_{B25}$ |
| II-1624. | $L_{A53}$ | $L_{B25}$ |
| II-1625. | $L_{A54}$ | $L_{B25}$ |
| II-1626. | $L_{A55}$ | $L_{B25}$ |
| II-1627. | $L_{A56}$ | $L_{B25}$ |
| II-1628. | $L_{A57}$ | $L_{B25}$ |
| II-1629. | $L_{A58}$ | $L_{B25}$ |
| II-1630. | $L_{A59}$ | $L_{B25}$ |
| II-1631. | $L_{A60}$ | $L_{B25}$ |
| II-1632. | $L_{A61}$ | $L_{B25}$ |
| II-1633. | $L_{A62}$ | $L_{B25}$ |
| II-1634. | $L_{A63}$ | $L_{B25}$ |
| II-1635. | $L_{A64}$ | $L_{B25}$ |
| II-1636. | $L_{A65}$ | $L_{B25}$ |
| II-1637. | $L_{A66}$ | $L_{B25}$ |
| II-1638. | $L_{A67}$ | $L_{B25}$ |
| II-1639. | $L_{A68}$ | $L_{B25}$ |
| II-1640. | $L_{A69}$ | $L_{B25}$ |
| II-1641. | $L_{A1}$ | $L_{B26}$ |
| II-1642. | $L_{A2}$ | $L_{B26}$ |
| II-1643. | $L_{A3}$ | $L_{B26}$ |
| II-1644. | $L_{A4}$ | $L_{B26}$ |
| II-1645. | $L_{A5}$ | $L_{B26}$ |
| II-1646. | $L_{A6}$ | $L_{B26}$ |
| II-1647. | $L_{A7}$ | $L_{B26}$ |
| II-1648. | $L_{A8}$ | $L_{B26}$ |
| II-1649. | $L_{A9}$ | $L_{B26}$ |
| II-1650. | $L_{A10}$ | $L_{B26}$ |
| II-1651. | $L_{A11}$ | $L_{B26}$ |
| II-1652. | $L_{A12}$ | $L_{B26}$ |
| II-1653. | $L_{A13}$ | $L_{B26}$ |

| Compound Number | $L_A$ | $L_B$ |
|---|---|---|
| II-1654. | $L_{A14}$ | $L_{B26}$ |
| II-1655. | $L_{A15}$ | $L_{B26}$ |
| II-1656. | $L_{A16}$ | $L_{B26}$ |
| II-1657. | $L_{A17}$ | $L_{B26}$ |
| II-1658. | $L_{A18}$ | $L_{B26}$ |
| II-1659. | $L_{A19}$ | $L_{B26}$ |
| II-1660. | $L_{A20}$ | $L_{B26}$ |
| II-1661. | $L_{A21}$ | $L_{B26}$ |
| II-1662. | $L_{A22}$ | $L_{B26}$ |
| II-1663. | $L_{A23}$ | $L_{B26}$ |
| II-1664. | $L_{A24}$ | $L_{B26}$ |
| II-1665. | $L_{A25}$ | $L_{B26}$ |
| II-1666. | $L_{A26}$ | $L_{B26}$ |
| II-1667. | $L_{A27}$ | $L_{B26}$ |
| II-1668. | $L_{A28}$ | $L_{B26}$ |
| II-1669. | $L_{A29}$ | $L_{B26}$ |
| II-1670. | $L_{A30}$ | $L_{B26}$ |
| II-1671. | $L_{A31}$ | $L_{B26}$ |
| II-1672. | $L_{A32}$ | $L_{B26}$ |
| II-1673. | $L_{A33}$ | $L_{B26}$ |
| II-1674. | $L_{A34}$ | $L_{B26}$ |
| II-1675. | $L_{A35}$ | $L_{B26}$ |
| II-1676. | $L_{A36}$ | $L_{B26}$ |
| II-1677. | $L_{A37}$ | $L_{B26}$ |
| II-1678. | $L_{A38}$ | $L_{B26}$ |
| II-1679. | $L_{A39}$ | $L_{B26}$ |
| II-1680. | $L_{A40}$ | $L_{B26}$ |
| II-1681. | $L_{A41}$ | $L_{B26}$ |
| II-1682. | $L_{A42}$ | $L_{B26}$ |
| II-1683. | $L_{A43}$ | $L_{B26}$ |
| II-1684. | $L_{A44}$ | $L_{B26}$ |
| II-1685. | $L_{A45}$ | $L_{B26}$ |
| II-1686. | $L_{A46}$ | $L_{B26}$ |
| II-1687. | $L_{A47}$ | $L_{B26}$ |
| II-1688. | $L_{A48}$ | $L_{B26}$ |
| II-1689. | $L_{A49}$ | $L_{B26}$ |
| II-1690. | $L_{A50}$ | $L_{B26}$ |
| II-1691. | $L_{A51}$ | $L_{B26}$ |
| II-1692. | $L_{A52}$ | $L_{B26}$ |
| II-1693. | $L_{A53}$ | $L_{B26}$ |
| II-1694. | $L_{A54}$ | $L_{B26}$ |
| II-1695. | $L_{A55}$ | $L_{B26}$ |
| II-1696. | $L_{A56}$ | $L_{B26}$ |
| II-1697. | $L_{A57}$ | $L_{B26}$ |
| II-1698. | $L_{A58}$ | $L_{B26}$ |
| II-1699. | $L_{A59}$ | $L_{B26}$ |
| II-1700. | $L_{A60}$ | $L_{B26}$ |
| II-1701. | $L_{A61}$ | $L_{B26}$ |
| II-1702. | $L_{A62}$ | $L_{B26}$ |
| II-1703. | $L_{A63}$ | $L_{B26}$ |
| II-1704. | $L_{A64}$ | $L_{B26}$ |
| II-1705. | $L_{A65}$ | $L_{B26}$ |
| II-1706. | $L_{A66}$ | $L_{B26}$ |
| II-1707. | $L_{A67}$ | $L_{B26}$ |
| II-1708. | $L_{A68}$ | $L_{B26}$ |
| II-1709. | $L_{A69}$ | $L_{B26}$ |
| II-1710. | $L_{A1}$ | $L_{B27}$ |
| II-1711. | $L_{A2}$ | $L_{B27}$ |
| II-1712. | $L_{A3}$ | $L_{B27}$ |
| II-1713. | $L_{A4}$ | $L_{B27}$ |
| II-1714. | $L_{A5}$ | $L_{B27}$ |
| II-1715. | $L_{A6}$ | $L_{B27}$ |
| II-1716. | $L_{A7}$ | $L_{B27}$ |
| II-1717. | $L_{A8}$ | $L_{B27}$ |
| II-1718. | $L_{A9}$ | $L_{B27}$ |
| II-1719. | $L_{A10}$ | $L_{B27}$ |
| II-1720. | $L_{A11}$ | $L_{B27}$ |
| II-1721. | $L_{A12}$ | $L_{B27}$ |
| II-1722. | $L_{A13}$ | $L_{B27}$ |
| II-1723. | $L_{A14}$ | $L_{B27}$ |
| II-1724. | $L_{A15}$ | $L_{B27}$ |
| II-1725. | $L_{A16}$ | $L_{B27}$ |
| II-1726. | $L_{A17}$ | $L_{B27}$ |
| II-1727. | $L_{A18}$ | $L_{B27}$ |
| II-1728. | $L_{A19}$ | $L_{B27}$ |
| II-1729. | $L_{A20}$ | $L_{B27}$ |
| II-1730. | $L_{A21}$ | $L_{B27}$ |
| II-1731. | $L_{A22}$ | $L_{B27}$ |
| II-1732. | $L_{A23}$ | $L_{B27}$ |
| II-1733. | $L_{A24}$ | $L_{B27}$ |
| II-1734. | $L_{A25}$ | $L_{B27}$ |
| II-1735. | $L_{A26}$ | $L_{B27}$ |
| II-1736. | $L_{A27}$ | $L_{B27}$ |
| II-1737. | $L_{A28}$ | $L_{B27}$ |
| II-1738. | $L_{A29}$ | $L_{B27}$ |
| II-1739. | $L_{A30}$ | $L_{B27}$ |
| II-1740. | $L_{A31}$ | $L_{B27}$ |
| II-1741. | $L_{A32}$ | $L_{B27}$ |
| II-1742. | $L_{A33}$ | $L_{B27}$ |
| II-1743. | $L_{A34}$ | $L_{B27}$ |
| II-1744. | $L_{A35}$ | $L_{B27}$ |
| II-1745. | $L_{A36}$ | $L_{B27}$ |
| II-1746. | $L_{A37}$ | $L_{B27}$ |
| II-1747. | $L_{A38}$ | $L_{B27}$ |
| II-1748. | $L_{A39}$ | $L_{B27}$ |
| II-1749. | $L_{A40}$ | $L_{B27}$ |
| II-1750. | $L_{A41}$ | $L_{B27}$ |
| II-1751. | $L_{A42}$ | $L_{B27}$ |
| II-1752. | $L_{A43}$ | $L_{B27}$ |
| II-1753. | $L_{A44}$ | $L_{B27}$ |
| II-1754. | $L_{A45}$ | $L_{B27}$ |
| II-1755. | $L_{A46}$ | $L_{B27}$ |
| II-1756. | $L_{A47}$ | $L_{B27}$ |
| II-1757. | $L_{A48}$ | $L_{B27}$ |
| II-1758. | $L_{A49}$ | $L_{B27}$ |
| II-1759. | $L_{A50}$ | $L_{B27}$ |
| II-1760. | $L_{A51}$ | $L_{B27}$ |
| II-1761. | $L_{A52}$ | $L_{B27}$ |
| II-1762. | $L_{A53}$ | $L_{B27}$ |
| II-1763. | $L_{A54}$ | $L_{B27}$ |
| II-1764. | $L_{A55}$ | $L_{B27}$ |
| II-1765. | $L_{A56}$ | $L_{B27}$ |
| II-1766. | $L_{A57}$ | $L_{B27}$ |
| II-1767. | $L_{A58}$ | $L_{B27}$ |
| II-1768. | $L_{A59}$ | $L_{B27}$ |
| II-1769. | $L_{A60}$ | $L_{B27}$ |
| II-1770. | $L_{A61}$ | $L_{B27}$ |
| II-1771. | $L_{A62}$ | $L_{B27}$ |
| II-1772. | $L_{A63}$ | $L_{B27}$ |
| II-1773. | $L_{A64}$ | $L_{B27}$ |
| II-1774. | $L_{A65}$ | $L_{B27}$ |
| II-1775. | $L_{A66}$ | $L_{B27}$ |
| II-1776. | $L_{A67}$ | $L_{B27}$ |
| II-1777. | $L_{A68}$ | $L_{B27}$ |
| II-1778. | $L_{A69}$ | $L_{B27}$ |
| II-1779. | $L_{A1}$ | $L_{B28}$ |
| II-1780. | $L_{A2}$ | $L_{B28}$ |
| II-1781. | $L_{A3}$ | $L_{B28}$ |
| II-1782. | $L_{A4}$ | $L_{B28}$ |
| II-1783. | $L_{A5}$ | $L_{B28}$ |
| II-1784. | $L_{A6}$ | $L_{B28}$ |
| II-1785. | $L_{A7}$ | $L_{B28}$ |
| II-1786. | $L_{A8}$ | $L_{B28}$ |
| II-1787. | $L_{A9}$ | $L_{B28}$ |
| II-1788. | $L_{A10}$ | $L_{B28}$ |
| II-1789. | $L_{A11}$ | $L_{B28}$ |
| II-1790. | $L_{A12}$ | $L_{B28}$ |
| II-1791. | $L_{A13}$ | $L_{B28}$ |
| II-1792. | $L_{A14}$ | $L_{B28}$ |
| II-1793. | $L_{A15}$ | $L_{B28}$ |
| II-1794. | $L_{A16}$ | $L_{B28}$ |
| II-1795. | $L_{A17}$ | $L_{B28}$ |
| II-1796. | $L_{A18}$ | $L_{B28}$ |
| II-1797. | $L_{A19}$ | $L_{B28}$ |
| II-1798. | $L_{A20}$ | $L_{B28}$ |
| II-1799. | $L_{A21}$ | $L_{B28}$ |
| II-1800. | $L_{A22}$ | $L_{B28}$ |
| II-1801. | $L_{A23}$ | $L_{B28}$ |
| II-1802. | $L_{A24}$ | $L_{B28}$ |
| II-1803. | $L_{A25}$ | $L_{B28}$ |
| II-1804. | $L_{A26}$ | $L_{B28}$ |
| II-1805. | $L_{A27}$ | $L_{B28}$ |

-continued

| Compound Number | $L_A$ | $L_B$ |
|---|---|---|
| II-1806. | $L_{A28}$ | $L_{B28}$ |
| II-1807. | $L_{A29}$ | $L_{B28}$ |
| II-1808. | $L_{A30}$ | $L_{B28}$ |
| II-1809. | $L_{A31}$ | $L_{B28}$ |
| II-1810. | $L_{A32}$ | $L_{B28}$ |
| II-1811. | $L_{A33}$ | $L_{B28}$ |
| II-1812. | $L_{A34}$ | $L_{B28}$ |
| II-1813. | $L_{A35}$ | $L_{B28}$ |
| II-1814. | $L_{A36}$ | $L_{B28}$ |
| II-1815. | $L_{A37}$ | $L_{B28}$ |
| II-1816. | $L_{A38}$ | $L_{B28}$ |
| II-1817. | $L_{A39}$ | $L_{B28}$ |
| II-1818. | $L_{A40}$ | $L_{B28}$ |
| II-1819. | $L_{A41}$ | $L_{B28}$ |
| II-1820. | $L_{A42}$ | $L_{B28}$ |
| II-1821. | $L_{A43}$ | $L_{B28}$ |
| II-1822. | $L_{A44}$ | $L_{B28}$ |
| II-1823. | $L_{A45}$ | $L_{B28}$ |
| II-1824. | $L_{A46}$ | $L_{B28}$ |
| II-1825. | $L_{A47}$ | $L_{B28}$ |
| II-1826. | $L_{A48}$ | $L_{B28}$ |
| II-1827. | $L_{A49}$ | $L_{B28}$ |
| II-1828. | $L_{A50}$ | $L_{B28}$ |
| II-1829. | $L_{A51}$ | $L_{B28}$ |
| II-1830. | $L_{A52}$ | $L_{B28}$ |
| II-1831. | $L_{A53}$ | $L_{B28}$ |
| II-1832. | $L_{A54}$ | $L_{B28}$ |
| II-1833. | $L_{A55}$ | $L_{B28}$ |
| II-1834. | $L_{A56}$ | $L_{B28}$ |
| II-1835. | $L_{A57}$ | $L_{B28}$ |
| II-1836. | $L_{A58}$ | $L_{B28}$ |
| II-1837. | $L_{A59}$ | $L_{B28}$ |
| II-1838. | $L_{A60}$ | $L_{B28}$ |
| II-1839. | $L_{A61}$ | $L_{B28}$ |
| II-1840. | $L_{A62}$ | $L_{B28}$ |
| II-1841. | $L_{A63}$ | $L_{B28}$ |
| II-1842. | $L_{A64}$ | $L_{B28}$ |
| II-1843. | $L_{A65}$ | $L_{B28}$ |
| II-1844. | $L_{A66}$ | $L_{B28}$ |
| II-1845. | $L_{A67}$ | $L_{B28}$ |
| II-1846. | $L_{A68}$ | $L_{B28}$ |
| II-1847. | $L_{A69}$ | $L_{B28}$ |

In one preferred embodiment, the heteroleptic iridium complex is selected from the group of compounds that have one or more deuterated ligands. The group consists of Compound II-11 through Compound II-43, Compound II-64 through Compound II-96, Compound II-130 through Compound II-163, Compound II-197 through Compound II-230, Compound II-263 through Compound II-296, Compound II-330 through Compound II-363, Compound II-397 through Compound II-430, Compound II-464 through Compound II-1031, Compound II-1065 through Compound II-1098, Compound II-1132 through Compound II-1165, Compound II-1199 through Compound II-1232, Compound II-1266 through Compound II-1299, Compound II-1333 through Compound II-1366, Compound II-1400 through Compound II-1846, and Compound II-1847.

In a more preferred embodiment, the heteroleptic iridium complex is selected from the group of compounds having one or more deuterated ligands, wherein the group consisting of Compound II-11, Compound II-12, Compound II-13, Compound II-16, Compound II-17, Compound II-18, Compound II-19, Compound II-27, Compound II-28, Compound II-29, Compound II-30, Compound II-33, Compound II-34, Compound II-35, Compound II-36, Compound II-263, Compound II-264, Compound II-265, Compound II-266, Compound II-269, Compound II-270, Compound II-271, Compound II-272, Compound II-280, Compound II-281, Compound II-282, Compound II-283, Compound II-286, Compound II-287, Compound II-288, Compound II-289, Compound II-529, Compound II-530, Compound II-531, Compound II-534, Compound II-535, Compound II-536, Compound II-537, Compound II-545, Compound II-546, Compound II-547, Compound II-550, Compound II-551, Compound II-552, Compound II-553, Compound II-730, Compound II-731, Compound II-732, Compound II-735, Compound II-736, Compound II-737, Compound II-738, Compound II-746, Compound II-747, Compound II-748, Compound II-751, Compound II-752, Compound II-753, Compound II-754, Compound II-1132, Compound II-1133, Compound II-1134, Compound II-1135, Compound II-1138, Compound II-1139, Compound II-1140, Compound II-1141, Compound II-1149, Compound II-1150, Compound II-1151, Compound II-1152, Compound II-1155, Compound II-1156, Compound II-1157, Compound II-1158, Compound II-1469, Compound II-1470, Compound II-1471, Compound II-1472, Compound II-1475, Compound II-1476, Compound II-1477, Compound II-1478, Compound II-1486, Compound II-1487, Compound II-1488, Compound II-1489, Compound II-1492, Compound II-1493, Compound II-1494, Compound II-1495, Compound II-1538, Compound II-1539, Compound II-1540, Compound II-1541, Compound II-1544, Compound II-1545, Compound II-1546, Compound II-1547, Compound II-1555, Compound II-1556, Compound II-1557, Compound II-1558, Compound II-1561, Compound II-1562, Compound II-1563, Compound II-1564, Compound II-1676, Compound II-1677, Compound II-1678, Compound II-1679, Compound II-1682, Compound II-1683, Compound II-1684, Compound II-1685, Compound II-1693, Compound II-1694, Compound II-1695, Compound II-1696, Compound II-1699, Compound II-1700, Compound II-1701, and Compound II-1702.

In one aspect, a formulation comprising the compound of the present invention is disclosed. The formulation comprises a heteroleptic iridium complex having the formula $IrL_A(L_B)_2$, wherein $L_A$ is selected from the group consisting of ligands $L_{A1}$ through $L_{A69}$, $L_B$ is selected from the group consisting of ligands $L_{B1}$ through $L_{B28}$, and the heteroleptic iridium complex is selected from the group consisting of Compound II-1 through Compound II-1847 as defined herein.

In one aspect, a first device is provided. The first device comprises a first organic light emitting device, and contains an anode, a cathode, and an organic layer, disposed between the anode and the cathode. The organic layer comprises a heteroleptic iridium complex having the formula $IrL_A(L_B)_2$, wherein $L_A$ is selected from the group consisting of the ligands $L_{A1}$ through $L_{A69}$ defined herein, $L_B$ is selected from the group consisting of the ligands $L_{B1}$ through $L_{B28}$, and the heteroleptic iridium complex is selected from the group consisting of Compound II-1 through Compound II-1846, and Compound II-1847 as defined herein.

In one preferred embodiment, the heteroleptic iridium complex in the organic layer of the first device is selected from a group of compounds having one or more deuterated ligands. Such group consists of Compound II-11 through Compound II-43, Compound II-64 through Compound II-96, Compound II-130 through Compound II-163, Compound II-197 through Compound II-230, Compound II-263 through Compound II-296, Compound II-330 through Compound II-363, Compound II-397 through Compound II-430, Compound II-464 through Compound II-1031, Compound II-1065 through Compound II-1098, Compound II-1132 through Compound II-1165, Compound II-1199 through Compound II-1232, Compound II-1266 through Compound II-1299, Compound II-1333 through Compound II-1366, Compound II-1400 through Compound II-1846, and Compound II-1847, as defined herein.

In one embodiment, the organic layer is an emissive layer and the compound is an emissive dopant. In another embodiment, the organic layer is an emissive layer and the compound is a non-emissive dopant.

In another embodiment, the organic layer further comprises a host. In one embodiment, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10. In one embodiment, the host has the formula:

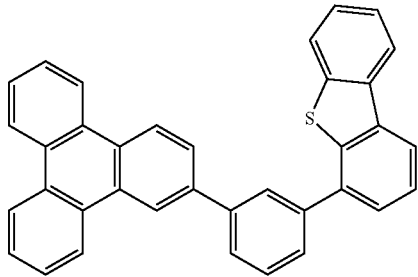

Compound H

In one embodiment, the host is a metal complex. Any of the metal complexes described herein are suitable hosts.

OLEDs that incorporate compounds of Formula I have broad yellow emission profiles, as well as high quantum efficiencies and long commercial lifetimes. A device capable of broad yellow emission is particularly desirable in white illumination sources.

The quality of white illumination sources can be fully described by a simple set of parameters. The color of the light source is given by its CIE chromaticity coordinates x and y (1931 2-degree standard observer CIE chromaticity). The CIE coordinates are typically represented on a two dimensional plot. Monochromatic colors fall on the perimeter of the horseshoe shaped curve starting with blue in the lower left, running through the colors of the spectrum in a clockwise direction to red in the lower right. The CIE coordinates of a light source of given energy and spectral shape will fall within the area of the curve. Summing light at all wavelengths uniformly gives the white or neutral point, found at the center of the diagram (CIE x,y-coordinates, 0.33, 0.33). Mixing light from two or more sources gives light whose color is represented by the intensity weighted average of the CIE coordinates of the independent sources. Thus, mixing light from two or more sources can be used to generate white light.

When considering the use of these white light sources for illumination, the CIE color rendering index (CRI) may be considered in addition to the CIE coordinates of the source. The CRI gives an indication of how well the light source will render colors of objects it illuminates. A perfect match of a given source to the standard illuminant gives a CRI of 100. Though a CRI value of at least 70 may be acceptable for certain applications, a preferred white light source may have a CRI of about 80 or higher.

The compounds of Formula I have yellow emission profiles with significant red and green components. The addition of a blue emitter, i.e. an emitter with a peak wavelength of between 400 to 500 nanometers, together with appropriate filters on OLEDs incorporating the compound of Formula I allows for the reproduction of the RGB spectrum. In some embodiments, OLEDs that incorporate compounds of Formula I are used for color displays (or lighting applications) using only two types of emissive compounds: a yellow emitter of Formula I and a blue emitter. A color display using only two emissive compounds: a broad yellow emitter of Formula I and a blue emitter, may employ a color filter to selectively pass the red, green, and blue color components of a display. The red and green components can both come from a broad yellow emitter of Formula I.

In one embodiment, the first device is a consumer product. In another embodiment, the first device is an organic light-emitting device. In another aspect, the first device comprises a lighting panel.

In one embodiment, the first device further comprises a second emissive dopant having a peak wavelength of between 400 to 500 nanometers. In one embodiment, the second emissive dopant is a fluorescent emitter. In another embodiment, the second emissive dopant is a phosphorescent emitter.

In one embodiment, the first device further comprises a first organic light-emitting device comprising a compound of Formula I and a second light emitting device separate from the first organic light-emitting device comprising an emissive dopant having a peak wavelength of between 400 to 500 nanometers. The first and second light-emitting devices can be placed in any suitable spatial arrangement, depending on the needs of the desired display or lighting application.

In another embodiment, the first device comprises an organic-light emitting device having a first emissive layer comprising a compound of Formula I and a second emissive layer comprising an emissive dopant having a peak wavelength of between 400 to 500 nanometers. The first emissive layer and the second emissive layer may have one or more other layers in between them.

Device Examples

All device examples were fabricated by high vacuum (<$10^{-7}$ Torr) thermal evaporation (VTE). The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound A as the hole injection layer (HIL), 300 Å of 4,4'-bis[N-(1- naphthyl)-N-phenylamino]biphenyl (alpha-NPD) as the hole transporting layer (HTL), 300 Å of 7-15 wt % of a compound of Formula I doped in with Compound H (as host) as the emissive layer (EML), 50 Å or 100 Å of Compound H as blocking layer (BL), 450 Å or 500 of Å Alq (tris-8-hydroxyquinoline aluminum) as the electron transport layer (ETL). The comparative example used 8 weight percent of Compound X in the EML. The device results and data are summarized in Table 1 and Table 2 from those devices. As used herein, NPD, Alq, Compound A, Compound H, and Compound X have the following structures:

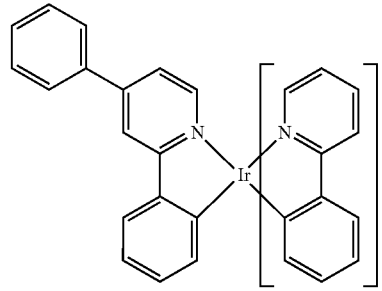
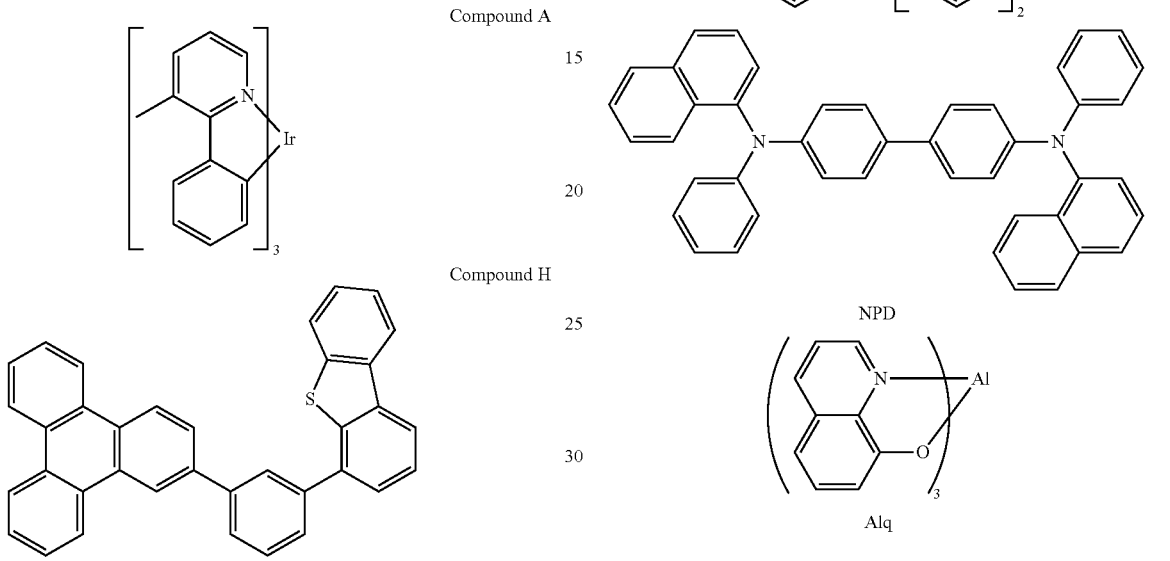

TABLE 2

VTE Phosphorescent OLEDs

| Example | HIL | HTL | EML (300 Å, doping %) | | BL | ETL |
|---|---|---|---|---|---|---|
| Comparative Example 1 | Compound A 100 Å | NPD 300 Å | Compound H | Compound X 8% | Compound H 50 Å | Alq 450 Å |
| Example 1 | Compound A 100 Å | NPD 300 Å | Compound H | Compound 3 12% | Compound H 50 Å | Alq 450 Å |
| Example 2 | Compound A 100 Å | NPD 300 Å | Compound H | Compound 4 12% | Compound H 50 Å | Alq 450 Å |
| Example 3 | Compound A 100 Å | NPD 300 Å | Compound H | Compound 5 10% | Compound H 50 Å | Alq 450 Å |
| Example 4 | Compound A 100 Å | NPD 300 Å | Compound H | Compound 6 7% | Compound H 50 Å | Alq 450 Å |
| Example 5 | Compound A 100 Å | NPD 300 Å | Compound H | Compound 7 10% | Compound H 50 Å | Alq 500 Å |
| Example 6 | Compound A 100 Å | NPD 300 Å | Compound H | Compound 8 7% | Compound H 50 Å | Alq 450 Å |

TABLE 3

VTE Device Data

| Example | x | y | $\lambda_{max}$ | FWHM (nm) | Voltage (V) | LE (Cd/A) | EQE (%) | PE (lm/W) | LT80% (h) |
|---|---|---|---|---|---|---|---|---|---|
| Comparative Example 1 | 0.435 | 0.550 | 556 | 84 | 5.9 | 58.3 | 17.3 | 31.3 | 510 |
| Example 1 | 0.458 | 0.532 | 562 | 82 | 5.0 | 66.8 | 20.5 | 42.2 | 900 |
| Example 2 | 0.460 | 0.530 | 562 | 82 | 5.1 | 61.6 | 19.0 | 38.2 | 1250 |
| Example 3 | 0.428 | 0.556 | 552 | 84 | 5.6 | 77.2 | 22.6 | 43.0 | 630 |
| Example 4 | 0.461 | 0.528 | 566 | 86 | 6.2 | 61.5 | 19.3 | 31.0 | 540 |

TABLE 3-continued

| | | | | VTE Device Data | | | | | |
|---|---|---|---|---|---|---|---|---|---|
| Example | x | y | $\lambda_{max}$ | FWHM (nm) | Voltage (V) | LE (Cd/A) | EQE (%) | PE (lm/W) | LT80% (h) |
| Example 5 | 0.485 | 0.508 | 570 | 84 | 5.0 | 64.6 | 21.2 | 40.4 | 4300 |
| Example 6 | 0.462 | 0.528 | 564 | 82 | 5.7 | 52.4 | 16.2 | 28.9 | 830 |

The device data show that compounds of Formula I are effective yellow emitters with broad line shape (desirable for use in white light devices), with high efficiency and commercially useful lifetimes. Devices made with compounds of Formula I (Examples 1-6) generally show higher luminous efficiencies (LE), external quantum efficiencies (EQE) and power efficiencies (PE) than the Comparative Example. Without being bound by theory, it is believed that the alkyl substitutions reduce the aggregation of the dopant in the device, change the charge transport properties, and lead to higher efficiencies versus the Comparative Example, which lacks alkyl groups. Additionally, Compounds 3-5, Compound 7, and Compound 8 all show lower turn-on voltages in the device than Comparative Compound X. Finally, the compounds of Formula I in Examples 1-6 show longer device lifetimes than the Comparative Example. For example, Compound 4 and Compound 7 had device lifetimes about 2.5 and 8 fold higher, respectively, than Comparative Compound X.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

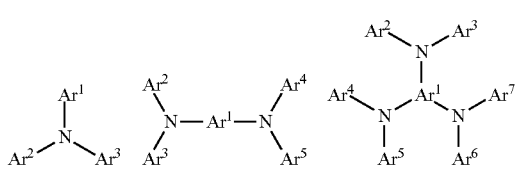

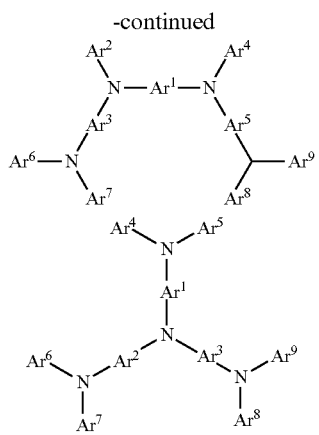

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

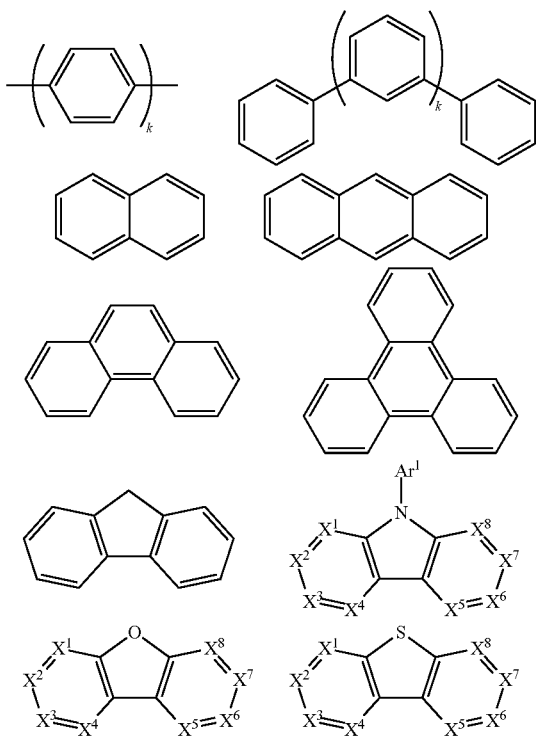

k is an integer from 1 to 20; $X^1$ to $X^8$ is C (including CH) or N; $Ar^1$ has the same group defined above.

Examples of metal complexes used in HIL or HTL include, but not limit to the following general formula:

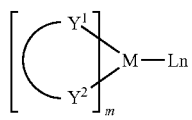

M is a metal, having an atomic weight greater than 40; ($Y^1$-$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$-$Y^2$) is a 2-phenylpyridine derivative.
In another aspect, ($Y^1$-$Y^2$) is a carbene ligand.
In another aspect, M is selected from Ir, Pt, Os, and Zn.
In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant.

Examples of metal complexes used as host are preferred to have the following general formula:

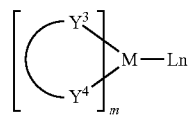

M is a metal; ($Y^3$-$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

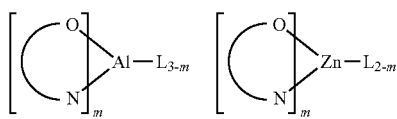

(O—N) is a bidentate ligand, having metal coordinated to atoms O and N.

In another aspect, M is selected from Ir and Pt.
In a further aspect, ($Y^3$-$Y^4$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

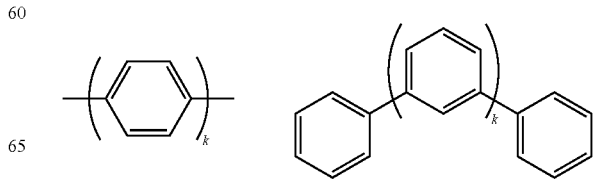

-continued

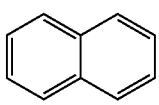 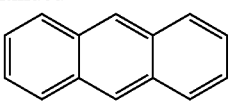

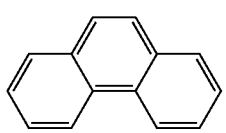 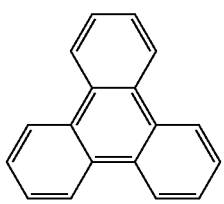

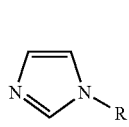 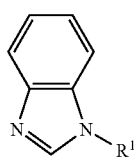 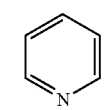 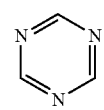

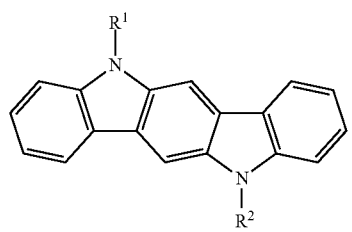

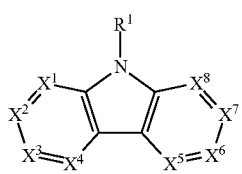

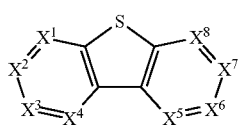

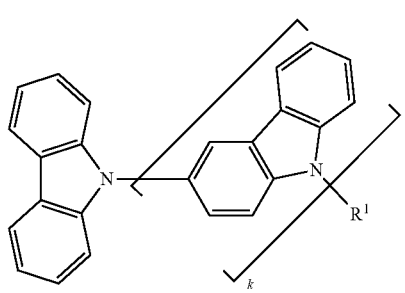

-continued

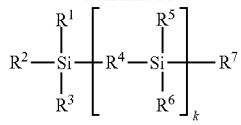

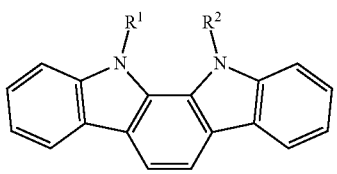

$R^1$ to $R^7$ is independently selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

k is an integer from 0 to 20.

$X^1$ to $X^8$ is selected from C (including CH) or N.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule used as host described above.

In another aspect, compound used in HBL contains at least one of the following groups in the molecule:

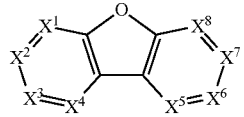

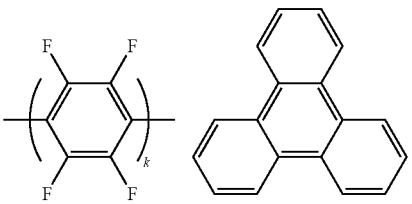

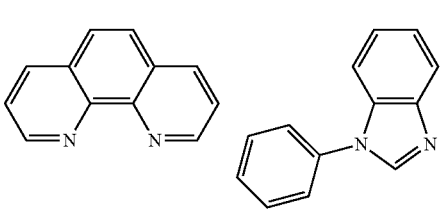

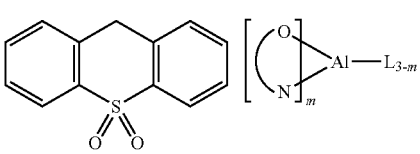

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

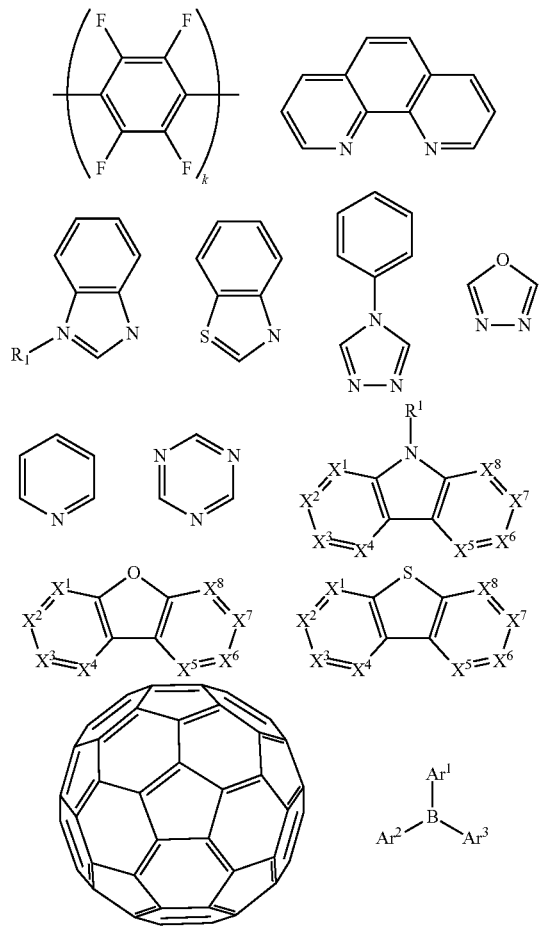

$R^1$ is selected from the group consisting of hydrogen, alkyl, alkoxy, amino, alkenyl, alkynyl, arylalkyl, heteroalkyl, aryl and heteroaryl, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

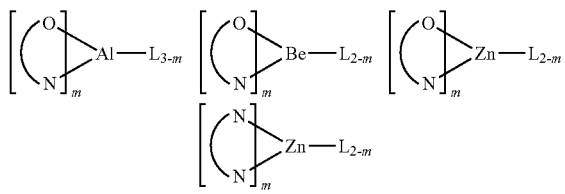

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
| --- | --- | --- |
| | Hole injection materials | |
| Phthalocyanine and porphryin compounds | | Appl. Phys. Lett. 69, 2160 (1996) |

TABLE 3-continued
| MATERIAL | EXAMPLES OF MATERIAL | PUBLICATIONS |
|---|---|---|
| Starburst triarylamines | 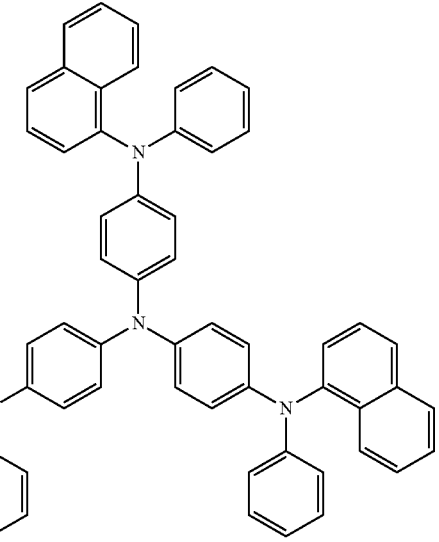 | J. Lumin. 72-74, 985 (1997) |
| $CF_x$ Fluorohydrocarbon polymer | $-(CH_xF_y)_n-$ | Appl. Phys. Lett. 78, 673 (2001) |
| Conducting polymers (e.g., PEDOT: PSS, polyaniline, polypthiophene) | 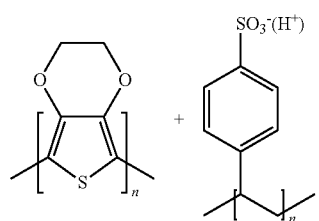 | Synth. Met. 87, 171 (1997) WO2007002683 |
| Phosphonic acid and sliane SAMs | 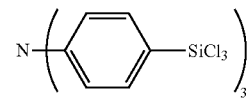 | US20030162053 |
| Triarylamine or polythiophene polymers with conductivity dopants | 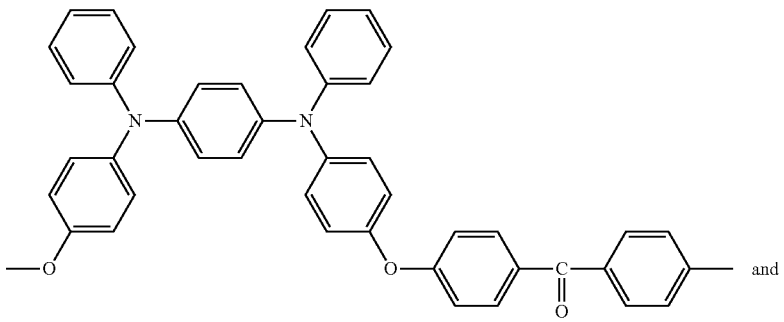 and | EP1725079A1 |

TABLE 3-continued
| MATERIAL | EXAMPLES OF MATERIAL | PUBLICATIONS |
|---|---|---|
| | 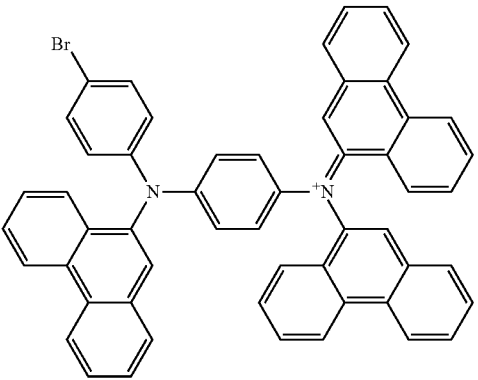 | |
| | 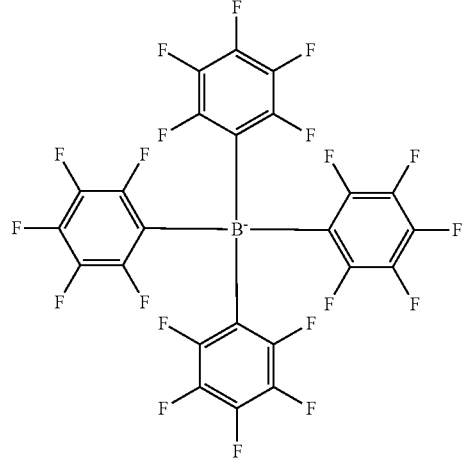 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Arylamines complexed with metal oxides such as molybdenum and tungsten oxides | 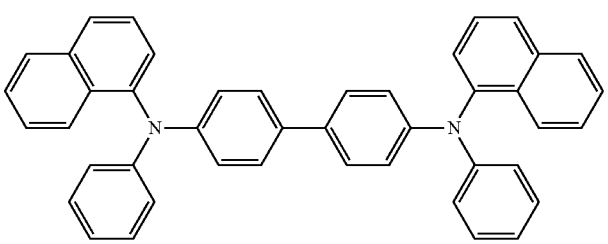 + $MoO_x$ | SID Symposium Digest, 37, 923 (2006) WO2009018009 |
| p-type semiconducting organic complexes | 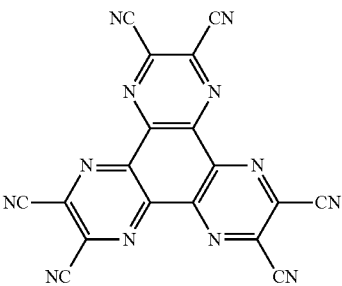 [SMILES: N#Cc1nc2c3nc(C#N)c(C#N)nc3c3nc(C#N)c(C#N)nc3c2nc1C#N] | US20020158242 |

TABLE 3-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |

Hole transporting materials

| | | |
| --- | --- | --- |
| Triarylamines (e.g., TPD, α-NPD) | | Appl. Phys. Lett. 51, 913 (1987) |
| | | U.S. Pat. No. 5,061,569 |

145 146
TABLE 3-continued
| MATERIAL | EXAMPLES OF MATERIAL | PUBLICATIONS |
|---|---|---|
| | 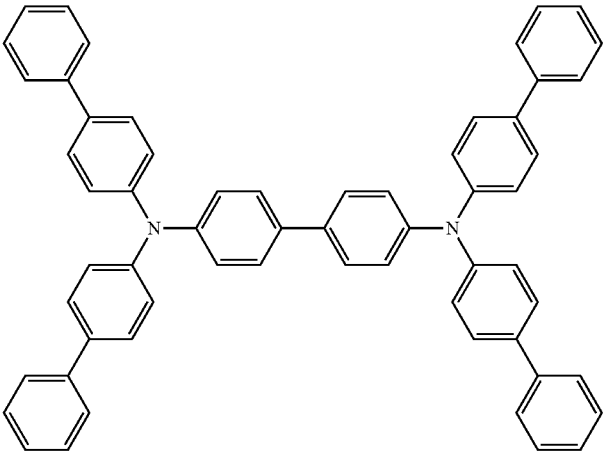 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 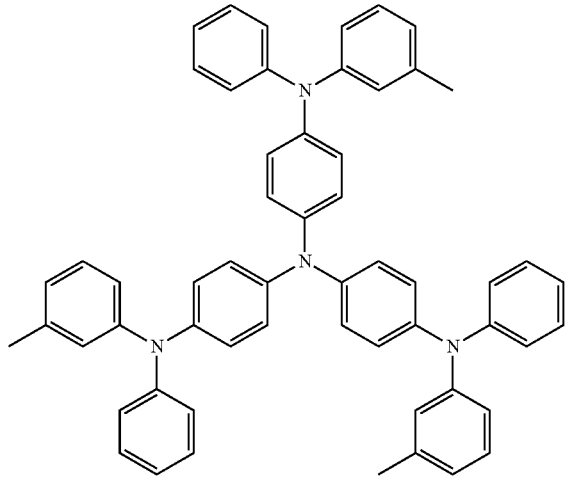 [SMILES: Cc1cccc(N(c2ccccc2)c2ccc(N(c3ccc(N(c4ccccc4)c4cccc(C)c4)cc3)c3ccc(N(c4ccccc4)c4cccc(C)c4)cc3)cc2)c1] | J. Mater. Chem. 3, 319 (1993) |
| | 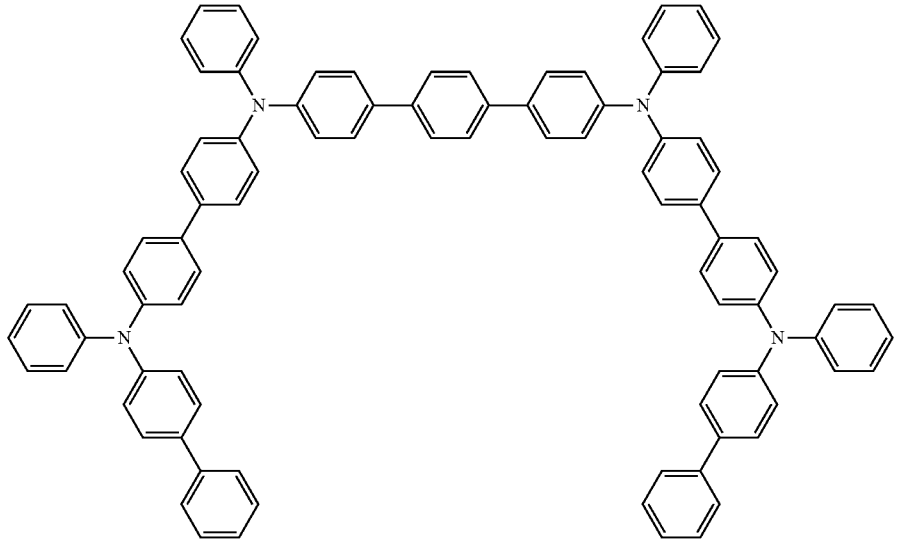 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

| MATERIAL | EXAMPLES OF MATERIAL | PUBLICATIONS |
|---|---|---|
| | 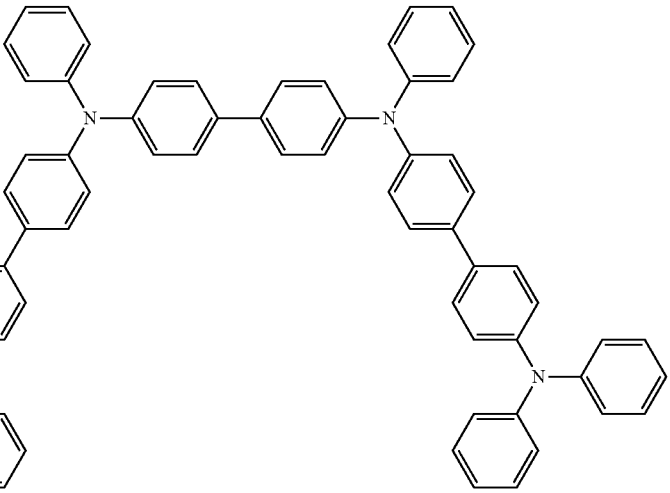 | Appl. Phys. Lett. 90, 183503 (2007) |
| Triaylamine on spirofluorene core | 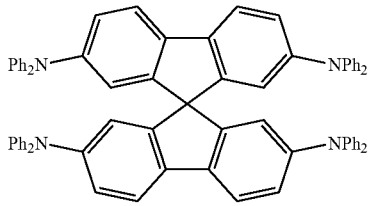 | Synth. Met. 91, 209 (1997) |
| Arylamine carbazole compounds | 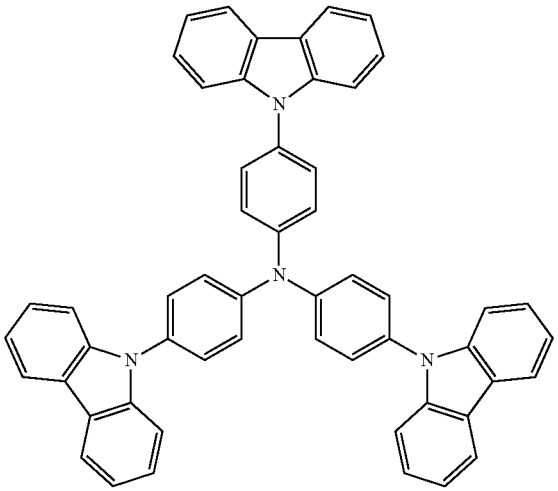 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/ (di)benzofuran | 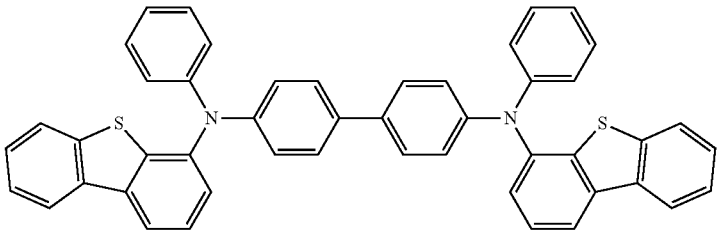 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 |

TABLE 3-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials

Red hosts

| | | |
| --- | --- | --- |
| Arylcarbazoles | | Appl. Phys. Lett. 78, 1622 (2001) |

TABLE 3-continued

| MATERIAL | EXAMPLES OF MATERIAL | PUBLICATIONS |
| --- | --- | --- |
| Metal 8-hydroxy-quinolates (e.g., Alq3, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 3-continued

| MATERIAL | EXAMPLES OF MATERIAL | PUBLICATIONS |
| --- | --- | --- |
| Zinc complexes | | WO2009062578 |

Green hosts

| MATERIAL | EXAMPLES OF MATERIAL | PUBLICATIONS |
| --- | --- | --- |
| Arylcarbazoles | | Appl. Phys. Lett. 78, 1622 (2001) |
| | | US20030175553 |
| | | WO2001039234 |
| Aryltriphenylene compounds | | US20060280965 |

TABLE 3-continued

| MATERIAL | EXAMPLES OF MATERIAL | PUBLICATIONS |
|---|---|---|
| | | US20060280965 |
| | | WO2009021126 |
| Donor acceptor type molecules | | WO2008056746 |
| Aza-carbazole/ DBT/DBF | | JP2008074939 |
| Polymers (e.g., PVK) | | Appl. Phys. Lett. 77, 2280 (2000) |

TABLE 3-continued

| MATERIAL | EXAMPLES OF MATERIAL | PUBLICATIONS |
| --- | --- | --- |
| Spirofluorene compounds | | WO2004093207 |
| Metal phenoxybenzo-oxazole compounds | | WO2005089025 |
| | | WO2006132173 |
| | | JP200511610 |
| Spirofluorene-carbazole compounds | | JP2007254297 |

TABLE 3-continued
| MATERIAL | EXAMPLES OF MATERIAL | PUBLICATIONS |
|---|---|---|
| | 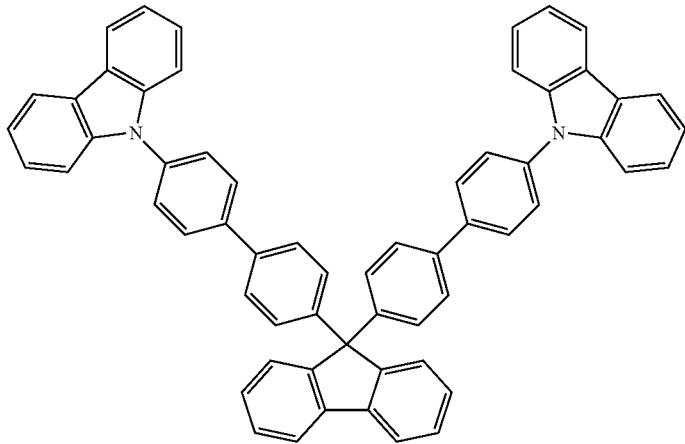 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolo-cabazoles | 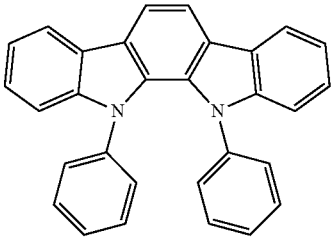 [SMILES: c1ccc(-n2c3ccccc3c3ccc4c5ccccc5n(-c5ccccc5)c4c32)cc1] | WO2007063796 |
| | 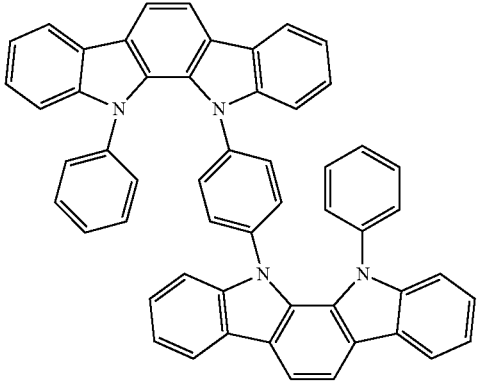 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 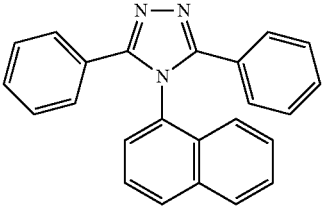 [SMILES: c1ccc(-c2nnc(-c3ccccc3)n2-c2cccc3ccccc23)cc1] | J. Appl. Phys. 90, 5048 (2001) |
| | 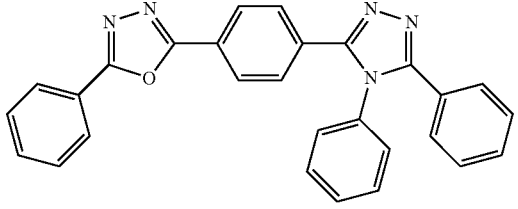 [SMILES: c1ccc(-c2nnc(-c3ccc(-c4nnc(-c5ccccc5)n4-c4ccccc4)cc3)o2)cc1] | WO2004107822 |

TABLE 3-continued
| MATERIAL | EXAMPLES OF MATERIAL | PUBLICATIONS |
|---|---|---|
| Tetraphenylene complexes | 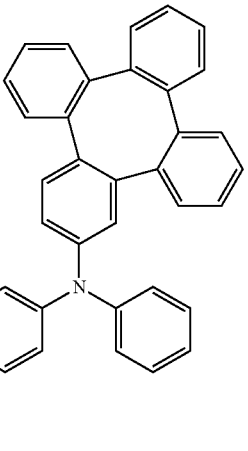 | US20050112407 |
| Metal phenoxy-pyridine compounds | 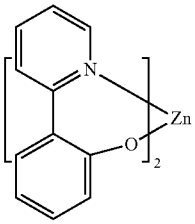 | WO2005030900 |
| Metal coordination complexes (e.g., Zn, Al with N^N ligands) | 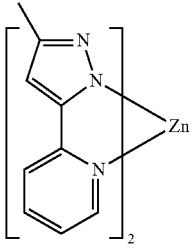 | US20040137268, US20040137267 |
| Blue hosts | | |
| Arylcarbazoles | 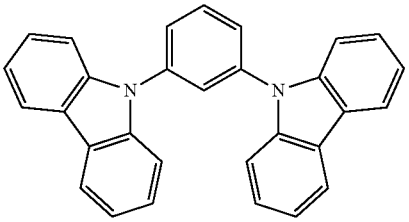 [SMILES: c1cc(-n2c3ccccc3c3ccccc32)cc(-n2c3ccccc3c3ccccc32)c1] | Appl. Phys. Lett. 82, 2422 (2003) |
| | 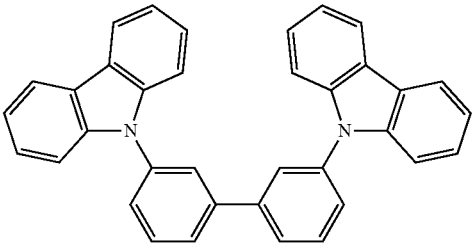 [SMILES: c1cc(-c2cccc(-n3c4ccccc4c4ccccc43)c2)cc(-n2c3ccccc3c3ccccc32)c1] | US20070190359 |

| MATERIAL | EXAMPLES OF MATERIAL | PUBLICATIONS |
|---|---|---|
| Dibenzothiophene/Dibenzofuran-carbazole compounds | 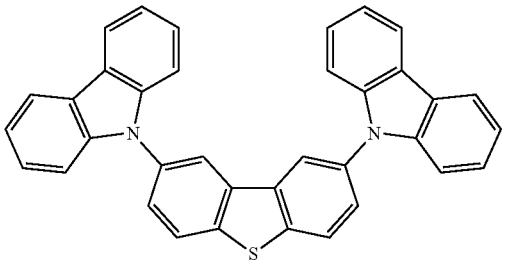 [SMILES: c1ccc2c(c1)c1ccccc1n2-c1ccc2sc3ccc(-n4c5ccccc5c5ccccc54)cc3c2c1] | WO2006114966, US20090167162 |
| | 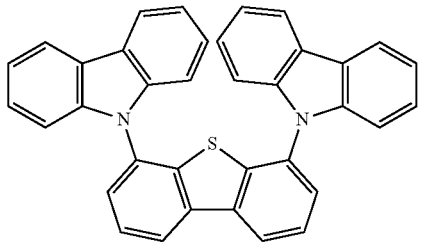 [SMILES: c1cc(-n2c3ccccc3c3ccccc32)c2sc3c(-n4c5ccccc5c5ccccc54)cccc3c2c1] | US20090167162 |
| | 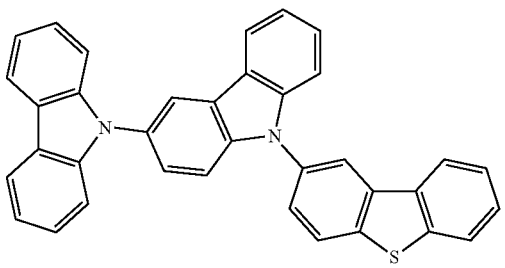 [SMILES: c1ccc2c(c1)sc1ccc(-n3c4ccccc4c4cc(-n5c6ccccc6c6ccccc65)ccc43)cc12] | WO2009086028 |
| | 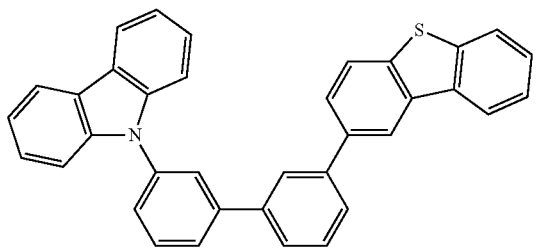 [SMILES: c1cc(-c2cccc(-n3c4ccccc4c4ccccc43)c2)cc(-c2ccc3sc4ccccc4c3c2)c1] | US20090030202, US20090017330 |
| Silicon aryl compounds | 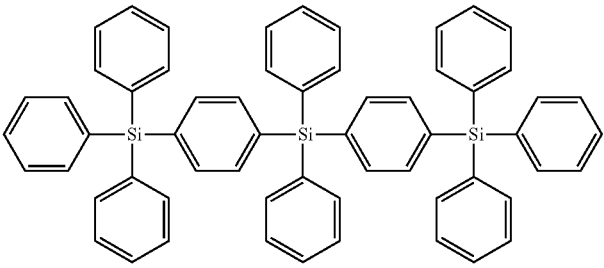 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 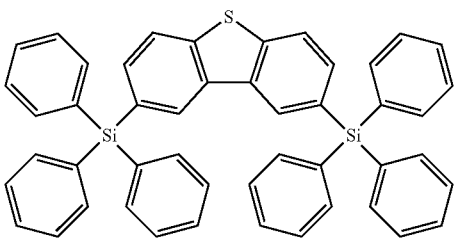 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
| --- | --- | --- |
| Silicon/ Germanium aryl compounds | | EP2034538A |
| Aryl benzoyl ester | | WO2006100298 |
| High triplet metal organometallic complex | | U.S. Pat. No. 7,154,114 |

Phosphorescent dopants
Red dopants

| | | |
| --- | --- | --- |
| Heavy metal porphyrins (e.g., PtOEP) | | Nature 395, 151 (1998) |
| Iridium(III) organometallic complexes | | Appl. Phys. Lett. 78, 1622 (2001) |

TABLE 3-continued

| MATERIAL | EXAMPLES OF MATERIAL | PUBLICATIONS |
|---|---|---|
| | | US2006835469 |
| | | US2006835469 |
| | | US20060202194 |
| | | US20060202194 |
| | | US20070087321 |

TABLE 3-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| Platinum(II) organometallic complexes | | WO2003040257 |

TABLE 3-continued

| MATERIAL | EXAMPLES OF MATERIAL | PUBLICATIONS |
|---|---|---|
| Osminum(III) complexes | (structure with $F_3C$, pyrazole-pyridine, $Os(PPhMe_2)_2$) | Chem. Mater. 17, 3532 (2005) |
| Ruthenium(II) complexes | (structure with $^tBu$, pyrazole-isoquinoline, $Ru(PPhMe_2)_2$) | Adv. Mater. 17, 1059 (2005) |
| Rhenium (I), (II), and (III) complexes | (structure with quinolinolate, $Re(CO)_4$) | US20050244673 |

Green dopants

| | | |
|---|---|---|
| Iridium(III) organometallic complexes | (tris-phenylpyridine Ir complex) and its derivatives | Inorg. Chem. 40, 1704 (2001) |
| | (bis-phenylpyridine Ir acac complex) | US20020034656 |

TABLE 3-continued
| MATERIAL | EXAMPLES OF MATERIAL | PUBLICATIONS |
| --- | --- | --- |
| | 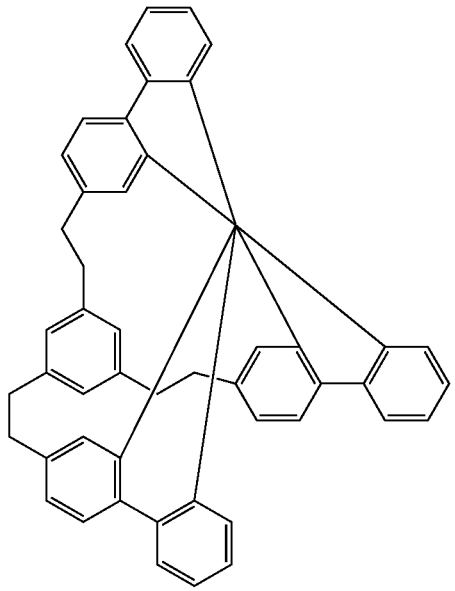 | U.S. Pat. No. 7,332,232 |
| | 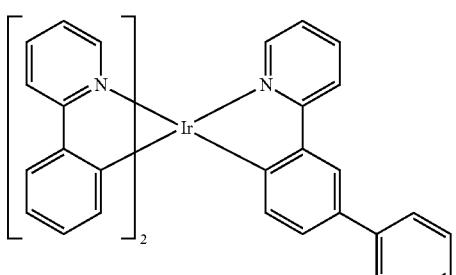 | US20090108737 |
| | 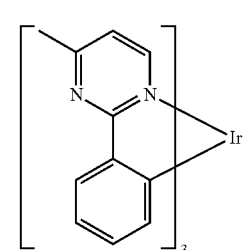 | US20090039776 |
| | 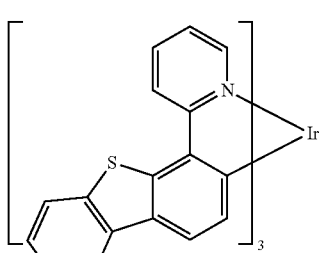 | U.S. Pat. No. 6,921,915 |

| MATERIAL | EXAMPLES OF MATERIAL | PUBLICATIONS |
|---|---|---|
| | 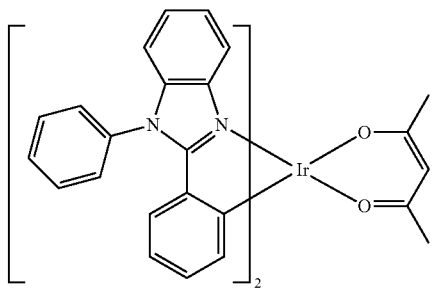 | U.S. Pat. No. 6,687,266 |
| | 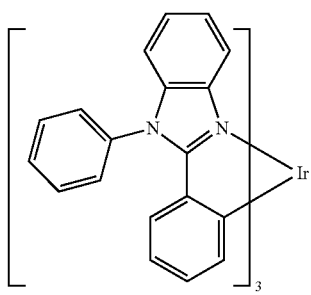 | Chem. Mater. 16, 2480 (2004) |
| | 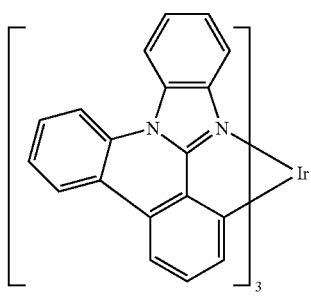 | US20070190359 |
| | 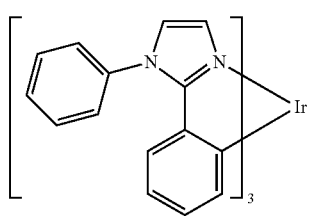 | US 20060008670 JP2007123392 |
| | 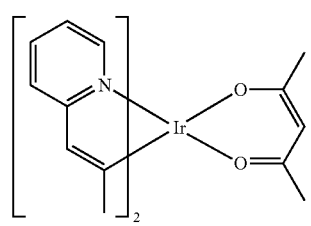 | Adv. Mater. 16, 2003 (2004) |

TABLE 3-continued
| MATERIAL | EXAMPLES OF MATERIAL | PUBLICATIONS |
|---|---|---|
| | 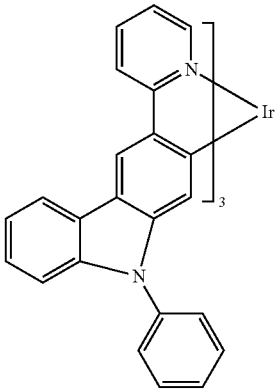 | Angew. Chem. Int. Ed. 2006, 45, 7800 |
| | 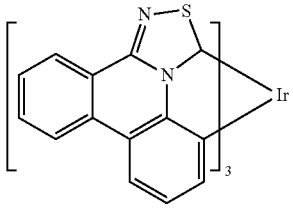 | WO2009050290 |
| | 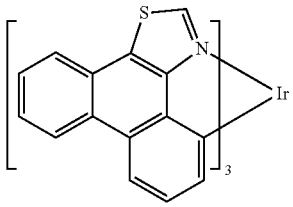 | US20090165846 |
| | 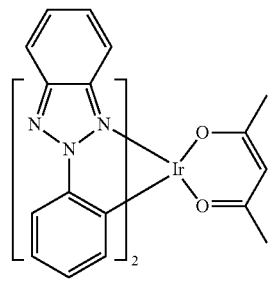 | US20080015355 |
| Monomer for polymeric metal organometallic compounds | 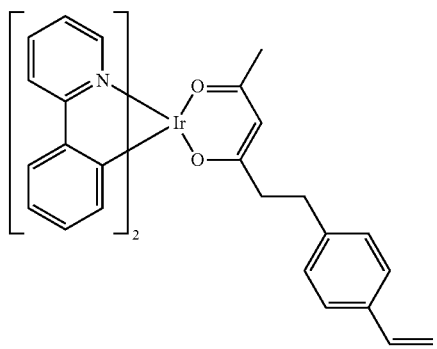 | U.S. Pat. No. 7,250,226, U.S. Pat. No. 7,396,598 |

TABLE 3-continued
| MATERIAL | EXAMPLES OF MATERIAL | PUBLICATIONS |
|---|---|---|
| Pt(II) organometallic complexes, including polydentated ligands | 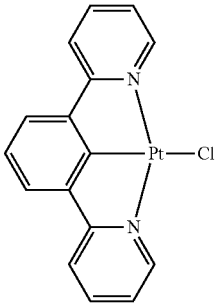 | Appl. Phys. Lett. 86, 153505 (2005) |
| | 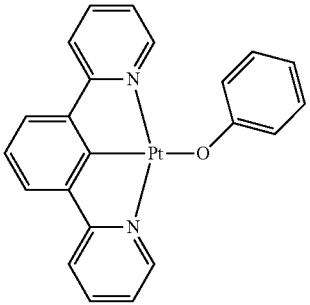 | Appl. Phys. Lett. 86, 153505 (2005) |
| | 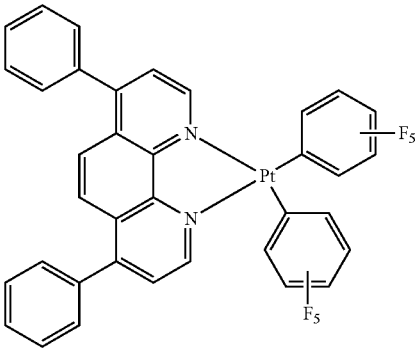 | Chem. Lett. 34, 592 (2005) |
| | 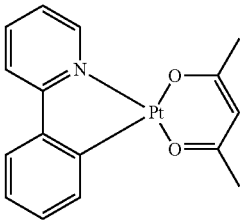 | WO2002015645 |
| | 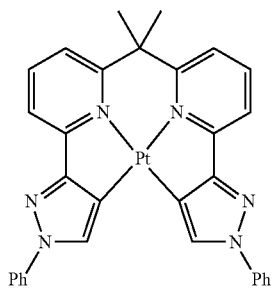 | US20060263635 |

TABLE 3-continued

| MATERIAL | EXAMPLES OF MATERIAL | PUBLICATIONS |
|---|---|---|
| Cu complexes | | WO2009000673 |
| Gold complexes | | Chem. Commun. 2906 (2005) |
| Rhenium(III) complexes | | Inorg. Chem. 42, 1248 (2003) |
| Deuterated organometallic complexes | | US20030138657 |

| MATERIAL | EXAMPLES OF MATERIAL | PUBLICATIONS |
|---|---|---|
| Organometallic complexes with two or more metal centers | 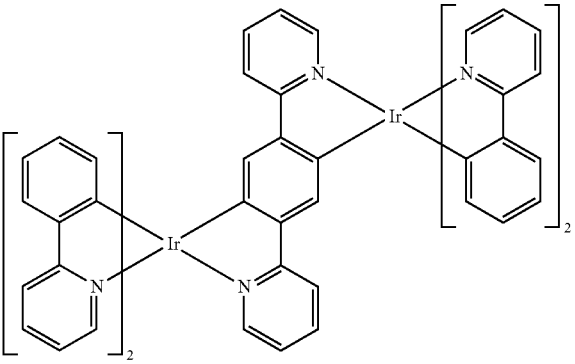 | US20030152802 |
| | 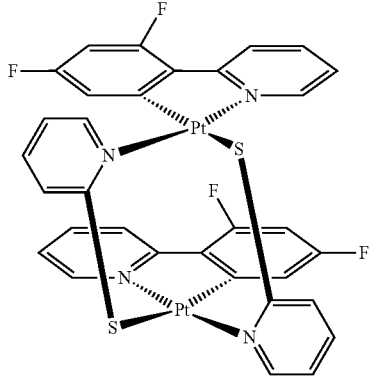 | U.S. Pat. No. 7,090,928 |
| Blue dopants | | |
| Iridium(III) organometallic complexes | 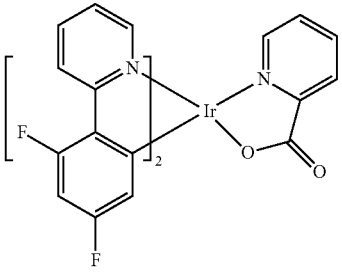 | WO2002002714 |
| | 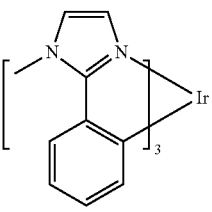 | WO2006009024 |
| | 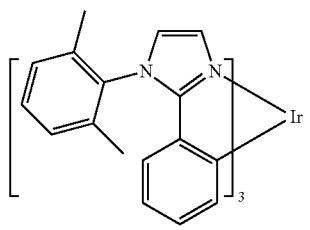 | US20060251923 |

TABLE 3-continued

| MATERIAL | EXAMPLES OF MATERIAL | PUBLICATIONS |
|---|---|---|
| | | U.S. Pat. No. 7,393,599, WO2006056418, US20050260441, WO2005019373 |
| | | U.S. Pat. No. 7,534,505 |
| | | U.S. Pat. No. 7,445,855 |
| | | US20070190359, US20080297033 |
| | | U.S. Pat. No. 7,338,722 |
| | | US20020134984 |

TABLE 3-continued

| MATERIAL | EXAMPLES OF MATERIAL | PUBLICATIONS |
|---|---|---|
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 3-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 3-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | 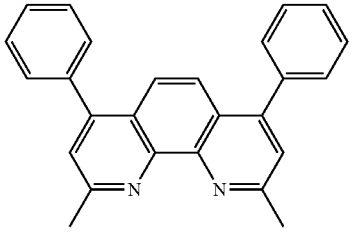 [SMILES: Cc1cc(-c2ccccc2)c2ccc3c(-c4ccccc4)cc(C)nc3c2n1] | Appl. Phys. Lett. 75, 4 (1999) |
| | 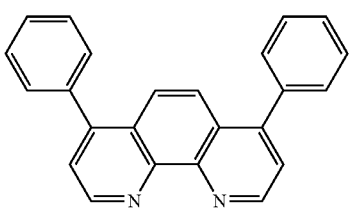 [SMILES: c1ccc(-c2ccnc3c2ccc2c(-c4ccccc4)ccnc23)cc1] | Appl. Phys. Lett. 79, 449 (2001) |
| Metal 8-hydroxy-quinolates (e.g., BAlq) | 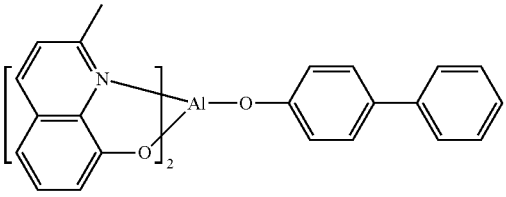 | Appl. Phys. Lett. 81, 162 (2002) |
| 5-member ring electron deficient heterocycles such as triazole, oxadiazole, imidazole, benzoimidazole | 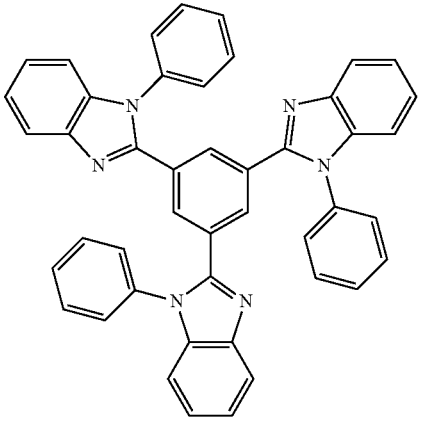 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 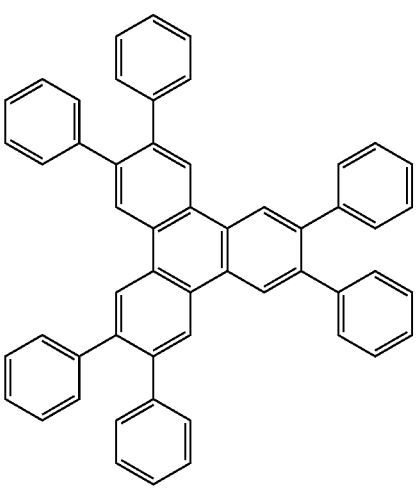 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |

TABLE 3-continued
| MATERIAL | EXAMPLES OF MATERIAL | PUBLICATIONS |
|---|---|---|
| Fluorinated aromatic compounds | 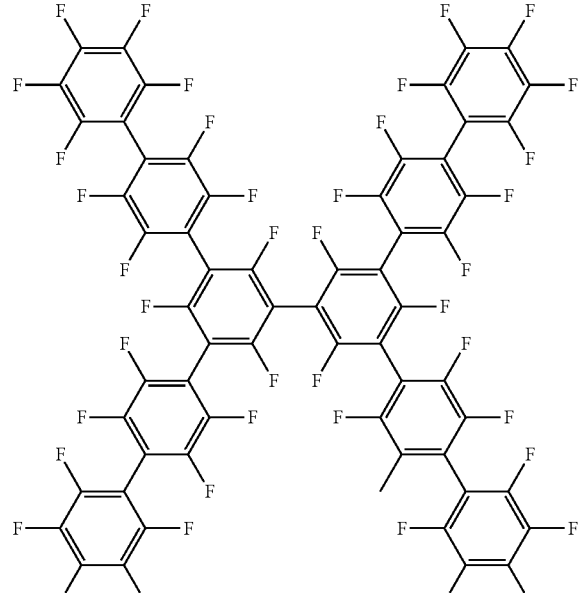 | Appl. Phys. Lett. 79, 156 (2001) |
| Phenothiazine-S-oxide | 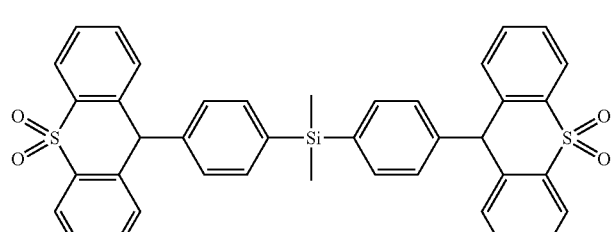 | WO2008132085 |
Electron transporting materials
| | | |
|---|---|---|
| Anthracene-benzoimidazole compounds | 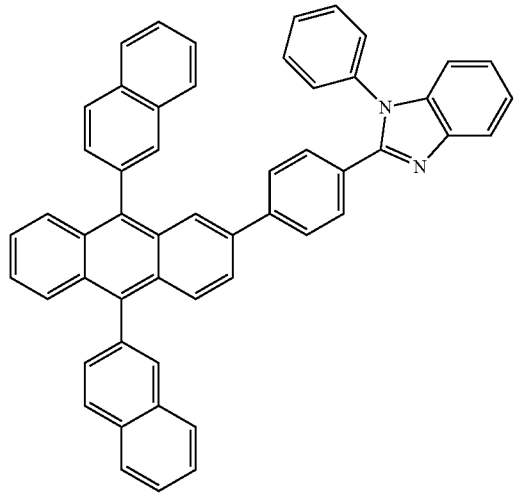 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |

TABLE 3-continued
| MATERIAL | EXAMPLES OF MATERIAL | PUBLICATIONS |
|---|---|---|
| | 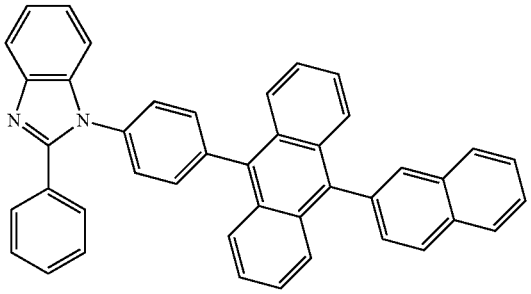 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 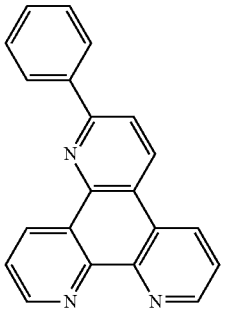 [SMILES: c1ccc(-c2ccc3c4cccnc4c4ncccc4c3n2)cc1] | US2009115316 |
| Anthracene-benzothiazole compounds | 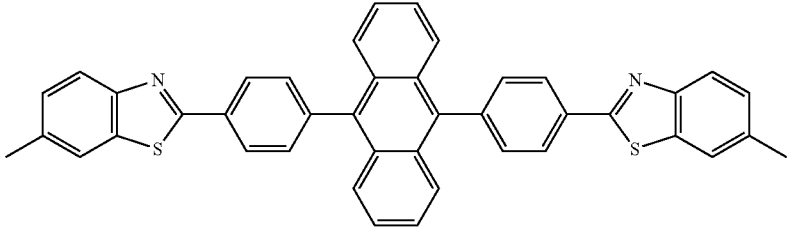 | Appl. Phys. Lett. 89, 063504 (2006) |
| Metal 8-hydroxy-quinolates (e.g., Alq$_3$, Zrq$_4$) | 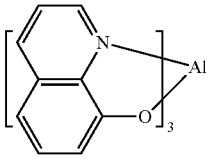 | Appl. Phys. Lett. 51, 913 (1987) U.S. Pat. No. 7,230,107 |
| Metal hydroxy-benoquinolates | 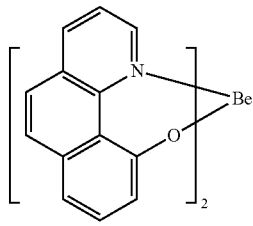 | Chem. Lett. 5, 905 (1993) |
| Bathocuprine compounds such as BCP, BPhen, etc | 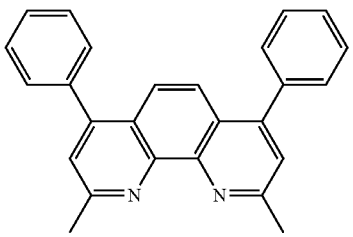 [SMILES: Cc1cc(-c2ccccc2)c2ccc3c(-c4ccccc4)cc(C)nc3c2n1] | Appl. Phys. Lett. 91, 263503 (2007) |

TABLE 3-continued
| MATERIAL | EXAMPLES OF MATERIAL | PUBLICATIONS |
|---|---|---|
| | 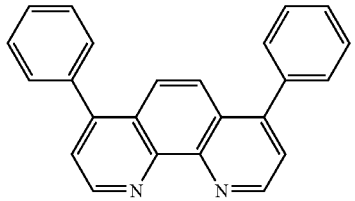 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 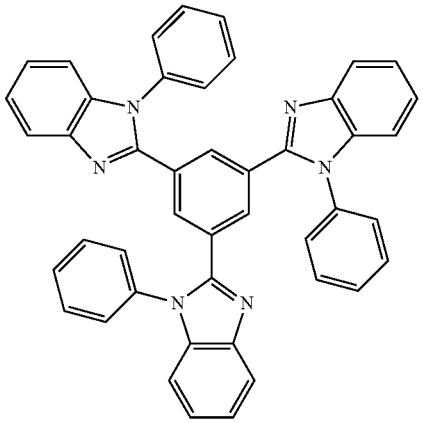 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 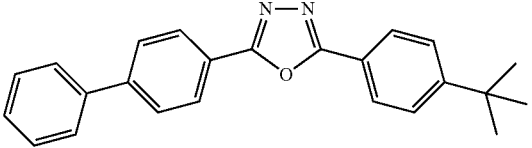 [SMILES: CC(C)(C)c1ccc(-c2nnc(-c3ccc(-c4ccccc4)cc3)o2)cc1] | Appl. Phys. Lett. 55, 1489 (1989) |
| | 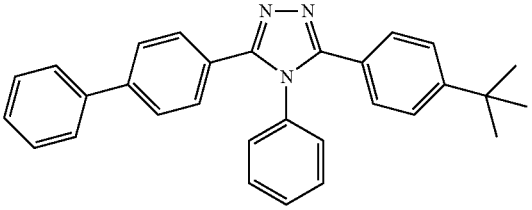 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 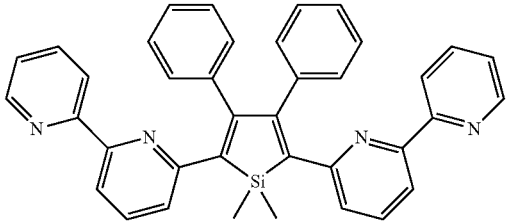 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 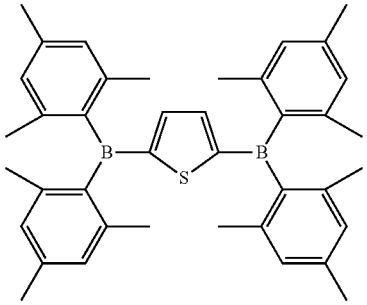 | J. Am. Chem. Soc. 120, 9714 (1998) |

TABLE 3-continued

| MATERIAL | EXAMPLES OF MATERIAL | PUBLICATIONS |
| --- | --- | --- |
| Fluorinated aromatic compounds | | J. Am. Chem. Soc. 122, 1832 (2000) |
| Fullerene (e.g., C60) | | US20090101870 |
| Triazine complexes | | US20040036077 |
| Zn (N^N) complexes | | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, S-Phos is dicyclohexyl(2',6'-dimethoxy-[1,1'-biphenyl]-3-yl)phosphine, THF is tetrahydrofuran, DCM is dichloromethane, PPh$_3$ is triphenylphosphine.

Synthesis of Compound 3

Step 1

Synthesis of 5-Methyl-2-phenylpyridine

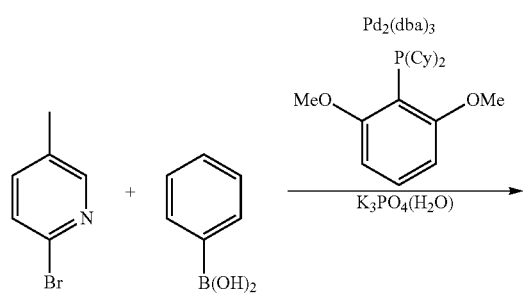

In a 1 L round bottom flask was added 2-bromo-5-methylpyridine (30 g, 174 mmol), phenylboronic acid (25.5 g, 209 mmol), dicyclohexyl(2',6'-dimethoxy-[1,1'-biphenyl]-2-yl)phosphine (2.86 g, 6.98 mmol) and potassium phosphate tribasic monohydrate (120 g, 523 mmol) with toluene (600 mL) and water (60 mL). The reaction mixture was degassed with N$_2$ for 20 min. Pd$_2$(dba)$_3$ (3.19 g, 3.49 mmol) was added and the reaction mixture was refluxed for 18 h. The reaction mixture was cooled, the aqueous layer was removed and the organic layer was concentrated to dryness to leave a residue. The residue was dissolved in EtOAc:hexane (1:3) and passed through a small silica gel plug and eluted with EtOAc:hexane (1:3). The solvent was removed and the crude product was purified by Kugelrohr at 150° C. to yield 26 g of 5-methyl-2-phenylpyridine, which was obtained as a white solid (HPLC purity: 99.2%).

Step 2

Synthesis of iridium chloro-bridged dimer:

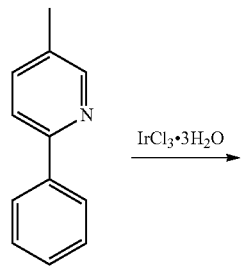

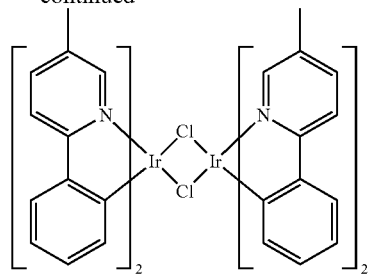

In a 500 mL round bottom flask was added 5-methyl-2-phenylpyridine (12 g, 70.9 mmol) and iridium(III) chloride hydrate (7.14 g, 20.2 mmol) with 2-ethoxyethanol (100 mL) and water (33.3 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 11.0 g (96% yield) of the desired product.

Synthesis of iridium trifluoromethanesulfonate salt:

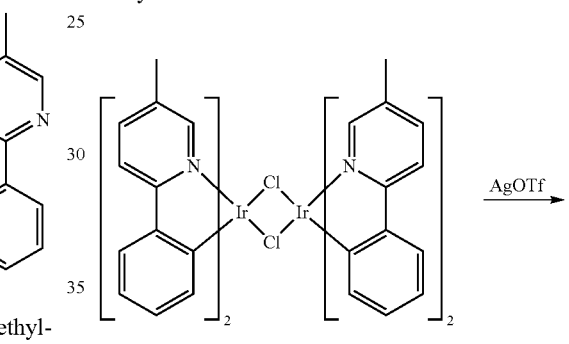

The iridium dimer (11 g, 9.75 mmol), as obtained in Step 2 above, was suspended in 600 mL of dichloromethane. In a separate flask, silver(I) trifluoromethanesulfonate (5.26 g, 20.48 mmol) was dissolved in MeOH (300 mL) and added slowly to the dichloromethane suspension with continuous stirring at room temperature. The reaction mixture was stirred overnight in the dark. The reaction mixture was filtered through a tightly packed Celite® bed and the solvent was removed under vacuum to give 15 g (100% yield) of product as a brownish green solid. The product was used without further purification.

Step 3

Synthesis of Compound 3:

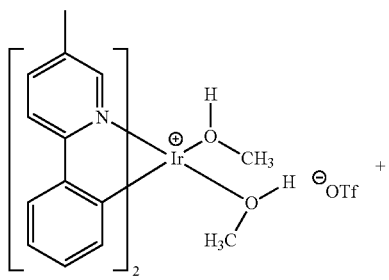

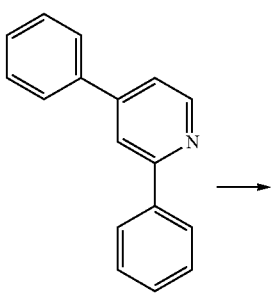

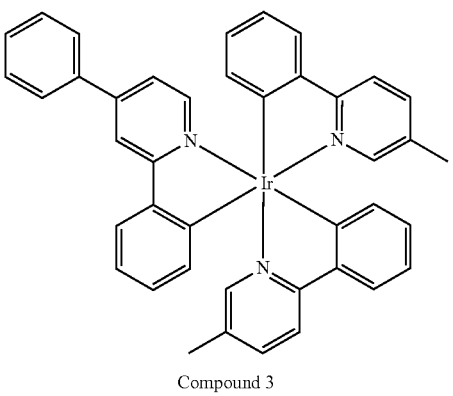

Compound 3

A mixture of iridium trifluormethanesulfonate complex (3.0 g, 4.04 mmol), as obtained from Step 2 above, and 2,4-diphenylpyridine (3.11 g, 13.45 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and hexane (3-4 times). The filtrate was discarded. The Celite®/silica plug was then washed with dichloromethane to elute the crude product. The crude product was chromatographed on silica gel with 1/1 (v/v) dichloromethane/hexane and later 4/1 (v/v) dichloromethane/hexane to yield 0.9 g of Compound 3 (28% yield), which was confirmed by HPLC (99.9% pure) and LC/MS.

Synthesis of Compound 4

Step 1

Synthesis of 4-chloro-2-phenylpyridine:

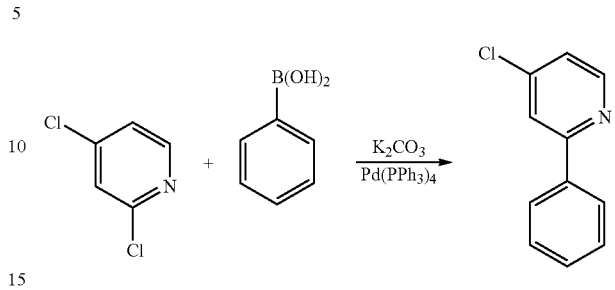

A 1 L round bottom flask was charged with 2,4-dichloropyridine (30 g, 203 mmol), phenylboronic acid (24.7 g, 203 mmol), potassium carbonate (84 g, 608 mmol), Pd(PPh$_3$)$_4$ (2.3 g, 2.0 mmol), dimethoxyethane (500 mL) and water (150 mL). The reaction mixture was degassed and heated to reflux for 20 h. After cooling and separation of the layers, the aqueous layer was extracted with EtOAc (2×100 mL). After removal of the solvent, the crude product was subjected to column chromatography (SiO$_2$, 5% EtOAc in hexane to 10% EtOAc in hexane) to get 34 g (88% yield) of pure product.

Step 2

Synthesis of 2-phenyl-4-(prop-1-en-2yl)pyridine:

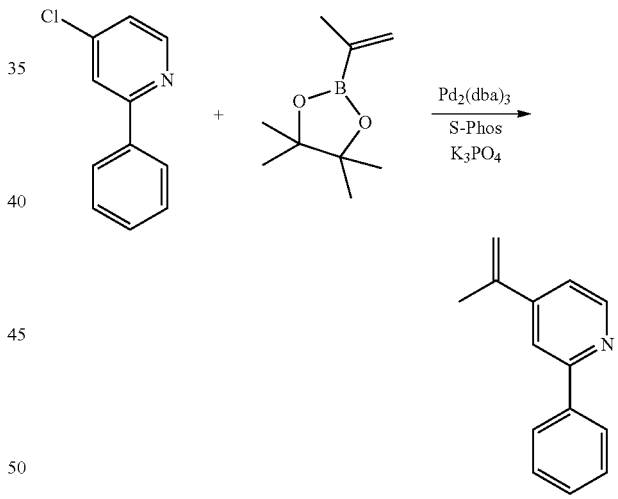

4-Chloro-2-phenylpyridine (14.0 g, 73.8 mmol) and potassium phosphate (51.0 g, 221 mmol) were dissolved in 300 mL of toluene and 30 mL of water. The reaction was purged with nitrogen for 20 minutes and then 4,4,5,5-tetramethyl-2-(prop-1-en-2-yl)-1,3,2-dioxaborolane (16.65 mL, 89 mmol), Pd$_2$(dba)$_3$ (1.35 g, 1.48 mmol) and S-Phos (2.42 g, 5.91 mmol) were added. The reaction was refluxed for 18 h. After cooling, 100 mL of water was added, the layers were separated, and the aqueous layer extracted twice with 100 mL of ethyl acetate. The organic layers were passed through a plug of silica gel, eluting with DCM. After evaporation of the solvent, the crude product was subjected to column chromatography (SiO$_2$, 5% EtOAc in hexane to 10% EtOAc in hexane) to get 13.5 g of pure product (90% yield).

Step 3
Synthesis of 2-phenyl-4-propylpyridine:

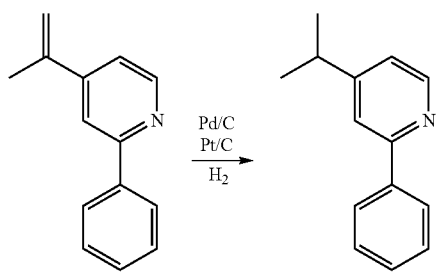

2-Phenyl-4-(prop-1-en-2-yl)pyridine (13.5 g, 69.1 mmol) was added to a hydrogenator bottle with EtOH (150 mL). The reaction mixture was degassed by bubbling $N_2$ for 10 min. Pd/C (0.736 g, 6.91 mmol) and Pt/C (0.674 g, 3.46 mmol) were added. The reaction mixture was placed on a Parr hydrogenator for 2 h ($H_2$~84 psi, according to theoretical calculations). The reaction mixture was filtered on a tightly packed Celite® bed and washed with dichloromethane. The solvent was evaporated and GC/MS confirmed complete hydrogenation. The crude product was adsorbed on Celite® for column chromatography. The crude product was chromatographed on silica gel with 10% EtOAc in hexane to yield 10 g (75% yield) of the desired product (HPLC purity: 99.8%). The product was confirmed by GC/MS.

Step 4
Synthesis of iridium chloro-bridged dimer:

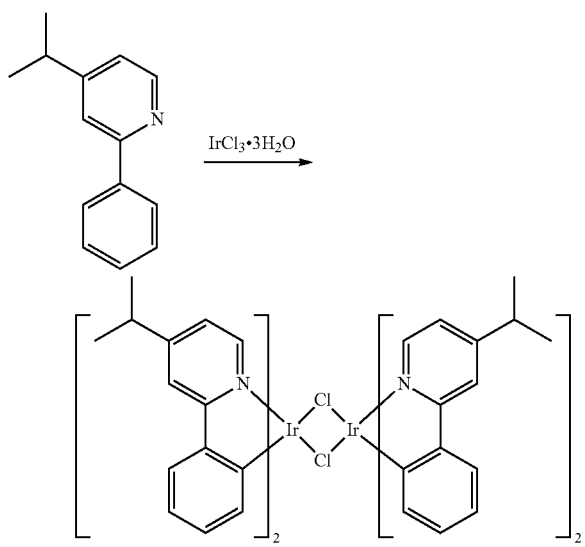

To a 500 mL round-bottom flask was added 4-isopropyl-2-phenylpyridine (8.0 g, 40.6 mmol) and iridium(III) chloride hydrate (7.4 g, 20.28 mmol) with 2-ethoxyethanol (90 mL) and water (30 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 6.1 g (95% yield) of the desired product.

Step 5
Synthesis of iridium trifluoromethanesulfonate salt:

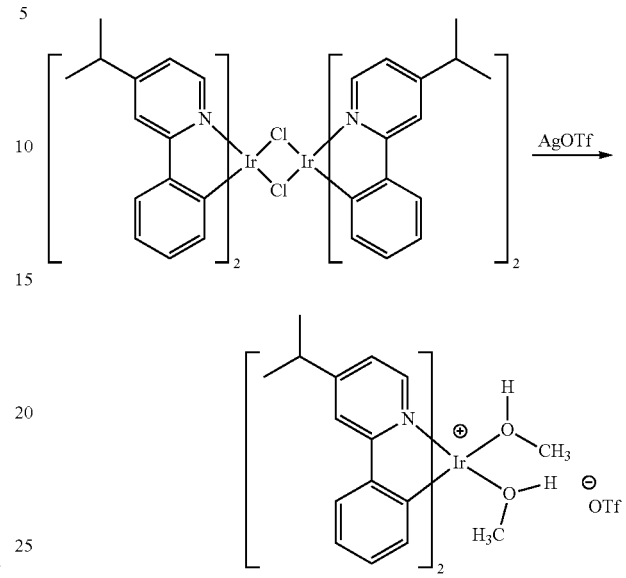

The iridium dimer (6.2 g, 4.94 mmol), obtained as in Step 4 above, was dissolved in 500 mL of dichloromethane. In a separate flask, silver(I) trifluoromethanesulfonate (2.66 g, 10.37 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 7.8 g (100% yield) of product as a brownish green solid. The product was used without further purification.

Step 6
Synthesis of Compound 4:

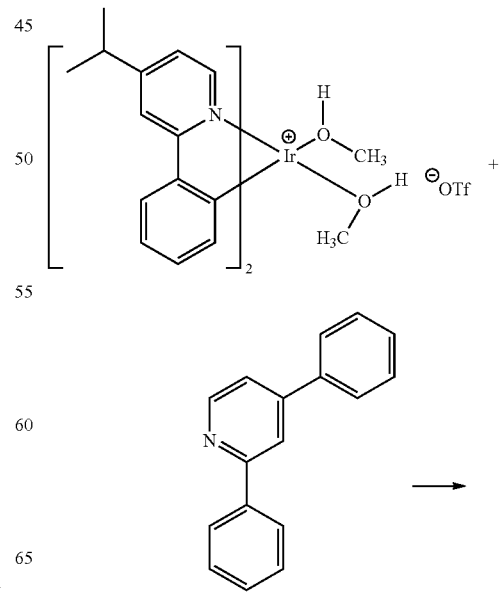

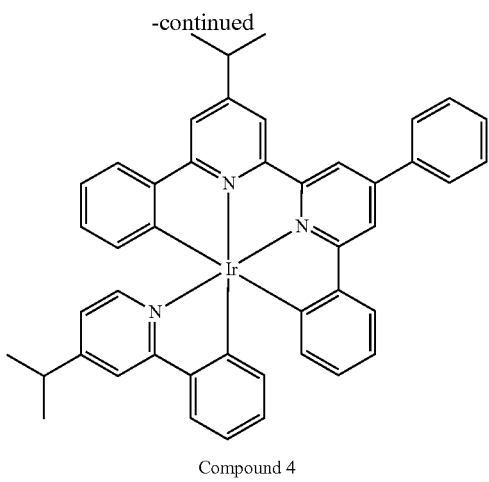

Compound 4

A mixture of iridium trifluormethanesulfonate complex (2.4 g, 3.01 mmol), obtained as in Step 5 above, and 2,4-diphenylpyridine (2.4 g, 10.38 mmol) in EtOH (30 mL) and MeOH (30 mL) was refluxed for 20 h under $N_2$ atmosphere. The reaction mixture was cooled to room temperature, diluted with ethanol, Celite® was added, and the mixture was stirred for 10 min. The mixture was filtered on a small silica gel plug and washed with ethanol (3-4 times) and with hexane (3-4 times). The filtrate was discarded. The Celite®/silica plug was then washed with dichloromethane to elute the product. The crude product was chromatographed on silica gel with 30% THF in hexanes to yield 1.24 g (51% yield) of Compound 4 as a yellow solid. The product was confirmed by HPLC (99.9% pure) and LC/MS.

Synthesis of Compound 5
Step 1
Synthesis of 4-(4-isobutylphenyl)-2-phenylpyridine:

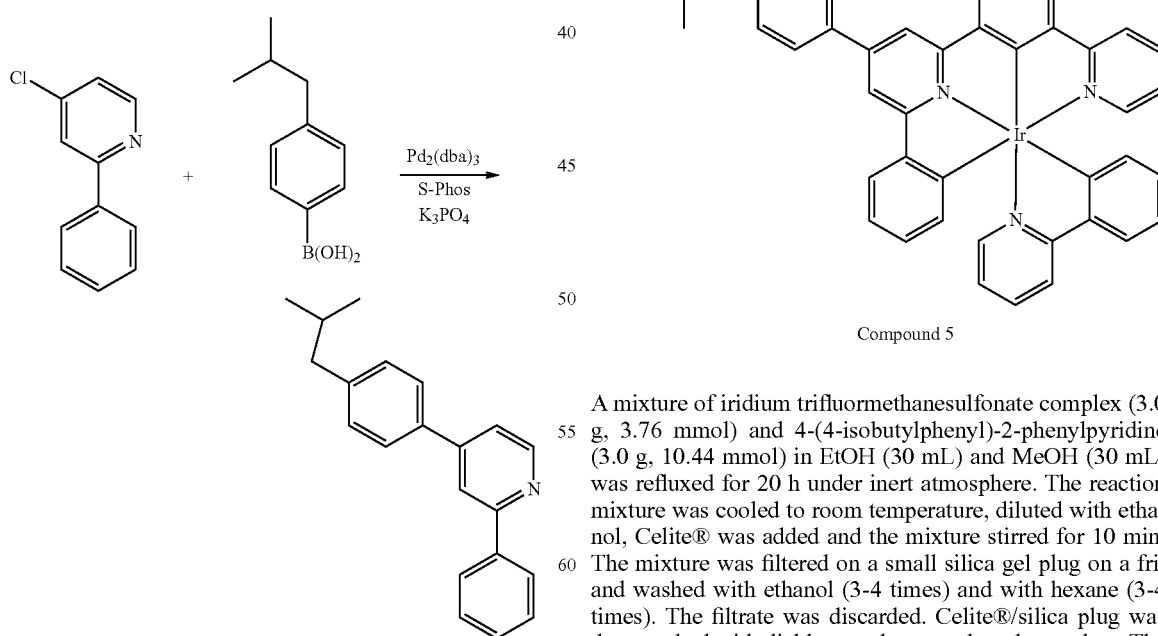

A 250 mL round-bottomed flask was charged with 4-chloro-2-phenylpyridine (5 g, 26.4 mmol), (4-isobutylphenyl)boronic acid (7.04 g, 39.5 mmol), $Pd_2(dba)_3$ (0.483 g, 0.527 mmol), dicyclohexyl(2',6'-dimethoxy-[1,1'-biphenyl]-3-yl)phosphine (S-Phos) (0.866 g, 2.109 mmol), $K_3PO_4$ (16.79 g, 79 mmol), toluene (100 mL) and water (10 mL) to give a yellow suspension. The suspension was heated to reflux for 21 hrs. The reaction mixture was poured into water and extracted with EtOAc. The organic layers were combined and subjected to column chromatography ($SiO_2$, 10% EtOAc in hexane) to yield 4-(4-isobutylphenyl)-2-phenylpyridine (6 g, 20.9 mmol, 79% yield).

Step 2
Synthesis of Compound 5:

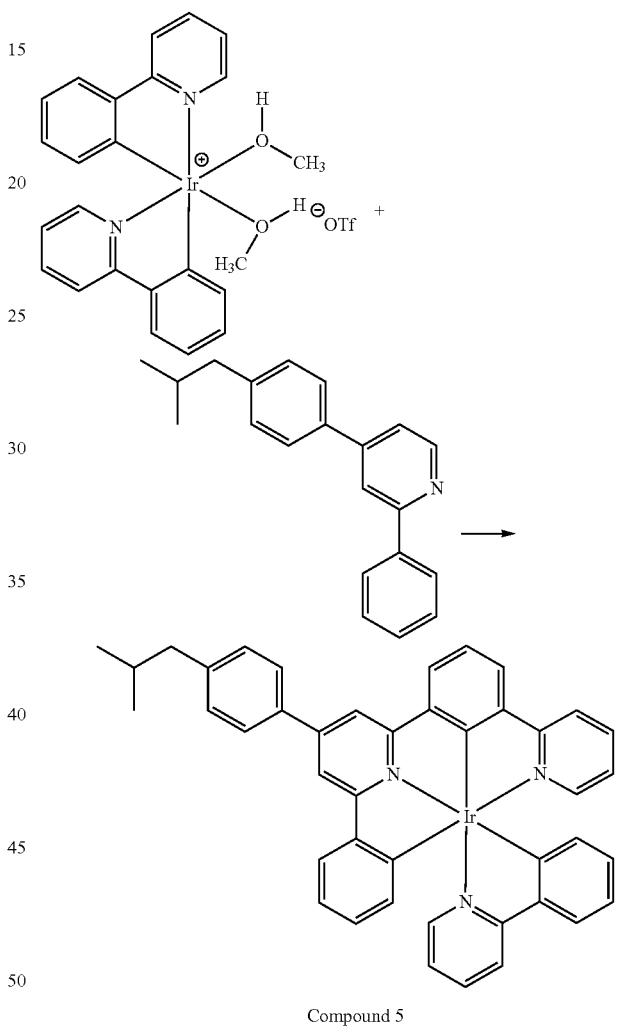

Compound 5

A mixture of iridium trifluormethanesulfonate complex (3.0 g, 3.76 mmol) and 4-(4-isobutylphenyl)-2-phenylpyridine (3.0 g, 10.44 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. Celite®/silica plug was then washed with dichloromethane to elute the product. The crude product was chromatographed on silica gel with 1/1 dichloromethane/hexane to yield 2.0 g (65% yield) of Compound 5 as a yellow solid. Compound 5 was confirmed by HPLC (99.8% pure) and LC/MS.

Synthesis of Compound 6
Step 1
Synthesis of iridium chloro-bridged dimer:

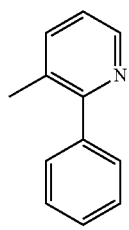

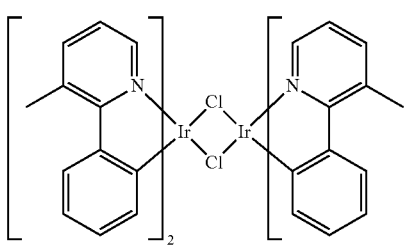

To a 500 mL round-bottom flask was added 3-methyl-2-phenylpyridine (5.7 g, 33.7 mmol) and iridium(III) chloride hydrate (5.94 g, 16.84 mmol), 2-ethoxyethanol (100 mL) and water (33.3 mL). The resulting reaction mixture was refluxed at 130° C. for 18 h under a nitrogen atmosphere. The resulting precipitate was filtered and washed with methanol (3-4 times) and hexane (3-4 times). The product obtained was dried to give 6.35 g (66% yield) of the desired product.

Step 2
Synthesis of iridium trifluoromethanesulfonate salt:

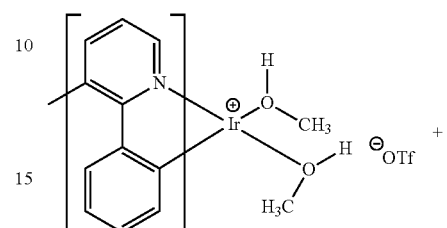

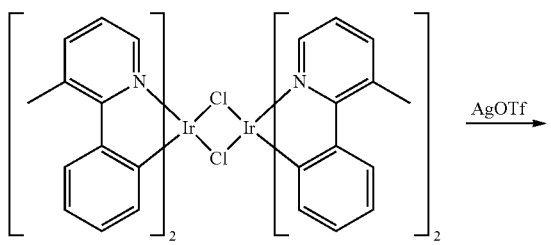

The iridium dimer (4.33 g, 3.84 mmol) was dissolved in 500 mL of dichloromethane. In a separate flask, silver(I) trifluoromethanesulfonate (2.07 g, 8.06 mmol) was dissolved in MeOH (250 mL) and was added slowly to the dichloromethane solution with continuous stirring at room temperature. The reaction mixture was stirred overnight in the dark. The reaction mixture was filtered through a tightly packed Celite® bed and the solvent was removed under vacuum to give 5.86 g (100% yield) of product as a brownish solid. The product was used without further purification.

Step 3
Synthesis of Compound 6:

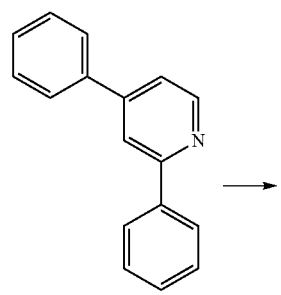

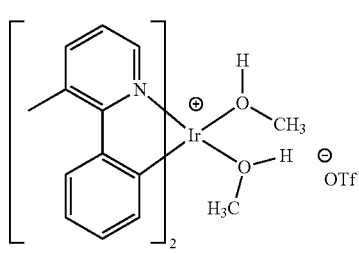

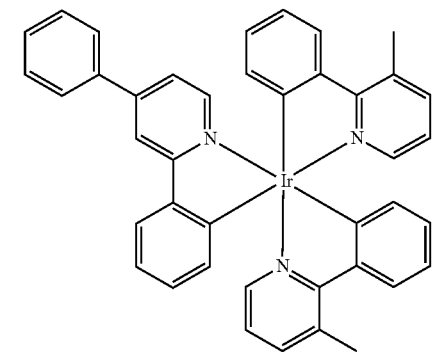

Compound 6

A mixture of iridium trifluormethanesulfonate complex (2.85 g, 3.84 mmol) and 2-(dibenzo[b,d]furan-4-yl)-4,5-dimethylpyridine (2.85 g, 12.33 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 (v/v) dichloromethane/hexane to yield 0.5 g (17% yield) of Compound 6 as a yellow solid. Compound 6 was confirmed by HPLC (99.8% pure) and LC/MS.

Synthesis of Compound 7

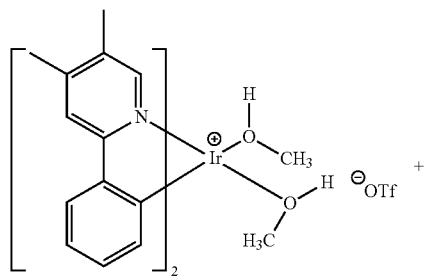

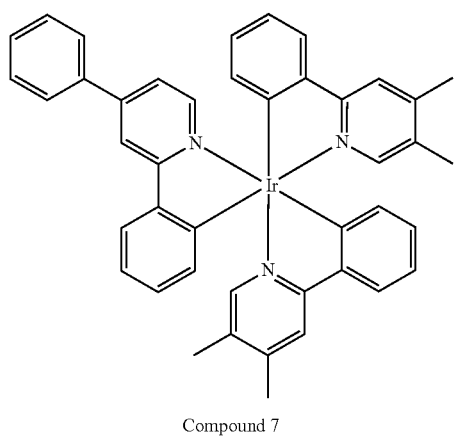

Compound 7

A mixture of iridium trifluormethanesulfonate complex (3.0 g, 3.76 mmol) and 4-(4-isobutylphenyl)-2-phenylpyridine (3.0 g, 10.44 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with toluene to yield 1.35 g (44% yield) of Compound 7 as a yellow solid. Compound 7 was confirmed by HPLC (99.9% pure) and LC/MS.

Synthesis of Compound 8

Step 1

Synthesis of 2-phenyl-5-(prop-1-en-2-yl)pyridine:

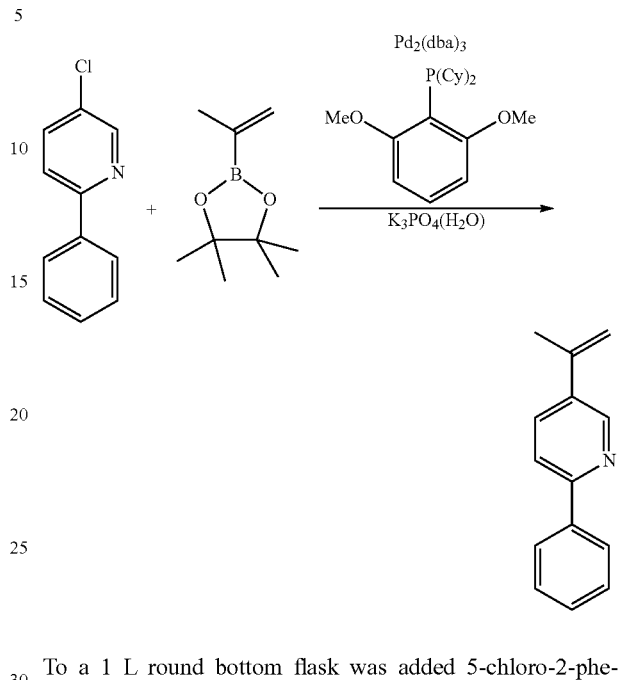

To a 1 L round bottom flask was added 5-chloro-2-phenylpyridine (10.15 g, 53.5 mmol), dicyclohexyl(2',6'-dimethoxy-[1,1'-biphenyl]-2-yl)phosphine (1.8 g, 4.3 mmol), potassium phosphate tribasic monohydrate (37.0 g, 161 mmol) with toluene (200 mL) and water (20 mL). The reaction mixture was degassed with $N_2$ for 20 minutes, then 4,4,5,5-tetramethyl-2-(prop-1-en-2-yl)-1,3,2-dioxaborolane (12.07 mL, 64.2 mmol) and $Pd_2(dba)_3$ (0.980 g, 1.070 mmol) were added and the reaction mixture was refluxed for 18 h. The aqueous layer was removed and the organic layer was concentrated to dryness. The crude product was chromatographed on silica gel with 0-20% EtOAc in hexane to yield 11 g of the desired product (HPLC purity: 95%). The product was confirmed by GC/MS.

Step 2

Synthesis of 2-phenyl-5-isopropylpyridine:

2-Phenyl-5-(prop-1-en-2-yl)pyridine (11 g, 56.3 mmol) was added to a hydrogenator bottle with EtOH (150 mL). The reaction mixture was degassed by bubbling $N_2$ for 10 min, after which, Pd/C (0.60 g, 5.63 mmol) and Pt/C (0.55 g, 2.82 mmol) were added. The reaction mixture was placed on the Parr hydrogenator for 1.5 h ($H_2$~70 psi, according to theoretical calculations). The reaction mixture was filtered on a tightly packed Celite® bed and washed with dichloromethane. The solvent was removed on a rotoevaporator and GC/MS confirmed complete conversion. The crude product was adsorbed on Celite® for column chromatography. The crude product was chromatographed on silica gel with 10% EtOAc in hexane to yield 6 g (54% yield) of the desired product (HPLC purity: 100%). The product was confirmed by GC/MS.

Step 3

Synthesis of iridium chloro-bridged dimer:

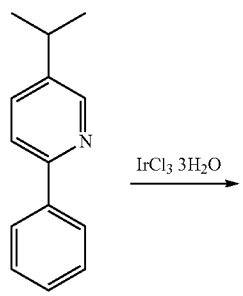

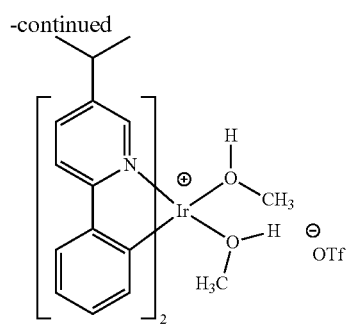

The iridium dimer (5.3 g, 4.27 mmol) was dissolved in 500 mL of dichloromethane. In a separate flask, silver(I) trifluoromethanesulfonate (2.3 g, 8.97 mmol) was dissolved in MeOH (250 mL) and added slowly to the dichloromethane solution with continuous stirring at room temperature. The reaction mixture was stirred overnight in the dark. The reaction mixture was filtered through a tightly packed Celite® bed and the solvent was removed under vacuum to give 6.9 g (100% yield) of product as a brownish solid. The product was used without further purification.

Step 5

Synthesis of Compound 8

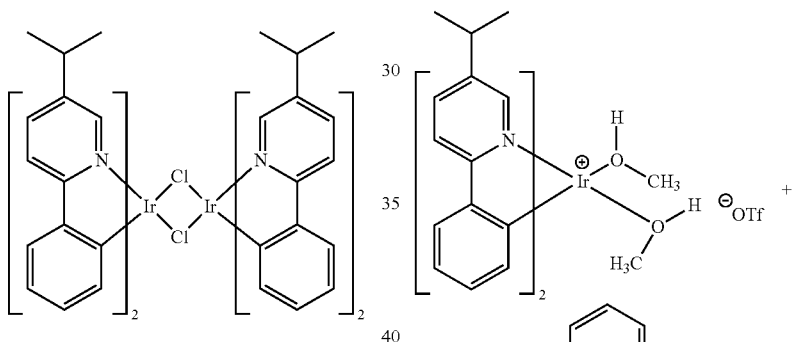

To a 500 mL round-bottom flask was added 5-isopropyl-2-phenylpyridine (6.0 g, 30.4 mmol) and iridium(III) chloride hydrate (3.57 g, 10.14 mmol) with 2-ethoxyethanol (100 mL) and water (33.3 mL) under a nitrogen atmosphere. The resulting reaction mixture was refluxed at 130° C. for 18 h. The resulting precipitate was filtered and washed with methanol (3-4 times) and hexane (3-4 times). The product obtained was dried to give 7 g (100% yield) of the desired product.

Step 4

Synthesis of iridium trifluoromethanesulfonate salt:

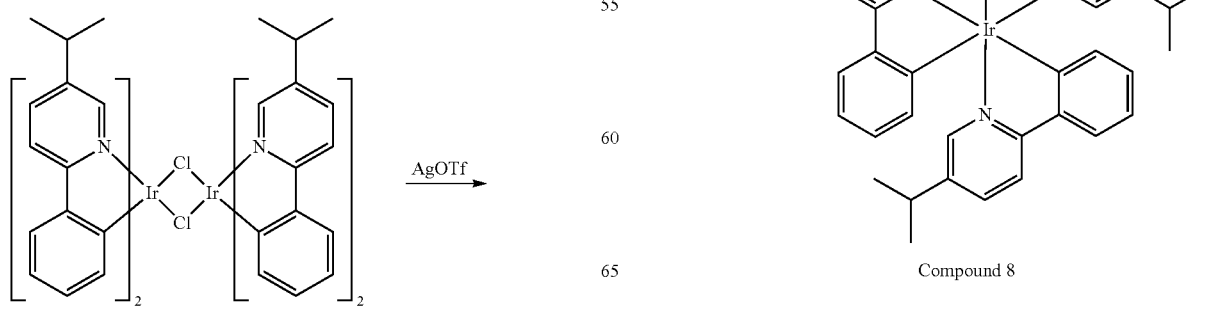

Compound 8

A mixture of iridium trifluoromethanesulfonate complex (3.0 g, 3.76 mmol) and 2-(dibenzo[b,d]furan-4-yl)-4,5-dimethylpyridine (3.0 g, 10.98 mmol) in EtOH (30 mL) and MeOH (30 mL) was refluxed for 20 h under inert atmosphere. The reaction mixture was cooled to room temperature, diluted with ethanol, Celite® was added and the mixture stirred for 10 min. The mixture was filtered on a small silica gel plug on a frit and washed with ethanol (3-4 times) and with hexane (3-4 times). The filtrate was discarded. The Celite®/silica plug was then washed with dichloromethane to elute the product. The crude product was chromatographed on silica gel with 1/1 dichloromethane/hexane to yield 2.1 g (65% yield) of Compound 8 as a yellow solid. The product was confirmed by HPLC (99.8% pure) and LC/MS.

Synthesis of Compound II-11

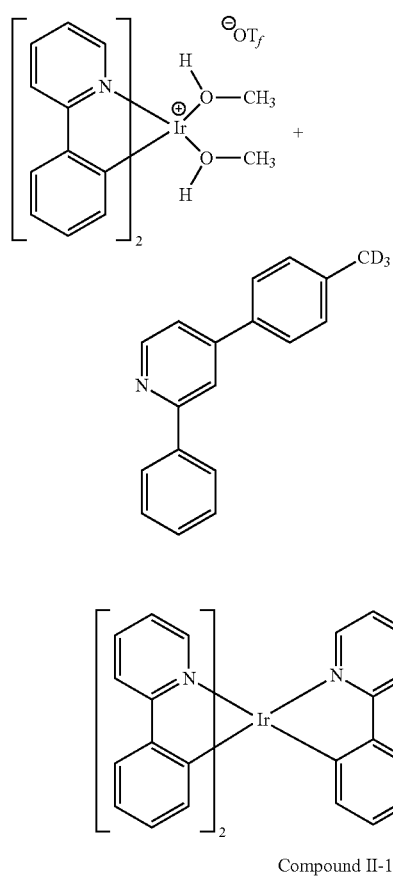

Compound II-11

Iridium intermediate (11.5 g, 17.6 mmol) and 2-phenyl-4-(4-methyl-d₃-phenyl)pyridine (13 g, 52.2 mmol) were suspended/dissolved in 1:1 methanol:ethanol (440 mL). The reaction was heated at reflux for 24 hours then cooled to room temperature. Celite® was added and the reaction was stirred for 10 minutes. The suspension was filtered through a pad of silica gel via vacuum filtration and the silica gel/Celite® pad was washed with ethanol. The receiving flask was changed and the Celite®/silica gel pad was washed with dichloromethane. The dichloromethane extracts were concentrated to give ~10 g of crude product of ~92% purity. The crude was purified by column chromatography to give desired product (4.7 g, 35% yield).

Synthesis of Compound II-232

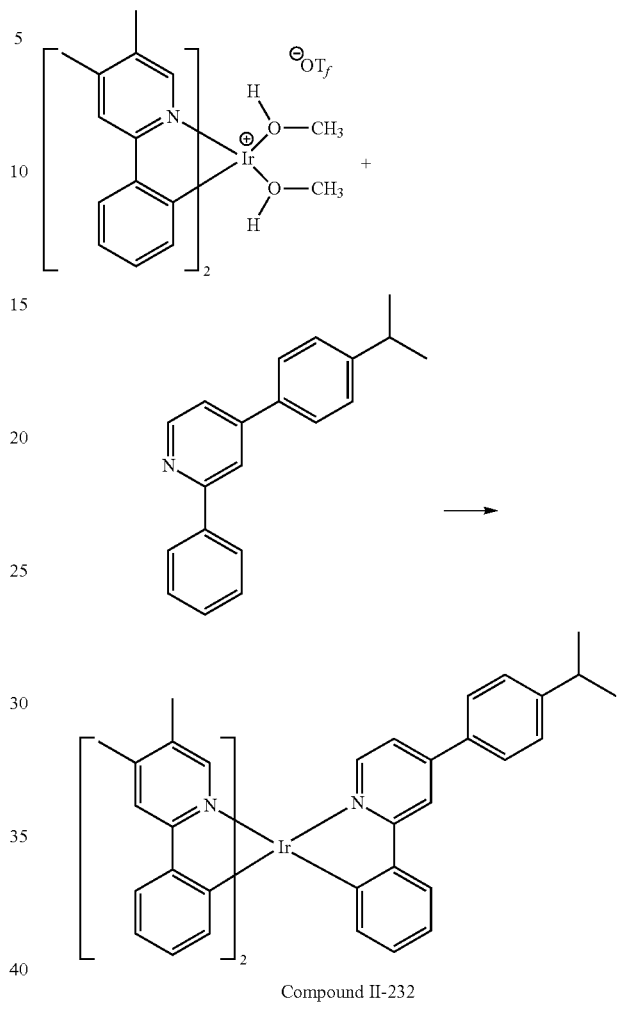

Compound II-232

A mixture of the iridium intermediate (3.01 g, 4.03 mmol), 4-(4-isopropylphenyl)-2-phenylpyridine (3.3 g, 12.08 mmol), methanol (100 mL) and ethanol (100 mL) was heated up at 65° C. (oil bath temperature) for 72 hours. The reaction was cooled down and filtered. The solid was washed thoroughly with methanol. The crude was run through a silica gel plug with dichloromethane, then purified by reverse phase column (C18) with 5% water in acetonitrile to obtain 1.2 g pure product (yield 36%).

Synthesis of Compound II-263

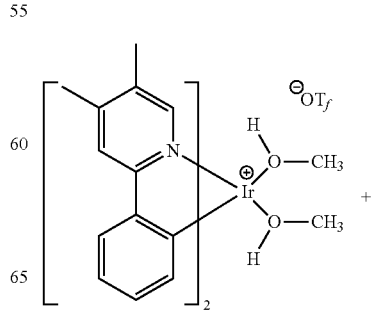

-continued

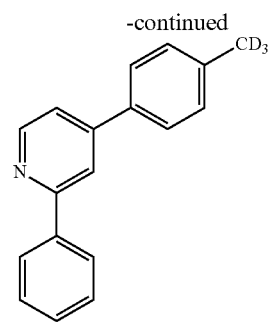

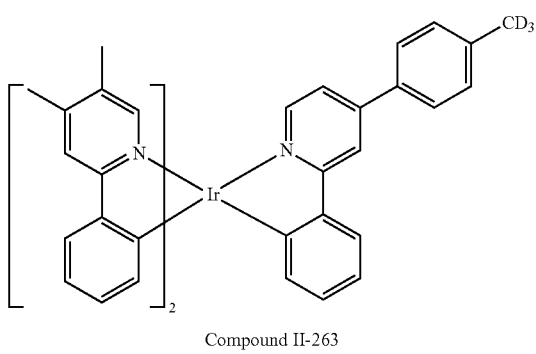

Compound II-263

A mixture of the iridium intermediate (2.5 g, 3.25 mmol), 2-phenyl-4-(4-methyl-d₃-phenyl)pyridine (2.41 g, 9.74 mmol), methanol (100 mL) and ethanol (100 mL) was heated up at 65° C. (oil bath T) for 72 hours. The reaction was cooled down and filtered. The solid was washed thoroughly with methanol. The solid was run through a silica plug with dichloromethane, then purified with reverse phase column (C18) with 10% water in Macetonitrile to obtain 0.670 g (26% yield) of pure product.

Synthesis of Compound II-242

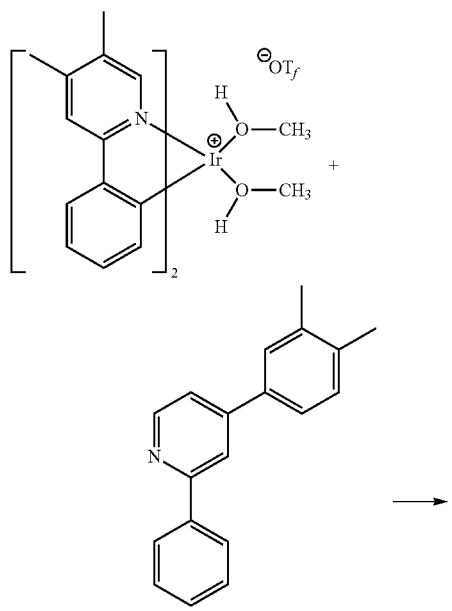

-continued

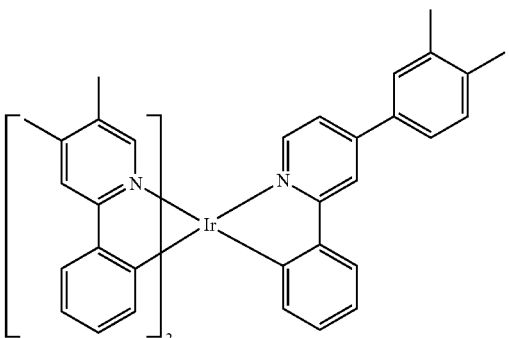

Compound II-242

A mixture of the iridium intermediate (3.2 g, 4.16 mmol), 4-(3,4-dimethylphenyl)-2-phenylpyridine (3.23 g, 12.47 mmol), methanol (100 mL) and ethanol (100 mL) was heated up at 65° C. (oil bath temperature) for 72 hours. The reaction was cooled down and filtered. The solid was washed thoroughly with methanol. The solid was run through a silica gel plug with dichloromethane, then purified with reverse phase column (C18) with 5% water in acetonitrile to obtain 2.2 g pure product (yield 64.9%).

Synthesis of Compound II-536

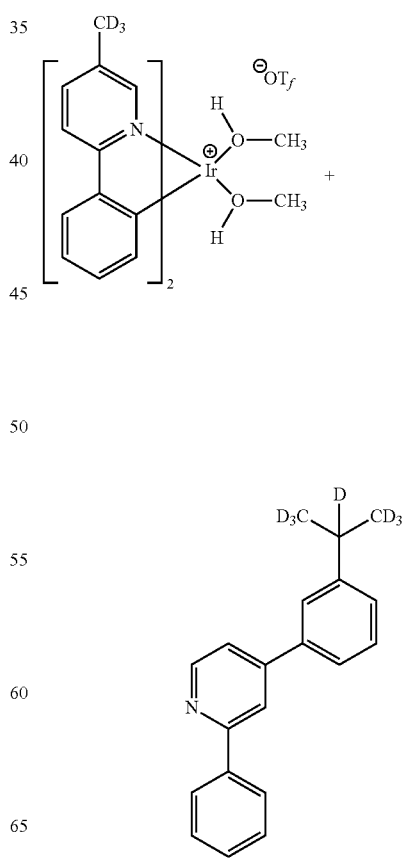

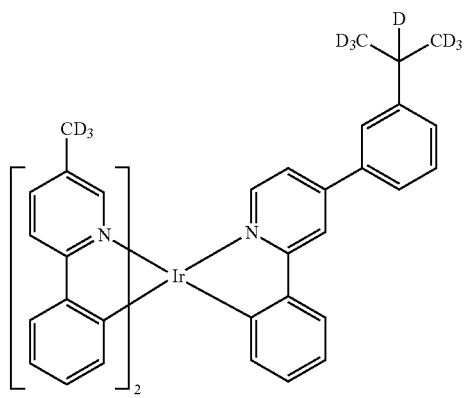

Compound II-536

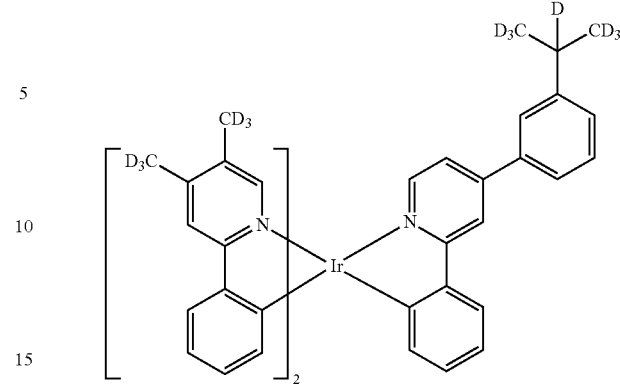

Compound II-737

A mixture of the iridium intermediate (1.6 g, 2.14 mmol), 4-(3-isopropyl-d7-phenyl)-2-phenylpyridine (1.8 g, 6.42 mmol), ethanol (60 mL) and methanol (60 mL) was heated at 65° C. for 72 hours. The reaction was cooled down and filtered through a small plug of silica gel and washed with dichloromethane. The solution was concentrated and chromatographed (1:1 heptane:DCM) to give desired product (0.4 g, 23% yield).

Synthesis of Compound II-737

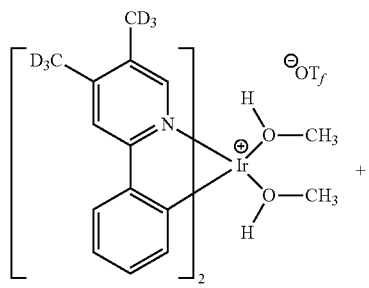

+

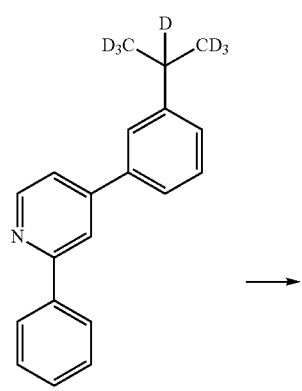

→

A mixture of the iridium intermediate (1.6 g, 2.05 mmol), 4-(3-isopropyl-d7-phenyl)-2-phenylpyridine (1.72 g, 6.14 mmol), ethanol (60 mL) and methanol (60 mL) was heated at 65° C. for 72 hours. The reaction was cooled down and filtered through a small plug of silica gel and washed with dichloromethane. The dichloromethane solution was concentrated and chromatographed with C18 reverse phase column 90-95% acetonitrile in water to give desired product (0.48 g, 28% yield).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:
1. A compound comprising a heteroleptic iridium complex having the formula $IrL_A(L_B)_2$, wherein the heteroleptic iridium complex is selected from the group consisting of compounds listed in the following table:

| Compound Number | $L_A$ | $L_B$ |
|---|---|---|
| II-234. | $L_{A6}$ | $L_{B5}$ |
| II-235. | $L_{A7}$ | $L_{B5}$ |
| II-240. | $L_{A12}$ | $L_{B5}$ |
| II-241. | $L_{A13}$ | $L_{B5}$ |
| II-242. | $L_{A14}$ | $L_{B5}$ |
| II-243. | $L_{A15}$ | $L_{B5}$ |
| II-244. | $L_{A16}$ | $L_{B5}$ |
| II-245. | $L_{A17}$ | $L_{B5}$ |
| II-246. | $L_{A18}$ | $L_{B5}$ |
| II-251. | $L_{A24}$ | $L_{B5}$ |
| II-252. | $L_{A25}$ | $L_{B5}$ |
| II-257. | $L_{A30}$ | $L_{B5}$ |
| II-258. | $L_{A31}$ | $L_{B5}$ |
| II-259. | $L_{A32}$ | $L_{B5}$ |
| II-260. | $L_{A33}$ | $L_{B5}$ |
| II-261. | $L_{A34}$ | $L_{B5}$ |
| II-262. | $L_{A35}$ | $L_{B5}$ |
| II-267. | $L_{A40}$ | $L_{B5}$ |
| II-268. | $L_{A41}$ | $L_{B5}$ |
| II-273. | $L_{A46}$ | $L_{B5}$ |
| II-274. | $L_{A47}$ | $L_{B5}$ |
| II-275. | $L_{A48}$ | $L_{B5}$ |

| Compound Number | $L_A$ | $L_B$ |
|---|---|---|
| II-276. | $L_{A49}$ | $L_{B5}$ |
| II-277. | $L_{A50}$ | $L_{B5}$ |
| II-278. | $L_{A51}$ | $L_{B5}$ |
| II-279. | $L_{A52}$ | $L_{B5}$ |
| II-284. | $L_{A57}$ | $L_{B5}$ |
| II-285. | $L_{A58}$ | $L_{B5}$ |
| II-290. | $L_{A63}$ | $L_{B5}$ |
| II-291. | $L_{A64}$ | $L_{B5}$ |
| II-292. | $L_{A65}$ | $L_{B5}$ |
| II-293. | $L_{A66}$ | $L_{B5}$ |
| II-294. | $L_{A67}$ | $L_{B5}$ |
| II-295. | $L_{A68}$ | $L_{B5}$ |
| II-296. | $L_{A69}$ | $L_{B5}$ |
| II-301. | $L_{A6}$ | $L_{B6}$ |
| II-302. | $L_{A7}$ | $L_{B6}$ |
| II-307. | $L_{A12}$ | $L_{B6}$ |
| II-308. | $L_{A13}$ | $L_{B6}$ |
| II-309. | $L_{A14}$ | $L_{B6}$ |
| II-310. | $L_{A15}$ | $L_{B6}$ |
| II-311. | $L_{A16}$ | $L_{B6}$ |
| II-312. | $L_{A17}$ | $L_{B6}$ |
| II-313. | $L_{A18}$ | $L_{B6}$ |
| II-318. | $L_{A24}$ | $L_{B6}$ |
| II-319. | $L_{A25}$ | $L_{B6}$ |
| II-324. | $L_{A30}$ | $L_{B6}$ |
| II-325. | $L_{A31}$ | $L_{B6}$ |
| II-326. | $L_{A32}$ | $L_{B6}$ |
| II-327. | $L_{A33}$ | $L_{B6}$ |
| II-328. | $L_{A34}$ | $L_{B6}$ |
| II-329. | $L_{A35}$ | $L_{B6}$ |
| II-334. | $L_{A40}$ | $L_{B6}$ |
| II-335. | $L_{A41}$ | $L_{B6}$ |
| II-340. | $L_{A46}$ | $L_{B6}$ |
| II-341. | $L_{A47}$ | $L_{B6}$ |
| II-342. | $L_{A48}$ | $L_{B6}$ |
| II-343. | $L_{A49}$ | $L_{B6}$ |
| II-344. | $L_{A50}$ | $L_{B6}$ |
| II-345. | $L_{A51}$ | $L_{B6}$ |
| II-346. | $L_{A52}$ | $L_{B6}$ |
| II-351. | $L_{A57}$ | $L_{B6}$ |
| II-352. | $L_{A58}$ | $L_{B6}$ |
| II-357. | $L_{A63}$ | $L_{B6}$ |
| II-358. | $L_{A64}$ | $L_{B6}$ |
| II-359. | $L_{A65}$ | $L_{B6}$ |
| II-360. | $L_{A66}$ | $L_{B6}$ |
| II-361. | $L_{A67}$ | $L_{B6}$ |
| II-362. | $L_{A68}$ | $L_{B6}$ |
| II-363. | $L_{A69}$ | $L_{B6}$ |
| II-368. | $L_{A6}$ | $L_{B7}$ |
| II-369. | $L_{A7}$ | $L_{B7}$ |
| II-374. | $L_{A12}$ | $L_{B7}$ |
| II-375. | $L_{A13}$ | $L_{B7}$ |
| II-376. | $L_{A14}$ | $L_{B7}$ |
| II-377. | $L_{A15}$ | $L_{B7}$ |
| II-378. | $L_{A16}$ | $L_{B7}$ |
| II-379. | $L_{A17}$ | $L_{B7}$ |
| II-380. | $L_{A18}$ | $L_{B7}$ |
| II-385. | $L_{A24}$ | $L_{B7}$ |
| II-386. | $L_{A25}$ | $L_{B7}$ |
| II-391. | $L_{A30}$ | $L_{B7}$ |
| II-392. | $L_{A31}$ | $L_{B7}$ |
| II-393. | $L_{A32}$ | $L_{B7}$ |
| II-394. | $L_{A33}$ | $L_{B7}$ |
| II-395. | $L_{A34}$ | $L_{B7}$ |
| II-396. | $L_{A35}$ | $L_{B7}$ |
| II-401. | $L_{A40}$ | $L_{B7}$ |
| II-402. | $L_{A41}$ | $L_{B7}$ |
| II-407. | $L_{A46}$ | $L_{B7}$ |
| II-408. | $L_{A47}$ | $L_{B7}$ |
| II-409. | $L_{A48}$ | $L_{B7}$ |
| II-410. | $L_{A49}$ | $L_{B7}$ |
| II-411. | $L_{A50}$ | $L_{B7}$ |
| II-412. | $L_{A51}$ | $L_{B7}$ |
| II-413. | $L_{A52}$ | $L_{B7}$ |
| II-418. | $L_{A57}$ | $L_{B7}$ |
| II-419. | $L_{A58}$ | $L_{B7}$ |
| II-424. | $L_{A63}$ | $L_{B7}$ |
| II-425. | $L_{A64}$ | $L_{B7}$ |
| II-426. | $L_{A65}$ | $L_{B7}$ |
| II-427. | $L_{A66}$ | $L_{B7}$ |
| II-428. | $L_{A67}$ | $L_{B7}$ |
| II-429. | $L_{A68}$ | $L_{B7}$ |
| II-430. | $L_{A69}$ | $L_{B7}$ |
| II-435. | $L_{A6}$ | $L_{B8}$ |
| II-436. | $L_{A7}$ | $L_{B8}$ |
| II-441. | $L_{A12}$ | $L_{B8}$ |
| II-442. | $L_{A13}$ | $L_{B8}$ |
| II-443. | $L_{A14}$ | $L_{B8}$ |
| II-444. | $L_{A15}$ | $L_{B8}$ |
| II-445. | $L_{A16}$ | $L_{B8}$ |
| II-446. | $L_{A17}$ | $L_{B8}$ |
| II-447. | $L_{A18}$ | $L_{B8}$ |
| II-452. | $L_{A24}$ | $L_{B8}$ |
| II-453. | $L_{A25}$ | $L_{B8}$ |
| II-458. | $L_{A30}$ | $L_{B8}$ |
| II-459. | $L_{A31}$ | $L_{B8}$ |
| II-460. | $L_{A32}$ | $L_{B8}$ |
| II-461. | $L_{A33}$ | $L_{B8}$ |
| II-462. | $L_{A34}$ | $L_{B8}$ |
| II-463. | $L_{A35}$ | $L_{B8}$ |
| II-468. | $L_{A40}$ | $L_{B8}$ |
| II-469. | $L_{A41}$ | $L_{B8}$ |
| II-474. | $L_{A46}$ | $L_{B8}$ |
| II-475. | $L_{A47}$ | $L_{B8}$ |
| II-476. | $L_{A48}$ | $L_{B8}$ |
| II-477. | $L_{A49}$ | $L_{B8}$ |
| II-478. | $L_{A50}$ | $L_{B8}$ |
| II-479. | $L_{A51}$ | $L_{B8}$ |
| II-480. | $L_{A52}$ | $L_{B8}$ |
| II-485. | $L_{A57}$ | $L_{B8}$ |
| II-486. | $L_{A58}$ | $L_{B8}$ |
| II-491. | $L_{A63}$ | $L_{B8}$ |
| II-492. | $L_{A64}$ | $L_{B8}$ |
| II-493. | $L_{A65}$ | $L_{B8}$ |
| II-494. | $L_{A66}$ | $L_{B8}$ |
| II-495. | $L_{A67}$ | $L_{B8}$ |
| II-496. | $L_{A68}$ | $L_{B8}$ |
| II-497. | $L_{A69}$ | $L_{B8}$ |
| II-702. | $L_{A6}$ | $L_{B12}$ |
| II-703. | $L_{A7}$ | $L_{B12}$ |
| II-708. | $L_{A12}$ | $L_{B12}$ |
| II-709. | $L_{A13}$ | $L_{B12}$ |
| II-710. | $L_{A14}$ | $L_{B12}$ |
| II-711. | $L_{A15}$ | $L_{B12}$ |
| II-712. | $L_{A16}$ | $L_{B12}$ |
| II-713. | $L_{A17}$ | $L_{B12}$ |
| II-714. | $L_{A18}$ | $L_{B12}$ |
| II-718. | $L_{A24}$ | $L_{B12}$ |
| II-719. | $L_{A25}$ | $L_{B12}$ |
| II-724. | $L_{A30}$ | $L_{B12}$ |
| II-725. | $L_{A31}$ | $L_{B12}$ |
| II-726. | $L_{A32}$ | $L_{B12}$ |
| II-727. | $L_{A33}$ | $L_{B12}$ |
| II-728. | $L_{A34}$ | $L_{B12}$ |
| II-729. | $L_{A35}$ | $L_{B12}$ |
| II-733. | $L_{A40}$ | $L_{B12}$ |
| II-734. | $L_{A41}$ | $L_{B12}$ |
| II-739. | $L_{A46}$ | $L_{B12}$ |
| II-740. | $L_{A47}$ | $L_{B12}$ |
| II-741. | $L_{A48}$ | $L_{B12}$ |
| II-742. | $L_{A49}$ | $L_{B12}$ |
| II-743. | $L_{A50}$ | $L_{B12}$ |
| II-744. | $L_{A51}$ | $L_{B12}$ |
| II-745. | $L_{A52}$ | $L_{B12}$ |
| II-749. | $L_{A57}$ | $L_{B12}$ |
| II-750. | $L_{A58}$ | $L_{B12}$ |
| II-755. | $L_{A63}$ | $L_{B12}$ |
| II-756. | $L_{A64}$ | $L_{B12}$ |
| II-757. | $L_{A65}$ | $L_{B12}$ |
| II-758. | $L_{A66}$ | $L_{B12}$ |
| II-759. | $L_{A67}$ | $L_{B12}$ |
| II-760. | $L_{A68}$ | $L_{B12}$ |

| Compound Number | $L_A$ | $L_B$ |
|---|---|---|
| II-761. | $L_{A69}$ | $L_{B12}$ |
| II-767. | $L_{A6}$ | $L_{B13}$ |
| II-768. | $L_{A7}$ | $L_{B13}$ |
| II-773. | $L_{A12}$ | $L_{B13}$ |
| II-774. | $L_{A13}$ | $L_{B13}$ |
| II-775. | $L_{A14}$ | $L_{B13}$ |
| II-776. | $L_{A15}$ | $L_{B13}$ |
| II-777. | $L_{A16}$ | $L_{B13}$ |
| II-778. | $L_{A17}$ | $L_{B13}$ |
| II-779. | $L_{A18}$ | $L_{B13}$ |
| II-785. | $L_{A24}$ | $L_{B13}$ |
| II-786. | $L_{A25}$ | $L_{B13}$ |
| II-791. | $L_{A30}$ | $L_{B13}$ |
| II-792. | $L_{A31}$ | $L_{B13}$ |
| II-793. | $L_{A32}$ | $L_{B13}$ |
| II-794. | $L_{A33}$ | $L_{B13}$ |
| II-795. | $L_{A34}$ | $L_{B13}$ |
| II-796. | $L_{A35}$ | $L_{B13}$ |
| II-801. | $L_{A40}$ | $L_{B13}$ |
| II-802. | $L_{A41}$ | $L_{B13}$ |
| II-807. | $L_{A46}$ | $L_{B13}$ |
| II-808. | $L_{A47}$ | $L_{B13}$ |
| II-809. | $L_{A48}$ | $L_{B13}$ |
| II-810. | $L_{A49}$ | $L_{B13}$ |
| II-811. | $L_{A50}$ | $L_{B13}$ |
| II-812. | $L_{A51}$ | $L_{B13}$ |
| II-813. | $L_{A52}$ | $L_{B13}$ |
| II-818. | $L_{A57}$ | $L_{B13}$ |
| II-819. | $L_{A58}$ | $L_{B13}$ |
| II-824. | $L_{A63}$ | $L_{B13}$ |
| II-825. | $L_{A64}$ | $L_{B13}$ |
| II-826. | $L_{A65}$ | $L_{B13}$ |
| II-827. | $L_{A66}$ | $L_{B13}$ |
| II-828. | $L_{A67}$ | $L_{B13}$ |
| II-829. | $L_{A68}$ | $L_{B13}$ |
| II-830. | $L_{A69}$ | $L_{B13}$ |
| II-836. | $L_{A6}$ | $L_{B14}$ |
| II-837. | $L_{A7}$ | $L_{B14}$ |
| II-842. | $L_{A12}$ | $L_{B14}$ |
| II-843. | $L_{A13}$ | $L_{B14}$ |
| II-844. | $L_{A14}$ | $L_{B14}$ |
| II-845. | $L_{A15}$ | $L_{B14}$ |
| II-846. | $L_{A16}$ | $L_{B14}$ |
| II-847. | $L_{A17}$ | $L_{B14}$ |
| II-848. | $L_{A18}$ | $L_{B14}$ |
| II-854. | $L_{A24}$ | $L_{B14}$ |
| II-855. | $L_{A25}$ | $L_{B14}$ |
| II-860. | $L_{A30}$ | $L_{B14}$ |
| II-861. | $L_{A31}$ | $L_{B14}$ |
| II-862. | $L_{A32}$ | $L_{B14}$ |
| II-863. | $L_{A33}$ | $L_{B14}$ |
| II-864. | $L_{A34}$ | $L_{B14}$ |
| II-865. | $L_{A35}$ | $L_{B14}$ |
| II-870. | $L_{A40}$ | $L_{B14}$ |
| II-871. | $L_{A41}$ | $L_{B14}$ |
| II-876. | $L_{A46}$ | $L_{B14}$ |
| II-877. | $L_{A47}$ | $L_{B14}$ |
| II-878. | $L_{A48}$ | $L_{B14}$ |
| II-879. | $L_{A49}$ | $L_{B14}$ |
| II-880. | $L_{A50}$ | $L_{B14}$ |
| II-881. | $L_{A51}$ | $L_{B14}$ |
| II-882. | $L_{A52}$ | $L_{B14}$ |
| II-887. | $L_{A57}$ | $L_{B14}$ |
| II-888. | $L_{A58}$ | $L_{B14}$ |
| II-893. | $L_{A63}$ | $L_{B14}$ |
| II-894. | $L_{A64}$ | $L_{B14}$ |
| II-895. | $L_{A65}$ | $L_{B14}$ |
| II-896. | $L_{A66}$ | $L_{B14}$ |
| II-897. | $L_{A67}$ | $L_{B14}$ |
| II-898. | $L_{A68}$ | $L_{B14}$ |
| II-899. | $L_{A69}$ | $L_{B14}$ |
| II-905. | $L_{A6}$ | $L_{B15}$ |
| II-906. | $L_{A7}$ | $L_{B15}$ |
| II-911. | $L_{A12}$ | $L_{B15}$ |
| II-912. | $L_{A13}$ | $L_{B15}$ |
| II-913. | $L_{A14}$ | $L_{B15}$ |
| II-914. | $L_{A15}$ | $L_{B15}$ |
| II-915. | $L_{A16}$ | $L_{B15}$ |
| II-916. | $L_{A17}$ | $L_{B15}$ |
| II-917. | $L_{A18}$ | $L_{B15}$ |
| II-923. | $L_{A24}$ | $L_{B15}$ |
| II-924. | $L_{A25}$ | $L_{B15}$ |
| II-929. | $L_{A30}$ | $L_{B15}$ |
| II-930. | $L_{A31}$ | $L_{B15}$ |
| II-931. | $L_{A32}$ | $L_{B15}$ |
| II-932. | $L_{A33}$ | $L_{B15}$ |
| II-933. | $L_{A34}$ | $L_{B15}$ |
| II-934. | $L_{A35}$ | $L_{B15}$ |
| II-939. | $L_{A40}$ | $L_{B15}$ |
| II-940. | $L_{A41}$ | $L_{B15}$ |
| II-945. | $L_{A46}$ | $L_{B15}$ |
| II-946. | $L_{A47}$ | $L_{B15}$ |
| II-947. | $L_{A48}$ | $L_{B15}$ |
| II-948. | $L_{A49}$ | $L_{B15}$ |
| II-949. | $L_{A50}$ | $L_{B15}$ |
| II-950. | $L_{A51}$ | $L_{B15}$ |
| II-951. | $L_{A52}$ | $L_{B15}$ |
| II-956. | $L_{A57}$ | $L_{B15}$ |
| II-957. | $L_{A58}$ | $L_{B15}$ |
| II-962. | $L_{A63}$ | $L_{B15}$ |
| II-963. | $L_{A64}$ | $L_{B15}$ |
| II-964. | $L_{A65}$ | $L_{B15}$ |
| II-965. | $L_{A66}$ | $L_{B15}$ |
| II-966. | $L_{A67}$ | $L_{B15}$ |
| II-967. | $L_{A68}$ | $L_{B15}$ |
| II-968. | $L_{A69}$ | $L_{B15}$ |
| II-972. | $L_{A6}$ | $L_{B16}$ |
| II-973. | $L_{A7}$ | $L_{B16}$ |
| II-978. | $L_{A12}$ | $L_{B16}$ |
| II-979. | $L_{A13}$ | $L_{B16}$ |
| II-980. | $L_{A14}$ | $L_{B16}$ |
| II-981. | $L_{A15}$ | $L_{B16}$ |
| II-982. | $L_{A16}$ | $L_{B16}$ |
| II-983. | $L_{A17}$ | $L_{B16}$ |
| II-984. | $L_{A18}$ | $L_{B16}$ |
| II-989. | $L_{A25}$ | $L_{B16}$ |
| II-990. | $L_{A26}$ | $L_{B16}$ |
| II-995. | $L_{A31}$ | $L_{B16}$ |
| II-996. | $L_{A32}$ | $L_{B16}$ |
| II-997. | $L_{A33}$ | $L_{B16}$ |
| II-998. | $L_{A34}$ | $L_{B16}$ |
| II-999. | $L_{A35}$ | $L_{B16}$ |
| II-1003. | $L_{A40}$ | $L_{B16}$ |
| II-1004. | $L_{A41}$ | $L_{B16}$ |
| II-1009. | $L_{A46}$ | $L_{B16}$ |
| II-1010. | $L_{A47}$ | $L_{B16}$ |
| II-1011. | $L_{A48}$ | $L_{B16}$ |
| II-1012. | $L_{A49}$ | $L_{B16}$ |
| II-1013. | $L_{A50}$ | $L_{B16}$ |
| II-1014. | $L_{A51}$ | $L_{B16}$ |
| II-1015. | $L_{A52}$ | $L_{B16}$ |
| II-1019. | $L_{A57}$ | $L_{B16}$ |
| II-1020. | $L_{A58}$ | $L_{B16}$ |
| II-1025. | $L_{A63}$ | $L_{B16}$ |
| II-1026. | $L_{A64}$ | $L_{B16}$ |
| II-1027. | $L_{A65}$ | $L_{B16}$ |
| II-1028. | $L_{A66}$ | $L_{B16}$ |
| II-1029. | $L_{A67}$ | $L_{B16}$ |
| II-1030. | $L_{A68}$ | $L_{B16}$ |
| II-1031. | $L_{A69}$ | $L_{B16}$ |
| II-1103. | $L_{A6}$ | $L_{B18}$ |
| II-1104. | $L_{A7}$ | $L_{B18}$ |
| II-1109. | $L_{A12}$ | $L_{B18}$ |
| II-1110. | $L_{A13}$ | $L_{B18}$ |
| II-1111. | $L_{A14}$ | $L_{B18}$ |
| II-1112. | $L_{A15}$ | $L_{B18}$ |
| II-1113. | $L_{A16}$ | $L_{B18}$ |
| II-1114. | $L_{A17}$ | $L_{B18}$ |
| II-1115. | $L_{A18}$ | $L_{B18}$ |
| II-1120. | $L_{A24}$ | $L_{B18}$ |
| II-1121. | $L_{A25}$ | $L_{B18}$ |
| II-1126. | $L_{A30}$ | $L_{B18}$ |

| Compound Number | $L_A$ | $L_B$ |
|---|---|---|
| II-1127. | $L_{A31}$ | $L_{B18}$ |
| II-1128. | $L_{A32}$ | $L_{B18}$ |
| II-1129. | $L_{A33}$ | $L_{B18}$ |
| II-1130. | $L_{A34}$ | $L_{B18}$ |
| II-1131. | $L_{A35}$ | $L_{B18}$ |
| II-1136. | $L_{A40}$ | $L_{B18}$ |
| II-1137. | $L_{A41}$ | $L_{B18}$ |
| II-1142. | $L_{A46}$ | $L_{B18}$ |
| II-1143. | $L_{A47}$ | $L_{B18}$ |
| II-1144. | $L_{A48}$ | $L_{B18}$ |
| II-1145. | $L_{A49}$ | $L_{B18}$ |
| II-1146. | $L_{A50}$ | $L_{B18}$ |
| II-1147. | $L_{A51}$ | $L_{B18}$ |
| II-1148. | $L_{A52}$ | $L_{B18}$ |
| II-1153. | $L_{A57}$ | $L_{B18}$ |
| II-1154. | $L_{A58}$ | $L_{B18}$ |
| II-1159. | $L_{A63}$ | $L_{B18}$ |
| II-1160. | $L_{A64}$ | $L_{B18}$ |
| II-1161. | $L_{A65}$ | $L_{B18}$ |
| II-1162. | $L_{A66}$ | $L_{B18}$ |
| II-1163. | $L_{A67}$ | $L_{B18}$ |
| II-1164. | $L_{A68}$ | $L_{B18}$ |
| II-1165. | $L_{A69}$ | $L_{B18}$ |
| II-1237. | $L_{A6}$ | $L_{B20}$ |
| II-1238. | $L_{A7}$ | $L_{B20}$ |
| II-1243. | $L_{A12}$ | $L_{B20}$ |
| II-1244. | $L_{A13}$ | $L_{B20}$ |
| II-1245. | $L_{A14}$ | $L_{B20}$ |
| II-1246. | $L_{A15}$ | $L_{B20}$ |
| II-1247. | $L_{A16}$ | $L_{B20}$ |
| II-1248. | $L_{A17}$ | $L_{B20}$ |
| II-1249. | $L_{A18}$ | $L_{B20}$ |
| II-1254. | $L_{A24}$ | $L_{B20}$ |
| II-1255. | $L_{A25}$ | $L_{B20}$ |
| II-1260. | $L_{A30}$ | $L_{B20}$ |
| II-1261. | $L_{A31}$ | $L_{B20}$ |
| II-1262. | $L_{A32}$ | $L_{B20}$ |
| II-1263. | $L_{A33}$ | $L_{B20}$ |
| II-1264. | $L_{A34}$ | $L_{B20}$ |
| II-1265. | $L_{A35}$ | $L_{B20}$ |
| II-1270. | $L_{A40}$ | $L_{B20}$ |
| II-1271. | $L_{A41}$ | $L_{B20}$ |
| II-1276. | $L_{A46}$ | $L_{B20}$ |
| II-1277. | $L_{A47}$ | $L_{B20}$ |
| II-1278. | $L_{A48}$ | $L_{B20}$ |
| II-1279. | $L_{A49}$ | $L_{B20}$ |
| II-1280. | $L_{A50}$ | $L_{B20}$ |
| II-1281. | $L_{A51}$ | $L_{B20}$ |
| II-1282. | $L_{A52}$ | $L_{B20}$ |
| II-1287. | $L_{A57}$ | $L_{B20}$ |
| II-1288. | $L_{A58}$ | $L_{B20}$ |
| II-1293. | $L_{A63}$ | $L_{B20}$ |
| II-1294. | $L_{A64}$ | $L_{B20}$ |
| II-1295. | $L_{A65}$ | $L_{B20}$ |
| II-1296. | $L_{A66}$ | $L_{B20}$ |
| II-1297. | $L_{A67}$ | $L_{B20}$ |
| II-1298. | $L_{A68}$ | $L_{B20}$ |
| II-1299. | $L_{A69}$ | $L_{B20}$ |
| II-1371. | $L_{A6}$ | $L_{B22}$ |
| II-1372. | $L_{A7}$ | $L_{B22}$ |
| II-1377. | $L_{A12}$ | $L_{B22}$ |
| II-1378. | $L_{A13}$ | $L_{B22}$ |
| II-1379. | $L_{A14}$ | $L_{B22}$ |
| II-1380. | $L_{A15}$ | $L_{B22}$ |
| II-1381. | $L_{A16}$ | $L_{B22}$ |
| II-1382. | $L_{A17}$ | $L_{B22}$ |
| II-1383. | $L_{A18}$ | $L_{B22}$ |
| II-1388. | $L_{A24}$ | $L_{B22}$ |
| II-1389. | $L_{A25}$ | $L_{B22}$ |
| II-1394. | $L_{A30}$ | $L_{B22}$ |
| II-1395. | $L_{A31}$ | $L_{B22}$ |
| II-1396. | $L_{A32}$ | $L_{B22}$ |
| II-1397. | $L_{A33}$ | $L_{B22}$ |
| II-1398. | $L_{A34}$ | $L_{B22}$ |
| II-1399. | $L_{A35}$ | $L_{B22}$ |
| II-1404. | $L_{A40}$ | $L_{B22}$ |
| II-1405. | $L_{A41}$ | $L_{B22}$ |
| II-1410. | $L_{A46}$ | $L_{B22}$ |
| II-1411. | $L_{A47}$ | $L_{B22}$ |
| II-1412. | $L_{A48}$ | $L_{B22}$ |
| II-1413. | $L_{A49}$ | $L_{B22}$ |
| II-1414. | $L_{A50}$ | $L_{B22}$ |
| II-1415. | $L_{A51}$ | $L_{B22}$ |
| II-1416. | $L_{A52}$ | $L_{B22}$ |
| II-1421. | $L_{A57}$ | $L_{B22}$ |
| II-1422. | $L_{A58}$ | $L_{B22}$ |
| II-1427. | $L_{A63}$ | $L_{B22}$ |
| II-1428. | $L_{A64}$ | $L_{B22}$ |
| II-1429. | $L_{A65}$ | $L_{B22}$ |
| II-1430. | $L_{A66}$ | $L_{B22}$ |
| II-1431. | $L_{A67}$ | $L_{B22}$ |
| II-1432. | $L_{A68}$ | $L_{B22}$ |
| II-1433. | $L_{A69}$ | $L_{B22}$, | and wherein $L_A$ is selected from the group consisting of

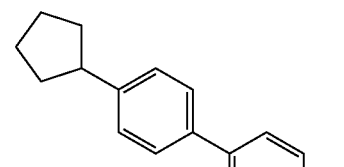

$L_{A6}$

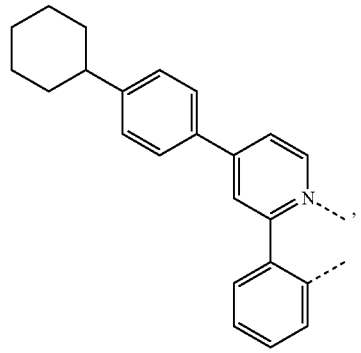

$L_{A7}$

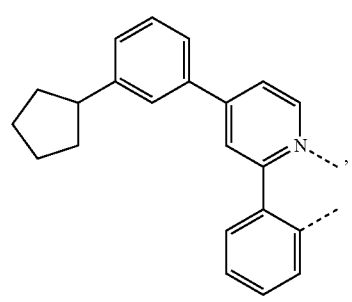

$L_{A12}$

L<sub>A13</sub>
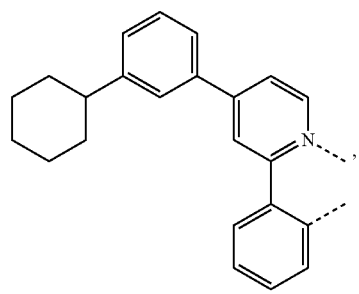
L<sub>A14</sub>
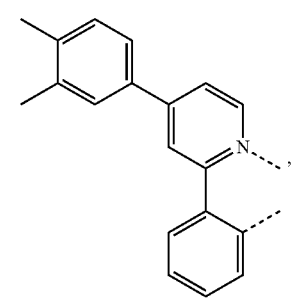
L<sub>A15</sub>
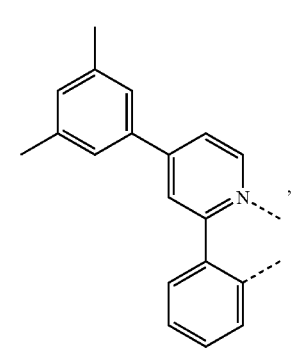
L<sub>A16</sub>
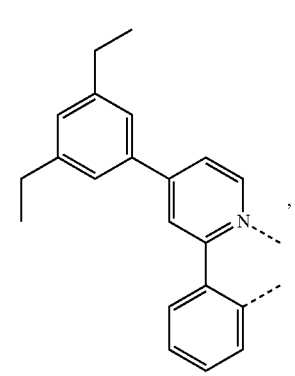
L<sub>A17</sub>
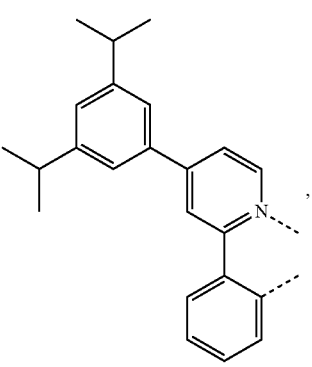
L<sub>A18</sub>
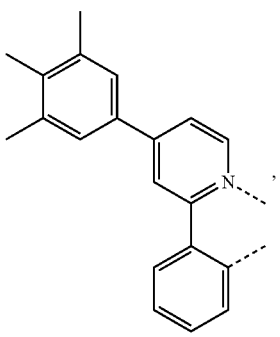
L<sub>A24</sub>
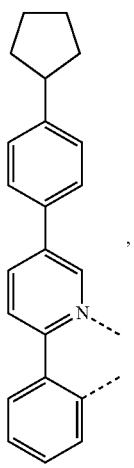
L<sub>A25</sub>
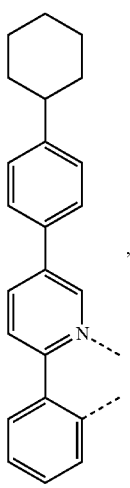

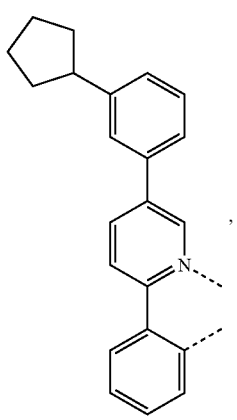
, L$_{A30}$
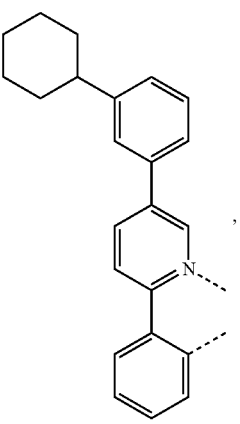
, L$_{A31}$
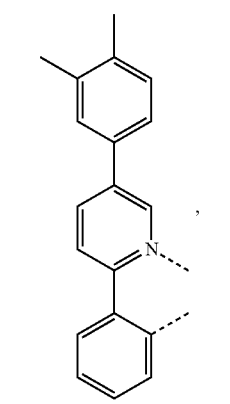
, L$_{A32}$
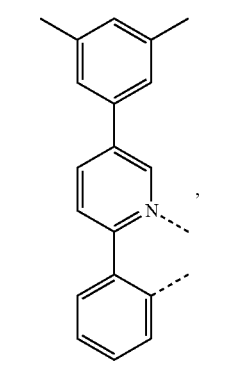
, L$_{A33}$
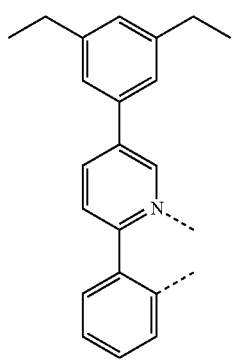
, L$_{A34}$
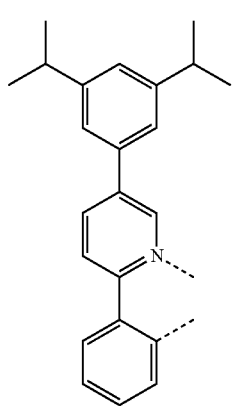
, L$_{A35}$
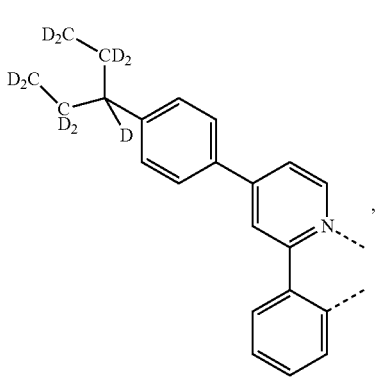
, L$_{A40}$
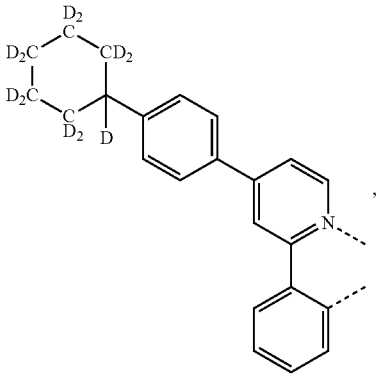
, L$_{A41}$

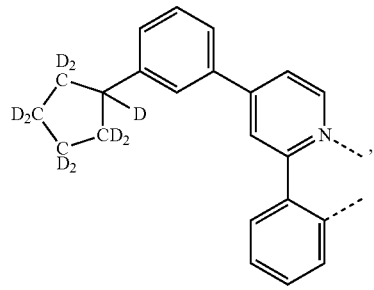 L$_{A46}$
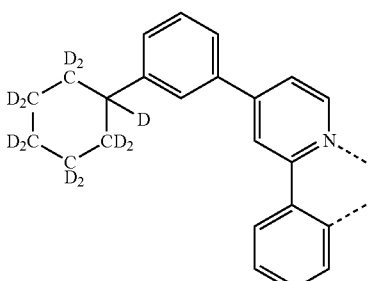 L$_{A47}$
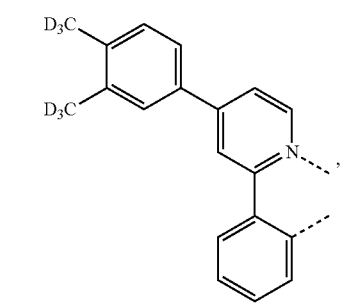 L$_{A48}$
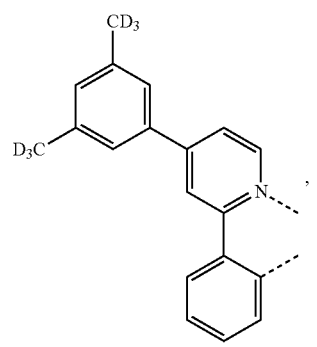 L$_{A49}$
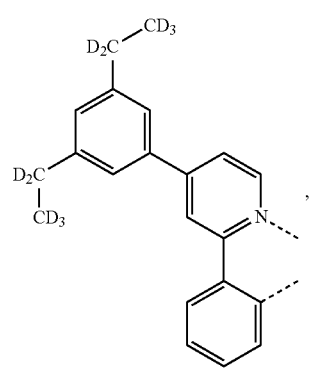 L$_{A50}$
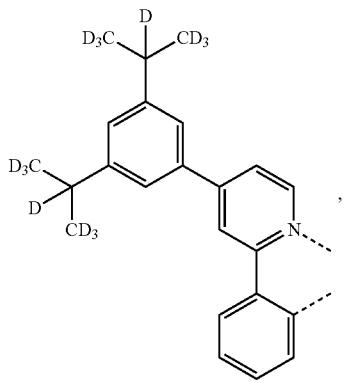 L$_{A51}$
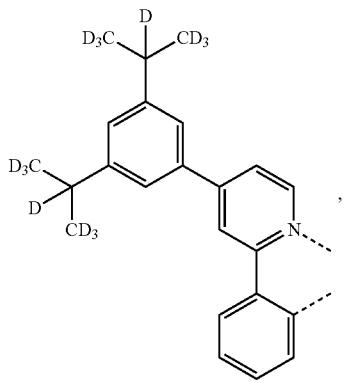 L$_{A52}$
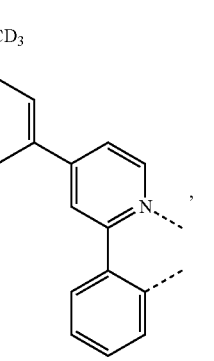 L$_{A57}$

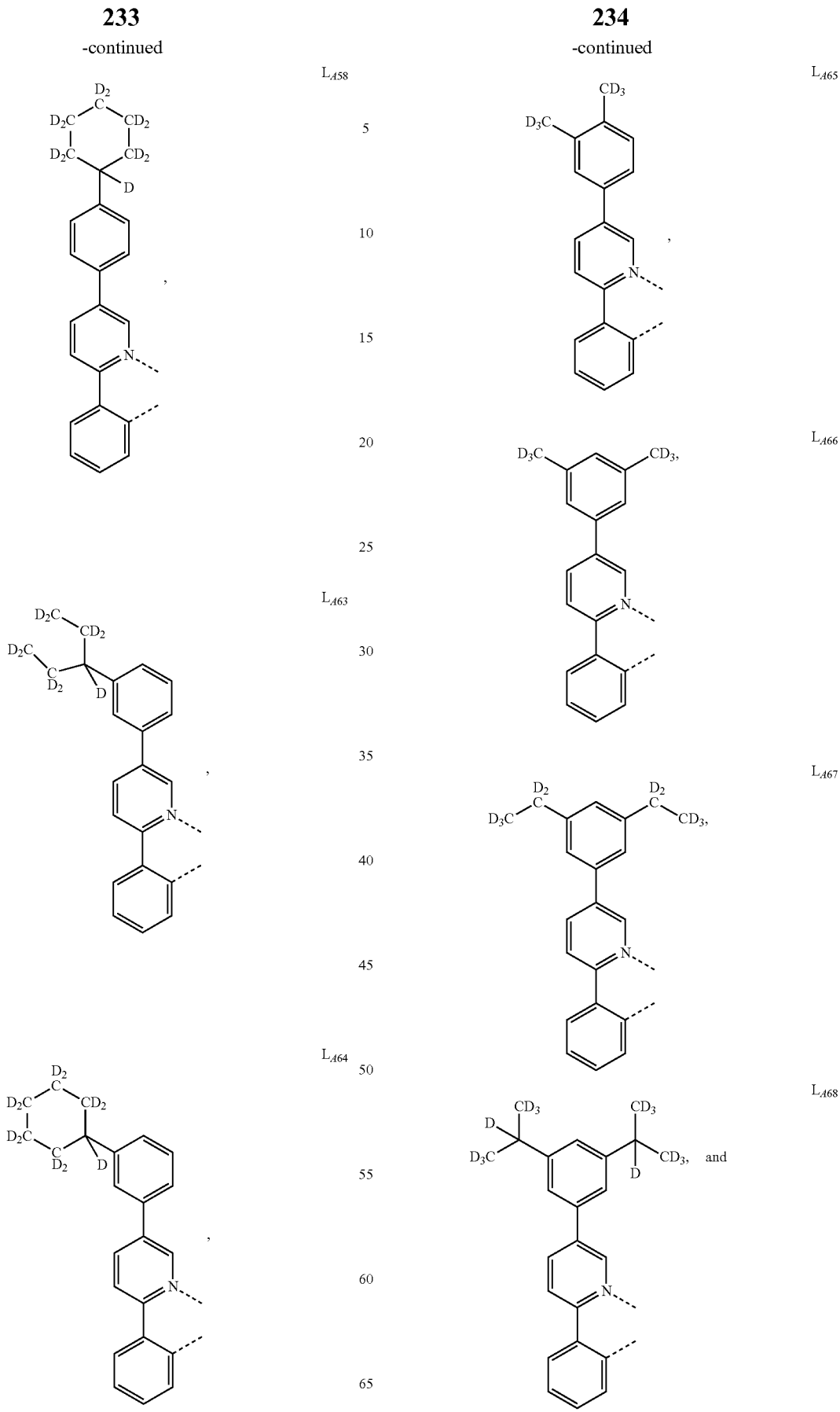

235
-continued
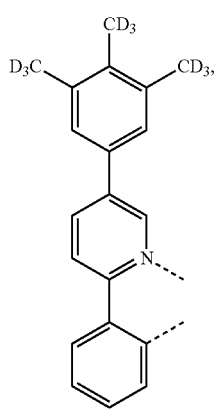
L_{A69}
L_B is selected from the group consisting of
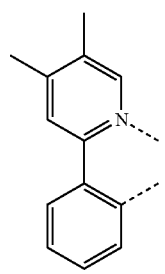
L_{B5}
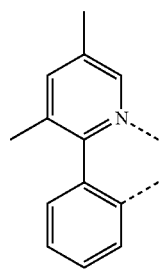
L_{B6}
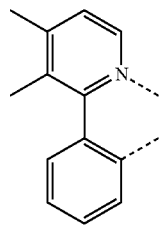
L_{B7}
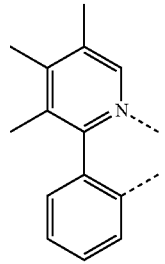
L_{B8}
236
-continued
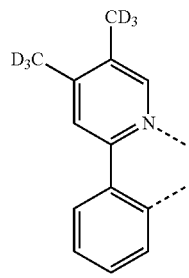
L_{B12}
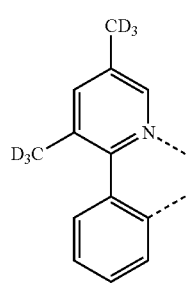
L_{B13}
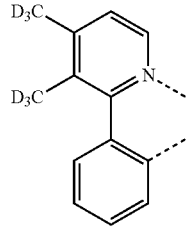
L_{B14}
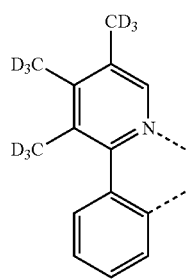
L_{B15}
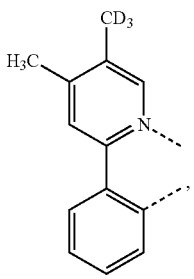
L_{B16}

-continued

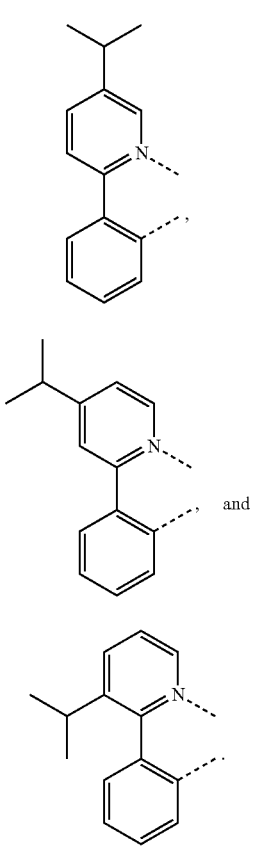

$L_{B18}$ $L_{B20}$

, and $L_{B22}$

2. The compound of claim 1, wherein the heteroleptic iridium complex is selected from the group consisting of Compound II-267 through Compound II-268, Compound II-273 through Compound II-279, Compound II-284 through Compound II-285, Compound II-290 through Compound II-296, Compound II-334 through Compound II-335, Compound II-340 through Compound II-346, Compound II-351 through Compound II-352, Compound II-357 through Compound II-363, Compound II-401 through Compound II-402, Compound II-407 through Compound II-413, Compound II-418 through Compound II-419, Compound II-424 through Compound II-430, Compound II-468 through Compound II-469, Compound II-474 through Compound II-480, Compound II-485 through Compound II-486, Compound II-491 through Compound II-497, Compound II-702 through Compound II-703, Compound II-708 through Compound II-714, Compound II-718 through Compound II-719, Compound II-724 through Compound II-729, Compound II-733 through Compound II-734, Compound II-739 through Compound II-745, Compound II-749 through Compound II-750, Compound II-755 through Compound II-761, Compound II-767 through Compound II-768, Compound II-773 through Compound II-779, Compound II-785 through Compound II-786, Compound II-791 through Compound II-796, Compound II-801 through Compound II-802, Compound II-807 through Compound II-813, Compound II-818 through Compound II-819, Compound II-824 through Compound II-830, Compound II-836 through Compound II-837, Compound II-842 through Compound II-848, Compound II-854 through Compound II-855, Compound II-860 through Compound II-865, Compound II-870 through Compound II-871, Compound II-876 through Compound II-882, Compound II-887 through Compound II-888, Compound II-893 through Compound II-899, Compound II-905 through Compound II-906, Compound II-911 through Compound II-917, Compound II-923 through Compound II-924, Compound II-929 through Compound II-934, Compound II-939 through Compound II-940, Compound II-945 through Compound II-951, Compound II-956 through Compound II-957, Compound II-962 through Compound II-968, Compound II-972 through Compound II-973, Compound II-978 through Compound II-984, Compound II-989 through Compound II-990, Compound II-995 through Compound II-999, Compound II-1003, Compound II-1004, Compound II-1009 through Compound II-1015, Compound II-1019 through Compound II-1020, Compound II-1025 through Compound II-1031, Compound II-1136 through Compound II-1137, Compound II-1142 through Compound II-1148, Compound II-1153 through Compound II-1154, Compound II-1159 through Compound II-1165, Compound II-1270 through Compound II-1271, Compound II-1276 through Compound II-1282, Compound II-1287 through Compound II-1288, Compound II-1293 through Compound II-1299, Compound II-1404 through Compound II-1405, Compound II-1410 through Compound II-1416, Compound II-1421 through Compound II-1422, and Compound II-1427 through Compound II-1433.

3. A first device comprising a first organic light emitting device, the first organic light emitting device further comprising:
an anode;
a cathode; and
an organic layer, disposed between the anode and the cathode, comprising a heteroleptic iridium complex having the formula $IrL_A(L_B)_2$, wherein the heteroleptic iridium complex is selected from the group consisting of compounds listed in the following table:

| Compound Number | $L_A$ | $L_B$ |
| --- | --- | --- |
| II-234. | $L_{A6}$ | $L_{B5}$ |
| II-235. | $L_{A7}$ | $L_{B5}$ |
| II-240. | $L_{A12}$ | $L_{B5}$ |
| II-241. | $L_{A13}$ | $L_{B5}$ |
| II-242. | $L_{A14}$ | $L_{B5}$ |
| II-243. | $L_{A15}$ | $L_{B5}$ |
| II-244. | $L_{A16}$ | $L_{B5}$ |
| II-245. | $L_{A17}$ | $L_{B5}$ |
| II-246. | $L_{A18}$ | $L_{B5}$ |
| II-251. | $L_{A24}$ | $L_{B5}$ |
| II-252. | $L_{A25}$ | $L_{B5}$ |
| II-257. | $L_{A30}$ | $L_{B5}$ |
| II-258. | $L_{A31}$ | $L_{B5}$ |
| II-259. | $L_{A32}$ | $L_{B5}$ |
| II-260. | $L_{A33}$ | $L_{B5}$ |
| II-261. | $L_{A34}$ | $L_{B5}$ |
| II-262. | $L_{A35}$ | $L_{B5}$ |
| II-267. | $L_{A40}$ | $L_{B5}$ |
| II-268. | $L_{A41}$ | $L_{B5}$ |
| II-273. | $L_{A46}$ | $L_{B5}$ |
| II-274. | $L_{A47}$ | $L_{B5}$ |
| II-275. | $L_{A48}$ | $L_{B5}$ |
| II-276. | $L_{A49}$ | $L_{B5}$ |
| II-277. | $L_{A50}$ | $L_{B5}$ |
| II-278. | $L_{A51}$ | $L_{B5}$ |
| II-279. | $L_{A52}$ | $L_{B5}$ |
| II-284. | $L_{A57}$ | $L_{B5}$ |
| II-285. | $L_{A58}$ | $L_{B5}$ |
| II-290. | $L_{A63}$ | $L_{B5}$ |
| II-291. | $L_{A64}$ | $L_{B5}$ |
| II-292. | $L_{A65}$ | $L_{B5}$ |
| II-293. | $L_{A66}$ | $L_{B5}$ |
| II-294. | $L_{A67}$ | $L_{B5}$ |

| Compound Number | $L_A$ | $L_B$ |
|---|---|---|
| II-295. | $L_{A68}$ | $L_{B5}$ |
| II-296. | $L_{A69}$ | $L_{B5}$ |
| II-301. | $L_{A6}$ | $L_{B6}$ |
| II-302. | $L_{A7}$ | $L_{B6}$ |
| II-307. | $L_{A12}$ | $L_{B6}$ |
| II-308. | $L_{A13}$ | $L_{B6}$ |
| II-309. | $L_{A14}$ | $L_{B6}$ |
| II-310. | $L_{A15}$ | $L_{B6}$ |
| II-311. | $L_{A16}$ | $L_{B6}$ |
| II-312. | $L_{A17}$ | $L_{B6}$ |
| II-313. | $L_{A18}$ | $L_{B6}$ |
| II-318. | $L_{A24}$ | $L_{B6}$ |
| II-319. | $L_{A25}$ | $L_{B6}$ |
| II-324. | $L_{A30}$ | $L_{B6}$ |
| II-325. | $L_{A31}$ | $L_{B6}$ |
| II-326. | $L_{A32}$ | $L_{B6}$ |
| II-327. | $L_{A33}$ | $L_{B6}$ |
| II-328. | $L_{A34}$ | $L_{B6}$ |
| II-329. | $L_{A35}$ | $L_{B6}$ |
| II-334. | $L_{A40}$ | $L_{B6}$ |
| II-335. | $L_{A41}$ | $L_{B6}$ |
| II-340. | $L_{A46}$ | $L_{B6}$ |
| II-341. | $L_{A47}$ | $L_{B6}$ |
| II-342. | $L_{A48}$ | $L_{B6}$ |
| II-343. | $L_{A49}$ | $L_{B6}$ |
| II-344. | $L_{A50}$ | $L_{B6}$ |
| II-345. | $L_{A51}$ | $L_{B6}$ |
| II-346. | $L_{A52}$ | $L_{B6}$ |
| II-351. | $L_{A57}$ | $L_{B6}$ |
| II-352. | $L_{A58}$ | $L_{B6}$ |
| II-357. | $L_{A63}$ | $L_{B6}$ |
| II-358. | $L_{A64}$ | $L_{B6}$ |
| II-359. | $L_{A65}$ | $L_{B6}$ |
| II-360. | $L_{A66}$ | $L_{B6}$ |
| II-361. | $L_{A67}$ | $L_{B6}$ |
| II-362. | $L_{A68}$ | $L_{B6}$ |
| II-363. | $L_{A69}$ | $L_{B6}$ |
| II-368. | $L_{A6}$ | $L_{B7}$ |
| II-369. | $L_{A7}$ | $L_{B7}$ |
| II-374. | $L_{A12}$ | $L_{B7}$ |
| II-375. | $L_{A13}$ | $L_{B7}$ |
| II-376. | $L_{A14}$ | $L_{B7}$ |
| II-377. | $L_{A15}$ | $L_{B7}$ |
| II-378. | $L_{A16}$ | $L_{B7}$ |
| II-379. | $L_{A17}$ | $L_{B7}$ |
| II-380. | $L_{A18}$ | $L_{B7}$ |
| II-385. | $L_{A24}$ | $L_{B7}$ |
| II-386. | $L_{A25}$ | $L_{B7}$ |
| II-391. | $L_{A30}$ | $L_{B7}$ |
| II-392. | $L_{A31}$ | $L_{B7}$ |
| II-393. | $L_{A32}$ | $L_{B7}$ |
| II-394. | $L_{A33}$ | $L_{B7}$ |
| II-395. | $L_{A34}$ | $L_{B7}$ |
| II-396. | $L_{A35}$ | $L_{B7}$ |
| II-401. | $L_{A40}$ | $L_{B7}$ |
| II-402. | $L_{A41}$ | $L_{B7}$ |
| II-407. | $L_{A46}$ | $L_{B7}$ |
| II-408. | $L_{A47}$ | $L_{B7}$ |
| II-409. | $L_{A48}$ | $L_{B7}$ |
| II-410. | $L_{A49}$ | $L_{B7}$ |
| II-411. | $L_{A50}$ | $L_{B7}$ |
| II-412. | $L_{A51}$ | $L_{B7}$ |
| II-413. | $L_{A52}$ | $L_{B7}$ |
| II-418. | $L_{A57}$ | $L_{B7}$ |
| II-419. | $L_{A58}$ | $L_{B7}$ |
| II-424. | $L_{A63}$ | $L_{B7}$ |
| II-425. | $L_{A64}$ | $L_{B7}$ |
| II-426. | $L_{A65}$ | $L_{B7}$ |
| II-427. | $L_{A66}$ | $L_{B7}$ |
| II-428. | $L_{A67}$ | $L_{B7}$ |
| II-429. | $L_{A68}$ | $L_{B7}$ |
| II-430. | $L_{A69}$ | $L_{B7}$ |
| II-435. | $L_{A6}$ | $L_{B8}$ |
| II-436. | $L_{A7}$ | $L_{B8}$ |
| II-441. | $L_{A12}$ | $L_{B8}$ |
| II-442. | $L_{A13}$ | $L_{B8}$ |
| II-443. | $L_{A14}$ | $L_{B8}$ |
| II-444. | $L_{A15}$ | $L_{B8}$ |
| II-445. | $L_{A16}$ | $L_{B8}$ |
| II-446. | $L_{A17}$ | $L_{B8}$ |
| II-447. | $L_{A18}$ | $L_{B8}$ |
| II-452. | $L_{A24}$ | $L_{B8}$ |
| II-453. | $L_{A25}$ | $L_{B8}$ |
| II-458. | $L_{A30}$ | $L_{B8}$ |
| II-459. | $L_{A31}$ | $L_{B8}$ |
| II-460. | $L_{A32}$ | $L_{B8}$ |
| II-461. | $L_{A33}$ | $L_{B8}$ |
| II-462. | $L_{A34}$ | $L_{B8}$ |
| II-463. | $L_{A35}$ | $L_{B8}$ |
| II-468. | $L_{A40}$ | $L_{B8}$ |
| II-469. | $L_{A41}$ | $L_{B8}$ |
| II-474. | $L_{A46}$ | $L_{B8}$ |
| II-475. | $L_{A47}$ | $L_{B8}$ |
| II-476. | $L_{A48}$ | $L_{B8}$ |
| II-477. | $L_{A49}$ | $L_{B8}$ |
| II-478. | $L_{A50}$ | $L_{B8}$ |
| II-479. | $L_{A51}$ | $L_{B8}$ |
| II-480. | $L_{A52}$ | $L_{B8}$ |
| II-485. | $L_{A57}$ | $L_{B8}$ |
| II-486. | $L_{A58}$ | $L_{B8}$ |
| II-491. | $L_{A63}$ | $L_{B8}$ |
| II-492. | $L_{A64}$ | $L_{B8}$ |
| II-493. | $L_{A65}$ | $L_{B8}$ |
| II-494. | $L_{A66}$ | $L_{B8}$ |
| II-495. | $L_{A67}$ | $L_{B8}$ |
| II-496. | $L_{A68}$ | $L_{B8}$ |
| II-497. | $L_{A69}$ | $L_{B8}$ |
| II-702. | $L_{A6}$ | $L_{B12}$ |
| II-703. | $L_{A7}$ | $L_{B12}$ |
| II-708. | $L_{A12}$ | $L_{B12}$ |
| II-709. | $L_{A13}$ | $L_{B12}$ |
| II-710. | $L_{A14}$ | $L_{B12}$ |
| II-711. | $L_{A15}$ | $L_{B12}$ |
| II-712. | $L_{A16}$ | $L_{B12}$ |
| II-713. | $L_{A17}$ | $L_{B12}$ |
| II-714. | $L_{A18}$ | $L_{B12}$ |
| II-718. | $L_{A24}$ | $L_{B12}$ |
| II-719. | $L_{A25}$ | $L_{B12}$ |
| II-724. | $L_{A30}$ | $L_{B12}$ |
| II-725. | $L_{A31}$ | $L_{B12}$ |
| II-726. | $L_{A32}$ | $L_{B12}$ |
| II-727. | $L_{A33}$ | $L_{B12}$ |
| II-728. | $L_{A34}$ | $L_{B12}$ |
| II-729. | $L_{A35}$ | $L_{B12}$ |
| II-733. | $L_{A40}$ | $L_{B12}$ |
| II-734. | $L_{A41}$ | $L_{B12}$ |
| II-739. | $L_{A46}$ | $L_{B12}$ |
| II-740. | $L_{A47}$ | $L_{B12}$ |
| II-741. | $L_{A48}$ | $L_{B12}$ |
| II-742. | $L_{A49}$ | $L_{B12}$ |
| II-743. | $L_{A50}$ | $L_{B12}$ |
| II-744. | $L_{A51}$ | $L_{B12}$ |
| II-745. | $L_{A52}$ | $L_{B12}$ |
| II-749. | $L_{A57}$ | $L_{B12}$ |
| II-750. | $L_{A58}$ | $L_{B12}$ |
| II-755. | $L_{A63}$ | $L_{B12}$ |
| II-756. | $L_{A64}$ | $L_{B12}$ |
| II-757. | $L_{A65}$ | $L_{B12}$ |
| II-758. | $L_{A66}$ | $L_{B12}$ |
| II-759. | $L_{A67}$ | $L_{B12}$ |
| II-760. | $L_{A68}$ | $L_{B12}$ |
| II-761. | $L_{A69}$ | $L_{B12}$ |
| II-767. | $L_{A6}$ | $L_{B13}$ |
| II-768. | $L_{A7}$ | $L_{B13}$ |
| II-773. | $L_{A12}$ | $L_{B13}$ |
| II-774. | $L_{A13}$ | $L_{B13}$ |
| II-775. | $L_{A14}$ | $L_{B13}$ |
| II-776. | $L_{A15}$ | $L_{B13}$ |
| II-777. | $L_{A16}$ | $L_{B13}$ |
| II-778. | $L_{A17}$ | $L_{B13}$ |
| II-779. | $L_{A18}$ | $L_{B13}$ |
| II-785. | $L_{A24}$ | $L_{B13}$ |

-continued

| Compound Number | $L_A$ | $L_B$ |
|---|---|---|
| II-786. | $L_{A25}$ | $L_{B13}$ |
| II-791. | $L_{A30}$ | $L_{B13}$ |
| II-792. | $L_{A31}$ | $L_{B13}$ |
| II-793. | $L_{A32}$ | $L_{B13}$ |
| II-794. | $L_{A33}$ | $L_{B13}$ |
| II-795. | $L_{A34}$ | $L_{B13}$ |
| II-796. | $L_{A35}$ | $L_{B13}$ |
| II-801. | $L_{A40}$ | $L_{B13}$ |
| II-802. | $L_{A41}$ | $L_{B13}$ |
| II-807. | $L_{A46}$ | $L_{B13}$ |
| II-808. | $L_{A47}$ | $L_{B13}$ |
| II-809. | $L_{A48}$ | $L_{B13}$ |
| II-810. | $L_{A49}$ | $L_{B13}$ |
| II-811. | $L_{A50}$ | $L_{B13}$ |
| II-812. | $L_{A51}$ | $L_{B13}$ |
| II-813. | $L_{A52}$ | $L_{B13}$ |
| II-818. | $L_{A57}$ | $L_{B13}$ |
| II-819. | $L_{A58}$ | $L_{B13}$ |
| II-824. | $L_{A63}$ | $L_{B13}$ |
| II-825. | $L_{A64}$ | $L_{B13}$ |
| II-826. | $L_{A65}$ | $L_{B13}$ |
| II-827. | $L_{A66}$ | $L_{B13}$ |
| II-828. | $L_{A67}$ | $L_{B13}$ |
| II-829. | $L_{A68}$ | $L_{B13}$ |
| II-830. | $L_{A69}$ | $L_{B13}$ |
| II-836. | $L_{A6}$ | $L_{B14}$ |
| II-837. | $L_{A7}$ | $L_{B14}$ |
| II-842. | $L_{A12}$ | $L_{B14}$ |
| II-843. | $L_{A13}$ | $L_{B14}$ |
| II-844. | $L_{A14}$ | $L_{B14}$ |
| II-845. | $L_{A15}$ | $L_{B14}$ |
| II-846. | $L_{A16}$ | $L_{B14}$ |
| II-847. | $L_{A17}$ | $L_{B14}$ |
| II-848. | $L_{A18}$ | $L_{B14}$ |
| II-854. | $L_{A24}$ | $L_{B14}$ |
| II-855. | $L_{A25}$ | $L_{B14}$ |
| II-860. | $L_{A30}$ | $L_{B14}$ |
| II-861. | $L_{A31}$ | $L_{B14}$ |
| II-862. | $L_{A32}$ | $L_{B14}$ |
| II-863. | $L_{A33}$ | $L_{B14}$ |
| II-864. | $L_{A34}$ | $L_{B14}$ |
| II-865. | $L_{A35}$ | $L_{B14}$ |
| II-870. | $L_{A40}$ | $L_{B14}$ |
| II-871. | $L_{A41}$ | $L_{B14}$ |
| II-876. | $L_{A46}$ | $L_{B14}$ |
| II-877. | $L_{A47}$ | $L_{B14}$ |
| II-878. | $L_{A48}$ | $L_{B14}$ |
| II-879. | $L_{A49}$ | $L_{B14}$ |
| II-880. | $L_{A50}$ | $L_{B14}$ |
| II-881. | $L_{A51}$ | $L_{B14}$ |
| II-882. | $L_{A52}$ | $L_{B14}$ |
| II-887. | $L_{A57}$ | $L_{B14}$ |
| II-888. | $L_{A58}$ | $L_{B14}$ |
| II-893. | $L_{A63}$ | $L_{B14}$ |
| II-894. | $L_{A64}$ | $L_{B14}$ |
| II-895. | $L_{A65}$ | $L_{B14}$ |
| II-896. | $L_{A66}$ | $L_{B14}$ |
| II-897. | $L_{A67}$ | $L_{B14}$ |
| II-898. | $L_{A68}$ | $L_{B14}$ |
| II-899. | $L_{A69}$ | $L_{B14}$ |
| II-905. | $L_{A6}$ | $L_{B15}$ |
| II-906. | $L_{A7}$ | $L_{B15}$ |
| II-911. | $L_{A12}$ | $L_{B15}$ |
| II-912. | $L_{A13}$ | $L_{B15}$ |
| II-913. | $L_{A14}$ | $L_{B15}$ |
| II-914. | $L_{A15}$ | $L_{B15}$ |
| II-915. | $L_{A16}$ | $L_{B15}$ |
| II-916. | $L_{A17}$ | $L_{B15}$ |
| II-917. | $L_{A18}$ | $L_{B15}$ |
| II-923. | $L_{A24}$ | $L_{B15}$ |
| II-924. | $L_{A25}$ | $L_{B15}$ |
| II-929. | $L_{A30}$ | $L_{B15}$ |
| II-930. | $L_{A31}$ | $L_{B15}$ |
| II-931. | $L_{A32}$ | $L_{B15}$ |
| II-932. | $L_{A33}$ | $L_{B15}$ |
| II-933. | $L_{A34}$ | $L_{B15}$ |

-continued

| Compound Number | $L_A$ | $L_B$ |
|---|---|---|
| II-934. | $L_{A35}$ | $L_{B15}$ |
| II-939. | $L_{A40}$ | $L_{B15}$ |
| II-940. | $L_{A41}$ | $L_{B15}$ |
| II-945. | $L_{A46}$ | $L_{B15}$ |
| II-946. | $L_{A47}$ | $L_{B15}$ |
| II-947. | $L_{A48}$ | $L_{B15}$ |
| II-948. | $L_{A49}$ | $L_{B15}$ |
| II-949. | $L_{A50}$ | $L_{B15}$ |
| II-950. | $L_{A51}$ | $L_{B15}$ |
| II-951. | $L_{A52}$ | $L_{B15}$ |
| II-956. | $L_{A57}$ | $L_{B15}$ |
| II-957. | $L_{A58}$ | $L_{B15}$ |
| II-962. | $L_{A63}$ | $L_{B15}$ |
| II-963. | $L_{A64}$ | $L_{B15}$ |
| II-964. | $L_{A65}$ | $L_{B15}$ |
| II-965. | $L_{A66}$ | $L_{B15}$ |
| II-966. | $L_{A67}$ | $L_{B15}$ |
| II-967. | $L_{A68}$ | $L_{B15}$ |
| II-968. | $L_{A69}$ | $L_{B15}$ |
| II-972. | $L_{A6}$ | $L_{B16}$ |
| II-973. | $L_{A7}$ | $L_{B16}$ |
| II-978. | $L_{A12}$ | $L_{B16}$ |
| II-979. | $L_{A13}$ | $L_{B16}$ |
| II-980. | $L_{A14}$ | $L_{B16}$ |
| II-981. | $L_{A15}$ | $L_{B16}$ |
| II-982. | $L_{A16}$ | $L_{B16}$ |
| II-983. | $L_{A17}$ | $L_{B16}$ |
| II-984. | $L_{A18}$ | $L_{B16}$ |
| II-989. | $L_{A25}$ | $L_{B16}$ |
| II-990. | $L_{A26}$ | $L_{B16}$ |
| II-995. | $L_{A31}$ | $L_{B16}$ |
| II-996. | $L_{A32}$ | $L_{B16}$ |
| II-997. | $L_{A33}$ | $L_{B16}$ |
| II-998. | $L_{A34}$ | $L_{B16}$ |
| II-999. | $L_{A35}$ | $L_{B16}$ |
| II-1003. | $L_{A40}$ | $L_{B16}$ |
| II-1004. | $L_{A41}$ | $L_{B16}$ |
| II-1009. | $L_{A46}$ | $L_{B16}$ |
| II-1010. | $L_{A47}$ | $L_{B16}$ |
| II-1011. | $L_{A48}$ | $L_{B16}$ |
| II-1012. | $L_{A49}$ | $L_{B16}$ |
| II-1013. | $L_{A50}$ | $L_{B16}$ |
| II-1014. | $L_{A51}$ | $L_{B16}$ |
| II-1015. | $L_{A52}$ | $L_{B16}$ |
| II-1019. | $L_{A57}$ | $L_{B16}$ |
| II-1020. | $L_{A58}$ | $L_{B16}$ |
| II-1025. | $L_{A63}$ | $L_{B16}$ |
| II-1026. | $L_{A64}$ | $L_{B16}$ |
| II-1027. | $L_{A65}$ | $L_{B16}$ |
| II-1028. | $L_{A66}$ | $L_{B16}$ |
| II-1029. | $L_{A67}$ | $L_{B16}$ |
| II-1030. | $L_{A68}$ | $L_{B16}$ |
| II-1031. | $L_{A69}$ | $L_{B16}$ |
| II-1103. | $L_{A6}$ | $L_{B18}$ |
| II-1104. | $L_{A7}$ | $L_{B18}$ |
| II-1109. | $L_{A12}$ | $L_{B18}$ |
| II-1110. | $L_{A13}$ | $L_{B18}$ |
| II-1111. | $L_{A14}$ | $L_{B18}$ |
| II-1112. | $L_{A15}$ | $L_{B18}$ |
| II-1113. | $L_{A16}$ | $L_{B18}$ |
| II-1114. | $L_{A17}$ | $L_{B18}$ |
| II-1115. | $L_{A18}$ | $L_{B18}$ |
| II-1120. | $L_{A24}$ | $L_{B18}$ |
| II-1121. | $L_{A25}$ | $L_{B18}$ |
| II-1126. | $L_{A30}$ | $L_{B18}$ |
| II-1127. | $L_{A31}$ | $L_{B18}$ |
| II-1128. | $L_{A32}$ | $L_{B18}$ |
| II-1129. | $L_{A33}$ | $L_{B18}$ |
| II-1130. | $L_{A34}$ | $L_{B18}$ |
| II-1131. | $L_{A35}$ | $L_{B18}$ |
| II-1136. | $L_{A40}$ | $L_{B18}$ |
| II-1137. | $L_{A41}$ | $L_{B18}$ |
| II-1142. | $L_{A46}$ | $L_{B18}$ |
| II-1143. | $L_{A47}$ | $L_{B18}$ |
| II-1144. | $L_{A48}$ | $L_{B18}$ |
| II-1145. | $L_{A49}$ | $L_{B18}$ |

-continued

| Compound Number | $L_A$ | $L_B$ |
|---|---|---|
| II-1146. | $L_{A50}$ | $L_{B18}$ |
| II-1147. | $L_{A51}$ | $L_{B18}$ |
| II-1148. | $L_{A52}$ | $L_{B18}$ |
| II-1153. | $L_{A57}$ | $L_{B18}$ |
| II-1154. | $L_{A58}$ | $L_{B18}$ |
| II-1159. | $L_{A63}$ | $L_{B18}$ |
| II-1160. | $L_{A64}$ | $L_{B18}$ |
| II-1161. | $L_{A65}$ | $L_{B18}$ |
| II-1162. | $L_{A66}$ | $L_{B18}$ |
| II-1163. | $L_{A67}$ | $L_{B18}$ |
| II-1164. | $L_{A68}$ | $L_{B18}$ |
| II-1165. | $L_{A69}$ | $L_{B18}$ |
| II-1237. | $L_{A6}$ | $L_{B20}$ |
| II-1238. | $L_{A7}$ | $L_{B20}$ |
| II-1243. | $L_{A12}$ | $L_{B20}$ |
| II-1244. | $L_{A13}$ | $L_{B20}$ |
| II-1245. | $L_{A14}$ | $L_{B20}$ |
| II-1246. | $L_{A15}$ | $L_{B20}$ |
| II-1247. | $L_{A16}$ | $L_{B20}$ |
| II-1248. | $L_{A17}$ | $L_{B20}$ |
| II-1249. | $L_{A18}$ | $L_{B20}$ |
| II-1254. | $L_{A24}$ | $L_{B20}$ |
| II-1255. | $L_{A25}$ | $L_{B20}$ |
| II-1260. | $L_{A30}$ | $L_{B20}$ |
| II-1261. | $L_{A31}$ | $L_{B20}$ |
| II-1262. | $L_{A32}$ | $L_{B20}$ |
| II-1263. | $L_{A33}$ | $L_{B20}$ |
| II-1264. | $L_{A34}$ | $L_{B20}$ |
| II-1265. | $L_{A35}$ | $L_{B20}$ |
| II-1270. | $L_{A40}$ | $L_{B20}$ |
| II-1271. | $L_{A41}$ | $L_{B20}$ |
| II-1276. | $L_{A46}$ | $L_{B20}$ |
| II-1277. | $L_{A47}$ | $L_{B20}$ |
| II-1278. | $L_{A48}$ | $L_{B20}$ |
| II-1279. | $L_{A49}$ | $L_{B20}$ |
| II-1280. | $L_{A50}$ | $L_{B20}$ |
| II-1281. | $L_{A51}$ | $L_{B20}$ |
| II-1282. | $L_{A52}$ | $L_{B20}$ |
| II-1287. | $L_{A57}$ | $L_{B20}$ |
| II-1288. | $L_{A58}$ | $L_{B20}$ |
| II-1293. | $L_{A63}$ | $L_{B20}$ |
| II-1294. | $L_{A64}$ | $L_{B20}$ |
| II-1295. | $L_{A65}$ | $L_{B20}$ |
| II-1296. | $L_{A66}$ | $L_{B20}$ |
| II-1297. | $L_{A67}$ | $L_{B20}$ |
| II-1298. | $L_{A68}$ | $L_{B20}$ |
| II-1299. | $L_{A69}$ | $L_{B20}$ |
| II-1371. | $L_{A6}$ | $L_{B22}$ |
| II-1372. | $L_{A7}$ | $L_{B22}$ |
| II-1377. | $L_{A12}$ | $L_{B22}$ |
| II-1378. | $L_{A13}$ | $L_{B22}$ |
| II-1379. | $L_{A14}$ | $L_{B22}$ |
| II-1380. | $L_{A15}$ | $L_{B22}$ |
| II-1381. | $L_{A16}$ | $L_{B22}$ |
| II-1382. | $L_{A17}$ | $L_{B22}$ |
| II-1383. | $L_{A18}$ | $L_{B22}$ |
| II-1388. | $L_{A24}$ | $L_{B22}$ |
| II-1389. | $L_{A25}$ | $L_{B22}$ |
| II-1394. | $L_{A30}$ | $L_{B22}$ |
| II-1395. | $L_{A31}$ | $L_{B22}$ |
| II-1396. | $L_{A32}$ | $L_{B22}$ |
| II-1397. | $L_{A33}$ | $L_{B22}$ |
| II-1398. | $L_{A34}$ | $L_{B22}$ |
| II-1399. | $L_{A35}$ | $L_{B22}$ |
| II-1404. | $L_{A40}$ | $L_{B22}$ |
| II-1405. | $L_{A41}$ | $L_{B22}$ |
| II-1410. | $L_{A46}$ | $L_{B22}$ |
| II-1411. | $L_{A47}$ | $L_{B22}$ |
| II-1412. | $L_{A48}$ | $L_{B22}$ |
| II-1413. | $L_{A49}$ | $L_{B22}$ |
| II-1414. | $L_{A50}$ | $L_{B22}$ |
| II-1415. | $L_{A51}$ | $L_{B22}$ |
| II-1416. | $L_{A52}$ | $L_{B22}$ |
| II-1421. | $L_{A57}$ | $L_{B22}$ |
| II-1422. | $L_{A58}$ | $L_{B22}$ |
| II-1427. | $L_{A63}$ | $L_{B22}$ |

-continued

| Compound Number | $L_A$ | $L_B$ |
|---|---|---|
| II-1428. | $L_{A64}$ | $L_{B22}$ |
| II-1429. | $L_{A65}$ | $L_{B22}$ |
| II-1430. | $L_{A66}$ | $L_{B22}$ |
| II-1431. | $L_{A67}$ | $L_{B22}$ |
| II-1432. | $L_{A68}$ | $L_{B22}$ |
| II-1433. | $L_{A69}$ | $L_{B22}$, | and wherein $L_A$ is selected from the group consisting of

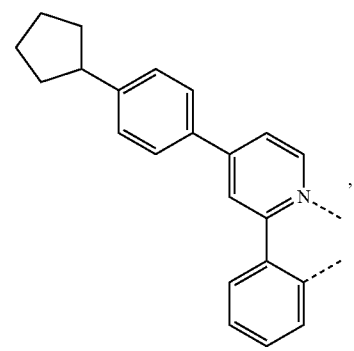

$L_{A6}$

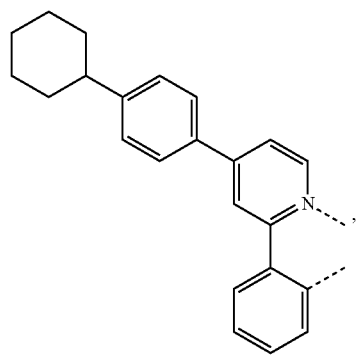

$L_{A7}$

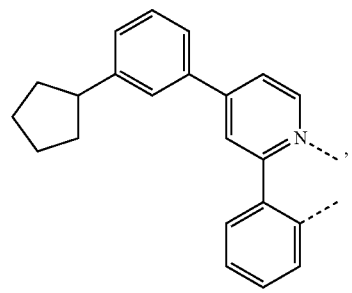

$L_{A12}$

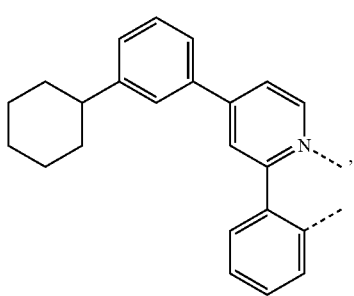

$L_{A13}$

L<sub>A14</sub>
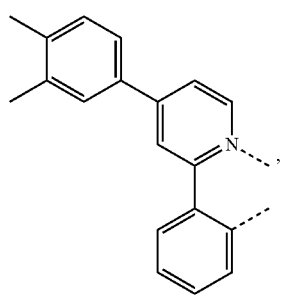
L<sub>A15</sub>
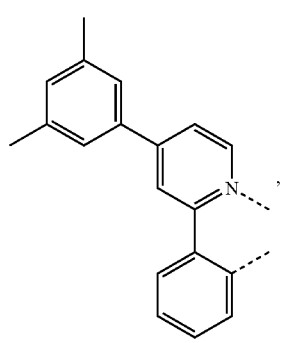
L<sub>A16</sub>
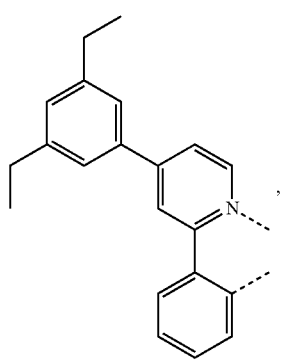
L<sub>A17</sub>
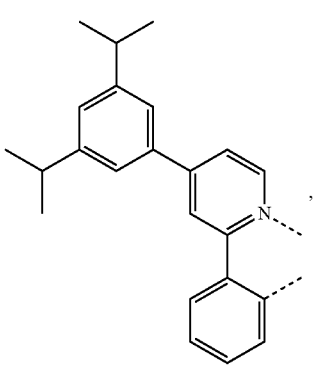
L<sub>A18</sub>
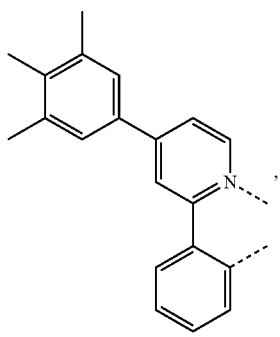
L<sub>A24</sub>
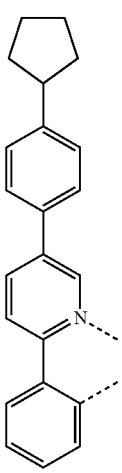
L<sub>A25</sub>
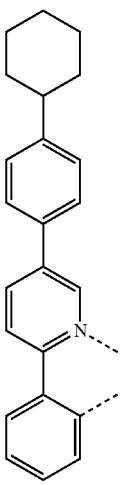

L_{A30}
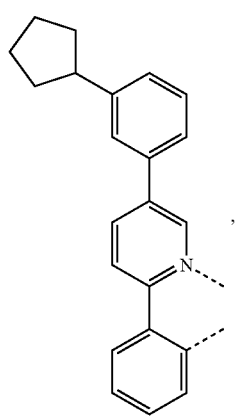
L_{A31}
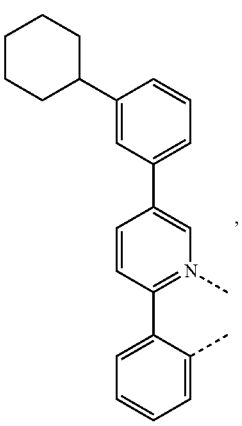
L_{A32}
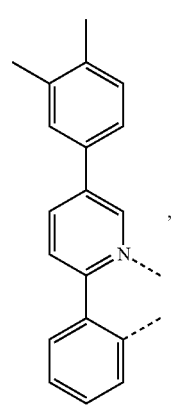
L_{A33}
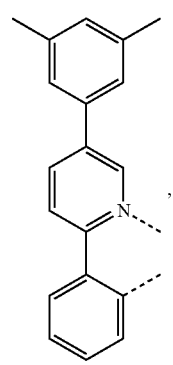
L_{A34}
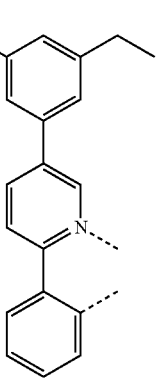
L_{A35}
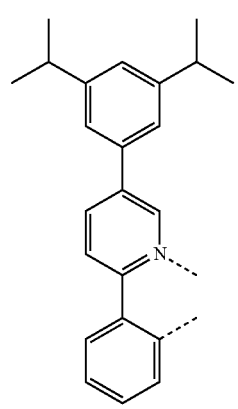
L_{A40}
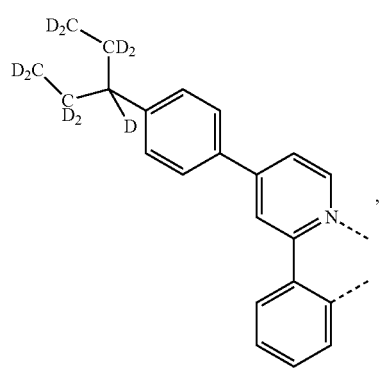
L_{A41}
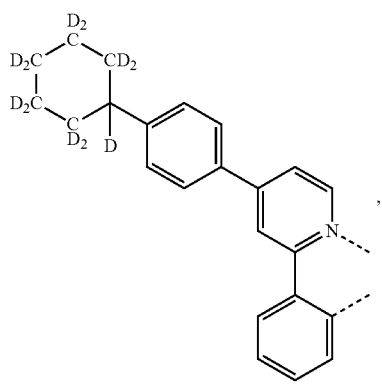

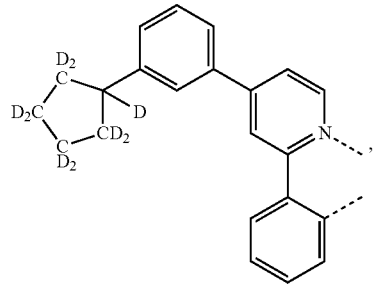 L<sub>A46</sub>
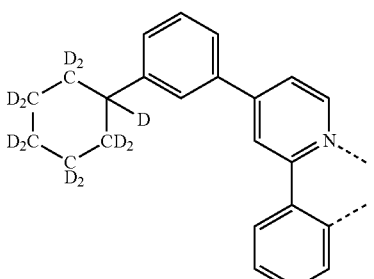 L<sub>A47</sub>
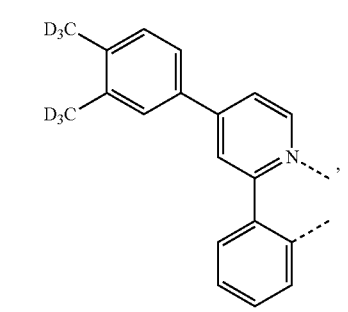 L<sub>A48</sub>
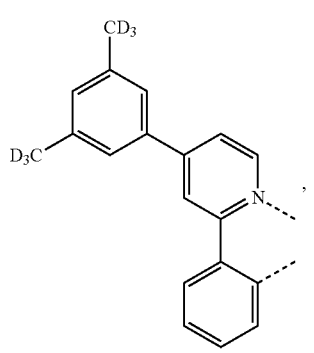 L<sub>A49</sub>
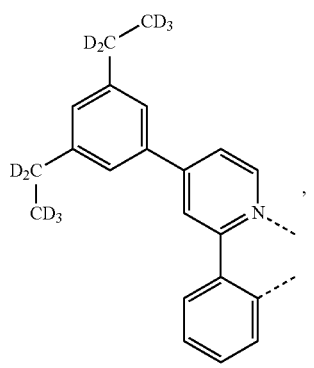 L<sub>A50</sub>
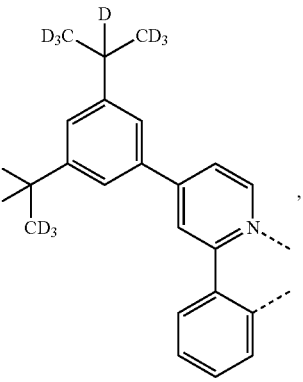 L<sub>A51</sub>
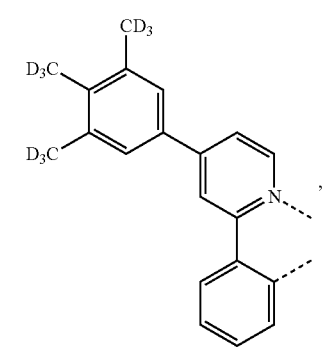 L<sub>A52</sub>
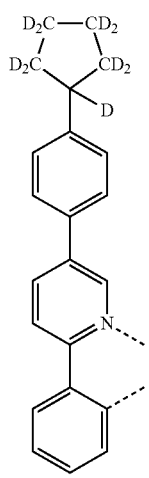 L<sub>A57</sub>

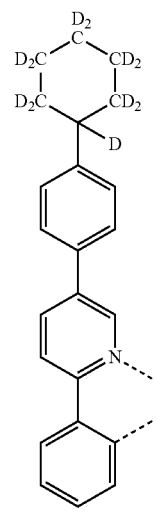
L_A58
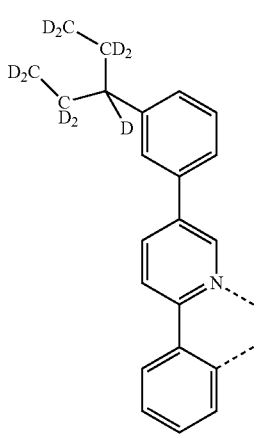
L_A63
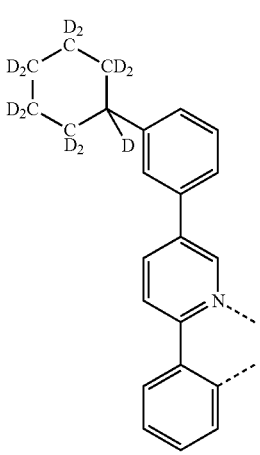
L_A64
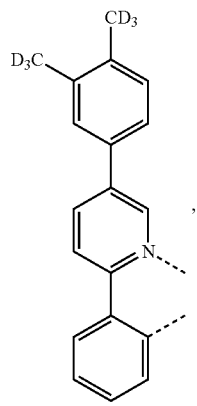
L_A65
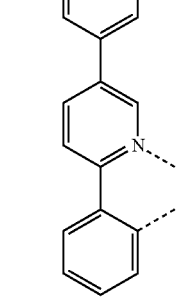
L_A66
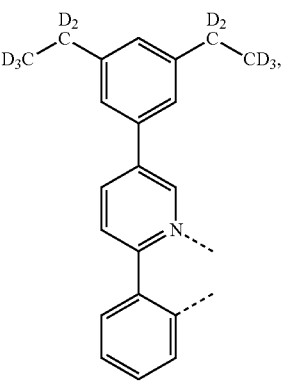
L_A67
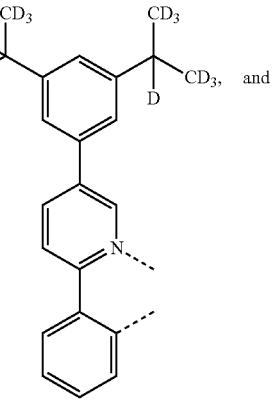
L_A68, and

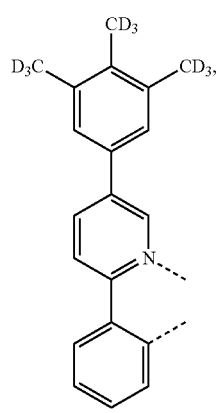
L_{A69}
L_B is selected from the group consisting of
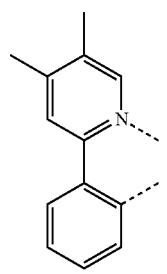
L_{B5}
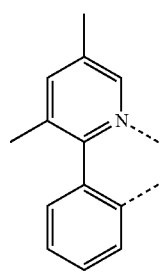
L_{B6}
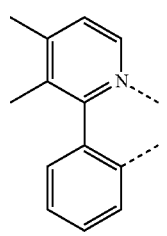
L_{B7}
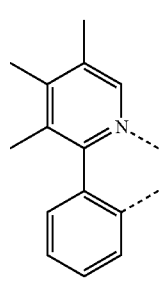
L_{B8}
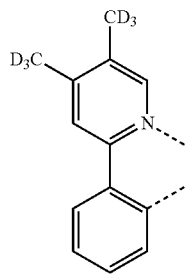
L_{B12}
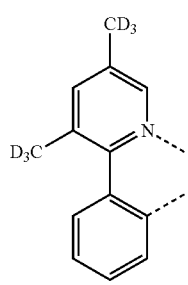
L_{B13}
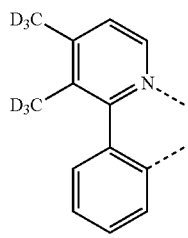
L_{B14}
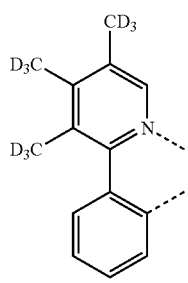
L_{B15}
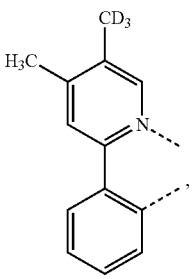
L_{B16}

L_{B18}

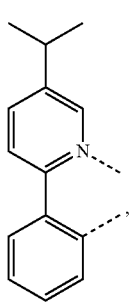

L_{B20}

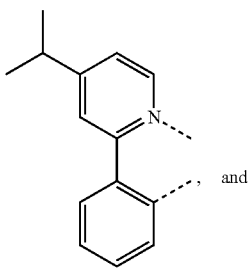, and

L_{B22}

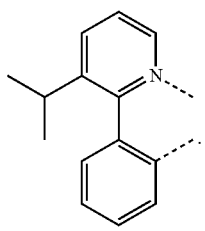

4. The first device of claim 3, wherein the heteroleptic iridium complex is selected from the group consisting of Compound II-267 through Compound II-268, Compound II-273 through Compound II-279, Compound II-284 through Compound II-285, Compound II-290 through Compound II-296, Compound II-334 through Compound II-335, Compound II-340 through Compound II-346, Compound II-351 through Compound II-352, Compound II-357 through Compound II-363, Compound II-401 through Compound II-402, Compound II-407 through Compound II-413, Compound II-418 through Compound II-419, Compound II-424 through Compound II-430, Compound II-468 through Compound II-469, Compound II-474 through Compound II-480, Compound II-485 through Compound II-486, Compound II-491 through Compound II-497, Compound II-702 through Compound II-703, Compound II-708 through Compound II-714, Compound II-718 through Compound II-719, Compound II-724 through Compound II-729, Compound II-733 through Compound II-734, Compound II-739 through Compound II-745, Compound II-749 through Compound II-750, Compound II-755 through Compound II-761, Compound II-767 through Compound II-768, Compound II-773 through Compound II-779, Compound II-785 through Compound II-786, Compound II-791 through Compound II-796, Compound II-801 through Compound II-802, Compound II-807 through Compound II-813, Compound II-818 through Compound II-819, Compound II-824 through Compound II-830, Compound II-836 through Compound II-837, Compound II-842 through Compound II-848, Compound II-854 through Compound II-855, Compound II-860 through Compound II-865, Compound II-870 through Compound II-871, Compound II-876 through Compound II-882, Compound II-887 through Compound II-888, Compound II-893 through Compound II-899, Compound II-905 through Compound II-906, Compound II-911 through Compound II-917, Compound II-923 through Compound II-924, Compound II-929 through Compound II-934, Compound II-939 through Compound II-940, Compound II-945 through Compound II-951, Compound II-956 through Compound II-957, Compound II-962 through Compound II-968, Compound II-972 through Compound II-973, Compound II-978 through Compound II-984, Compound II-989 through Compound II-990, Compound II-995 through Compound II-999, Compound II-1003, Compound II-1004, Compound II-1009 through Compound II-1015, Compound II-1019 through Compound II-1020, Compound II-1025 through Compound II-1031, Compound II-1136 through Compound II-1137, Compound II-1142 through Compound II-1148, Compound II-1153 through Compound II-1154, Compound II-1159 through Compound II-1165, Compound II-1270 through Compound II-1271, Compound II-1276 through Compound II-1282, Compound II-1287 through Compound II-1288, Compound II-1293 through Compound II-1299, Compound II-1404 through Compound II-1405, Compound II-1410 through Compound II-1416, Compound II-1421 through Compound II-1422, and Compound II-1427 through Compound II-1433.

5. The first device of claim 3, wherein the organic layer is an emissive layer and the compound is an emissive dopant.

6. The first device of claim 3, wherein the organic layer is an emissive layer and the compound is a non-emissive dopant.

7. The first device of claim 3, wherein the organic layer further comprises a host.

8. The first device of claim 7, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH^{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, and $C_nH_{2n}-Ar_1$, or the host has no substitution;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

9. The first device of claim 8, wherein the host has the formula:

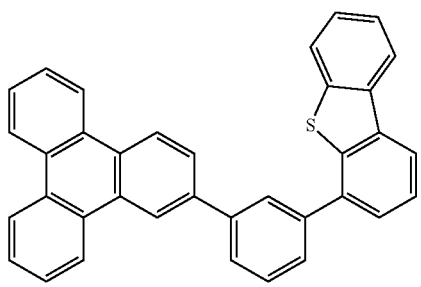

Compound H

10. The first device of claim 7, wherein the host is a metal complex.

11. The first device of claim 3, wherein the first device is a consumer product.

12. The first device of claim 3, wherein the first device is an organic light-emitting device.

13. The first device of claim 3, wherein the first device further comprises a second emissive dopant having a peak wavelength of between 400 to 500 nanometers.

14. The first device of claim 13, wherein the second emissive dopant is a fluorescent emitter.

15. The first device of claim 13, wherein the second emissive dopant is a phosphorescent emitter.

16. The first device of claim 3, wherein the first device comprises a lighting panel.

17. The first device of claim 3, wherein the first device further comprises a first organic light-emitting device comprising a compound of Formula I and a second light emitting device separate from the first organic light-emitting device comprising an emissive dopant having a peak wavelength of between 400 to 500 nanometers.

18. The first device of claim 3, wherein the first device comprises an organic-light emitting device having a first emissive layer and a second emissive layer;
wherein the first emissive layer comprises a compound of Formula I; and
wherein the second emissive layer comprises an emissive dopant having a peak wavelength of between 400 to 500 nanometers.

19. A formulation comprising a compound comprising a heteroleptic iridium complex having the formula $IrL_A(L_B)_2$, wherein the heteroleptic iridium complex is selected from the group consisting of the compounds listed in the following table:

| Compound Number | $L_A$ | $L_B$ |
|---|---|---|
| II-234. | $L_{A6}$ | $L_{B5}$ |
| II-235. | $L_{A7}$ | $L_{B5}$ |
| II-240. | $L_{A12}$ | $L_{B5}$ |
| II-241. | $L_{A13}$ | $L_{B5}$ |
| II-242. | $L_{A14}$ | $L_{B5}$ |
| II-243. | $L_{A15}$ | $L_{B5}$ |
| II-244. | $L_{A16}$ | $L_{B5}$ |
| II-245. | $L_{A17}$ | $L_{B5}$ |
| II-246. | $L_{A18}$ | $L_{B5}$ |
| II-251. | $L_{A24}$ | $L_{B5}$ |
| II-252. | $L_{A25}$ | $L_{B5}$ |
| II-257. | $L_{A30}$ | $L_{B5}$ |
| II-258. | $L_{A31}$ | $L_{B5}$ |
| II-259. | $L_{A32}$ | $L_{B5}$ |
| II-260. | $L_{A33}$ | $L_{B5}$ |
| II-261. | $L_{A34}$ | $L_{B5}$ |
| II-262. | $L_{A35}$ | $L_{B5}$ |
| II-267. | $L_{A40}$ | $L_{B5}$ |
| II-268. | $L_{A41}$ | $L_{B5}$ |
| II-273. | $L_{A46}$ | $L_{B5}$ |
| II-274. | $L_{A47}$ | $L_{B5}$ |
| II-275. | $L_{A48}$ | $L_{B5}$ |
| II-276. | $L_{A49}$ | $L_{B5}$ |
| II-277. | $L_{A50}$ | $L_{B5}$ |
| II-278. | $L_{A51}$ | $L_{B5}$ |
| II-279. | $L_{A52}$ | $L_{B5}$ |
| II-284. | $L_{A57}$ | $L_{B5}$ |
| II-285. | $L_{A58}$ | $L_{B5}$ |
| II-290. | $L_{A63}$ | $L_{B5}$ |
| II-291. | $L_{A64}$ | $L_{B5}$ |
| II-292. | $L_{A65}$ | $L_{B5}$ |
| II-293. | $L_{A66}$ | $L_{B5}$ |
| II-294. | $L_{A67}$ | $L_{B5}$ |
| II-295. | $L_{A68}$ | $L_{B5}$ |
| II-296. | $L_{A69}$ | $L_{B5}$ |
| II-301. | $L_{A6}$ | $L_{B6}$ |
| II-302. | $L_{A7}$ | $L_{B6}$ |
| II-307. | $L_{A12}$ | $L_{B6}$ |
| II-308. | $L_{A13}$ | $L_{B6}$ |
| II-309. | $L_{A14}$ | $L_{B6}$ |
| II-310. | $L_{A15}$ | $L_{B6}$ |
| II-311. | $L_{A16}$ | $L_{B6}$ |
| II-312. | $L_{A17}$ | $L_{B6}$ |
| II-313. | $L_{A18}$ | $L_{B6}$ |
| II-318. | $L_{A24}$ | $L_{B6}$ |
| II-319. | $L_{A25}$ | $L_{B6}$ |
| II-324. | $L_{A30}$ | $L_{B6}$ |
| II-325. | $L_{A31}$ | $L_{B6}$ |
| II-326. | $L_{A32}$ | $L_{B6}$ |
| II-327. | $L_{A33}$ | $L_{B6}$ |
| II-328. | $L_{A34}$ | $L_{B6}$ |
| II-329. | $L_{A35}$ | $L_{B6}$ |
| II-334. | $L_{A40}$ | $L_{B6}$ |
| II-335. | $L_{A41}$ | $L_{B6}$ |
| II-340. | $L_{A46}$ | $L_{B6}$ |
| II-341. | $L_{A47}$ | $L_{B6}$ |
| II-342. | $L_{A48}$ | $L_{B6}$ |
| II-343. | $L_{A49}$ | $L_{B6}$ |
| II-344. | $L_{A50}$ | $L_{B6}$ |
| II-345. | $L_{A51}$ | $L_{B6}$ |
| II-346. | $L_{A52}$ | $L_{B6}$ |
| II-351. | $L_{A57}$ | $L_{B6}$ |
| II-352. | $L_{A58}$ | $L_{B6}$ |
| II-357. | $L_{A63}$ | $L_{B6}$ |
| II-358. | $L_{A64}$ | $L_{B6}$ |
| II-359. | $L_{A65}$ | $L_{B6}$ |
| II-360. | $L_{A66}$ | $L_{B6}$ |
| II-361. | $L_{A67}$ | $L_{B6}$ |
| II-362. | $L_{A68}$ | $L_{B6}$ |
| II-363. | $L_{A69}$ | $L_{B6}$ |
| II-368. | $L_{A6}$ | $L_{B7}$ |
| II-369. | $L_{A7}$ | $L_{B7}$ |
| II-374. | $L_{A12}$ | $L_{B7}$ |
| II-375. | $L_{A13}$ | $L_{B7}$ |
| II-376. | $L_{A14}$ | $L_{B7}$ |
| II-377. | $L_{A15}$ | $L_{B7}$ |
| II-378. | $L_{A16}$ | $L_{B7}$ |
| II-379. | $L_{A17}$ | $L_{B7}$ |
| II-380. | $L_{A18}$ | $L_{B7}$ |
| II-385. | $L_{A24}$ | $L_{B7}$ |
| II-386. | $L_{A25}$ | $L_{B7}$ |
| II-391. | $L_{A30}$ | $L_{B7}$ |
| II-392. | $L_{A31}$ | $L_{B7}$ |
| II-393. | $L_{A32}$ | $L_{B7}$ |
| II-394. | $L_{A33}$ | $L_{B7}$ |
| II-395. | $L_{A34}$ | $L_{B7}$ |
| II-396. | $L_{A35}$ | $L_{B7}$ |
| II-401. | $L_{A40}$ | $L_{B7}$ |
| II-402. | $L_{A41}$ | $L_{B7}$ |
| II-407. | $L_{A46}$ | $L_{B7}$ |
| II-408. | $L_{A47}$ | $L_{B7}$ |
| II-409. | $L_{A48}$ | $L_{B7}$ |
| II-410. | $L_{A49}$ | $L_{B7}$ |
| II-411. | $L_{A50}$ | $L_{B7}$ |
| II-412. | $L_{A51}$ | $L_{B7}$ |
| II-413. | $L_{A52}$ | $L_{B7}$ |
| II-418. | $L_{A57}$ | $L_{B7}$ |
| II-419. | $L_{A58}$ | $L_{B7}$ |
| II-424. | $L_{A63}$ | $L_{B7}$ |
| II-425. | $L_{A64}$ | $L_{B7}$ |
| II-426. | $L_{A65}$ | $L_{B7}$ |
| II-427. | $L_{A66}$ | $L_{B7}$ |
| II-428. | $L_{A67}$ | $L_{B7}$ |
| II-429. | $L_{A68}$ | $L_{B7}$ |
| II-430. | $L_{A69}$ | $L_{B7}$ |
| II-435. | $L_{A6}$ | $L_{B8}$ |
| II-436. | $L_{A7}$ | $L_{B8}$ |
| II-441. | $L_{A12}$ | $L_{B8}$ |
| II-442. | $L_{A13}$ | $L_{B8}$ |
| II-443. | $L_{A14}$ | $L_{B8}$ |
| II-444. | $L_{A15}$ | $L_{B8}$ |
| II-445. | $L_{A16}$ | $L_{B8}$ |
| II-446. | $L_{A17}$ | $L_{B8}$ |

-continued

| Compound Number | $L_A$ | $L_B$ |
|---|---|---|
| II-447. | $L_{A18}$ | $L_{B8}$ |
| II-452. | $L_{A24}$ | $L_{B8}$ |
| II-453. | $L_{A25}$ | $L_{B8}$ |
| II-458. | $L_{A30}$ | $L_{B8}$ |
| II-459. | $L_{A31}$ | $L_{B8}$ |
| II-460. | $L_{A32}$ | $L_{B8}$ |
| II-461. | $L_{A33}$ | $L_{B8}$ |
| II-462. | $L_{A34}$ | $L_{B8}$ |
| II-463. | $L_{A35}$ | $L_{B8}$ |
| II-468. | $L_{A40}$ | $L_{B8}$ |
| II-469. | $L_{A41}$ | $L_{B8}$ |
| II-474. | $L_{A46}$ | $L_{B8}$ |
| II-475. | $L_{A47}$ | $L_{B8}$ |
| II-476. | $L_{A48}$ | $L_{B8}$ |
| II-477. | $L_{A49}$ | $L_{B8}$ |
| II-478. | $L_{A50}$ | $L_{B8}$ |
| II-479. | $L_{A51}$ | $L_{B8}$ |
| II-480. | $L_{A52}$ | $L_{B8}$ |
| II-485. | $L_{A57}$ | $L_{B8}$ |
| II-486. | $L_{A58}$ | $L_{B8}$ |
| II-491. | $L_{A63}$ | $L_{B8}$ |
| II-492. | $L_{A64}$ | $L_{B8}$ |
| II-493. | $L_{A65}$ | $L_{B8}$ |
| II-494. | $L_{A66}$ | $L_{B8}$ |
| II-495. | $L_{A67}$ | $L_{B8}$ |
| II-496. | $L_{A68}$ | $L_{B8}$ |
| II-497. | $L_{A69}$ | $L_{B8}$ |
| II-702. | $L_{A6}$ | $L_{B12}$ |
| II-703. | $L_{A7}$ | $L_{B12}$ |
| II-708. | $L_{A12}$ | $L_{B12}$ |
| II-709. | $L_{A13}$ | $L_{B12}$ |
| II-710. | $L_{A14}$ | $L_{B12}$ |
| II-711. | $L_{A15}$ | $L_{B12}$ |
| II-712. | $L_{A16}$ | $L_{B12}$ |
| II-713. | $L_{A17}$ | $L_{B12}$ |
| II-714. | $L_{A18}$ | $L_{B12}$ |
| II-718. | $L_{A24}$ | $L_{B12}$ |
| II-719. | $L_{A25}$ | $L_{B12}$ |
| II-724. | $L_{A30}$ | $L_{B12}$ |
| II-725. | $L_{A31}$ | $L_{B12}$ |
| II-726. | $L_{A32}$ | $L_{B12}$ |
| II-727. | $L_{A33}$ | $L_{B12}$ |
| II-728. | $L_{A34}$ | $L_{B12}$ |
| II-729. | $L_{A35}$ | $L_{B12}$ |
| II-733. | $L_{A40}$ | $L_{B12}$ |
| II-734. | $L_{A41}$ | $L_{B12}$ |
| II-739. | $L_{A46}$ | $L_{B12}$ |
| II-740. | $L_{A47}$ | $L_{B12}$ |
| II-741. | $L_{A48}$ | $L_{B12}$ |
| II-742. | $L_{A49}$ | $L_{B12}$ |
| II-743. | $L_{A50}$ | $L_{B12}$ |
| II-744. | $L_{A51}$ | $L_{B12}$ |
| II-745. | $L_{A52}$ | $L_{B12}$ |
| II-749. | $L_{A57}$ | $L_{B12}$ |
| II-750. | $L_{A58}$ | $L_{B12}$ |
| II-755. | $L_{A63}$ | $L_{B12}$ |
| II-756. | $L_{A64}$ | $L_{B12}$ |
| II-757. | $L_{A65}$ | $L_{B12}$ |
| II-758. | $L_{A66}$ | $L_{B12}$ |
| II-759. | $L_{A67}$ | $L_{B12}$ |
| II-760. | $L_{A68}$ | $L_{B12}$ |
| II-761. | $L_{A69}$ | $L_{B12}$ |
| II-767. | $L_{A6}$ | $L_{B13}$ |
| II-768. | $L_{A7}$ | $L_{B13}$ |
| II-773. | $L_{A12}$ | $L_{B13}$ |
| II-774. | $L_{A13}$ | $L_{B13}$ |
| II-775. | $L_{A14}$ | $L_{B13}$ |
| II-776. | $L_{A15}$ | $L_{B13}$ |
| II-777. | $L_{A16}$ | $L_{B13}$ |
| II-778. | $L_{A17}$ | $L_{B13}$ |
| II-779. | $L_{A18}$ | $L_{B13}$ |
| II-785. | $L_{A24}$ | $L_{B13}$ |
| II-786. | $L_{A25}$ | $L_{B13}$ |
| II-791. | $L_{A30}$ | $L_{B13}$ |
| II-792. | $L_{A31}$ | $L_{B13}$ |
| II-793. | $L_{A32}$ | $L_{B13}$ |
| II-794. | $L_{A33}$ | $L_{B13}$ |
| II-795. | $L_{A34}$ | $L_{B13}$ |
| II-796. | $L_{A35}$ | $L_{B13}$ |
| II-801. | $L_{A40}$ | $L_{B13}$ |
| II-802. | $L_{A41}$ | $L_{B13}$ |
| II-807. | $L_{A46}$ | $L_{B13}$ |
| II-808. | $L_{A47}$ | $L_{B13}$ |
| II-809. | $L_{A48}$ | $L_{B13}$ |
| II-810. | $L_{A49}$ | $L_{B13}$ |
| II-811. | $L_{A50}$ | $L_{B13}$ |
| II-812. | $L_{A51}$ | $L_{B13}$ |
| II-813. | $L_{A52}$ | $L_{B13}$ |
| II-818. | $L_{A57}$ | $L_{B13}$ |
| II-819. | $L_{A58}$ | $L_{B13}$ |
| II-824. | $L_{A63}$ | $L_{B13}$ |
| II-825. | $L_{A64}$ | $L_{B13}$ |
| II-826. | $L_{A65}$ | $L_{B13}$ |
| II-827. | $L_{A66}$ | $L_{B13}$ |
| II-828. | $L_{A67}$ | $L_{B13}$ |
| II-829. | $L_{A68}$ | $L_{B13}$ |
| II-830. | $L_{A69}$ | $L_{B13}$ |
| II-836. | $L_{A6}$ | $L_{B14}$ |
| II-837. | $L_{A7}$ | $L_{B14}$ |
| II-842. | $L_{A12}$ | $L_{B14}$ |
| II-843. | $L_{A13}$ | $L_{B14}$ |
| II-844. | $L_{A14}$ | $L_{B14}$ |
| II-845. | $L_{A15}$ | $L_{B14}$ |
| II-846. | $L_{A16}$ | $L_{B14}$ |
| II-847. | $L_{A17}$ | $L_{B14}$ |
| II-848. | $L_{A18}$ | $L_{B14}$ |
| II-854. | $L_{A24}$ | $L_{B14}$ |
| II-855. | $L_{A25}$ | $L_{B14}$ |
| II-860. | $L_{A30}$ | $L_{B14}$ |
| II-861. | $L_{A31}$ | $L_{B14}$ |
| II-862. | $L_{A32}$ | $L_{B14}$ |
| II-863. | $L_{A33}$ | $L_{B14}$ |
| II-864. | $L_{A34}$ | $L_{B14}$ |
| II-865. | $L_{A35}$ | $L_{B14}$ |
| II-870. | $L_{A40}$ | $L_{B14}$ |
| II-871. | $L_{A41}$ | $L_{B14}$ |
| II-876. | $L_{A46}$ | $L_{B14}$ |
| II-877. | $L_{A47}$ | $L_{B14}$ |
| II-878. | $L_{A48}$ | $L_{B14}$ |
| II-879. | $L_{A49}$ | $L_{B14}$ |
| II-880. | $L_{A50}$ | $L_{B14}$ |
| II-881. | $L_{A51}$ | $L_{B14}$ |
| II-882. | $L_{A52}$ | $L_{B14}$ |
| II-887. | $L_{A57}$ | $L_{B14}$ |
| II-888. | $L_{A58}$ | $L_{B14}$ |
| II-893. | $L_{A63}$ | $L_{B14}$ |
| II-894. | $L_{A64}$ | $L_{B14}$ |
| II-895. | $L_{A65}$ | $L_{B14}$ |
| II-896. | $L_{A66}$ | $L_{B14}$ |
| II-897. | $L_{A67}$ | $L_{B14}$ |
| II-898. | $L_{A68}$ | $L_{B14}$ |
| II-899. | $L_{A69}$ | $L_{B14}$ |
| II-905. | $L_{A6}$ | $L_{B15}$ |
| II-906. | $L_{A7}$ | $L_{B15}$ |
| II-911. | $L_{A12}$ | $L_{B15}$ |
| II-912. | $L_{A13}$ | $L_{B15}$ |
| II-913. | $L_{A14}$ | $L_{B15}$ |
| II-914. | $L_{A15}$ | $L_{B15}$ |
| II-915. | $L_{A16}$ | $L_{B15}$ |
| II-916. | $L_{A17}$ | $L_{B15}$ |
| II-917. | $L_{A18}$ | $L_{B15}$ |
| II-923. | $L_{A24}$ | $L_{B15}$ |
| II-924. | $L_{A25}$ | $L_{B15}$ |
| II-929. | $L_{A30}$ | $L_{B15}$ |
| II-930. | $L_{A31}$ | $L_{B15}$ |
| II-931. | $L_{A32}$ | $L_{B15}$ |
| II-932. | $L_{A33}$ | $L_{B15}$ |
| II-933. | $L_{A34}$ | $L_{B15}$ |
| II-934. | $L_{A35}$ | $L_{B15}$ |
| II-939. | $L_{A40}$ | $L_{B15}$ |
| II-940. | $L_{A41}$ | $L_{B15}$ |
| II-945. | $L_{A46}$ | $L_{B15}$ |

-continued

| Compound Number | $L_A$ | $L_B$ |
|---|---|---|
| II-946. | $L_{A47}$ | $L_{B15}$ |
| II-947. | $L_{A48}$ | $L_{B15}$ |
| II-948. | $L_{A49}$ | $L_{B15}$ |
| II-949. | $L_{A50}$ | $L_{B15}$ |
| II-950. | $L_{A51}$ | $L_{B15}$ |
| II-951. | $L_{A52}$ | $L_{B15}$ |
| II-956. | $L_{A57}$ | $L_{B15}$ |
| II-957. | $L_{A58}$ | $L_{B15}$ |
| II-962. | $L_{A63}$ | $L_{B15}$ |
| II-963. | $L_{A64}$ | $L_{B15}$ |
| II-964. | $L_{A65}$ | $L_{B15}$ |
| II-965. | $L_{A66}$ | $L_{B15}$ |
| II-966. | $L_{A67}$ | $L_{B15}$ |
| II-967. | $L_{A68}$ | $L_{B15}$ |
| II-968. | $L_{A69}$ | $L_{B15}$ |
| II-972. | $L_{A6}$ | $L_{B16}$ |
| II-973. | $L_{A7}$ | $L_{B16}$ |
| II-978. | $L_{A12}$ | $L_{B16}$ |
| II-979. | $L_{A13}$ | $L_{B16}$ |
| II-980. | $L_{A14}$ | $L_{B16}$ |
| II-981. | $L_{A15}$ | $L_{B16}$ |
| II-982. | $L_{A16}$ | $L_{B16}$ |
| II-983. | $L_{A17}$ | $L_{B16}$ |
| II-984. | $L_{A18}$ | $L_{B16}$ |
| II-989. | $L_{A25}$ | $L_{B16}$ |
| II-990. | $L_{A26}$ | $L_{B16}$ |
| II-995. | $L_{A31}$ | $L_{B16}$ |
| II-996. | $L_{A32}$ | $L_{B16}$ |
| II-997. | $L_{A33}$ | $L_{B16}$ |
| II-998. | $L_{A34}$ | $L_{B16}$ |
| II-999. | $L_{A35}$ | $L_{B16}$ |
| II-1003. | $L_{A40}$ | $L_{B16}$ |
| II-1004. | $L_{A41}$ | $L_{B16}$ |
| II-1009. | $L_{A46}$ | $L_{B16}$ |
| II-1010. | $L_{A47}$ | $L_{B16}$ |
| II-1011. | $L_{A48}$ | $L_{B16}$ |
| II-1012. | $L_{A49}$ | $L_{B16}$ |
| II-1013. | $L_{A50}$ | $L_{B16}$ |
| II-1014. | $L_{A51}$ | $L_{B16}$ |
| II-1015. | $L_{A52}$ | $L_{B16}$ |
| II-1019. | $L_{A57}$ | $L_{B16}$ |
| II-1020. | $L_{A58}$ | $L_{B16}$ |
| II-1025. | $L_{A63}$ | $L_{B16}$ |
| II-1026. | $L_{A64}$ | $L_{B16}$ |
| II-1027. | $L_{A65}$ | $L_{B16}$ |
| II-1028. | $L_{A66}$ | $L_{B16}$ |
| II-1029. | $L_{A67}$ | $L_{B16}$ |
| II-1030. | $L_{A68}$ | $L_{B16}$ |
| II-1031. | $L_{A69}$ | $L_{B16}$ |
| II-1103. | $L_{A6}$ | $L_{B18}$ |
| II-1104. | $L_{A7}$ | $L_{B18}$ |
| II-1109. | $L_{A12}$ | $L_{B18}$ |
| II-1110. | $L_{A13}$ | $L_{B18}$ |
| II-1111. | $L_{A14}$ | $L_{B18}$ |
| II-1112. | $L_{A15}$ | $L_{B18}$ |
| II-1113. | $L_{A16}$ | $L_{B18}$ |
| II-1114. | $L_{A17}$ | $L_{B18}$ |
| II-1115. | $L_{A18}$ | $L_{B18}$ |
| II-1120. | $L_{A24}$ | $L_{B18}$ |
| II-1121. | $L_{A25}$ | $L_{B18}$ |
| II-1126. | $L_{A30}$ | $L_{B18}$ |
| II-1127. | $L_{A31}$ | $L_{B18}$ |
| II-1128. | $L_{A32}$ | $L_{B18}$ |
| II-1129. | $L_{A33}$ | $L_{B18}$ |
| II-1130. | $L_{A34}$ | $L_{B18}$ |
| II-1131. | $L_{A35}$ | $L_{B18}$ |
| II-1136. | $L_{A40}$ | $L_{B18}$ |
| II-1137. | $L_{A41}$ | $L_{B18}$ |
| II-1142. | $L_{A46}$ | $L_{B18}$ |
| II-1143. | $L_{A47}$ | $L_{B18}$ |
| II-1144. | $L_{A48}$ | $L_{B18}$ |
| II-1145. | $L_{A49}$ | $L_{B18}$ |
| II-1146. | $L_{A50}$ | $L_{B18}$ |
| II-1147. | $L_{A51}$ | $L_{B18}$ |
| II-1148. | $L_{A52}$ | $L_{B18}$ |
| II-1153. | $L_{A57}$ | $L_{B18}$ |

-continued

| Compound Number | $L_A$ | $L_B$ |
|---|---|---|
| II-1154. | $L_{A58}$ | $L_{B18}$ |
| II-1159. | $L_{A63}$ | $L_{B18}$ |
| II-1160. | $L_{A64}$ | $L_{B18}$ |
| II-1161. | $L_{A65}$ | $L_{B18}$ |
| II-1162. | $L_{A66}$ | $L_{B18}$ |
| II-1163. | $L_{A67}$ | $L_{B18}$ |
| II-1164. | $L_{A68}$ | $L_{B18}$ |
| II-1165. | $L_{A69}$ | $L_{B18}$ |
| II-1237. | $L_{A6}$ | $L_{B20}$ |
| II-1238. | $L_{A7}$ | $L_{B20}$ |
| II-1243. | $L_{A12}$ | $L_{B20}$ |
| II-1244. | $L_{A13}$ | $L_{B20}$ |
| II-1245. | $L_{A14}$ | $L_{B20}$ |
| II-1246. | $L_{A15}$ | $L_{B20}$ |
| II-1247. | $L_{A16}$ | $L_{B20}$ |
| II-1248. | $L_{A17}$ | $L_{B20}$ |
| II-1249. | $L_{A18}$ | $L_{B20}$ |
| II-1254. | $L_{A24}$ | $L_{B20}$ |
| II-1255. | $L_{A25}$ | $L_{B20}$ |
| II-1260. | $L_{A30}$ | $L_{B20}$ |
| II-1261. | $L_{A31}$ | $L_{B20}$ |
| II-1262. | $L_{A32}$ | $L_{B20}$ |
| II-1263. | $L_{A33}$ | $L_{B20}$ |
| II-1264. | $L_{A34}$ | $L_{B20}$ |
| II-1265. | $L_{A35}$ | $L_{B20}$ |
| II-1270. | $L_{A40}$ | $L_{B20}$ |
| II-1271. | $L_{A41}$ | $L_{B20}$ |
| II-1276. | $L_{A46}$ | $L_{B20}$ |
| II-1277. | $L_{A47}$ | $L_{B20}$ |
| II-1278. | $L_{A48}$ | $L_{B20}$ |
| II-1279. | $L_{A49}$ | $L_{B20}$ |
| II-1280. | $L_{A50}$ | $L_{B20}$ |
| II-1281. | $L_{A51}$ | $L_{B20}$ |
| II-1282. | $L_{A52}$ | $L_{B20}$ |
| II-1287. | $L_{A57}$ | $L_{B20}$ |
| II-1288. | $L_{A58}$ | $L_{B20}$ |
| II-1293. | $L_{A63}$ | $L_{B20}$ |
| II-1294. | $L_{A64}$ | $L_{B20}$ |
| II-1295. | $L_{A65}$ | $L_{B20}$ |
| II-1296. | $L_{A66}$ | $L_{B20}$ |
| II-1297. | $L_{A67}$ | $L_{B20}$ |
| II-1298. | $L_{A68}$ | $L_{B20}$ |
| II-1299. | $L_{A69}$ | $L_{B20}$ |
| II-1371. | $L_{A6}$ | $L_{B22}$ |
| II-1372. | $L_{A7}$ | $L_{B22}$ |
| II-1377. | $L_{A12}$ | $L_{B22}$ |
| II-1378. | $L_{A13}$ | $L_{B22}$ |
| II-1379. | $L_{A14}$ | $L_{B22}$ |
| II-1380. | $L_{A15}$ | $L_{B22}$ |
| II-1381. | $L_{A16}$ | $L_{B22}$ |
| II-1382. | $L_{A17}$ | $L_{B22}$ |
| II-1383. | $L_{A18}$ | $L_{B22}$ |
| II-1388. | $L_{A24}$ | $L_{B22}$ |
| II-1389. | $L_{A25}$ | $L_{B22}$ |
| II-1394. | $L_{A30}$ | $L_{B22}$ |
| II-1395. | $L_{A31}$ | $L_{B22}$ |
| II-1396. | $L_{A32}$ | $L_{B22}$ |
| II-1397. | $L_{A33}$ | $L_{B22}$ |
| II-1398. | $L_{A34}$ | $L_{B22}$ |
| II-1399. | $L_{A35}$ | $L_{B22}$ |
| II-1404. | $L_{A40}$ | $L_{B22}$ |
| II-1405. | $L_{A41}$ | $L_{B22}$ |
| II-1410. | $L_{A46}$ | $L_{B22}$ |
| II-1411. | $L_{A47}$ | $L_{B22}$ |
| II-1412. | $L_{A48}$ | $L_{B22}$ |
| II-1413. | $L_{A49}$ | $L_{B22}$ |
| II-1414. | $L_{A50}$ | $L_{B22}$ |
| II-1415. | $L_{A51}$ | $L_{B22}$ |
| II-1416. | $L_{A52}$ | $L_{B22}$ |
| II-1421. | $L_{A57}$ | $L_{B22}$ |
| II-1422. | $L_{A58}$ | $L_{B22}$ |
| II-1427. | $L_{A63}$ | $L_{B22}$ |
| II-1428. | $L_{A64}$ | $L_{B22}$ |
| II-1429. | $L_{A65}$ | $L_{B22}$ |
| II-1430. | $L_{A66}$ | $L_{B22}$ |
| II-1431. | $L_{A67}$ | $L_{B22}$ |

-continued
| Compound Number | $L_A$ | $L_B$ |
|---|---|---|
| II-1432. | $L_{A68}$ | $L_{B22}$ |
| II-1433. | $L_{A69}$ | $L_{B22}$, |
and wherein $L_A$ is selected from the group consisting of
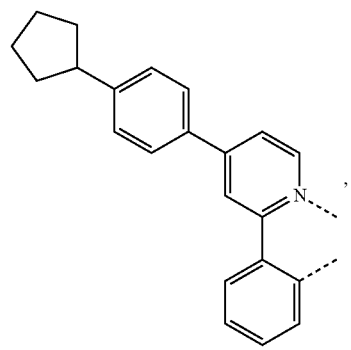
$L_{A6}$
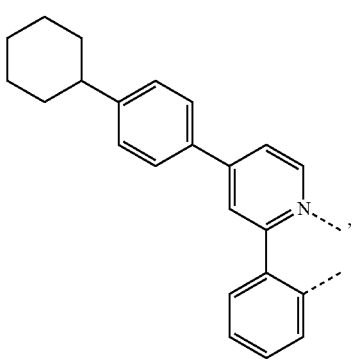
$L_{A7}$
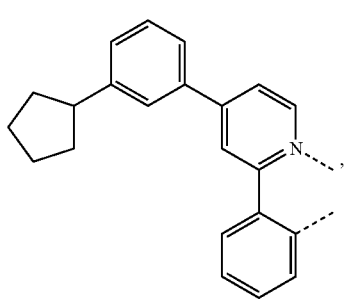
$L_{A12}$
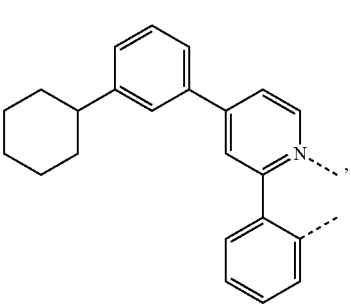
$L_{A13}$
-continued
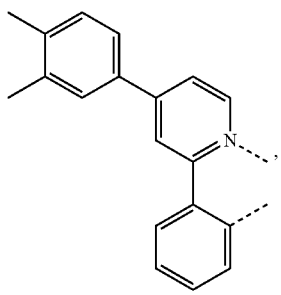
$L_{A14}$
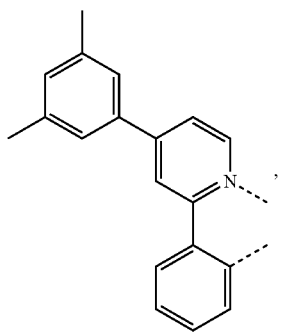
$L_{A15}$
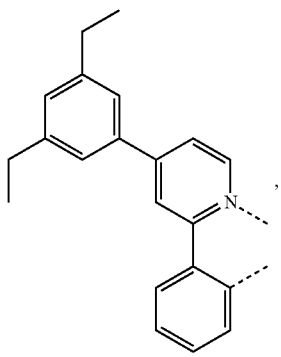
$L_{A16}$
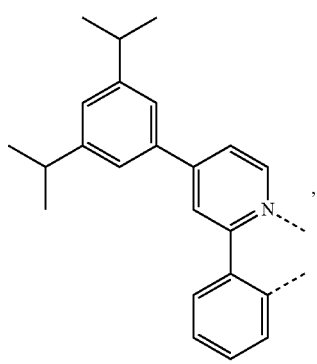
$L_{A17}$

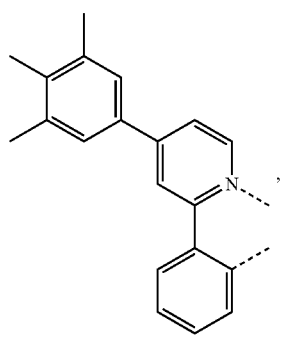   L<sub>A18</sub>
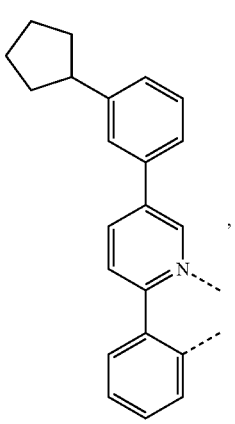   L<sub>A30</sub>
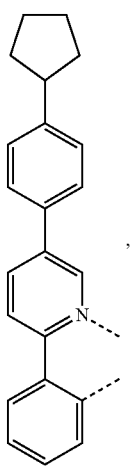   L<sub>A24</sub>
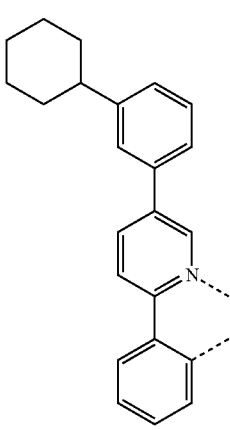   L<sub>A31</sub>
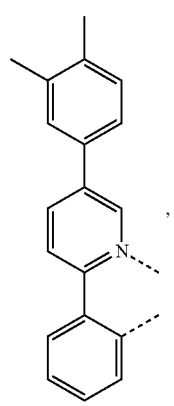   L<sub>A32</sub>
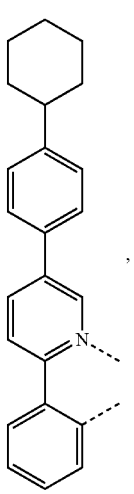   L<sub>A25</sub>
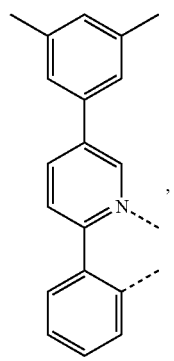   L<sub>A33</sub>

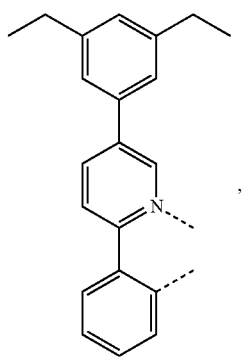
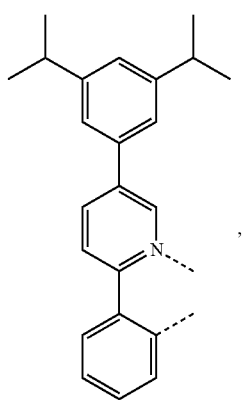
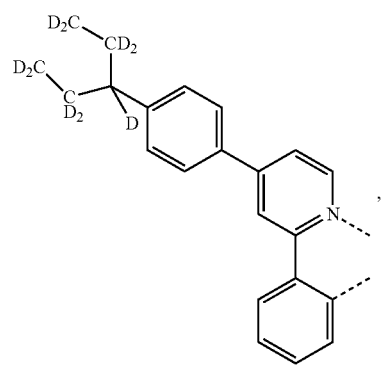
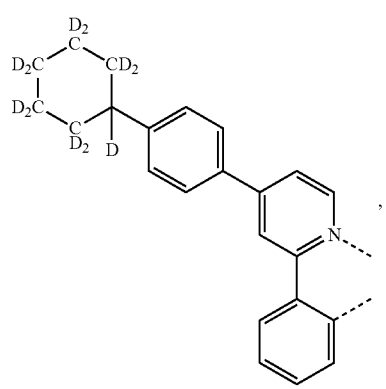
L<sub>A34</sub>
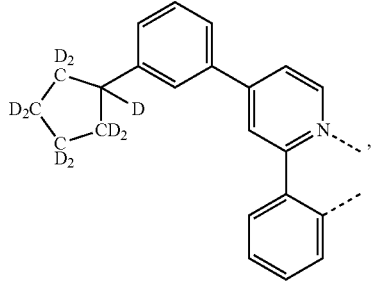
L<sub>A446</sub>
L<sub>A35</sub>
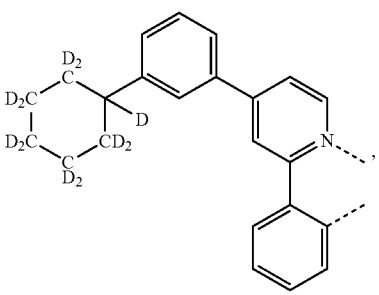
L<sub>A447</sub>
L<sub>A40</sub>
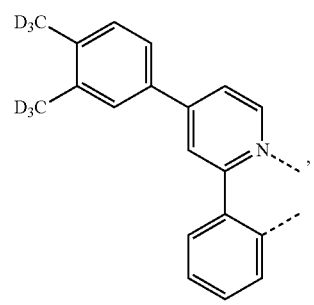
L<sub>A448</sub>
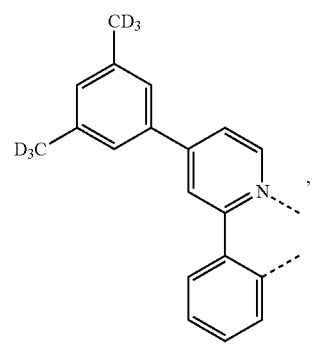
L<sub>A449</sub>
L<sub>A41</sub>
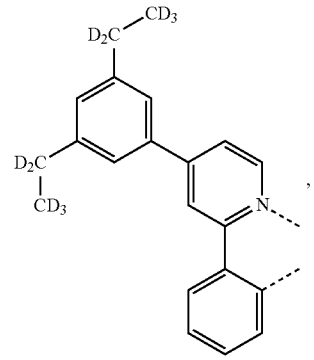
L<sub>A450</sub>

L_{A51}
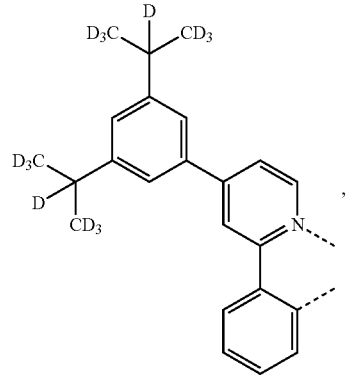
L_{A52}
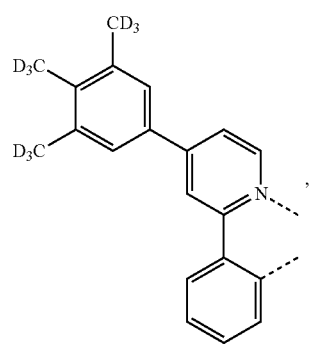
L_{A57}
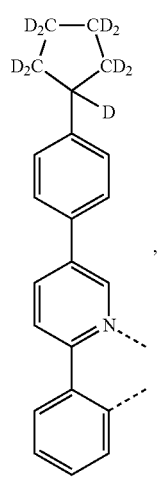
L_{A58}
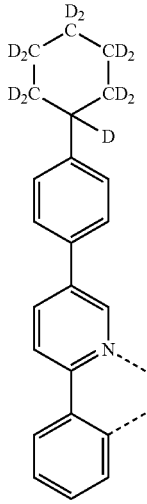
L_{A63}
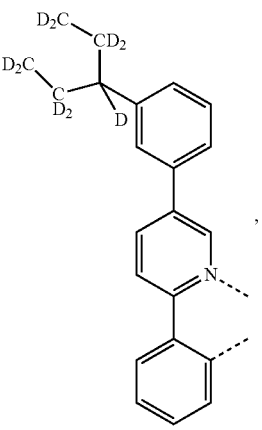
L_{A64}
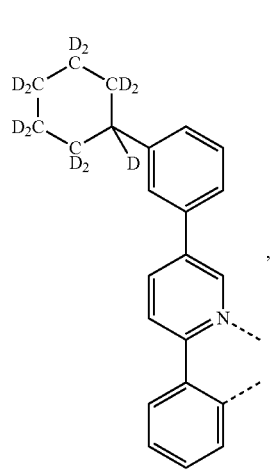

L<sub>A65</sub>
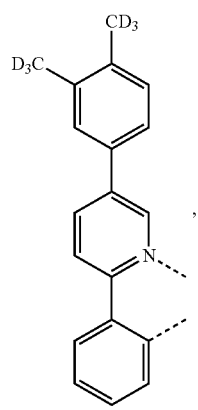
L<sub>A66</sub>
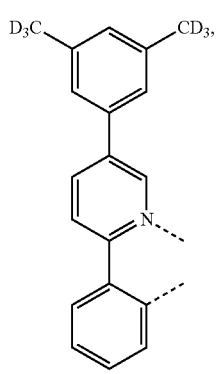
L<sub>A67</sub>
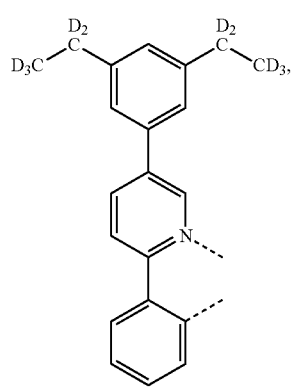
L<sub>A68</sub>
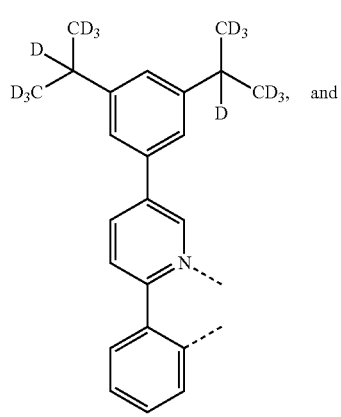, and
L<sub>A69</sub>
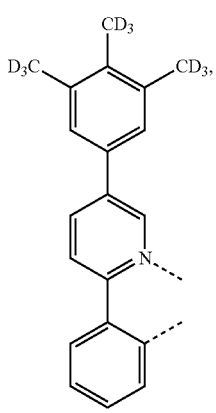
L<sub>B</sub> is selected from the group consisting of
L<sub>B5</sub>
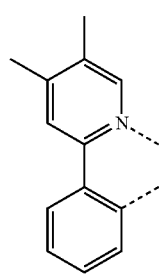
L<sub>B6</sub>
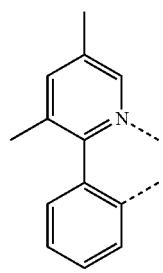
L<sub>B7</sub>
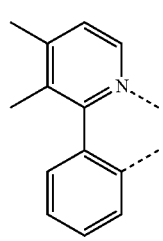
L<sub>B8</sub>
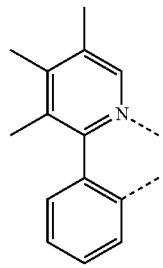

-continued
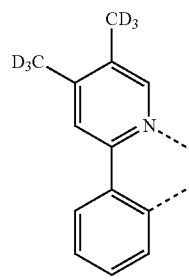
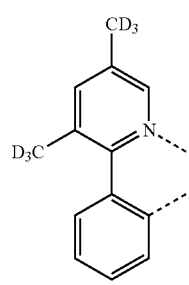
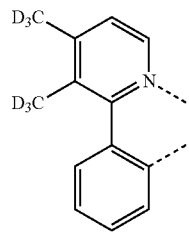
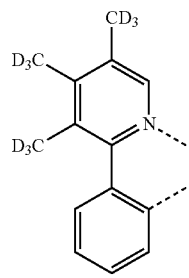
$L_{B12}$
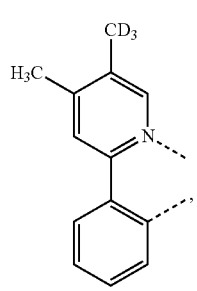
$L_{B13}$
$L_{B14}$
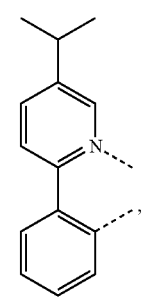
$L_{B15}$
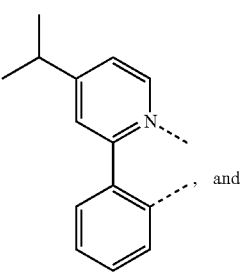
and
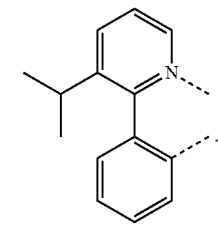
$L_{B16}$
$L_{B18}$
$L_{B20}$
$L_{B22}$
* * * * *